United States Patent
Lavoie et al.

(10) Patent No.: US 12,146,145 B2
(45) Date of Patent: Nov. 19, 2024

(54) ENDOGENOUS PLANT EXPRESSION ENHANCER

(71) Applicants: MITSUBISHI TANABE PHARMA CORPORATION, Osaka (JP); MEDICAGO INC., Québec (CA); NATIONAL UNIVERSITY CORPORATION NARA INSTITUTE OF SCIENCE AND TECHNOLOGY, Ikoma (JP)

(72) Inventors: Pierre-Olivier Lavoie, Quebec (CA); Marc-Andre D'Aoust, Quebec (CA); Ko Kato, Ikoma (JP); Shotaro Yamasaki, Ikoma (JP)

(73) Assignee: Aramis Biotechnologies Inc., Quebec City (CA)

( * ) Notice: Subject to any disclaimer, the term of this patent is extended or adjusted under 35 U.S.C. 154(b) by 331 days.

(21) Appl. No.: 17/439,155

(22) PCT Filed: Mar. 14, 2019

(86) PCT No.: PCT/CA2019/050319
§ 371 (c)(1),
(2) Date: Sep. 14, 2021

(87) PCT Pub. No.: WO2020/181354
PCT Pub. Date: Sep. 17, 2020

(65) Prior Publication Data
US 2022/0154195 A1 May 19, 2022

(51) Int. Cl.
*C12N 15/82* (2006.01)
(52) U.S. Cl.
CPC ..... *C12N 15/8216* (2013.01); *C12N 15/8258* (2013.01)
(58) Field of Classification Search
CPC ............ C12N 15/8216; C12N 15/8258; C12N 2760/16122; C12N 2760/16123; C12N 2760/16222; C12N 2760/16223; C12N 2770/16022; C12N 2770/16023; C12N 2770/18022; C07K 14/005; C12P 21/02
See application file for complete search history.

(56) References Cited

U.S. PATENT DOCUMENTS 8,674,084 B2   3/2014  Sainsbury

FOREIGN PATENT DOCUMENTS

| CA | 2984402 A1 | 11/2016 | |
|----|-----------|---------|---|
| WO | 2007135480 A1 | 11/2007 | |
| WO | 2009087391 A1 | 7/2009 | |
| WO | WO-2014153674 A1 * | 10/2014 | ............ A61K 39/12 |
| WO | 2015103704 A1 | 7/2015 | |
| WO | 2015143567 A1 | 10/2015 | |
| WO | 2016175132 A1 | 11/2016 | |
| WO | 2020168424 A1 | 8/2020 | |

OTHER PUBLICATIONS

Goodin MM, Zaitlin D, Naidu RA, Lommel SA. Nicotiana benthamiana: its history and future as a model for plant-pathogen interactions. Mol Plant Microbe Interact. Aug. 2008;21(8):1015-26. doi: 10.1094/MPMI-21-8-1015. PMID: 18616398.*
Ludwig, Michael Z., et al. "Consequences of eukaryotic enhancer architecture for gene expression dynamics, development, and fitness." PLoS genetics 7.11 (2011): e1002364. (Year: 2011).*
Long, Hannah K., Sara L. Prescott, and Joanna Wysocka. "Ever-changing landscapes: transcriptional enhancers in development and evolution." Cell 167.5 (2016): 1170-1187. (Year: 2016).*
Levo, Michal, and Eran Segal. "In pursuit of design principles of regulatory sequences." Nature Reviews Genetics 15.7 (2014): 453-468. (Year: 2014).*
Harth-Hertle, Marie L., et al. "Inactivation of intergenic enhancers by EBNA3A initiates and maintains polycomb signatures across a chromatin domain encoding CXCL10 and CXCL9." PLoS pathogens 9.9 (2013): e1003638. (Year: 2013).*
Whyte, Warren A., et al. "Enhancer decommissioning by LSD1 during embryonic stem cell differentiation." Nature 482.7384 (2012): 221-225. (Year: 2012).*
Oka, R., Zicola, J., Weber, B. et al. Genome-wide mapping of transcriptional enhancer candidates using DNA and chromatin features in maize. Genome Biol 18, 137 (2017). https://doi.org/10.1186/s13059-017-1273-4 (Year: 2017).*
Farh, Kyle Kai-How, et al. "Genetic and epigenetic fine mapping of causal autoimmune disease variants." Nature 518.7539 (2015): 337-343. (Year: 2015).*
Karnuta, Jaret M, and Peter C Scacheri. "Enhancers: bridging the gap between gene control and human disease." Human molecular genetics vol. 27,R2 (2018): R219-R227. doi:10.1093/hmg/ddy167 (Year: 2018).*
Lin, Y., Meng, F., Fang, C. et al. Rapid validation of transcriptional enhancers using agrobacterium-mediated transient assay. Plant Methods 15, 21 (2019). https://doi.org/10.1186/s13007-019-0407-y (Year: 2019).*
Sainsbury, F., et al. Expression of multiple proteins using full-length and deleted versions of cowpea mosaic virus RNA-2. Plant Biotechnology Journal, vol. 6, 2008, pp. 82-92.
Sainsbury, F., et al. pEAQ: versatile expression vectors for easy and quick transient expression of heterologous proteins in plants. Plant Biotechnology Journal (2009), 7, pp. 682-693.

(Continued)

*Primary Examiner* — Charles Logsdon
*Assistant Examiner* — Kelsey L McWilliams
(74) *Attorney, Agent, or Firm* — Ballard Spahr LLP

(57) ABSTRACT

An isolated expression enhancer active in a plant, portion of a plant or plant cell, the expression enhancer is provided. The isolated expression enhancer may be selected from the group consisting of nbEPI42 (SEQ ID NO:1); nbSNS46 (SEQ ID NO:2); nbCSY65 (SEQ ID NO:3); nbHEL40 (SEQ ID NO:4); and nbSEP44 (SEQ ID NO:5). Methods for using the isolated expression enhancer are also provided.

19 Claims, 54 Drawing Sheets

Specification includes a Sequence Listing.

(56) References Cited

OTHER PUBLICATIONS

Sainsbury F. et al. Cowpea Mosaic Virus-Based Systems for the Expression of Antigens and Antibodies in Plants, Methods in Molecular Biology, Recombinant Proteins From Plants, vol. 483: 25-39, 2009.

Sainsbury & Lomonossoff Extremely high-level and rapid transient protein production in plants without the use of viral replication. Plant Physiology. (2008) vol. 148, 1212-1218.

Dvir, S. et al., Deciphering the rules by which 5'-UTR sequences affect protein expression in yeast. 2013 PNAS, published online Jul. 5, 2013, E2792-E2801.

Leppek K et. al., Functional 5' UTR mRNA structures in eukaryotic translation regulation and how to find them. Nature Reviews Mol. Cell Biol. 19:158-174, Mar. 2018.

Yamasaki, S., et al. *Arabidopsis thaliana* cold-regulated 47 gene 5'-untranslated region enables stable high-level expression of transgenes. Journal of Bioscience and Bioengineering, 2018, vol. 125(1), pp. 124-130.

Diamos, A.G. et al. T' and 3' Untranslated Regions Strongly Enhance Performance of Geminiviral Replicons in Nicotiana benthamiana Leaves. Frontiers in Plant Science, vol. 7, Article 200, Feb. 2016.

Suzuki, S. and Noguchi S., FS437376 normalized full-length tobacco cDNA library Nicotiana tabacum cDNA clone TBK02GR0101_2_F02 5' mRNA sequence. GenBank, 2009.

Accession DR233261, created Feb. 24, 2006, last updated Feb. 15, 2011.

Mardanova, et al. Efficient Transient Expression of Recombinant Proteins in Plants by the Novel pEff Vector Based on the Genome of Potato Virus X. Frontiers in Plant Science, vol. 8, Article 247, Feb. 2017.

International Search Report and Written Opinion for PCT/CA2019/050319 mailed Nov. 20, 2019.

\* cited by examiner

PRIOR ART (WO2015/103704)
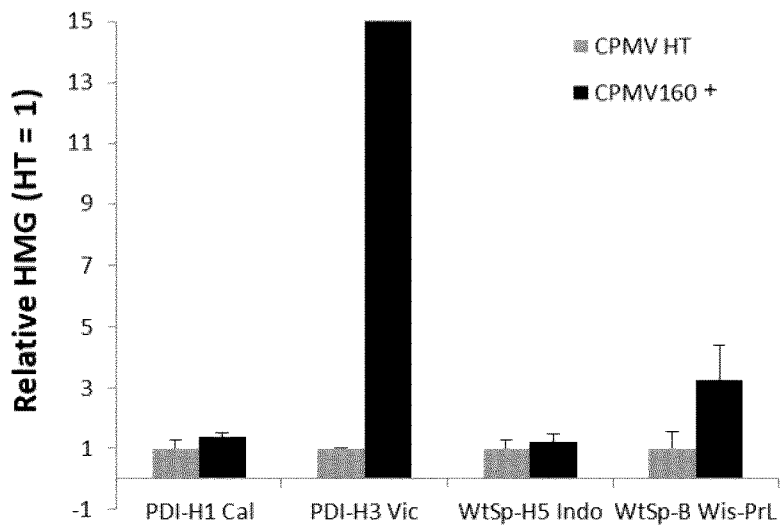
Figure 1B
PRIOR ART (WO2015/103704)
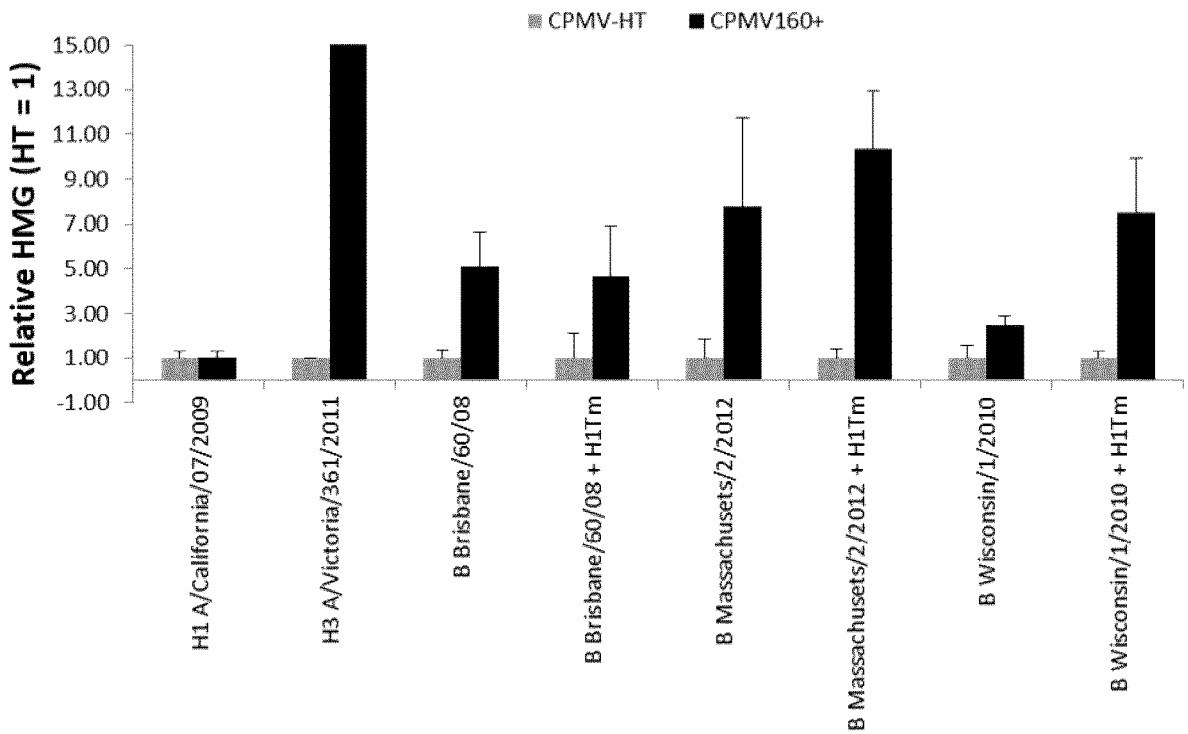

FIGURE 9A   nbEPI42 (SEQ ID NO:1)

ACTTTAATTTGCTGATTTTCAACAAAATCAAGAATTTCAGCA

FIGURE 9B   nbSNS46 (SEQ ID NO:2)

ATTCAGTGCTTAACTGGTTATTGAGTAAGTTATCAAAAAGCAAAAA

FIGURE 9C   nbCSY65 (SEQ ID NO:3)

ACTTTTCTAATCAATCATCAAACAGAACGCAGAAAATTTCCTAAAAACAAAAAAAAGGCATACAA

FIGURE 9D   nbHEL40 (SEQ ID NO;4)

ACTCCATTTGAATCTATCAAACCAAAACACATTGAGCAAA

FIGURE 9E   nbSEP44 (SEQ ID NO: 5)

ACTTCAATCACTCCACACTTTATTCTCTTTCAAAACCTACACTC

FIGURE 9F   CPMV 160 (SEQ ID NO:6) PRIOR ART:

TATTAAAATCTTAATAGGTTTTGATAAAAGCGAACGTGGGGAAACCCGAACCAAACCTTCTTCTAAACTCTCTCTCATCTCTCTTAAAGCAAACTTCTCTCTTGTCTTTCTTGCGTGAGCGATCTTCAACGTTGTCAGATCGTGCTTCGGCACCAGTACA

Figure 9G   nbMT78 (SEQ ID NO:7);

ACACAATTTGCTTTAGTGATTAAACTTTCTTTTACAACAAATTAAAGGTCTATTATCTCCCAACAACATAAGAAAACA

FIGURE 9H   atHSP69 (SEQ ID NO:8);

AAATTCAAAATTTAACACACAAACACAAACACACACACCAAAAAAAACACAGACCTTAAAAAAATAAAA

FIGURE 10A   IF-(2X35S+C)_CPMV160.c   (SEQ ID NO:9)

TTTCATTTGGAGAGGCTATTAAAATCTTAATAGGTTTTGATAAAAGCG

FIGURE 10B   IF-Dasher(27-609).r   (SEQ ID NO:10)

ACTAAAGAAAATAGGCCTTTACTGATAGGTATCGAGATCGACGGCCTTGACCACTT

FIGURE 10C   CPMV 160 5'UTR-Dasher DNA sequence   (SEQ ID NO:11)

```
    TATTAAAATCTTAATAGGTTTTGATAAAAGCGAACGTGGGGAAACCCGAACCAAACCTTCTTCTA
AACTCTCTCTCATCTCTCTTAAAGCAAACTTCTCTCTTGTCTTTCTTGCGTGAGCGATCTTCAACGTTGT
CAGATCGTGCTTCGGCACCAGTACAATGACTGCCCTGACCGAAGGTGCTAAGCTGTTTGAGAAGGAGATT
CCGTACATCACCGAGCTGGAAGGGGACGTCGAAGGAATGAAGTTCATCATCAAGGGAGAAGGAACCGGGG
ACGCTACGACTGGAACCATTAAGGCCAAGTATATCTGTACCACTGGAGATCTGCCAGTGCCTTGGGCCAC
CCTTGTGTCAACCCTCTCGTATGGAGTGCAGTGTTTTGCTAAGTACCCTAGCCACATTAAGGACTTCTTC
AAATCCGCCATGCCGGAAGGTTATACCCAAGAGCGCACCATTTCTTTTGAGGGAGATGGAGTGTACAAGA
CCCGCGCGATGGTCACCTATGAGAGGGGATCTATCTACAACCGGGTGACTCTGACTGGAGAAAACTTTAA
GAAGGACGGGCATATTCTTCGGAAGAATGTCGCCTTCCAGTGCCCTCCCAGCATCCTTTACATTCTCCCC
GACACTGTGAACAACGGAATCCGCGTGGAGTTCAATCAAGCCTACGACATCGAGGGGGTGACGGAGAAGC
TGGTGACCAAGTGTAGCCAGATGAATCGGCCACTGGCCGGTTCAGCGGCTGTCCACATTCCGCGCTACCA
TCATATCACTTATCACACTAAGCTCTCCAAAGACCGCGATGAGAGGAGAGATCACATGTGCCTGGTGGAA
GTGGTCAAGGCCGTCGATCTCGATACCTATCAGTAA
```

FIGURE 10D   Dasher DNA sequence   (SEQ ID NO:12)

```
        ATGACTGCCCTGACCGAAGGTGCTAAGCTGTTTGAGAAGGAGATTCCGTACATCACCGAGCTGGA
AGGGGACGTCGAAGGAATGAAGTTCATCATCAAGGGAGAAGGAACCGGGGACGCTACGACTGGAACCATT
AAGGCCAAGTATATCTGTACCACTGGAGATCTGCCAGTGCCTTGGGCCACCCTTGTGTCAACCCTCTCGT
ATGGAGTGCAGTGTTTTGCTAAGTACCCTAGCCACATTAAGGACTTCTTCAAATCCGCCATGCCGGAAGG
TTATACCCAAGAGCGCACCATTTCTTTTGAGGGAGATGGAGTGTACAAGACCCGCGCGATGGTCACCTAT
GAGAGGGGATCTATCTACAACCGGGTGACTCTGACTGGAGAAAACTTTAAGAAGGACGGGCATATTCTTC
GGAAGAATGTCGCCTTCCAGTGCCCTCCCAGCATCCTTTACATTCTCCCCGACACTGTGAACAACGGAAT
CCGCGTGGAGTTCAATCAAGCCTACGACATCGAGGGGGTGACGGAGAAGCTGGTGACCAAGTGTAGCCAG
ATGAATCGGCCACTGGCCGGTTCAGCGGCTGTCCACATTCCGCGCTACCATCATATCACTTATCACACTA
AGCTCTCCAAAGACCGCGATGAGAGGAGAGATCACATGTGCCTGGTGGAAGTGGTCAAGGCCGTCGATCT
CGATACCTATCAGTAA
```

FIGURE 10E   Dasher protein sequence   (SEQ ID NO:13)

```
    MTALTEGAKLFEKEIPYITELEGDVEGMKFIIKGEGTGDATTGTIKAKYICTTGDLPVPWATLVS
TLSYGVQCFAKYPSHIKDFFKSAMPEGYTQERTISFEGDGVYKTRAMVTYERGSIYNRVTLTGENFKKDG
HILRKNVAFQCPPSILYILPDTVNNGIRVEFNQAYDIEGVTEKLVTKCSQMNRPLAGSAAVHIPRYHHIT
YHTKLSKDRDERRDHMCLVEVVKAVDLDTYQ
```

FIGURE 10F  IF-nbMT78.c  (SEQ ID NO:14)

TTTCATTTGGAGAGGCACACAATTTGCTTTAGTGATTAAACTTTCTTTTACAACAAATTAAAGGT
CTATTATCTCCCAACAACATAAGA

FIGURE 10G  nbMT78_Dasher.c  (SEQ ID NO: 15)

TTAAAGGTCTATTATCTCCCAACAACATAAGAAAACAATGACTGCCCTGACCGAAGGTG

FIGURE 10H  atHSP69_Dasher.c  (SEQ ID NO: 16)

CCAAAAAAAACACAGACCTTAAAAAAATAAAAATGACTGCCCTGACCGAAGGTGCTAAG

FIGURE 10I  IF-atHSP69.c  (SEQ ID NO: 17)

TTTCATTTGGAGAGGCAAATTCAAAATTTAACACACAAACACAAACACACACACCAAAAAAAACA
CAGACCTTAAAAAAATAAA

FIGURE 10J  nbEPI42+Dasher.c  (SEQ ID NO: 18)

TTTCAACAAAATCAAGAATTTCAGCAATGACTGCCCTGACCGAAGGTGCTAA

FIGURE 10K  IF-nbEPI42.c  (SEQ ID NO: 19)

ATTTCATTTGGAGAGGCACTTTAATTTGCTGATTTTCAACAAAATCAAGAATTTCAGCA

FIGURE 10L  nbSNS46+Dasher.c  (SEQ ID NO: 20)

TTGAGTAAGTTATCAAAAAGCAAAAAATGACTGCCCTGACCGAAGGTGCTAA

FIGURE 10M  IF-nbSNS46.c  (SEQ ID NO: 21)

ATTTCATTTGGAGAGGCATTCAGTGCTTAACTGGTTATTGAGTAAGTTATCAAAAGCAAAAA

FIGURE 10N  nbCSY65+Dasher.c  (SEQ ID NO: 22)

CCTAAAAACAAAAAAAAGGCATACAAATGACTGCCCTGACCGAAGGTGCTAA

FIGURE 10O  IF-nbCSY65.c  (SEQ ID NO: 23)

ATTTCATTTGGAGAGGCACTTTTCTAATCAATCATCAAACAGAACGCAGAAAATTTCCTAAAAAC
AAAAAAAAGGCATACAA

FIGURE 10P  nbHEL40+Dasher.c  (SEQ ID NO: 24)

CTATCAAACCAAAACACATTGAGCAAAATGACTGCCCTGACCGAAGGTGCTAA

FIGURE 10Q  IF-nbHEL40.c  (SEQ ID NO: 25)

ATTTCATTTGGAGAGGCACTCCATTTGAATCTATCAAACCAAAACACATTGAGCAA

FIGURE 10R  nbSEP44+Dasher.c  (SEQ ID NO: 26)

TTTATTCTCTTTCAAAACCTACACTCATGACTGCCCTGACCGAAGGTGCTAAG

FIGURE 10S  IF-nbSEP44.c  (SEQ ID NO: 27)

ATTTCATTTGGAGAGGCACTTCAATCACTCCACACTTTATTCTCTTTCAAAACCTACACTC

FIGURE 11A  IF-GII4Syd12VP1.r  (SEQ ID NO: 28)

ACTAAAGAAAATAGGCCTTCAGACAGCCCTGCGTCTGCCAGTCCCATT

FIGURE 11B  CPMV 160 5'UTR-VP1 (GII.4) DNA sequence  (SEQ ID NO:29)

TATTAAAATCTTAATAGGTTTTGATAAAAGCGAACGTGGGGAAACCCGAACCAAACCTTCTTCTA
AACTCTCTCTCATCTCTCTTAAAGCAAACTTCTCTCTTGTCTTTCTTGCGTGAGCGATCTTCAACGTTGT
CAGATCGTGCTTCGGCACCAGTACAATGAAAATGGCCTCGAGTGACGCTAACCCTAGTGACGGCAGCGCC
GCCAATCTTGTGCCTGAGGTTAATAATGAGGTGATGGCCCTGGAGCCTGTGGTGGGCGCAGCCATAGCAG
CGCCCGTGGCCGGTCAGCAGAATGTGATTGACCCGTGGATACGCAACAATTTTGTCCAAGCCCCTGGTGG
GGAGTTCACCGTTAGCCCGAGAAATGCGCCAGGAGAAATCCTGTGGTCGGCCAGCTTGGGACCCGATCTG
AACCCCTATTTGTCACATCTCGCTCGGATGTACAACGGGTATGCCGGCGGATTTGAAGTGCAGGTGATTC
TGGCTGGGAACGCGTTCACTGCTGGCAAAGTGATCTTTGCAGCGGTGCCTCCCAACTTCCCCACTGAAGG
ACTGTCTCCAAGCCAGGTCACAATGTTTCCACACATCGTGGTGGACGTACGGCAGCTAGAGCCTGTCCTG
ATTCCCCTCCCTGATGTACGCAATAATTTCTACCACTACAATCAATCCAATGATCCGACCATTAAACTCA
TCGCGATGTTGTACACCCCTCTGCGCGCTAACAATGCTGGAGACGACGTATTCACCGTGTCATGCAGAGT
GCTCACCAGACCTTCACCAGACTTTGACTTTATCTTCTTAGTGCCCCCCACTGTTGAGAGCCGAACCAAG
CCCTTTAGTGTCCCCGTACTCACAGTCGAGGAGATGACAAATAGCCGCTTTCCAATCCCCCTTGAGAAAC
TGTTCACAGGACCTTCCTCGGCATTCGTGGTTCAGCCACAGAACGGACGCTGCACAACTGACGGCGTGCT

FIGURE 11B (CONT.)

```
GCTCGGAACCACCCAGCTTAGCCCTGTTAATATCTGTACGTTTAGAGGCGACGTAACTCACATAACTGGC
TCACGGAACTATACCATGAATCTGGCATCACAGAATTGGAATGACTACGACCCAACCGAAGAGATTCCCG
CACCTCTTGGAACCCCCGACTTTGTGGGAAAAATACAGGGCGTCCTGACACAAACCACCAGAACCGATGG
CTCCACACGGGGACACAAGGCAACCGTCTACACTGGCTCTGCCGATTTTGCCCCGAAACTGGGTAGAGTG
CAGTTTGAGACCGACACTGACCGGGACTTTGAAGCCAATCAGAATACTAAGTTCACACCTGTAGGAGTGA
TTCAGGACGGGGGCACCACTCACCGGAACGAGCCGCAACAATGGGTCCTGCCCTCTTATAGCGGGAGGAA
TACTCATAATGTGCATTTGGCTCCTGCAGTGGCTCCCACGTTTCCCGGGGAACAACTGCTCTTTTTTCGT
TCAACCATGCCTGGATGCTCCGGATATCCCAATATGGATCTCGATTGCCTGCTCCCACAGGAATGGGTGC
AGTATTTTTATCAAGAGGCCGCACCAGCCCAATCCGACGTCGCACTTCTGCGGTTCGTGAATCCAGACAC
AGGCCGCGTGTTGTTTGAGTGCAAATTGCACAAATCAGGATACGTTACAGTGGCTCATACTGGACAGCAT
GACCTGGTGATCCCACCCAACGGATATTTTAGGTTCGACTCCTGGGTGAATCAGTTTTATACATTAGCCC
CCATGGGGAATGGGACTGGCAGACGCAGGGCTGTCTGA
```

FIGURE 11C   VP1 (GII.4) DNA sequence   (SEQ ID NO:30)

```
ATGAAAATGGCCTCGAGTGACGCTAACCCTAGTGACGGCAGCGCCGCCAATCTTGTGCCTGAGGT
TAATAATGAGGTGATGGCCCTGGAGCCTGTGGTGGGCGCAGCCATAGCAGCGCCCGTGGCCGGTCAGCAG
AATGTGATTGACCCGTGGATACGCAACAATTTTGTCCAAGCCCCTGGTGGGGAGTTCACCGTTAGCCCGA
GAAATGCGCCAGGAGAAATCCTGTGGTCGGCCAGCTTGGGACCCGATCTGAACCCCTATTTGTCACATCT
CGCTCGGATGTACAACGGGTATGCCGGCGGATTTGAAGTGCAGGTGATTCTGGCTGGGAACGCGTTCACT
GCTGGCAAAGTGATCTTTGCAGCGGTGCCTCCCAACTTCCCCACTGAAGGACTGTCTCCAAGCCAGGTCA
CAATGTTTCCACACATCGTGGTGGACGTACGGCAGCTAGAGCCTGTCCTGATTCCCCTCCCTGATGTACG
CAATAATTTCTACCACTACAATCAATCCAATGATCCGACCATTAAACTCATCGCGATGTTGTACACCCCT
CTGCGCGCTAACAATGCTGGAGACGACGTATTCACCGTGTCATGCAGAGTGCTCACCAGACCTTCACCAG
ACTTTGACTTTATCTTCTTAGTGCCCCCCACTGTTGAGAGCCGAACCAAGCCCTTTAGTGTCCCCGTACT
CACAGTCGAGGAGATGACAAATAGCCGCTTTCCAATCCCCCTTGAGAAACTGTTCACAGGACCTTCCTCG
GCATTCGTGGTTCAGCCACAGAACGGACGCTGCACAACTGACGGCGTGCTGCTCGGAACCACCCAGCTTA
GCCCTGTTAATATCTGTACGTTTAGAGGCGACGTAACTCACATAACTGGCTCACGGAACTATACCATGAA
TCTGGCATCACAGAATTGGAATGACTACGACCCAACCGAAGAGATTCCCGCACCTCTTGGAACCCCCGAC
TTTGTGGGAAAAATACAGGGCGTCCTGACACAAACCACCAGAACCGATGGCTCCACACGGGGACACAAGG
CAACCGTCTACACTGGCTCTGCCGATTTTGCCCCGAAACTGGGTAGAGTGCAGTTTGAGACCGACACTGA
CCGGGACTTTGAAGCCAATCAGAATACTAAGTTCACACCTGTAGGAGTGATTCAGGACGGGGGCACCACT
CACCGGAACGAGCCGCAACAATGGGTCCTGCCCTCTTATAGCGGGAGGAATACTCATAATGTGCATTTGG
CTCCTGCAGTGGCTCCCACGTTTCCCGGGGAACAACTGCTCTTTTTTCGTTCAACCATGCCTGGATGCTC
CGGATATCCCAATATGGATCTCGATTGCCTGCTCCCACAGGAATGGGTGCAGTATTTTTATCAAGAGGCC
GCACCAGCCCAATCCGACGTCGCACTTCTGCGGTTCGTGAATCCAGACACAGGCCGCGTGTTGTTTGAGT
GCAAATTGCACAAATCAGGATACGTTACAGTGGCTCATACTGGACAGCATGACCTGGTGATCCCACCCAA
CGGATATTTTAGGTTCGACTCCTGGGTGAATCAGTTTTATACATTAGCCCCCATGGGGAATGGGACTGGC
AGACGCAGGGCTGTCTGA
```

FIGURE 11D   VP1 (GII.4) protein sequence   (SEQ ID NO:31)

```
    MKMASSDANPSDGSAANLVPEVNNEVMALEPVVGAAIAAPVAGQQNVIDPWIRNNFVQAPGGEFT
VSPRNAPGEILWSASLGPDLNPYLSHLARMYNGYAGGFEVQVILAGNAFTAGKVIFAAVPPNFPTEGLSP
SQVTMFPHIVVDVRQLEPVLIPLPDVRNNFYHYNQSNDPTIKLIAMLYTPLRANNAGDDVFTVSCRVLTR
PSPDFDFIFLVPPTVESRTKPFSVPVLTVEEMTNSRFPIPLEKLFTGPSSAFVVQPQNGRCTTDGVLLGT
```

FIGURE 11D (CONT)

TQLSPVNICTFRGDVTHITGSRNYTMNLASQNWNDYDPTEEIPAPLGTPDFVGKIQGVLTQTTRTDGSTR
GHKATVYTGSADFAPKLGRVQFETDTDRDFEANQNTKFTPVGVIQDGGTTHRNEPQQWVLPSYSGRNTHN
VHLAPAVAPTFPGEQLLFFRSTMPGCSGYPNMDLDCLLPQEWVQYFYQEAAPAQSDVALLRFVNPDTGRV
LFECKLHKSGYVTVAHTGQHDLVIPPNGYFRFDSWVNQFYTLAPMGNGTGRRRAV*

FIGURE 11E  nbMT78+GII4Syd12.c  (SEQ ID NO:32)

TCTATTATCTCCCAACAACATAAGAAAACAATGAAAATGGCCTCGAGTGACGCTAACCC

FIGURE 11F  atHSP69+GII4Syd12.c  (SEQ ID NO:33)

AAACACAGACCTTAAAAAAATAAAAATGAAAATGGCCTCGAGTGACGCTAACCCTAGTG

FIGURE 11G  nbEPI42+GII4Syd12.c  (SEQ ID NO:34)

TGATTTTCAACAAAATCAAGAATTTCAGCAATGAAAATGGCCTCGAGTGACGCTAA

FIGURE 11H  nbSNS46+GII4Syd12.c  (SEQ ID NO:35)

TTGAGTAAGTTATCAAAAGCAAAAAATGAAAATGGCCTCGAGTGACGCTAA

FIGURE 11I  nbCSY65+GII4Syd12.c  (SEQ ID NO:36)

TCCTAAAAACAAAAAAAAGGCATACAAATGAAAATGGCCTCGAGTGACGCTAA

FIGURE 11J  nbHEL40+GII4Syd12.c  (SEQ ID NO:37)

TCTATCAAACCAAAACACATTGAGCAAAATGAAAATGGCCTCGAGTGACGCTAACC

FIGURE 11K  nbSEP44+GII4Syd12.c  (SEQ ID NO:38)

CTTTATTCTCTTTCAAAACCTACACTCATGAAAATGGCCTCGAGTGACGCTAA

FIGURE 12A  IF**-HC(Ritux).s1-6r  (SEQ ID NO:39)

ACTAAAGAAAATAGGCCTTCACTTTCCAGGAGAAAGAGAAAGGGACTTTTG

FIGURE 12B   CPMV 160 5'UTR-PDI+Rituximab HC DNA sequence   (SEQ ID NO:40)

TATTAAAATCTTAATAGGTTTTGATAAAAGCGAACGTGGGGAAACCCGAACCAAACCTTCTTCTA
AACTCTCTCTCATCTCTCTTAAAGCAAACTTCTCTCTTGTCTTTCTTGCGTGAGCGATCTTCAACGTTGT
CAGATCGTGCTTCGGCACCAGTACAATGGCGAAAAACGTTGCGATTTTCGGCTTATTGTTTTCTCTTCTT
GTGTTGGTTCCTTCTCAGATCTTCGCGCAGGTACAACTGCAGCAGCCTGGGGCTGAGCTGGTGAAGCCTG
GGGCCTCAGTGAAGATGTCCTGCAAGGCTTCTGGCTACACATTTACCAGTTACAATATGCACTGGGTAAA
ACAGACACCTGGTCGGGGCCTGGAATGGATTGGAGCTATTTATCCCGGAAATGGTGATACTTCCTACAAT
CAGAAGTTCAAAGGCAAGGCCACATTGACTGCAGACAAATCCTCCAGCACAGCCTACATGCAGCTCAGCA
GCCTGACATCTGAGGACTCTGCGGTCTATTACTGTGCAAGATCGACTTACTACGGCGGTGACTGGTACTT
CAATGTCTGGGGCGCAGGGACCACGGTCACCGTCTCTGCAGCTAGCACCAAGGGCCCATCGGTCTTCCCC
CTGGCACCCTCCTCCAAGAGCACCTCTGGGGGCACAGCGGCCCTGGGCTGCCTGGTCAAGGACTACTTCC
CCGAACCGGTGACGGTGTCGTGGAACTCAGGCGCCCTGACCAGCGGCGTGCACACCTTCCCGGCTGTCCT
ACAGTCCTCAGGACTCTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAAAGTTGAGCCCAAATCTTGTG
ACAAAACTCACACATGCCCACCGTGCCCAGCACCTGAACTCCTGGGGGGACCGTCAGTCTTCCTCTTCCC
CCCAAAACCCAAGGACACCCTCATGATCTCCCGGACCCCTGAGGTCACATGCGTGGTGGTGGACGTGAGC
CACGAAGACCCTGAGGTCAAGTTCAACTGGTACGTGGACGGCGTGGAGGTGCATAATGCCAAGACAAAGC
CGCGGGAGGAGCAGTACAACAGCACGTACCGTGTGGTCAGCGTCCTCACCGTCCTGCACCAGGACTGGCT
GAATGGCAAGGAGTACAAGTGCAAGGTCTCCAACAAAGCCCTCCCAGCCCCCATCGAGAAAACCATCTCC
AAAGCCAAAGGGCAGCCTAGGGAACCACAAGTGTACACTCTTCCACCATCTAGGGATGAGCTTACTAAGA
ACCAAGTTTCTCTTACTTGTCTTGTGAAGGGATTTTATCCATCTGACATCGCCGTGGAATGGGAATCCAA
CGGACAACCAGAGAACAATTACAAGACTACTCCACCAGTTCTTGATTCTGATGGATCCTTCTTTCTTTAT
TCCAAGCTTACTGTTGATAAGTCCAGATGGCAGCAAGGAAATGTGTTCTCTTGTTCTGTTATGCACGAAG
CTCTTCATAATCATTATACTCAAAAGTCCCTTTCTCTTTCTCCTGGAAAGTGA

FIGURE 12C  PDI+Rituximab HC DNA sequence   (SEQ ID NO:41)

ATGGCGAAAAACGTTGCGATTTTCGGCTTATTGTTTTCTCTTCTTGTGTTGGTTCCTTCTCAGAT
CTTCGCGCAGGTACAACTGCAGCAGCCTGGGGCTGAGCTGGTGAAGCCTGGGGCCTCAGTGAAGATGTCC
TGCAAGGCTTCTGGCTACACATTTACCAGTTACAATATGCACTGGGTAAAACAGACACCTGGTCGGGGCC
TGGAATGGATTGGAGCTATTTATCCCGGAAATGGTGATACTTCCTACAATCAGAAGTTCAAAGGCAAGGC
CACATTGACTGCAGACAAATCCTCCAGCACAGCCTACATGCAGCTCAGCAGCCTGACATCTGAGGACTCT
GCGGTCTATTACTGTGCAAGATCGACTTACTACGGCGGTGACTGGTACTTCAATGTCTGGGGCGCAGGGA
CCACGGTCACCGTCTCTGCAGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGGTGTCG
TGGAACTCAGGCGCCCTGACCAGCGGCGTGCACACCTTCCCGGCTGTCCTACAGTCCTCAGGACTCTACT
CCCTCAGCAGCGTGGTGACCGTGCCCTCCAGCAGCTTGGGCACCCAGACCTACATCTGCAACGTGAATCA
CAAGCCCAGCAACACCAAGGTGGACAAGAAAGTTGAGCCCAAATCTTGTGACAAAACTCACACATGCCCA
CCGTGCCCAGCACCTGAACTCCTGGGGGGACCGTCAGTCTTCCTCTTCCCCCCAAAACCCAAGGACACCC
TCATGATCTCCCGGACCCCTGAGGTCACATGCGTGGTGGTGGACGTGAGCCACGAAGACCCTGAGGTCAA
GTTCAACTGGTACGTGGACGGCGTGGAGGTGCATAATGCCAAGACAAAGCCGCGGGAGGAGCAGTACAAC
AGCACGTACCGTGTGGTCAGCGTCCTCACCGTCCTGCACCAGGACTGGCTGAATGGCAAGGAGTACAAGT
GCAAGGTCTCCAACAAAGCCCTCCCAGCCCCCATCGAGAAAACCATCTCCAAAGCCAAAGGGCAGCCTAG
GGAACCACAAGTGTACACTCTTCCACCATCTAGGGATGAGCTTACTAAGAACCAAGTTTCTCTTACTTGT

FIGURE 12C (CONT.)

```
CTTGTGAAGGGATTTTATCCATCTGACATCGCCGTGGAATGGGAATCCAACGGACAACCAGAGAACAATT
ACAAGACTACTCCACCAGTTCTTGATTCTGATGGATCCTTCTTTCTTTATTCCAAGCTTACTGTTGATAA
GTCCAGATGGCAGCAAGGAAATGTGTTCTCTTGTTCTGTTATGCACGAAGCTCTTCATAATCATTATACT
CAAAAGTCCCTTTCTCTTTCTCCTGGAAAGTGA
```

FIGURE 12D   PDI+Rituximab HC protein sequence   (SEQ ID NO:42)

```
        MAKNVAIFGLLFSLLVLVPSQIFAQVQLQQPGAELVKPGASVKMSCKASGYTFTSYNMHWVKQTP
GRGLEWIGAIYPGNGDTSYNQKFKGKATLTADKSSSTAYMQLSSLTSEDSAVYYCARSTYYGGDWYFNVW
GAGTTVTVSAASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLSLSPGK
```

FIGURE 12E   IF-LC(Ritux).s1-6r   (SEQ ID NO:43)**

```
        ACTAAAGAAAATAGGCCTTCAACACTCTCCCCTGTTGAAGCTCTTTGTGAC
```

FIGURE 12F   CPMV 160 5'UTR-PDI+Rituximab LC DNA sequence   (SEQ ID NO:44)

```
        TATTAAAATCTTAATAGGTTTTGATAAAAGCGAACGTGGGGAAACCCGAACCAAACCTTCTTCTA
AACTCTCTCTCATCTCTCTTAAAGCAAACTTCTCTCTTGTCTTTCTTGCGTGAGCGATCTTCAACGTTGT
CAGATCGTGCTTCGGCACCAGTACAATGGCGAAAAACGTTGCGATTTTCGGCTTATTGTTTTCTCTTCTT
GTGTTGGTTCCTTCTCAGATCTTCGCGCAAATTGTTCTCTCCAGTCTCCAGCAATCCTGTCTGCATCTC
CAGGGGAGAAGGTCACAATGACTTGCAGGGCCAGCTCAAGTGTAAGTTACATCCACTGGTTCCAGCAGAA
GCCAGGATCCTCCCCCAAACCCTGGATTTATGCCACATCCAACCTGGCTTCTGGAGTCCCTGTTCGCTTC
AGTGGCAGTGGGTCTGGGACTTCTTACTCTCTCACAATCAGCAGAGTGGAGGCTGAAGATGCTGCCACTT
ATTACTGCCAGCAGTGGACTAGTAACCCACCCACGTTCGGAGGGGGGACCAAGCTGGAAATCAAACGTAC
GGTGGCTGCACCATCTGTCTTCATCTTCCCGCCATCTGATGAGCAGTTGAAATCTGGAACTGCCTCTGTT
GTGTGCCTGCTGAATAACTTCTATCCCAGAGAGGCCAAAGTACAGTGGAAGGTGGATAACGCCCTCCAAT
CGGGTAACTCCCAGGAGAGTGTCACAGAGCAGGACAGCAAGGACAGCACCTACAGCCTCAGCAGCACCCT
GACGCTGAGCAAAGCAGACTACGAGAAACACAAAGTCTACGCCTGCGAAGTCACCCATCAGGGCCTGAGC
TCGCCCGTCACAAAGAGCTTCAACAGGGGAGAGTGTTGA
```

FIGURE 12G   PDI+Rituximab LC DNA sequence   (SEQ ID NO:45)

```
        ATGGCGAAAAACGTTGCGATTTTCGGCTTATTGTTTTCTCTTCTTGTGTTGGTTCCTTCTCAGAT
CTTCGCGCAAATTGTTCTCTCCAGTCTCCAGCAATCCTGTCTGCATCTCCAGGGGAGAAGGTCACAATG
ACTTGCAGGGCCAGCTCAAGTGTAAGTTACATCCACTGGTTCCAGCAGAAGCCAGGATCCTCCCCCAAAC
CCTGGATTTATGCCACATCCAACCTGGCTTCTGGAGTCCCTGTTCGCTTCAGTGGCAGTGGGTCTGGGAC
TTCTTACTCTCTCACAATCAGCAGAGTGGAGGCTGAAGATGCTGCCACTTATTACTGCCAGCAGTGGACT
```

FIGURE 12g (CONT)

AGTAACCCACCCACGTTCGGAGGGGGGACCAAGCTGGAAATCAAACGTACGGTGGCTGCACCATCTGTCT
TCATCTTCCCGCCATCTGATGAGCAGTTGAAATCTGGAACTGCCTCTGTTGTGTGCCTGCTGAATAACTT
CTATCCCAGAGAGGCCAAAGTACAGTGGAAGGTGGATAACGCCCTCCAATCGGGTAACTCCCAGGAGAGT
GTCACAGAGCAGGACAGCAAGGACAGCACCTACAGCCTCAGCAGCACCCTGACGCTGAGCAAAGCAGACT
ACGAGAAACACAAAGTCTACGCCTGCGAAGTCACCCATCAGGGCCTGAGCTCGCCCGTCACAAAGAGCTT
CAACAGGGGAGAGTGTTGA

FIGURE 12H    PDI+Rituximab LC protein sequence    (SEQ ID NO:46)

MAKNVAIFGLLFSLLVLVPSQIFAQIVLSQSPAILSASPGEKVTMTCRASSSVSYIHWFQQKPGS
SPKPWIYATSNLASGVPVRFSGSGSGTSYSLTISRVEAEDAATYYCQQWTSNPPTFGGGTKLEIKRTVAA
PSVFIFPPSDEQLKSGTASVVCLLNNFYPREAKVQWKVDNALQSGNSQESVTEQDSKDSTYSLSSTLTLS
KADYEKHKVYACEVTHQGLSSPVTKSFNRGEC

FIGURE 12I    nbMT78_SpPDI.c    (SEQ ID NO:47)

TATTATCTCCCAACAACATAAGAAAACAATGGCGAAAAACGTTGCGATTTTCGGCTTAT

FIGURE 12J    atHSP69_SpPDI.c    (SEQ ID NO:48)

CAAAAAAAACACAGACCTTAAAAAAATAAAAATGGCGAAAAACGTTGCGATTTTCGGCT

FIGURE 12K    nbEPI42+PDI.c    (SEQ ID NO:49)

TTTCAACAAAATCAAGAATTTCAGCAATGGCGAAAAACGTTGCGATTTTCGGCT

FIGURE 12L    nbSNS46+PDI.c    (SEQ ID NO:50)

TTGAGTAAGTTATCAAAAAGCAAAAAATGGCGAAAAACGTTGCGATTTTCGGC

FIGURE 12M    nbCSY65+PDI.c    (SEQ ID NO:51)

CCTAAAAACAAAAAAAAGGCATACAAATGGCGAAAAACGTTGCGATTTTCGGC

FIGURE 12N    nbHEL40+PDI.c    (SEQ ID NO:52)

CTATCAAACCAAAACACATTGAGCAAAATGGCGAAAAACGTTGCGATTTTCGGCT

FIGURE 12O  nbSEP44+PDI.c  (SEQ ID NO:53)

TTTATTCTCTTTCAAAACCTACACTCATGGCGAAAAACGTTGCGATTTTCGGCTTAT

FIGURE 13A  IF-H1cTMCT.s1-4r  (SEQ ID NO:54)

ACTAAAGAAAATAGGCCTTTAAATACATATTCTACACTGTAGAGAC

FIGURE 13B  CPMV 160 5'UTR-PDI+H1 Mich DNA sequence  (SEQ ID NO:55)

TATTAAAATCTTAATAGGTTTTGATAAAAGCGAACGTGGGGAAACCCGAACCAAACCTTCTTCTA
AACTCTCTCTCATCTCTCTTAAAGCAAACTTCTCTCTTGTCTTTCTTGCGTGAGCGATCTTCAACGTTGT
CAGATCGTGCTTCGGCACCAGTACAATGGCGAAAAACGTTGCGATTTTCGGCTTATTGTTTTCTCTTCTT
GTGTTGGTTCCTTCTCAGATCTTCGCGGACACATTATGTATAGGTTATCATGCGAACAATTCAACAGACA
CTGTAGACACAGTACTAGAAAAGAATGTAACAGTAACACACTCTGTTAACCTTCTGGAAGACAAGCATAA
CGGAAAACTATGCAAACTAAGAGGGGTAGCCCCATTGCATTTGGGTAAATGTAACATTGCTGGCTGGATC
CTGGGAAATCCAGAGTGTGAATCACTCTCCACAGCAAGTTCATGGTCCTACATTGTGGAAACATCTAATT
CAGACAATGGAACGTGTTACCCAGGAGATTTCATCAATTATGAGGAGCTAAGAGAGCAATTGAGCTCAGT
GTCATCATTTGAAAGGTTTGAGATATTCCCCAAGACAAGTTCATGGCCCAATCATGACTCGAACAAAGGT
GTAACGGCAGCATGTCCTCACGCTGGAGCAAAAAGCTTCTACAAAACTTGATATGGCTAGTTAAAAAAG
GAAATTCATACCCAAAGCTTAACCAATCCTACATTAATGATAAAGGGAAAGAAGTCCTCGTGCTGTGGGG
CATTCACCATCCATCTACTACTGCTGACCAACAAAGTCTCTATCAGAATGCAGATGCATATGTTTTGTG
GGGACATCAAGATACAGCAAGAAGTTCAAGCCGGAAATAGCAACAAGACCCAAAGTGAGGGATCAAGAAG
GGAGAATGAACTATTACTGGACACTAGTAGAGCCGGGAGACAAAATAACATTCGAAGCAACTGGAAATCT
AGTGGTACCGAGATATGCATTCACAATGGAAAGAAATGCTGGATCTGGTATTATCATTTCAGATACACCA
GTCCACGATTGCAATACAACTTGTCAGACACCCGAGGGTGCTATAAACACCAGCCTCCCATTTCAGAATA
TACATCCGATCACAATTGGAAAATGTCCAAAGTATGTAAAAAGCACAAAATTGAGACTGGCCACAGGATT
GAGGAATGTTCCGTCTATTCAATCTAGAGGCCTATTCGGGGCCATTGCCGGCTTCATTGAAGGGGGTGG
ACAGGGATGGTAGATGGATGGTACGGTTATCACCATCAAAATGAGCAGGGGTCAGGATATGCAGCCGACC
TGAAGAGCACACAAAATGCCATTGACAAGATTACTAACAAAGTAAATTCTGTTATTGAAAAGATGAATAC
ACAGGACACAGCAGTGGGTAAAGAGTTCAACCACCTGGAAAAAGAATAGAGAATCTAAATAAAAAGTT
GATGATGGTTTCCTGGACATTTGGACTTACAATGCCGAACTGTTGGTTCTAATGGAAAATGAAAGAACTT
TGGACTATCACGATTCAAATGTGAAGAACTTGTATGAAAAGTAAGAAACCAGTTAAAAAACAATGCCAA
GGAAATTGGAAACGGCTGCTTTGAATTTTACCACAAATGCGATAACACGTGCATGGAAAGTGTCAAAAAT
GGGACTTATGACTACCCAAAATACTCAGAGGAAGCAAAATTAAACAGAGAAAAAATAGATGGGGTAAAGC
TGGAATCAACAAGGATTTACCAGATTTTGGCGATCTATTCAACTGTCGCCAGTTCATTGGTACTGGTAGT
CTCCCTGGGGGCAATCAGCTTCTGGATGTGCTCTAATGGGTCTCTACAGTGTAGAATATGTATTTAA

FIGURE 13C  PDI+H1 Mich DNA sequence  (SEQ ID NO:56)

ATGGCGAAAAACGTTGCGATTTTCGGCTTATTGTTTTCTCTTCTTGTGTTGGTTCCTTCTCAGAT
CTTCGCGGACACATTATGTATAGGTTATCATGCGAACAATTCAACAGACACTGTAGACACAGTACTAGAA
AAGAATGTAACAGTAACACACTCTGTTAACCTTCTGGAAGACAAGCATAACGGAAAACTATGCAAACTAA
GAGGGGTAGCCCCATTGCATTTGGGTAAATGTAACATTGCTGGCTGGATCCTGGGAAATCCAGAGTGTGA

FIGURE 13C (CONT)

```
ATCACTCTCCACAGCAAGTTCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTTG
AGATATTCCCCAAGACAAGTTCATGGCCCAATCATGACTCGAACAAAGGTGTAACGGCAGCATGTCCTCA
CGCTGGAGCAAAAAGCTTCTACAAAAACTTGATATGGCTAGTTAAAAAAGGAAATTCATACCCAAAGCTT
AACCAATCCTACATTAATGATAAAGGGAAAGAAGTCCTCGTGCTGTGGGCATTCACCATCCATCTACTA
CTGCTGACCAACAAAGTCTCTATCAGAATGCAGATGCATATGTTTTTGTGGGGACATCAAGATACAGCAA
GAAGTTCAAGCCGGAAATAGCAACAAGACCCAAAGTGAGGGATCAAGAAGGGAGAATGAACTATTACTGG
ACACTAGTAGAGCCGGGAGACAAAATAACATTCGAAGCAACTGGAAATCTAGTGGTACCGAGATATGCAT
TCACAATGGAAGAAATGCTGGATCTGGTATTATCATTTCAGATACACCAGTCCACGATTGCAATACAAC
TTGTCAGACACCCGAGGGTGCTATAAACACCAGCCTCCCATTTCAGAATATACATCCGATCACAATTGGA
AAATGTCCAAAGTATGTAAAAAGCACAAAATTGAGACTGGCCACAGGATTGAGGAATGTTCCGTCTATTC
AATCTAGAGGCCTATTCGGGGCCATTGCCGGCTTCATTGAAGGGGGTGGACAGGGATGGTAGATGGATG
GTACGGTTATCACCATCAAAATGAGCAGGGGTCAGGATATGCAGCCGACCTGAAGAGCACACAAAATGCC
ATTGACAAGATTACTAACAAAGTAAATTCTGTTATTGAAAGATGAATACACAGGACACAGCAGTGGGTA
AAGAGTTCAACCACCTGGAAAAAGAATAGAGAATCTAAATAAAAAGTTGATGATGGTTTCCTGGACAT
TTGGACTTACAATGCCGAACTGTTGGTTCTAATGGAAAATGAAAGAACTTTGGACTATCACGATTCAAAT
GTGAAGAACTTGTATGAAAAAGTAAGAAACCAGTTAAAAAACAATGCCAAGGAAATTGGAAACGGCTGCT
TTGAATTTTACCACAAATGCGATAACACGTGCATGGAAAGTGTCAAAAATGGGACTTATGACTACCCAAA
ATACTCAGAGGAAGCAAAATTAAACAGAGAAAAAATAGATGGGGTAAAGCTGGAATCAACAAGGATTTAC
CAGATTTTGGCGATCTATTCAACTGTCGCCAGTTCATTGGTACTGGTAGTCTCCCTGGGGGCAATCAGCT
TCTGGATGTGCTCTAATGGGTCTCTACAGTGTAGAATATGTATTTAA
```

FIGURE 13D  PDI+H1 Mich protein sequence   (SEQ ID NO:57)

```
MAKNVAIFGLLFSLLVLVPSQIFADTLCIGYHANNSTDTVDTVLEKNVTVTHSVNLLEDKHNGKL
CKLRGVAPLHLGKCNIAGWILGNPECESLSTASSWSYIVETSNSDNGTCYPGDFINYEELREQLSSVSSF
ERFEIFPKTSSWPNHDSNKGVTAACPHAGAKSFYKNLIWLVKKGNSYPKLNQSYINDKGKEVLVLWGIHH
PSTTADQQSLYQNADAYVFVGTSRYSKKFKPEIATRPKVRDQEGRMNYYWTLVEPGDKITFEATGNLVVP
RYAFTMERNAGSGIIISDTPVHDCNTTCQTPEGAINTSLPFQNIHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQDT
AVGKEFNHLEKRIENLNKKVDDGFLDIWTYNAELLVLMENERTLDYHDSNVKNLYEKVRNQLKNNAKEIG
NGCFEFYHKCDNTCMESVKNGTYDYPKYSEEAKLNREKIDGVKLESTRIYQILAIYSTVASSLVLVVSLG
AISFWMCSNGSLQCRICI
```

FIGURE 14A  IF-H3Minn15.r   (SEQ ID NO:58)

```
ACTAAAGAAAATAGGCCTTCAAATGCAAATGTTGCATCTAATGTTGCCCTTTTGG
```

FIGURE 14B  CPMV 160 5'UTR-PDI+H3 sing DNA sequence  (SEQ ID NO:59)

```
TATTAAAATCTTAATAGGTTTTGATAAAAGCGAACGTGGGGAAACCCGAACCAAACCTTCTTCTA
AACTCTCTCTCATCTCTCTTAAAGCAAACTTCTCTCTTGTCTTTCTTGCGTGAGCGATCTTCAACGTTGT
CAGATCGTGCTTCGGCACCAGTACAATGGCGAAAAACGTTGCGATTTTCGGCTTATTGTTTTCTCTTCTT
GTGTTGGTTCCTTCTCAGATCTTCGCGCAAAAAATTCCTGGAAATGACAATAGCACGGCAACGCTGTGCC
TTGGGCACCATGCAGTACCAAACGGAACGATAGTGAAAACAATCACAAATGACCGAATTGAAGTTACTAA
TGCTACTGAGTTGGTTCAGAATTCCTCAATAGGTGAAATATGCGACAGTCCTCATCAGATCCTTGATGGA
GAGAACTGCACACTAATAGATGCTCTATTGGGAGACCCTCAGTGTGATGGCTTTCAAAATAAGAAATGGG
ACCTTTTTGTTGAACGAAGCAAAGCCTACAGCAACTGTTACCCTTATGATGTGCCGGATTATGCCTCCCT
TAGGTCACTAGTTGCCTCATCCGGCACACTGGAGTTTAAAAATGAAAGCTTCAATTGGACTGGAGTCACT
CAAAACGGAACAAGTTCTGCTTGCATAAGGGGCTCTAGTAGTAGTTTCTTTAGTAGATTAAATTGGTTGA
CCCACTTAAACTACACATATCCAGCATTGAACGTGACTATGCCAAACAAGGAACAATTTGACAAATTGTA
CATTTGGGGGGTTCACCACCCGGGTACGGACAAGGACCAAATCTTCCTGTATGCTCAATCATCAGGAAGA
ATCACAGTATCTACCAAAAGAAGCCAACAAGCTGTAATCCCAAATATCGGATCTAGACCCAGAATAAGGG
ATATCCCTAGCAGAATAAGCATCTATTGGACAATAGTAAAACCGGGAGACATACTTTTGATTAACAGCAC
AGGGAATCTAATTGCTCCTAGGGGTTACTTCAAAATACGAAGTGGGAAAAGCTCAATAATGAGATCAGAT
GCACCCATTGGCAAATGCAAGTCTGAATGCATCACTCCAAATGGAAGCATTCCCAATGACAAACCATTCC
AAAATGTAAACAGGATCACATACGGGGCCTGTCCCAGATATGTTAAGCATAGCACTCTGAAATTGGCAAC
AGGAATGCGAAATGTACCAGAGAAACAAACTAGAGGCATATTTGGCGCAATAGCGGGTTTCATAGAAAAT
GGTTGGGAGGGAATGGTGGATGGTTGGTACGGTTTCAGGCATCAAAATTCTGAGGGAAGAGGACAAGCAG
CAGATCTCAAAAGCACTCAAGCAGCAATCGATCAAATCAATGGGAAGCTGGCTCGGGTGATCGGGAAAAC
CAACGAGAAATTCCATCAGATTGAAAAGAATTCTCAGAAGTAGAAGGAAGAGTTCAAGACCTTGAGAAA
TATGTTGAGGACACTAAAATAGATCTCTGGTCATACAACGCGGAGCTTCTTGTTGCCCTGGAGAACCAAC
ATACAATTGATCTAACTGACTCAGAAATGAACAAACTGTTTGAAAAAACAAAGAAGCAACTGAGGGAAAA
TGCTGAGGATATGGGAAATGGTTGTTTCAAAATATACCACAAATGTGACAATGCCTGCATAGGATCAATA
AGAAATGAAACTTATGACCACAATGTGTACAGGGATGAAGCATTAAACAACCGGTTCCAGATCAAGGGAG
TTGAGCTGAAGTCAGGGTACAAAGATTGGATCCTATGGATTTCCTTTGCCATATCATCCCTTGTACTGTT
AGTTGCTTTGTTGGGGTTCATCATGTGGGCCTGCCAAAAGGGCAACATTAGATGCAACATTTGCATTTGA
```

FIGURE 14C  PDI+H3 sing DNA sequence  (SEQ ID NO:60)

```
ATGGCGAAAAACGTTGCGATTTTCGGCTTATTGTTTTCTCTTCTTGTGTTGGTTCCTTCTCAGAT
CTTCGCGCAAAAAATTCCTGGAAATGACAATAGCACGGCAACGCTGTGCCTTGGGCACCATGCAGTACCA
AACGGAACGATAGTGAAAACAATCACAAATGACCGAATTGAAGTTACTAATGCTACTGAGTTGGTTCAGA
ATTCCTCAATAGGTGAAATATGCGACAGTCCTCATCAGATCCTTGATGGAGAGAACTGCACACTAATAGA
TGCTCTATTGGGAGACCCTCAGTGTGATGGCTTTCAAAATAAGAAATGGGACCTTTTTGTTGAACGAAGC
AAAGCCTACAGCAACTGTTACCCTTATGATGTGCCGGATTATGCCTCCCTTAGGTCACTAGTTGCCTCAT
CCGGCACACTGGAGTTTAAAAATGAAAGCTTCAATTGGACTGGAGTCACTCAAAACGGAACAAGTTCTGC
TTGCATAAGGGGCTCTAGTAGTAGTTTCTTTAGTAGATTAAATTGGTTGACCCACTTAAACTACACATAT
CCAGCATTGAACGTGACTATGCCAAACAAGGAACAATTTGACAAATTGTACATTTGGGGGGTTCACCACC
CGGGTACGGACAAGGACCAAATCTTCCTGTATGCTCAATCATCAGGAAGAATCACAGTATCTACCAAAAG
AAGCCAACAAGCTGTAATCCCAAATATCGGATCTAGACCCAGAATAAGGGATATCCCTAGCAGAATAAGC
ATCTATTGGACAATAGTAAAACCGGGAGACATACTTTTGATTAACAGCACAGGGAATCTAATTGCTCCTA
GGGGTTACTTCAAAATACGAAGTGGGAAAAGCTCAATAATGAGATCAGATGCACCCATTGGCAAATGCAA
GTCTGAATGCATCACTCCAAATGGAAGCATTCCCAATGACAAACCATTCCAAAATGTAAACAGGATCACA
TACGGGGCCTGTCCCAGATATGTTAAGCATAGCACTCTGAAATTGGCAACAGGAATGCGAAATGTACCAG
```

FIGURE 14C (CONT)

```
AGAAACAAACTAGAGGCATATTTGGCGCAATAGCGGGTTTCATAGAAAATGGTTGGGAGGGAATGGTGGA
TGGTTGGTACGGTTTCAGGCATCAAAATTCTGAGGGAAGAGGACAAGCAGCAGATCTCAAAAGCACTCAA
GCAGCAATCGATCAAATCAATGGGAAGCTGGCTCGGGTGATCGGGAAAACCAACGAGAAATTCCATCAGA
TTGAAAAAGAATTCTCAGAAGTAGAAGGAAGAGTTCAAGACCTTGAGAAATATGTTGAGGACACTAAAAT
AGATCTCTGGTCATACAACGCGGAGCTTCTTGTTGCCCTGGAGAACCAACATACAATTGATCTAACTGAC
TCAGAAATGAACAAACTGTTTGAAAAACAAAGAAGCAACTGAGGGAAAATGCTGAGGATATGGGAAATG
GTTGTTTCAAATATACCACAAATGTGACAATGCCTGCATAGGATCAATAAGAAATGAAACTTATGACCA
CAATGTGTACAGGGATGAAGCATTAAACAACCGGTTCCAGATCAAGGGAGTTGAGCTGAAGTCAGGGTAC
AAAGATTGGATCCTATGGATTTCCTTTGCCATATCATCCCTTGTACTGTTAGTTGCTTTGTTGGGGTTCA
TCATGTGGGCCTGCCAAAAGGGCAACATTAGATGCAACATTTGCATTTGA
```

FIGURE 14D   PDI+H3 sing protein sequence   (SEQ ID NO:61)

```
        MAKNVAIFGLLFSLLVLVPSQIFAQKIPGNDNSTATLCLGHHAVPNGTIVKTITNDRIEVTNATE
LVQNSSIGEICDSPHQILDGENCTLIDALLGDPQCDGFQNKKWDLFVERSKAYSNCYPYDVPDYASLRSL
VASSGTLEFKNESFNWTGVTQNGTSSACIRGSSSSFFSRLNWLTHLNYTYPALNVTMPNKEQFDKLYIWG
VHHPGTDKDQIFLYAQSSGRITVSTKRSQQAVIPNIGSRPRIRDIPSRISIYWTIVKPGDILLINSTGNL
IAPRGYFKIRSGKSSIMRSDAPIGKCKSECITPNGSIPNDKPFQNVNRITYGACPRYVKHSTLKLATGMR
NVPEKQTRGIFGAIAGFIENGWEGMVDGWYGFRHQNSEGRGQAADLKSTQAAIDQINGKLARVIGKTNEK
FHQIEKEFSEVEGRVQDLEKYVEDTKIDLWSYNAELLVALENQHTIDLTDSEMNKLFEKTKKQLRENAED
MGNGCFKIYHKCDNACIGSIRNETYDHNVYRDEALNNRFQIKGVELKSGYKDWILWISFAISSLVLLVAL
LGFIMWACQKGNIRCNICI
```

FIGURE 15A   Cloning vector 1666 from left to right T-DNA   (SEQ ID NO:62)

```
        TGGCAGGATATATTGTGGTGTAAACAAATTGACGCTTAGACAACTTAATAACACATTGCGGACGT
TTTTAATGTACTGAATTAACGCCGAATCCCGGGCTGGTATATTTATATGTTGTCAAATAACTCAAAAACC
ATAAAAGTTTAAGTTAGCAAGTGTGTACATTTTTACTTGAACAAAAATATTCACCTACTACTGTTATAAA
TCATTATTAAACATTAGAGTAAAGAAATATGGATGATAAGAACAAGAGTAGTGATATTTTGACAACAATT
TTGTTGCAACATTTGAGAAATTTTGTTGTTCTCTCTTTTCATTGGTCAAAAACAATAGAGAGAGAAAAA
GGAAGAGGGAGAATAAAAACATAATGTGAGTATGAGAGAGAAAGTTGTACAAAAGTTGTACCAAAATAGT
TGTACAAATATCATTGAGGAATTTGACAAAAGCTACACAAATAAGGGTTAATTGCTGTAAATAAATAAGG
ATGACGCATTAGAGAGATGTACCATTAGAGAATTTTTGGCAAGTCATTAAAAAGAAAGAATAAATTATTT
TTAAAATTAAAAGTTGAGTCATTTGATTAAACATGTGATTATTTAATGAATTGATGAAAGAGTTGGATTA
AAGTTGTATTAGTAATTAGAATTTGGTGTCAAATTTAATTTGACATTTGATCTTTTCCTATATATTGCCC
CATAGAGTCAGTTAACTCATTTTTATATTTCATAGATCAAATAAGAGAAATAACGGTATATTAATCCCTC
CAAAAAAAAAAACGGTATATTTACTAAAAAATCTAAGCCACGTAGGAGGATAACAGGATCCCGTAGGA
GGATAACATCCAATCCAACCAATCACAACAATCCTGATGAGATAACCCACTTTAAGCCCACGCATCTGTG
GCACATCTACATTATCTAAATCACACATTCTTCCACACATCTGAGCCACACAAAAACCAATCCACATCTT
TATCACCCATTCTATAAAAATCACACTTTGTGAGTCTACACTTTGATTCCCTTCAAACACATACAAAGA
GAAGAGACTAATTAATTAATTAATCATCTTGAGAGAAATGGAACGAGCTATCAAGGAAACGACGCTAG
GGAACAAGCTAACAGTGAACGTTGGGATGGAGGATCAGGAGGTACCACTTCTCCCTTCAAACTTCCTGAC
GAAAGTCCGAGTTGGACTGAGTGGCGGCTACATAACGATGAGACGAATTCGAATCAAGATAATCCCCTTG
GTTTCAAGGAAAGCTGGGGTTTCGGGAAAGTTGTATTTAAGAGATATCTCAGATACGACAGGACGGAAGC
```

FIGURE 15A (CONT)

```
TTCACTGCACAGAGTCCTTGGATCTTGGACGGGAGATTCGGTTAACTATGCAGCATCTCGATTTTTCGGT
TTCGACCAGATCGGATGTACCTATAGTATTCGGTTTCGAGGAGTTAGTATCACCGTTTCTGGAGGGTCGC
GAACTCTTCAGCATCTCTGTGAGATGGCAATTCGGTCTAAGCAAGAACTGCTACAGCTTGCCCCAATCGA
AGTGGAAAGTAATGTATCAAGAGGATGCCCTGAAGGTACTCAAACCTTCGAAAAAGAAAGCGAGTAAGTT
AAAATGCTTCTTCGTCTCCTATTTATAATATGGTTTGTTATTGTTAATTTTGTTCTTGTAGAAGAGCTTA
ATTAATCGTTGTTGTTATGAAATACTATTTGTATGAGATGAACTGGTGTAATGTAATTCATTTACATAAG
TGGAGTCAGAATCAGAATGTTTCCTCCATAACTAACTAGACATGAAGACCTGCCGCGTACAATTGTCTTA
TATTTGAACAACTAAAATTGAACATCTTTTGCCACAACTTTATAAGTGGTTAATATAGCTCAAATATATG
GTCAAGTTCAATAGATTAATAATGGAAATATCAGTTATCGAAATTCATTAACAATCAACTTAACGTTATT
AACTACTAATTTTATATCATCCCCTTTGATAAATGATAGTACACCAATTAGGAAGGAGCATGCTCGCCTA
GGAGATTGTCGTTTCCCGCCTTCAGTTTGCAAGCTGCTCTAGCCGTGTAGCCAATACGCAAACCGCCTCT
CCCCGCGCGTTGGGAATTACTAGCGCGTGTCGACAAGCTTGCATGCCGGTCAACATGGTGGAGCACGACA
CACTTGTCTACTCCAAAAATATCAAAGATACAGTCTCAGAAGACCAAAGGGCAATTGAGACTTTTCAACA
AAGGGTAATATCCGGAAACCTCCTCGGATTCCATTGCCCAGCTATCTGTCACTTTATTGTGAAGATAGTG
GAAAAGGAAGGTGGCTCCTACAAATGCCATCATTGCGATAAAGGAAAGGCCATCGTTGAAGATGCCTCTG
CCGACAGTGGTCCCAAAGATGGACCCCCACCCACGAGGAGCATCGTGGAAAAAGAAGACGTTCCAACCAC
GTCTTCAAAGCAAGTGGATTGATGTGATAACATGGTGGAGCACGACACACTTGTCTACTCCAAAAATATC
AAAGATACAGTCTCAGAAGACCAAAGGGCAATTGAGACTTTTCAACAAAGGGTAATATCCGGAAACCTCC
TCGGATTCCATTGCCCAGCTATCTGTCACTTTATTGTGAAGATAGTGGAAAAGGAAGGTGGCTCCTACAA
ATGCCATCATTGCGATAAAGGAAAGGCCATCGTTGAAGATGCCTCTGCCGACAGTGGTCCCAAAGATGGA
CCCCCACCCACGAGGAGCATCGTGGAAAAAGAAGACGTTCCAACCACGTCTTCAAAGCAAGTGGATTGAT
GTGATATCTCCACTGACGTAAGGGATGACGCACAATCCCACTATCCTTCGCAAGACCCTTCCTCTATATA
AGGAAGTTCATTTCATTTGGAGAGGACGTCACTCCTCAGCCAAAACGACACCCCATCTGTCTATCCACT
GGCCCCTGGATCTGCTGCCCAAACTAACTCCATGGTGACCCTGGGATGCCTGGTCAAGGGCTATTTCCCT
GAGCCAGTGACAGTGACCTGGAACTCTGGATCCCTGTCCAGCGGTGTGCACACCTTCCCAGCTGTCCTGC
AGTCTGACCTCTACACTCTGAGCAGCTCAGTGACTGTCCCCTCCAGCACCTGGCCCAGCGAGACCGTCAC
CTGCAACGTTGCCCACCCGGCCAGCAGCACCAAGGTGGACAAGAAAATTGTGCCCAGGGATTGTGGTTGT
AAGCCTTGCATATGTACAGTCCCAGAAGTATCATCTGTCTTCATCTTCCCCCCAAAGCCCAAGGATGTGC
TCACCATTACTCTGACTCCTAAGGTCACGTGTGTTGTGGTAGACATCAGCAAGGATGATCCCGAGGTCCA
GTTCAGCTGGTTTGTAGATGATGTGGAGGTGCACACAGCTCAGACGCAACCCCGGGAGGAGCAGTTCAAC
AGCACTTTCCGCTCAGTCAGTGAACTTCCCATCATGCACCAGGACTGGCTCAATGGCAAGGAGACGTCCA
GATTTTGGCGATCTATTCAACTGTCGCCAGTTCATTGGTACTGGTAGTCTCCCTGGGGGCAATCAGTTTC
TGGATGTGCTCTAATGGGTCTCTACAGTGTAGAATATGTATTTAAAGGCCTATTTTCTTTAGTTTGAATT
TACTGTTATTCGGTGTGCATTTCTATGTTTGGTGAGCGGTTTTCTGTGCTCAGAGTGTGTTTATTTATG
TAATTTAATTTCTTTGTGAGCTCCTGTTTAGCAGGTCGTCCCTTCAGCAAGGACACAAAAAGATTTTAAT
TTTATTATCGTTCAAACATTTGGCAATAAAGTTTCTTAAGATTGAATCCTGTTGCCGGTCTTGCGATGAT
TATCATATAATTTCTGTTGAATTACGTTAAGCATGTAATAATTAACATGTAATGCATGACGTTATTTATG
AGATGGGTTTTTATGATTAGAGTCCCGCAATTATACATTTAATACGCGATAGAAAACAAAATATAGCGCG
CAAACTAGGATAAATTATCGCGCGCGGTGTCATCTATGTTACTAGATCTCTAGAGTCTCAAGCTTGGCGC
GCCCACGTGACTAGTGGCACTGGCCGTCGTTTTACAACGTCGTGACTGGGAAAACCCTGGCGTTACCCAA
CTTAATCGCCTTGCAGCACATCCCCCTTTCGCCAGCTGGCGTAATAGCGAAGAGGCCCGCACCGATCGCC
CTTCCCAACAGTTGCGCAGCCTGAATGGCGAATGCTAGAGCAGCTTGAGCTTGGATCAGATTGTCGTTTC
CCGCCTTCAGTTTAAACTATCAGTGTTTGACAGGATATATTGGCGGGTAAACCTAAGAGAAAAGAGCGTT
TA
```

FIGURE 15B  Construct 4467 from 2X35S promoter to NOS terminator   (SEQ ID NO:63)

```
GTCAACATGGTGGAGCACGACACACTTGTCTACTCCAAAAATATCAAAGATACAGTCTCAGAAGA
CCAAAGGGCAATTGAGACTTTTCAACAAAGGGTAATATCCGGAAACCTCCTCGGATTCCATTGCCCAGCT
ATCTGTCACTTTATTGTGAAGATAGTGGAAAAGGAAGGTGGCTCCTACAAATGCCATCATTGCGATAAAG
GAAAGGCCATCGTTGAAGATGCCTCTGCCGACAGTGGTCCCAAAGATGGACCCCCACCCACGAGGAGCAT
CGTGGAAAAGAAGACGTTCCAACCACGTCTTCAAAGCAAGTGGATTGATGTGATAACATGGTGGAGCAC
GACACACTTGTCTACTCCAAAAATATCAAAGATACAGTCTCAGAAGACCAAAGGGCAATTGAGACTTTTC
AACAAAGGGTAATATCCGGAAACCTCCTCGGATTCCATTGCCCAGCTATCTGTCACTTTATTGTGAAGAT
AGTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAGAAGACGTTCCAA
CCACGTCTTCAAAGCAAGTGGATTGATGTGATATCTCCACTGACGTAAGGGATGACGCACAATCCCACTA
TCCTTCGCAAGACCCTTCCTCTATATAAGGAAGTTCATTTCATTTGGAGAGGCACACAATTTGCTTTAGT
GATTAAACTTTCTTTTACAACAAATTAAAGGTCTATTATCTCCCAACAACATAAGAAAACAATGACTGCC
CTGACCGAAGGTGCTAAGCTGTTTGAGAAGGAGATTCCGTACATCACCGAGCTGGAAGGGGACGTCGAAG
GAATGAAGTTCATCATCAAGGGAGAAGGAACCGGGGACGCTACGACTGGAACCATTAAGGCCAAGTATAT
CTGTACCACTGGAGATCTGCCAGTGCCTTGGGCCACCCTTGTGTCAACCCTCTCGTATGGAGTGCAGTGT
TTTGCTAAGTACCCTAGCCACATTAAGGACTTCTTCAAATCCGCCATGCCGGAAGGTTATACCCAAGAGC
GCACCATTTCTTTTGAGGGAGATGGAGTGTACAAGACCCGCGCGATGGTCACCTATGAGAGGGGATCTAT
CTACAACCGGGTGACTCTGACTGGAGAAAACTTTAAGAAGGACGGGCATATTCTTCGGAAGAATGTCGCC
TTCCAGTGCCCTCCCAGCATCCTTTACATTCTCCCCGACACTGTGAACAACGGAATCCGCGTGGAGTTCA
ATCAAGCCTACGACATCGAGGGGGTGACGGAGAAGCTGGTGACCAAGTGTAGCCAGATGAATCGGCCACT
GGCCGGTTCAGCGGCTGTCCACATTCCGCGCTACCATCATATCACTTATCACACTAAGCTCTCCAAAGAC
CGCGATGAGAGGAGAGATCACATGTGCCTGGTGGAAGTGGTCAAGGCCGTCGATCTCGATACCTATCAGT
AAAGGCCTATTTTCTTTAGTTTGAATTTACTGTTATTCGGTGTGCATTTCTATGTTTGGTGAGCGGTTTT
CTGTGCTCAGAGTGTGTTTATTTTATGTAATTTAATTTCTTTGTGAGCTCCTGTTTAGCAGGTCGTCCCT
TCAGCAAGGACACAAAAAGATTTTAATTTTATTATCGTTCAAACATTTGGCAATAAAGTTTCTTAAGATT
GAATCCTGTTGCCGGTCTTGCGATGATTATCATATAATTTCTGTTGAATTACGTTAAGCATGTAATAATT
AACATGTAATGCATGACGTTATTTATGAGATGGGTTTTTATGATTAGAGTCCCGCAATTATACATTTAAT
ACGCGATAGAAAACAAAATATAGCGCGCAAACTAGGATAAATTATCGCGCGCGGTGTCATCTATGTTACT
AGAT
```

FIGURE 15C  Cloning vector 4160 from left to right T-DNA   (SEQ ID NO:64)

```
TGGCAGGATATATTGTGGTGTAAACAAATTGACGCTTAGACAACTTAATAACACATTGCGGACGT
TTTTAATGTACTGAATTAACGCCGAATCCCGGGCTGGTATATTTATATGTTGTCAAATAACTCAAAAACC
ATAAAAGTTTAAGTTAGCAAGTGTGTACATTTTTACTTGAACAAAAATATTCACCTACTACTGTTATAAA
TCATTATTAAACATTAGAGTAAAGAAATATGGATGATAAGAACAAGAGTAGTGATATTTTGACAACAATT
TTGTTGCAACATTTGAGAAAATTTTGTTGTTCTCTCTTTTCATTGGTCAAAAACAATAGAGAGAGAAAAA
GGAAGAGGGAGAATAAAAACATAATGTGAGTATGAGAGAGAAAGTTGTACAAAAGTTGTACCAAAATAGT
TGTACAAATATCATTGAGGAATTTGACAAAAGCTACACAAATAAGGGTTAATTGCTGTAAATAAATAAGG
ATGACGCATTAGAGAGATGTACCATTAGAGAATTTTTGGCAAGTCATTAAAAAGAAAGAATAAATTATTT
TTAAAATTAAAAGTTGAGTCATTTGATTAAACATGTGATTATTTAATGAATTGATGAAAGAGTTGGATTA
AAGTTGTATTAGTAATTAGAATTTGGTGTCAAATTTAATTTGACATTTGATCTTTTCCTATATATTGCCC
CATAGAGTCAGTTAACTCATTTTTATATTTCATAGATCAAATAAGAGAAATAACGGTATATTAATCCCTC
CAAAAAAAAAAACGGTATATTTACTAAAAAATCTAAGCCACGTAGGAGGATAACAGGATCCCCGTAGGA
GGATAACATCCAATCCAACCAATCACAACAATCCTGATGAGATAACCCACTTTAAGCCCACGCATCTGTG
```

FIGURE 15C (CONT)

```
GCACATCTACATTATCTAAATCACACATTCTTCCACACATCTGAGCCACACAAAAACCAATCCACATCTT
TATCACCCATTCTATAAAAAATCACACTTTGTGAGTCTACACTTTGATTCCCTTCAAACACATACAAAGA
GAAGAGACTAATTAATTAATTAATCATCTTGAGAGAAAATGGAACGAGCTATACAAGGAAACGACGCTAG
GGAACAAGCTAACAGTGAACGTTGGGATGGAGGATCAGGAGGTACCACTTCTCCCTTCAAACTTCCTGAC
GAAAGTCCGAGTTGGACTGAGTGGCGGCTACATAACGATGAGACGAATTCGAATCAAGATAATCCCCTTG
GTTTCAAGGAAAGCTGGGGTTTCGGGAAAGTTGTATTTAAGAGATATCTCAGATACGACAGGACGGAAGC
TTCACTGCACAGAGTCCTTGGATCTTGGACGGGAGATTCGGTTAACTATGCAGCATCTCGATTTTTCGGT
TTCGACCAGATCGGATGTACCTATAGTATTCGGTTTCGAGGAGTTAGTATCACCGTTTCTGGAGGGTCGC
GAACTCTTCAGCATCTCTGTGAGATGGCAATTCGGTCTAAGCAAGAACTGCTACAGCTTGCCCCAATCGA
AGTGGAAAGTAATGTATCAAGAGGATGCCCTGAAGGTACTCAAACCTTCGAAAAGAAAGCGAGTAAGTT
AAAATGCTTCTTCGTCTCCTATTTATAATATGGTTTGTTATTGTTAATTTTGTTCTTGTAGAAGAGCTTA
ATTAATCGTTGTTGTTATGAAATACTATTTGTATGAGATGAACTGGTGTAATGTAATTCATTTACATAAG
TGGAGTCAGAATCAGAATGTTTCCTCCATAACTAACTAGACATGAAGACCTGCCGCGTACAATTGTCTTA
TATTTGAACAACTAAAATTGAACATCTTTTGCCACAACTTTATAAGTGGTTAATATAGCTCAAATATATG
GTCAAGTTCAATAGATTAATAATGGAAATATCAGTTATCGAAATTCATTAACAATCAACTTAACGTTATT
AACTACTAATTTTATATCATCCCCTTTGATAAATGATAGTACACCAATTAGGAAGGAGCATGCTCGCCTA
GGAGATTGTCGTTTCCCGCCTTCAGTTTGCAAGCTGCTCTAGCCGTGTAGCCAATACGCAAACCGCCTCT
CCCCGCGCGTTGGGAATTACTAGCGCGTGTCGACACGCGTGGCGCGCCCTGGTATATTTATATGTTGTCA
ATAACTCAAAAACCATAAAAGTTTAAGTTAGCAAGTGTGTACATTTTTACTTGAACAAAAATATTCACC
TACTACTGTTATAAATCATTATTAAACATTAGAGTAAAGAAATATGGATGATAAGAACAAGAGTAGTGAT
ATTTTGACAACAATTTTGTTGCAACATTTGAGAAAATTTTGTTGTTCTCTCTTTTCATTGGTCAAAAACA
ATAGAGAGAGAAAAAGGAAGAGGGAGAATAAAAACATAATGTGAGTATGAGAGAGAAAGTTGTACAAAAG
TTGTACCAAAATAGTTGTACAAATATCATTGAGGAATTTGACAAAAGCTACACAAATAAGGGTTAATTGC
TGTAAATAAATAAGGATGACGCATTAGAGAGATGTACCATTAGAGAATTTTTGGCAAGTCATTAAAAAGA
AAGAATAAATTATTTTAAAATTAAAAGTTGAGTCATTTGATTAAACATGTGATTATTTAATGAATTGAT
GAAAGAGTTGGATTAAAGTTGTATTAGTAATTAGAATTTGGTGTCAAATTTAATTTGACATTTGATCTTT
TCCTATATATTGCCCCATAGAGTCAGTTAACTCATTTTTATATTTCATAGATCAAATAAGAGAAATAACG
GTATATTAATCCCTCCAAAAAAAAAAACGGTATATTTACTAAAAAATCTAAGCCACGTAGGAGGATAAC
AGGATCCCCGTAGGAGGATAACATCCAATCCAACCAATCACAACAATCCTGATGAGATAACCCACTTTAA
GCCCACGCATCTGTGGCACATCTACATTATCTAAATCACACATTCTTCCACACATCTGAGCCACACAAAA
ACCAATCCACATCTTTATCACCCATTCTATAAAAAATCACACTTTGTGAGTCTACACTTTGATTCCCTTC
AAACACATACAAAGAGAAGAGACTAATTAATTAATTAATCATCTTGAGAGAAAATGAGTCTTCTAACCGA
GGTCGAAACGCCTATCAGAAACGAATGGGGGTGCAGATGCAACGATTCAAGTGATCCTCTTGTTGTTGCC
GCAAGTATAATTGGGATTGTGCACCTGATATTGTGGATTATTGATCGCCTTTTTCCAAAAGCATTTATC
GTATCTTTAAACACGGTTTAAAAAGAGGGCCTTCTACGGAAGGAGTACCAGAGTCTATGAGGGAAGAATA
TCGAGAGGAACAGCAGAATGCTGTGGATGCTGACGATGGTCATTTTGTCAGCATAGAGCTGGAGTAAGAG
CTCTAAGTTAAAATGCTTCTTCGTCTCCTATTTATAATATGGTTTGTTATTGTTAATTTTGTTCTTGTAG
AAGAGCTTAATTAATCGTTGTTGTTATGAAATACTATTTGTATGAGATGAACTGGTGTAATGTAATTCAT
TTACATAAGTGGAGTCAGAATCAGAATGTTTCCTCCATAACTAACTAGACATGAAGACCTGCCGCGTACA
ATTGTCTTATATTTGAACAACTAAAATTGAACATCTTTTGCCACAACTTTATAAGTGGTTAATATAGCTC
AAATATATGGTCAAGTTCAATAGATTAATAATGGAAATATCAGTTATCGAAATTCATTAACAATCAACTT
AACGTTATTAACTACTAATTTTATATCATCCCCTTTGATAAATGATAGTACACCAATTAGGAAGGAACTA
GGAGATTGTCGTTTCCCGCCTTCAGTTTGCAAGCTGCTCTAGCCGTGTAGCCAATACGCAAACCGCCTCT
CCCCGCGCGTTGGGAATTACTAGCGCGTGTCGACAAGCTTGCATGCCGGTCAACATGGTGGAGCACGACA
CACTTGTCTACTCCAAAAATATCAAAGATACAGTCTCAGAAGACCAAAGGGCAATTGAGACTTTTCAACA
AAGGGTAATATCCGGAAACCTCCTCGGATTCCATTGCCCAGCTATCTGTCACTTTATTGTGAAGATAGTG
```

FIGURE 15C (CONT)

GAAAAGGAAGGTGGCTCCTACAAATGCCATCATTGCGATAAAGGAAAGGCCATCGTTGAAGATGCCTCTG
CCGACAGTGGTCCCAAAGATGGACCCCCACCCACGAGGAGCATCGTGGAAAAGAAGACGTTCCAACCAC
GTCTTCAAAGCAAGTGGATTGATGTGATAACATGGTGGAGCACGACACACTTGTCTACTCCAAAAATATC
AAAGATACAGTCTCAGAAGACCAAAGGGCAATTGAGACTTTTCAACAAAGGGTAATATCCGGAAACCTCC
TCGGATTCCATTGCCCAGCTATCTGTCACTTTATTGTGAAGATAGTGGAAAAGGAAGGTGGCTCCTACAA
ATGCCATCATTGCGATAAAGGAAAGGCCATCGTTGAAGATGCCTCTGCCGACAGTGGTCCCAAAGATGGA
CCCCCACCCACGAGGAGCATCGTGGAAAAGAAGACGTTCCAACCACGTCTTCAAAGCAAGTGGATTGAT
GTGATATCTCCACTGACGTAAGGGATGACGCACAATCCCACTATCCTTCGCAAGACCCTTCCTCTATATA
AGGAAGTTCATTTCATTTGGAGAGACGTCACTCCTCAGCCAAAACGACACCCCATCTGTCTATCCACTG
GCCCCTGGATCTGCTGCCCAAACTAACTCCATGGTGACCCTGGGATGCCTGGTCAAGGGCTATTTCCCTG
AGCCAGTGACAGTGACCTGGAACTCTGGATCCCTGTCCAGCGGTGTGCACACCTTCCCAGCTGTCCTGCA
GTCTGACCTCTACACTCTGAGCAGCTCAGTGACTGTCCCCTCCAGCACCTGGCCCAGCGAGACCGTCACC
TGCAACGTTGCCCACCCGGCCAGCAGCACCAAGGTGGACAAGAAAATTGTGCCCAGGGATTGTGGTTGTA
AGCCTTGCATATGTACAGTCCCAGAAGTATCATCTGTCTTCATCTTCCCCCCAAAGCCCAAGGATGTGCT
CACCATTACTCTGACTCCTAAGGTCACGTGTGTTGTGGTAGACATCAGCAAGGATGATCCCGAGGTCCAG
TTCAGCTGGTTTGTAGATGATGTGGAGGTGCACACAGCTCAGACGCAACCCCGGGAGGAGCAGTTCAACA
GCACTTTCCGCTCAGTCAGTGAACTTCCCATCATGCACCAGGACTGGCTCAATGGCAAGGAGACGTCCAG
ATTTTGGCGATCTATTCAACTGTCGCCAGTTCATTGGTACTGGTAGTCTCCCTGGGGCAATCAGTTTCT
GGATGTGCTCTAATGGGTCTCTACAGTGTAGAATATGTATTTAAAGGCCTATTTTCTTTAGTTTGAATTT
ACTGTTATTCGGTGTGCATTTCTATGTTTGGTGAGCGGTTTTCTGTGCTCAGAGTGTGTTTATTTTATGT
AATTTAATTTCTTTGTGAGCTCCTGTTTAGCAGGTCGTCCCTTCAGCAAGGACACAAAAAGATTTTAATT
TTATTATCGTTCAAACATTTGGCAATAAAGTTTCTTAAGATTGAATCCTGTTGCCGGTCTTGCGATGATT
ATCATATAATTTCTGTTGAATTACGTTAAGCATGTAATAATTAACATGTAATGCATGACGTTATTTATGA
GATGGGTTTTTATGATTAGAGTCCCGCAATTATACATTTAATACGCGATAGAAAACAAAATATAGCGCGC
AAACTAGGATAAATTATCGCGCGCGGTGTCATCTATGTTACTAGATCTCTAGAGTCTCAAGCTTGGCGCG
CCCACGTGACTAGTGGCACTGGCCGTCGTTTTACAACGTCGTGACTGGGAAAACCCTGGCGTTACCCAAC
TTAATCGCCTTGCAGCACATCCCCCTTTCGCCAGCTGGCGTAATAGCGAAGAGGCCCGCACCGATCGCCC
TTCCCAACAGTTGCGCAGCCTGAATGGCGAATGCTAGAGCAGCTTGAGCTTGGATCAGATTGTCGTTTCC
CGCCTTCAGTTTAAACTATCAGTGTTTGACAGGATATATTGGCGGGTAAACCTAAGAGAAAAGAGCGTTT
A

FIGURE 15D Cloning vector 4170 from left to right T-DNA (SEQ ID NO:65)

TGGCAGGATATATTGTGGTGTAAACAAATTGACGCTTAGACAACTTAATAACACATTGCGGACGT
TTTTAATGTACTGAATTAACGCCGAATCCCGGGCTGGTATATTTATATGTTGTCAAATAACTCAAAAACC
ATAAAAGTTTAAGTTAGCAAGTGTGTACATTTTACTTGAACAAAAATATTCACCTACTACTGTTATAAA
TCATTATTAAACATTAGAGTAAAGAAATATGGATGATAAGAACAAGAGTAGTGATATTTTGACAACAATT
TTGTTGCAACATTTGAGAAAATTTTGTTGTTCTCTCTTTTCATTGGTCAAAAACAATAGAGAGAGAAAAA
GGAAGAGGGAGAATAAAAACATAATGTGAGTATGAGAGAGAAAGTTGTACAAAAGTTGTACCAAAATAGT
TGTACAAATATCATTGAGGAATTTGACAAAAGCTACACAAATAAGGGTTAATTGCTGTAAATAAATAAGG
ATGACGCATTAGAGAGATGTACCATTAGAGAATTTTTGGCAAGTCATTAAAAAGAAAGAATAAATTATTT
TTAAAATTAAAAGTTGAGTCATTTGATTAAACATGTGATTATTTAATGAATTGATGAAAGAGTTGGATTA
AAGTTGTATTAGTAATTAGAATTTGGTGTCAAATTTAATTTGACATTTGATCTTTTCCTATATATTGCCC
CATAGAGTCAGTTAACTCATTTTTATATTTCATAGATCAAATAAGAGAAATAACGGTATATTAATCCCTC
CAAAAAAAAAAAACGGTATATTTACTAAAAAATCTAAGCCACGTAGGAGGATAACAGGATCCCCGTAGGA

FIGURE 15D (CONT)

```
GGATAACATCCAATCCAACCAATCACAACAATCCTGATGAGATAACCCACTTTAAGCCCACGCATCTGTG
GCACATCTACATTATCTAAATCACACATTCTTCCACACATCTGAGCCACACAAAAACCAATCCACATCTT
TATCACCCATTCTATAAAAATCACACTTTGTGAGTCTACACTTTGATTCCCTTCAAACACATACAAAGA
GAAGAGACTAATTAATTAATTAATCATCTTGAGAGAAAATGGAACGAGCTATACAAGGAAACGACGCTAG
GGAACAAGCTAACAGTGAACGTTGGGATGGAGGATCAGGAGGTACCACTTCTCCCTTCAAACTTCCTGAC
GAAAGTCCGAGTTGGACTGAGTGGCGGCTACATAACGATGAGACGAATTCGAATCAAGATAATCCCCTTG
GTTTCAAGGAAAGCTGGGGTTTCGGGAAAGTTGTATTTAAGAGATATCTCAGATACGACAGGACGGAAGC
TTCACTGCACAGAGTCCTTGGATCTTGGACGGGAGATTCGGTTAACTATGCAGCATCTCGATTTTCGGT
TTCGACCAGATCGGATGTACCTATAGTATTCGGTTTCGAGGAGTTAGTATCACCGTTTCTGGAGGGTCGC
GAACTCTTCAGCATCTCTGTGAGATGGCAATTCGGTCTAAGCAAGAACTGCTACAGCTTGCCCCAATCGA
AGTGGAAAGTAATGTATCAAGAGGATGCCCTGAAGGTACTCAAACCTTCGAAAAAGAAAGCGAGTAAGTT
AAAATGCTTCTTCGTCTCCTATTTATAATATGGTTTGTTATTGTTAATTTTGTTCTTGTAGAAGAGCTTA
ATTAATCGTTGTTGTTATGAAATACTATTTGTATGAGATGAACTGGTGTAATGTAATTCATTTACATAAG
TGGAGTCAGAATCAGAATGTTTCCTCCATAACTAACTAGACATGAAGACCTGCCGCGTACAATTGTCTTA
TATTTGAACAACTAAAATTGAACATCTTTTGCCACAACTTTATAAGTGGTTAATATAGCTCAAATATATG
GTCAAGTTCAATAGATTAATAATGGAAATATCAGTTATCGAAATTCATTAACAATCAACTTAACGTTATT
AACTACTAATTTTATATCATCCCCTTTGATAAATGATAGTACACCAATTAGGAAGGAGCATGCTCGCCTA
GGAGATTGTCGTTTCCCGCCTTCAGTTTGCAAGCTGCTCTAGCCGTGTAGCCAATACGCAAACCGCCTCT
CCCCGCGCGTTGGGAATTACTAGCGCGTGTCGACAAGCTTGCATGCCGGTCAACATGGTGGAGCACGACA
CACTTGTCTACTCCAAAAATATCAAAGATACAGTCTCAGAAGACCAAAGGGCAATTGAGACTTTTCAACA
AAGGGTAATATCCGGAAACCTCCTCGGATTCCATTGCCCAGCTATCTGTCACTTTATTGTGAAGATAGTG
GAAAAGGAAGGTGGCTCCTACAAATGCCATCATTGCGATAAAGGAAAGGCCATCGTTGAAGATGCCTCTG
CCGACAGTGGTCCCAAAGATGGACCCCCACCCACGAGGAGCATCGTGGAAAAAGAAGACGTTCCAACCAC
GTCTTCAAAGCAAGTGGATTGATGTGATAACATGGTGGAGCACGACACACTTGTCTACTCCAAAAATATC
AAAGATACAGTCTCAGAAGACCAAAGGGCAATTGAGACTTTTCAACAAAGGGTAATATCCGGAAACCTCC
TCGGATTCCATTGCCCAGCTATCTGTCACTTTATTGTGAAGATAGTGGAAAAGGAAGGTGGCTCCTACAA
ATGCCATCATTGCGATAAAGGAAAGGCCATCGTTGAAGATGCCTCTGCCGACAGTGGTCCCAAAGATGGA
CCCCCACCCACGAGGAGCATCGTGGAAAAAGAAGACGTTCCAACCACGTCTTCAAAGCAAGTGGATTGAT
GTGATATCTCCACTGACGTAAGGGATGACGCACAATCCCACTATCCTTCGCAAGACCCTTCCTCTATATA
AGGAAGTTCATTTCATTTGGAGAGACGTCACTCCTCAGCCAAAACGACACCCCATCTGTCTATCCACTG
GCCCCTGGATCTGCTGCCCAAACTAACTCCATGGTGACCCTGGGATGCCTGGTCAAGGGCTATTTCCCTG
AGCCAGTGACAGTGACCTGGAACTCTGGATCCCTGTCCAGCGGTGTGCACACCTTCCCAGCTGTCCTGCA
GTCTGACCTCTACACTCTGAGCAGCTCAGTGACTGTCCCCTCCAGCACCTGGCCCAGCGAGACCGTCACC
TGCAACGTTGCCCACCCGGCCAGCAGCACCAAGGTGGACAAGAAATTGTGCCCAGGGATTGTGGTTGTA
AGCCTTGCATATGTACAGTCCCAGAAGTATCATCTGTCTTCATCTTCCCCCAAAGCCCAAGGATGTGCT
CACCATTACTCTGACTCCTAAGGTCACGTGTGTTGTGGTAGACATCAGCAAGGATGATCCCGAGGTCCAG
TTCAGCTGGTTTGTAGATGATGTGGAGGTGCACACAGCTCAGACGCAACCCCGGGAGGAGCAGTTCAACA
GCACTTTCCGCTCAGTCAGTGAACTTCCCATCATGCACCAGGACTGGCTCAATGGCAAGGAGACGTCCAG
ATTTTGGCGATCTATTCAACTGTCGCCAGTTCATTGGTACTGGTAGTCTCCCTGGGGCAATCAGTTTCT
GGATGTGCTCTAATGGGTCTCTACAGTGTAGAATATGTATTTAAAGGCCTATTTTCTTTAGTTTGAATTT
ACTGTTATTCGGTGTGCATTTCTATGTTTGGTGAGCGGTTTTCTGTGCTCAGAGTGTGTTTATTTTATGT
AATTTAATTTCTTTGTGAGCTCCTGTTTAGCAGGTCGTCCCTTCAGCAAGGACACAAAAAGATTTTAATT
TTATTATCGTTCAAACATTTGGCAATAAAGTTTCTTAAGATTGAATCCTGTTGCCGGTCTTGCGATGATT
ATCATATAATTTCTGTTGAATTACGTTAAGCATGTAATAATTAACATGTAATGCATGACGTTATTTATGA
GATGGGTTTTTATGATTAGAGTCCCGCAATTATACATTTAATACGCGATAGAAAACAAAATATAGCGCGC
AAACTAGGATAAATTATCGCGCGCGGTGTCATCTATGTTACTAGATCTCTAGGTAAAAATCCCAATTATA
```

FIGURE 15D (CONT)

```
TTTGGTCTAATTTAGTTTGGTATTGAGTAAAACAAATTCGAACCAAACCAAAATATAAATATATAGTTTT
TATATATATGCCTTTAAGACTTTTTATAGAATTTTCTTTAAAAAATATCAAGAAATATTTGCGACTCTTC
TGGCATGTAATATTTCGTTAAATATGAAGTGCTCCATTTTTATTAACTTTAAATAATTGGTTGTACGATC
ACTTTCTTATCAAGTGTTACTAAAATGCGTCAATCTCTTTGTTCTTCCATATTCATATGTCAAAATCTAT
CAAAATTCTTATATATCTTTTTCGAATTTGAAGTGAAATTTCGATAATTTAAAATTAAATAGAACATATC
ATTATTTAGGTATCATATTGATTTTTATACTTAATTACTAAATTTGGTTAACTTTGAAAGTGTACATCAA
CGAAAAATTAGTCAAACGACTAAAATAAATAAATATCATGTGTTATTAAGAAAATTCTCCTATAAGAATA
TTTTAATAGATCATATGTTTGTAAAAAAATTAATTTTTACTAACACATATATTTACTTATCAAAAATTT
GACAAAGTAAGATTAAAATAATATTCATCTAACAAAAAAAAACCAGAAAATGCTGAAAACCCGGCAAAA
CCGAACCAATCCAAACCGATATAGTTGGTTTGGTTTGATTTTGATATAAACCGAACCAACTCGGTCCATT
TGCACCCCTAATCATAATAGCTTTAATATTTCAAGATATTATTAAGTTAACGTTGTCAATATCCTGGAAA
TTTTGCAAAATGAATCAAGCCTATATGGCTGTAATATGAATTTAAAAGCAGCTCGATGTGGTGGTAATAT
GTAATTTACTTGATTCTAAAAAAATATCCCAAGTATTAATAATTTCTGCTAGGAAGAAGGTTAGCTACGA
TTTACAGCAAAGCCAGAATACAAAGAACCATAAAGTGATTGAAGCTCGAAATATACGAAGGAACAAATAT
TTTTAAAAAAATACGCAATGACTTGGAACAAAAGAAAGTGATATATTTTTGTTCTTAAACAAGCATCCC
CTCTAAAGAATGGCAGTTTTCCTTTGCATGTAACTATTATGCTCCCTTCGTTACAAAAATTTTGGACTAC
TATTGGGAACTTCTTCTGAAAATTCTAGAGTCTCAAGCTTGGCGCGCCCACGTGACTAGTGGCACTGGCC
GTCGTTTTACAACGTCGTGACTGGGAAAACCCTGGCGTTACCCAACTTAATCGCCTTGCAGCACATCCCC
CTTTCGCCAGCTGGCGTAATAGCGAAGAGGCCCGCACCGATCGCCCTTCCCAACAGTTGCGCAGCCTGAA
TGGCGAATGCTAGAGCAGCTTGAGCTTGGATCAGATTGTCGTTTCCCGCCTTCAGTTTAAACTATCAGTG
TTTGACAGGATATATTGGCGGGTAAACCTAAGAGAAAGAGCGTTTA
```

ENDOGENOUS PLANT EXPRESSION ENHANCER

CROSS-REFERENCE TO RELATED APPLICATIONS

The present application is a national phase filing under 35 U.S.C. § 371 of International Application No. PCT/CA2019/050319, filed on Mar. 14, 2019, the contents of which is incorporated herein by reference in its entirety.

INCORPORATION OF THE SEQUENCE LISTING

The present application contains a sequence listing that is submitted via EFS-Web concurrent with the filing of the application, containing the file name "18636_0018U1Sequence_Listing.txt," which is 80,259 bytes in size, created on Sep. 13, 2021, and is herein incorporated by reference in its entirety pursuant to 37 C.F.R. § 1.52 (e)(5).

FIELD OF INVENTION

The present invention relates to expression enhancers that are active in plants. The present invention also relates to the expression of proteins of interest in plants and provides methods and compositions for production of proteins of interest in plants.

BACKGROUND OF THE INVENTION

Plants offer great potential as production systems for recombinant proteins. One approach to producing foreign proteins in plants is to generate stable transgenic plant lines. However this is a time consuming and labor intensive process. An alternative to transgenic plants is the use of plant virus-based expression vectors. Plant virus-based vectors allow for the rapid, high level, transient expression of proteins in plants.

High level transient expression of foreign proteins in plants has been obtained using of vectors based on RNA plant viruses, including comoviruses, such as Cowpea mosaic virus (CPMV; see, for example, WO2007/135480; WO2009/087391; US 2010/0287670, Sainsbury F. et al., 2008, *Plant Physiology;* 148: 121-1218; Sainsbury F. et al., 2008, *Plant Biotechnology Journal;* 6: 82-92; Sainsbury F. et al., 2009, *Plant Biotechnology Journal;* 7: 682-693; Sainsbury F. et al. 2009, *Methods in Molecular Biology, Recombinant Proteins From Plants*, vol. 483: 25-39).

Modifications of the 5'UTR of the RNA-2 of the comovirus cowpea mosaic virus (CPMV) have resulted in additional expression enhancer activity (as determined level of expression of a nucleic acid of interest or a protein of interest), when compared to the wild type CPMV 5'UTR. For example, mutation of the start codon at position 161 in a CPMV RNA-2 vector (U162C; HT) increases the levels of expression of a protein encoded by a sequence inserted after the start codon at position 512. This permits the production of high levels of foreign proteins without the need for viral replication and was termed the CPMV-HT system (WO2009/087391; Sainsbury and Lomonossoff, 2008, Plant Physiol. 148, 1212-1218). In pEAQ expression plasmids (Sainsbury et al., 2009, *Plant Biotechnology Journal*, 7, pp 682-693; US 2010/0287670), the sequence to be expressed is positioned between the 5'UTR and the 3' UTR. The 5'UTR in the pEAQ series carries the U162C (HT) mutation.

Additional modification of the CPMV 5' UTR region, have been described that further increase expression of a nucleic acid of interest within a plant. For example, "CMPV HT+" (comprising nucleotides 1-160 of the CPMV 5' UTR with modified ATGs at position 115-117, and at position 161-163; WO2015/143567; which is incorporated herein by reference), and "CPMVX" (where X=160, 155, 150, or 114 nucleic acids in length; WO 2015/103704; which is incorporated herein by reference). An example of CMPVX is the expression enhancer "CPMV 160". Expression of a nucleic acid sequence operatively linked to CPMV HT+" resulted in a significant increase in production of a protein of interest that was encoded by the nucleic acid sequence, when compared to the production of the same protein of interest using the same nucleic acid sequence operatively linked to the "CPMV HT" expression enhancer (see FIGS. 2 and 3 of WO2015/143567). Furthermore, expression of a nucleic acid sequence operatively linked to the "CPMV 160" expression enhancer resulted in a significant increase in production of a protein of interest encoded by the nucleic acid sequence, when compared to the production of the same protein of interest using the same nucleic acid sequence operatively linked to the "CPMV HT+" expression enhancer (see FIGS. 2 and 3 of WO2015/143567).

Diamos et. al (Frontiers in Plant Science. 2016, vol 7 pp. 1-15; which is incorporated herein by reference) describe several expression enhancers that may be used to increase production of proteins in plants (see Table 2 of Diamos et. al.), including the expression enhancer NbPsaK2 3'. As shown in FIG. 4 of Diamos et. al. (2016), production of protein of interest encoded by a nucleci acid that was operatively linked to NbPsaK2 3' resulted in enhanced protein production when compared to the production of the same protein encoded by the same nucleic acid sequence operatively linked to other truncated psaK expression enhancers.

SUMMARY OF THE INVENTION

The present invention relates to expression enhancers that are active in plants. The present invention also relates to the expression of proteins of interest in plants, and provides methods and compositions for the production of proteins of interest in plants.

It is an object of the invention to provide an improved expression enhancer active in a plant.

According to the present invention there is provided an isolated expression enhancer active in a plant, the expression enhancer selected from the group consisting of:
  nbEPI42 (SEQ ID NO:1);
  nbSNS46 (SEQ ID NO:2);
  nbCSY65 (SEQ ID NO:3);
  nbHEL40 (SEQ ID NO:4);
  nbSEP44 (SEQ ID NO:5); and
a nucleic acid having from 90-100% sequence identity to the nucleotide sequence set forth in any one of SEQ ID NO's: 1-5. Wherein, the expression enhancer, when operatively linked to a nucleic acid of interest, for example a heterologous nucleic acid of interest, results in expression of the nucleic acid of interest. Additionally, the expression enhancer, when operatively linked to a nucleic acid of interest, for example a heterologous nucleic acid of interest, may increase the level of expression of the nucleic acid of interest, or the heterologous nucleic acid of interest, when compared to the level of expression of the same nucleic acid or heterologous nucleic acid of interest that is not operatively linked to the expression enhancer, or for example, when operatively linked to the prior art expression enhancer CPMV 160 (SEQ ID NO:6).

The present disclosure also provides for a nucleic acid sequence comprising one of the isolated expression enhancers as described above, the expression enhancer operatively linked with a heterologous nucleotide sequence encoding a protein of interest. The heterologous nucleotide sequence may encode a viral protein or an antibody, for example which is not to be considered limiting, the viral protein may be an influenza protein or a norovirus protein. If the protein of interest is an influenza protein then it may include M2, a hemagglutinin protein selected from the group of H1, H2, H3, H4, H5, H6, H7, H8, H9, H10, H11, H12, H13, H14, H15, H16, an influenza type B hemagglutinin, or a combination thereof. If the protein of interest is a norovirus protein, then it may include a VP1 protein, a VP2 protein, or a combination thereof, selected from the group of GI.1, GI.2, GI.3, GI.5, GI.7, GII.1, GII.2, GII.3, GII.4, GII.5, GII.6, GII.7, GII.12, GII.13, GII.14, GII.17 and GII.21.

The present invention also provides a plant expression system comprising one or more than one of the nucleic acid sequence described above. The plant expression system may further comprise a comovirus 3' UTR.

The present invention also provides a plant expression system comprising one or more than one of the isolated nucleic acid sequence operatively linked with a heterologous nucleic acid, or nucleotide sequence, as described above. The plant expression system may further comprise a comovirus 3' UTR.

Also disclosed herein is a method of producing a protein of interest in a plant or in a portion of a plant comprising, introducing into the plant or in the portion of a plant the plant expression system as described above, comprising the one or more than one of nucleic acid sequence, and incubating the plant, the portion of a plant, or plant cell, under conditions that permit expression of each of the heterologous nucleotide sequence encoding the protein of interest. For example, the protein of interest may be a viral protein, such as an influenza protein or a norovirus protein. If the protein of interest is an influenza protein then it may include M2, a hemagglutinin protein selected from the group of H1, H2, H3, H4, H5, H6, H7, H8, H9, H10, H11, H12, H13, H14, H15, H16, an influenza type B hemagglutinin, and a combination thereof. If the protein of interest is a norovirus protein, then it may include a VP1 protein, a VP2 protein, or a combination thereof, selected from the group of GI.1, GI.2, GI.3, GI.5, GII.1, GII.2, GII.3, GII.4, GII.5, GII.6, GII.7, GII.12, GII.13, GII.14, GII.17 and GII.21.

A method of producing a multimeric protein of interest, is also described herein. The method involves co-expressing two or more than two of the nucleic acid sequence as described above, in a plant, the portion of a plant, or plant cell, in a transient or stable manner, wherein each of the two or more than two of the nucleic acid sequence encodes a component of the multimeric protein, and incubating the plant, the portion of a plant, or plant cell, under conditions that permit expression of each of the heterologous nucleotide sequence encoding the multimeric protein of interest.

Also provided herein is a plant, a portion of a plant, or plant cell that is transiently transformed, or stably transformed, with plant expression system as described above.

A plant-based expression system comprising an expression enhancer as described herein results in expression of the nucleic acid of interest. Furthermore, the plant-based expression system comprising an expression enhancer as described herein may result in increasing or enhancing expression of a nucleotide sequence encoding a heterologous open reading frame that is operatively linked to the expression enhancer, as described herein. The increase in expression may be determined by comparing the level of expression obtained using the expression enhancer as described herein with the level of expression of the same nucleotide sequence encoding the heterologous open reading frame but not operatively linked to an expression enhancer, or for example, when operatively linked to the prior art expression enhancer CPMV 160 (SEQ ID NO: 6).

The plant based expression systems, vectors, constructs and nucleic acids comprising one or more than one expression enhancer as described herein may also have a number of properties such as, for example, containing convenient cloning sites for genes or nucleotide sequences of interest, they may be used to easily transform plants in a cost-effective manner, they may cause efficient local or systemic transformation of inoculated plants. In addition, the transformation of a plant should provide a good yield of useful protein material.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1A is prior art and shows the relative titer of influenza H1 California, H3 Victoria, H5 Indonesia and B Wisconsin produced in plants by expressing a nucleic acid encoding each of these proteins wherein the nucleic acid is operatively linked to CPMV HT expression enhancer (described in WO 2009/087391) or to a CPMV 160+ expression enhancer (described in WO 2015/103704). FIG. 1B is prior art and shows the relative titer of H1 California, H3 Victoria, B Brisbane, B Brisbane+H1Tm, B Massachusetts, B Massachusetts+H1Tm, B Wisconsin and B Wisconsin+H1Tm, produced in plants by expressing a nucleic acid encoding each of these proteins wherein the nucleic acid is operatively linked to a CPMV HT expression enhancer (described in WO 2009/087391) or to a CPMV 160+ expression enhancer (described in WO 2015/103704).

FIG. 2A shows relative activity of the Dasher protein (Dasher GFP; FPB-27 269; from ATUM), a cytosolic protein, produced in plants by expressing a nucleic acid encoding the Dasher protein wherein the nucleic acid encoding Dasher is operatively linked to expression enhancers CPMV 160 (SEQ ID NO:6; described in WO 2015/103704), nbMT78 (SEQ ID NO:7; described in U.S. Provisional Application No. 62/643,053 Filed Mar. 14, 2018); atHSP69 (SEQ ID NO:8; described in U.S. Provisional Application No. 62/643,053 Filed Mar. 14, 2018); nbEPI42 (SEQ ID NO:1); nbSNS46 (SEQ ID NO:2); nbCSY65 (SEQ ID NO:3); nbHEL40 (SEQ ID NO:4); and nbSEP44 (SEQ ID NO:5). FIG. 2B shows relative yield of the cytosolic norovirus GII.4/Sydney 2012 VP1 VLPs, following gradient centrifugation, the VLPs produced in plants by expressing a nucleic acid encoding the norovirus VP1 protein wherein each of the nucleic acid encoding the VP1 protein is operatively linked to: the expression enhancer CPMV 160 (SEQ ID NO: 6; described in WO 2015/103704), nbMT78 (SEQ ID NO:7; described in U.S. Provisional Application No. 62/643,053, filed Mar. 14, 2018, which is incorporated herein by reference); atHSP69 (SEQ ID NO:8; described in U.S. Provisional Application No. 62/643,053, filed Mar. 14, 2018, which is incorporated herein by reference); nbEPI42

(SEQ ID NO:1); nbSNS46 (SEQ ID NO:2); nbCSY65 (SEQ ID NO:3); nbHEL40 (SEQ ID NO:4); and nbSEP44 (SEQ ID NO:5).

FIG. 9A shows the nucleic acid sequence of nbEPI42 (SEQ ID NO:1); FIG. 9B shows the nucleic acid sequence of nbSNS46 (SEQ ID NO:2); FIG. 9C shows the nucleic acid sequence of nbCSY65 (SEQ ID NO:3); FIG. 9D shows the nucleic acid sequence of nbHEL40 (SEQ ID NO:4); FIG. 9E shows the nucleic acid sequence of nbSEP44 (SEQ ID NO:5); FIG. 9F shows the nucleic acid sequence of CPMV 160 (SEQ ID NO:6; prior art; described in WO 2015/103704); FIG. 9G shows the nucleic acid sequence of nbMT78 (SEQ ID NO:7; described in U.S. Provisional Application No. 62/643,053 Filed Mar. 14, 2018); FIG. 9H shows the nucleic acid sequence of atHSP69 (SEQ ID NO:8; described in U.S. Provisional Application No. 62/643,053 Filed Mar. 14, 2018).

FIGS. 10A-10S show the nucleic acid sequences pertaining to Dasher constructs: FIG. 10A shows the nucleic acid sequence of IF-(2X35S+C)_CPMV160.c (SEQ ID NO:9); FIG. 10B shows the nucleic acid sequence of IF-Dasher (27-609).r (SEQ ID NO:10); FIG. 10C shows the amino acid sequence of CPMV 160 5'UTR-Dasher DNA sequence (SEQ ID NO:11); FIG. 10D shows the nucleic acid sequence of Dasher DNA sequence (SEQ ID NO:12); FIG. 10E shows the amino acid sequence of Dasher protein sequence (SEQ ID NO:13); FIG. 10F shows the nucleic acid sequence of IF-nbMT78.c (SEQ ID NO:14); FIG. 10G shows the nucleic acid sequence of nbMT78_Dasher.c (SEQ ID NO:15); FIG. 10H shows the nucleic acid sequence of atHSP69_Dasher.c (SEQ ID NO: 16); FIG. 10I shows the nucleic acid sequence of IF-atHSP69.c (SEQ ID NO: 17); FIG. 10J shows the nucleic acid sequence of nbEPI42+Dasher.c (SEQ ID NO: 18); FIG. 10K shows the nucleic acid sequence of IF-nbEPI42.c (SEQ ID NO: 19); FIG. 10L shows the nucleic acid sequence of nbSNS46+Dasher.c (SEQ ID NO: 20); FIG. 10M shows the nucleic acid sequence of IF-nbSNS46.c (SEQ ID NO: 21); FIG. 10N shows the nucleic acid sequence of nbCSY65+Dasher.c (SEQ ID NO: 22); FIG. 10O shows the nucleic acid sequence of IF-nbCSY65.c (SEQ ID NO: 23); FIG. 10P shows the nucleic acid sequence of nbHEL40+Dasher.c (SEQ ID NO: 24); FIG. 10Q shows the nucleic acid sequence of IF-nbHEL40.c (SEQ ID NO: 25); FIG. 10R shows the nucleic acid sequence of nbSEP44+Dasher.c (SEQ ID NO: 26); FIG. 10S shows the nucleic acid sequence of IF-nbSEP44.c (SEQ ID NO: 27).

FIGS. 11A-11K show the nucleic acid sequence relating to GII.4 Syd 12 VP1 constructs: FIG. 11A shows the nucleic acid sequence of IF-GII4Syd12VP1.r (SEQ ID NO: 28); FIG. 11B shows the nucleic acid sequence of CPMV 160 5'UTR-VP1 (GII.4) DNA sequence (SEQ ID NO:29); FIG. 11C shows the nucleic acid sequence of VP1 (GII.4) DNA sequence (SEQ ID NO:30); FIG. 11D shows the amino acid sequence of VP1 (GII.4) protein sequence (SEQ ID NO:31); FIG. 11E shows the nucleic acid sequence of nbMT78+GII4Syd12.c (SEQ ID NO:32); FIG. 11F shows the nucleic acid sequence of atHSP69+GII4Syd12.c (SEQ ID NO:33); FIG. 11G shows the nucleic acid sequence of nbEPI42+GII4Syd12.c (SEQ ID NO:34); FIG. 11H shows the nucleic acid sequence of nbSNS46+GII4Syd12.c (SEQ ID NO:35); FIG. 11I shows the nucleic acid sequence of nbCSY65+GII4Syd12.c (SEQ ID NO:36); FIG. 11J shows the nucleic acid sequence of nbHEL40+GII4Syd12.c (SEQ ID NO:37); FIG. 11K shows the nucleic acid sequence of nbSEP44+GII4Syd12.c (SEQ ID NO:38).

FIGS. 12A-12O show the nucleic acid sequence relating to Rituximab LC and HC constructs: FIG. 12A shows the nucleic acid sequence of IF -HC (Ritux).s1-6r (SEQ ID NO:39); FIG. 12B shows the nucleic acid sequence of CPMV 160 5'UTR-PDI+Rituximab HC DNA sequence (SEQ ID NO:40); FIG. 12C shows the nucleic acid sequence of PDI+Rituximab HC DNA sequence (SEQ ID NO:41); FIG. 12D shows the amino acid sequence of PDI+Rituximab HC protein sequence (SEQ ID NO:42); FIG. 12E shows the nucleic acid sequence of IF -LC (Ritux).s1-6r (SEQ ID NO:43); FIG. 12F shows the nucleic acid sequence of CPMV 160 5'UTR-PDI+Rituximab LC DNA sequence (SEQ ID NO: 44); FIG. 12G shows the nucleic acid sequence of PDI+Rituximab LC DNA sequence (SEQ ID NO:45); FIG. 12H shows the amino acid sequence of PDI+Rituximab LC protein sequence (SEQ ID NO:46); FIG. 12I shows the nucleic acid sequence of nbMT78_SpPDI.c (SEQ ID NO:47); FIG. 12J shows the nucleic acid sequence of atHSP69_SpPDI.c (SEQ ID NO: 48); FIG. 12K shows the nucleic acid sequence of nbEPI42+PDI.c (SEQ ID NO:49); FIG. 12L shows the nucleic acid sequence of nbSNS46+PDI.c (SEQ ID NO:50); FIG. 12M shows the nucleic acid sequence of nbCSY65+PDI.c (SEQ ID NO:51); FIG. 12N shows the nucleic acid sequence of nbHEL40+PDI.c (SEQ ID NO:52); FIG. 12O shows the nucleic acid sequence of nbSEP44+PDI.c (SEQ ID NO:53).

FIGS. 13A-13D show the nucleic acid sequence relating to H1 a Michigan 45/2015 constructs: FIG. 13A shows the nucleic acid sequence of IF-H1cTMCT.s1-4r (SEQ ID NO:54); FIG. 13B shows the nucleic acid sequence of CPMV 160 5'UTR-PDI+H1 Mich DNA sequence (SEQ ID NO:55); FIG. 13C shows the nucleic acid sequence of PDI+H1 Mich DNA sequence (SEQ ID NO:56); FIG. 13D shows the amino acid sequence of PDI+H1 Mich protein sequence (SEQ ID NO:57).

FIGS. 14A-14D show the nucleic acid sequence relating to H3 A/Singapore 19-0019-16 constructs: FIG. 14A shows the nucleic acid sequence of IF-H3Minn15.r (SEQ ID NO:58); FIG. 14B shows the nucleic acid sequence of CPMV 160 5'UTR-PDI+H3 sing DNA sequence (SEQ ID NO:59); FIG. 14C shows the nucleic acid sequence of PDI+H3 sing DNA sequence (SEQ ID NO:60); FIG. 14D shows the amino acid sequence of PDI+H3 sing protein sequence (SEQ ID NO:61).

FIGS. 15A-14D shows the nucleic acid sequence of cloning vectors, constructs 1666, 4467, 4160 and 4170: FIG. 15A shows the nucleic acid sequence of cloning vector 1666 from left to right T-DNA (SEQ ID NO:62); FIG. 15B shows the nucleic acid sequence of construct 4467 from 2X35S promoter to NOS terminator (SEQ ID NO: 63); FIG. 15C shows the nucleic acid sequence of cloning vector 4160 from left to right T-DNA (SEQ ID NO:64); FIG. 15D shows the nucleic acid sequence of cloning vector 4170 from left to right T-DNA (SEQ ID NO:65).

DETAILED DESCRIPTION

Figure 2A:
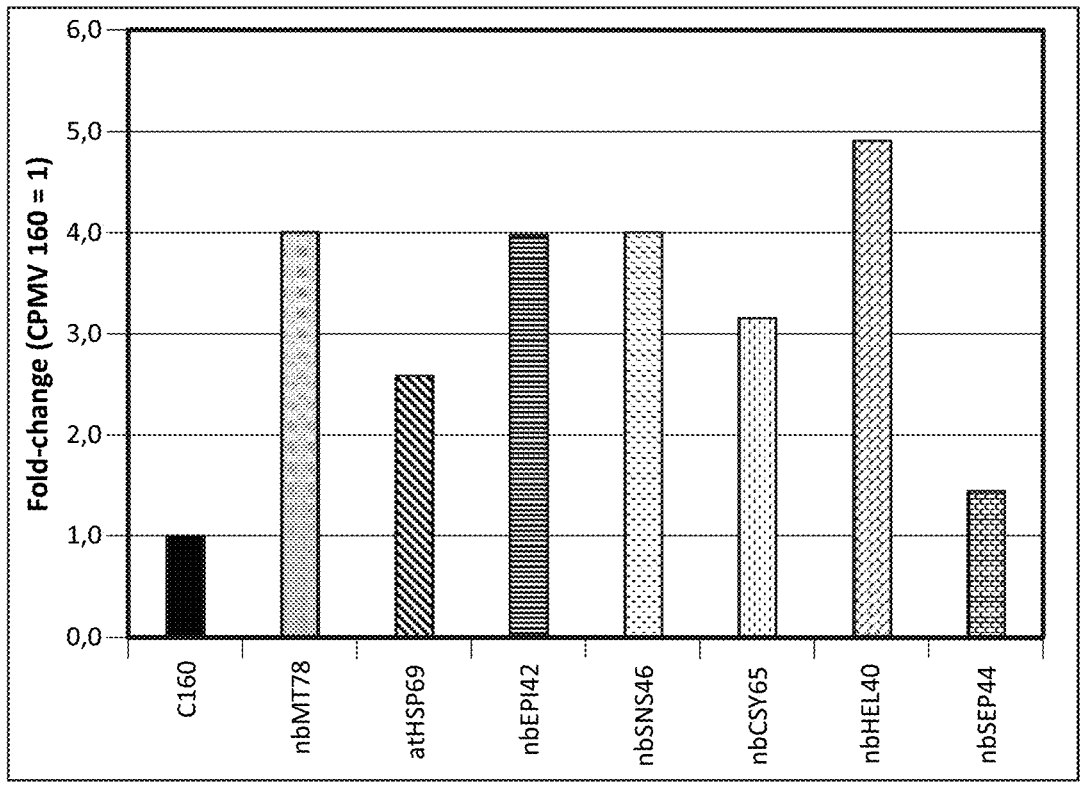

The following description is of a preferred embodiment.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments, consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The term "plant", "portion of a plant", "plant portion', "plant matter", "plant biomass", "plant material", plant extract", or "plant leaves", as used herein, may comprise an entire plant, tissue, cells, or any fraction thereof, intracellular plant components, extracellular plant components, liquid or solid extracts of plants, or a combination thereof, that are capable of providing the transcriptional, translational, and post-translational machinery for expression of one or more than one nucleic acids described herein, and/or from which an expressed protein of interest or VLP may be extracted and purified. Plants may include, but are not limited to, agricultural crops including for example canola, *Brassica* spp., maize, *Nicotiana* spp., (tobacco) for example, *Nicotiana benthamiana, Nicotiana rustica, Nicotiana tabacum, Nicotiana alata, Arabidopsis thaliana*, alfalfa, potato, sweet potato (*Ipomoea batatus*), ginseng, pea, oat, rice, soybean, wheat, barley, sunflower, cotton, corn, rye (*Secale cereale*), sorghum (*Sorghum bicolor, Sorghum vulgare*), safflower (Carthamus tinctorius).

The term "plant portion", as used herein, refers to any part of the plant including but not limited to leaves, stem, root, flowers, fruits, callus tissue or cell cultured plant tissue, a cluster of plant cells, a plant cell, for example a plant cell, cluster of plants cells callus or cultured plant tissue obtained from leaves, stem, root, flowers, fruits, a plant extract obtained from leaves, stem, root, flowers, fruits, or a combination thereof. The term plant cell refers to a cell of plant that is bounded by a plasma membrane and may or may not comprise a cell wall. A plant cell includes a protoplast (or spheroplast) that comprises an enzymatically digested cell and that may be obtained using techniques well known in the art (e.g. Davey M R et al., 2005, Biotechnology Advances 23:131-171; which is incorporated herein by reference). Callus plant tissue or cultured plant tissue may be produced using methods well known in the art (e.g. M K Razdan 2$^{nd}$ Ed., Science Publishers, 2003; which is incorporated herein by reference) The term "plant extract", as used herein, refers to a plant-derived product that is obtained following treating a plant, a portion of a plant, a plant cell, or a combination thereof, physically (for example by freezing followed by extraction in a suitable buffer), mechanically (for example by grinding or homogenizing the plant or portion of the plant followed by extraction in a suitable buffer), enzymatically (for example using cell wall degrading enzymes), chemically (for example using one or more chelators or buffers), or a combination thereof. A plant extract may be further processed to remove undesired plant components for example cell wall debris. A plant extract may be obtained to assist in the recovery of one or more components from the plant, portion of the plant or plant cell, for example a protein (including protein complexes, protein surprastructures and/ or VLPs), a nucleic acid, a lipid, a carbohydrate, or a combination thereof from the plant, portion of the plant, or plant cell. If the plant extract comprises proteins, then it may be referred to as a protein extract. A protein extract may be a crude plant extract, a partially purified plant or protein extract, or a purified product, that comprises one or more proteins, protein complexes, protein suprastructures, and/or VLPs, from the plant tissue. If desired a protein extract, or a plant extract, may be partially purified using techniques known to one of skill in the art, for example, the extract may be subjected to salt or pH precipitation, centrifugation, gradient density centrifugation, filtration, chromatography, for example, size exclusion chromatography, ion exchange chromatography, affinity chromatography, or a combination thereof. A protein extract may also be purified, using techniques that are known to one of skill in the art.

By "nucleotide (or nucleic acid) sequence of interest", or "coding region of interest", it is meant any nucleotide sequence, or coding region (these terms may be used interchangeably) that is to be expressed within a plant, portion of a plant, or a plant cell, to produce a protein of interest. Such a nucleotide sequence of interest may encode, but is not limited to, native or modified proteins, an industrial enzyme or a modified industrial enzyme, an agricultural protein or a modified agricultural protein, a helper protein, a protein supplement, a pharmaceutically active protein, a nutraceutical, a value-added product, or a fragment thereof for feed, food, or both feed and food use.

The protein of interest may comprise a native, or a non-native signal peptide; the non-native signal peptide may be of plant origin. For example, which is not to be considered limiting, the non-native signal peptide may be obtained from alfalfa protein disulfide isomerase (PDI SP; nucleotides 32-103 of Accession No. Z11499), potato patatin (PatA SP; located nucleotides 1738-1806 of GenBank Accession number A08215), Kiwi actinidin (Act), Tobacco cysteine proteinase 3 precursor (CP23), Corn ΔZein (ΔZein), Papaya proteinase I (Papain; Pap) and Thale cress cysteine proteinase RD21A (RD21). The native signal peptide may correspond to that of the protein of interest being expressed.

The nucleotide sequence of interest, or coding region of interest may also include a nucleotide sequence that encodes a pharmaceutically active protein, for example growth factors, growth regulators, antibodies, antigens, and fragments thereof, or their derivatives useful for immunization or vaccination and the like. Such proteins include, but are not limited to a protein that is a human pathogen, a viral protein, for example but not limited to virus like particle (VLP)-forming antigens, one or more proteins from Norovirus, Respiratory syncytial virus (RSV), Rotavirus, influenza virus, human immunodeficiency virus (HIV), Rabies virus, human papiloma virus (HPV), Enterovirus 71 (EV71), or interleukins, for example one or more than one of IL-1 to IL-24, IL-26 and IL-27, cytokines, Erythropoietin (EPO), insulin, G-CSF, GM-CSF, hPG-CSF, M-CSF or combinations thereof, interferons, for example, interferon-alpha, interferon-beta, interferon-gama, blood clotting factors, for example, Factor VIII, Factor IX, or tPA hGH, receptors, receptor agonists, antibodies for example but not limited to rituximab, neuropolypeptides, insulin, vaccines, growth factors for example but not limited to epidermal growth factor, keratinocyte growth factor, transformation growth factor, growth regulators, antigens, autoantigens, fragments thereof, or combinations thereof.

The protein of interest may include an influenza hemagglutinin (HA; see WO 2009/009876, WO 2009/076778, WO 2010/003225, which are incorporated herein by reference). HA is a homotrimeric membrane type I glycoprotein, generally comprising a signal peptide, an HA1 domain, and an HA2 domain comprising a membrane-spanning anchor site at the C-terminus and a small cytoplasmic tail. Nucleotide sequences encoding HA are well known and are available (see, for example, the BioDefense and Public Health Database (Influenza Research Database; Squires et al., 2008, Nucleic Acids Research 36:D497-D503) at URL: biohealthbase.org/GSearch/home.do?decorator=Influenza; or the databases maintained by the National Center for Biotechnology Information (see URL: ncbi.nlm.nih.gov), both of which are incorporated herein by reference).

An HA protein may be of a type A influenza, a type B influenza, or is a subtype of type A influenza HA selected from the group of H1, H2, H3, H4, H5, H6, H7, H8, H9, H10, H11, H12, H13, H14, H15, H16. H17 and H18. In some aspects of the invention, the HA may be from a type A influenza, selected from the group H1, H2, H3, H5, H6, H7 and H9. Fragments of the HAs listed above may also be considered a protein of interest. Furthermore, domains from an HA type or subtype listed above may be combined to produce chimeric HA's (see for example WO2009/076778 which is incorporated herein by reference).

Examples of subtypes comprising HA proteins include A/New Caledonia/20/99 (H1N1), A/Indonesia/5/2006 (H5N1), A/PuertoRico/8/34 (H1N1), A/Brisbane/59/2007 (H1N1), A/Solomon Islands 3/2006 (H1N1), A/California/04/2009 (H1N1), A/California/07/2009 (H1N1), A/chicken/New York/1995, A/Singapore/1/57 (H2N2), A/herring gull/DE/677/88 (H2N8), A/Texas/32/2003, A/mallard/MN/33/00, A/duck/Shanghai/1/2000, A/northern pintail/TX/828189/02, A/Brisbane 10/2007 (H3N2), A/Wisconsin/67/2005 (H3N2), A/Victoria/361/2011 (H3N2), A/Texas/50/2012 (H3N2), A/Hawaii/22/2012 (H3N2), A/New York/39/2012 (H3N2), A/Perth/16/2009 (H3N2), C/Johannesburg/66, A/Anhui/1/2005 (H5N1), A/Vietnam/1194/2004 (H5N1), A/Teal/HongKong/W312/97 (H6N1), A/Equine/Prague/56 (H7N7), A/Turkey/Ontario/6118/68 (H8N4), H7 A/Hangzhou/1/2013, A/Anhui/1/2013 (H7N9), A/Shanghai/2/2013 (H7N9), A/shoveler/Iran/G54/03, A/HongKong/1073/99 (H9N2), A/chicken/Germany/N/1949 (H10N7), A/duck/England/56 (H11N6), A/duck/Alberta/60/76 (H12N5), A/Gull/Maryland/704/77 (H13N6), A/Mallard/Gurjev/263/82, A/duck/Australia/341/83 (H15N8), A/black-headed gull/Sweden/5/99 (H16N3), B/Malaysia/2506/2004, B/Florida/4/2006, B/Brisbane/60/08, B/Massachusetts/2/2012-like virus (Yamagata lineage), B/Wisconsin/1/2010 (Yamagata lineage), or B/Lee/40.

The HA may also be a modified or chimeric HA, for example, the native transmembrane domain of the HA may be replaced with a heterologous transmembrane domain (WO 2010/148511; which is incorporated herein by reference), the HA may comprise a chimeric ectodomain (WO2012/083445, which is incorporated herein by reference), or the HA may comprises a proteolytic loop deletion (WO 2014/153647, which is incorporated herein by reference).

The protein of interest may also include a norovirus protein or a modified norovirus protein as described in WO2018/170603; which is incorporated herein by reference), or U.S. provisional application 62/593,006 (filed Nov. 11, 2017; which is incorporated herein by reference). Norovirus is a non-enveloped viral strain of the genus norovirus of the family Caliciviridae that is characterized as having a single-stranded, positive-sense RNA. Norovirus strains may include any known norovirus strain, but also modifications to known norovirus strains that are known to develop on a regular basis over time. For example, norovirus strains may include, GI.1, GI.2, GI.3, GI.5, GI.7, GII.1, GII.2, GII.3, GII.4, GII.5, GII.6, GII.7, GII.12, GII.13, GII.14, GII.17 and GII.21, for example but not limited to Hu/GI.1/United States/Norwalk/1968, Hu/GI.2/Leuven/2003/BEL, Hu/GI.3/S29/2008/Lilla Edet/Sweden, Hu/GI.5/Siklos/Hun5407/2013/HUN, Hu/GII.1/Ascension208/2010/USA, Hu/GII.2/CGMH47/2011/TW, Hu/GII.3/Jingzhou/2013402/CHN, Hu/GII.4/Sydney/NSW0514/2012/AU, US96/GII.4/Dresden174/1997/DE AY741811, FH02/GII.4/FarmingtonHills/2002/US AY502023, Hnt04:GII.4/Hunter-NSW504D/2004/AU_DQ078814, 2006b: GII.4/Shellharbour-NSW696T/2006/AU_EF684915, N009: GII.4/Orange-NSW001P/2008/AU_GQ845367, Hu/GII.5/AlbertaEI390/2013/CA, Hu/GII.6/Ohio/490/2012/USA, GII.7/Musa/2010/A1173774, Hu/GII.12/H5206/2010/USA, GII.13/VA173/2010/H9AWU4, GII.14_Saga_2008_JPN_ADE28701 native VP1, Hu/GII.17/Kawasaki323/2014/JP, and Hu/GII.21/Salisbury150/2011/USA. Norovirus strains also include strains having from about 30-100% or any amount therebetween, amino acid sequence identity, to the VP1 protein, the VP2 protein, or both the VP1 and the VP2 proteins, with any of the above norovirus strains.

The terms "percent similarity", "sequence similarity", "percent identity", or "sequence identity", when referring to a particular sequence, are used for example as set forth in the University of Wisconsin GCG software program, or by manual alignment and visual inspection (see, e.g., Current Protocols in Molecular Biology, Ausubel et al., eds. 1995 supplement). Methods of alignment of sequences for comparison are well-known in the art. Optimal alignment of sequences for comparison can be conducted, using for example the algorithm of Smith & Waterman, (1981, Adv. Appl. Math. 2:482), by the alignment algorithm of Needleman & Wunsch, (1970, J. Mol. Biol. 48:443), by the search for similarity method of Pearson & Lipman, (1988, Proc. Natl. Acad. Sci. USA 85:2444), by computerized implementations of these algorithms (for example: GAP, BESTFIT, FASTA, and TFASTA in the Wisconsin Genetics Software Package, Genetics Computer Group (GCG), 575 Science Dr., Madison, Wis.).

An example of an algorithm suitable for determining percent sequence identity and sequence similarity are the BLAST and BLAST 2.0 algorithms, which are described in Altschul et al., (1977, Nuc. Acids Res. 25:3389-3402) and Altschul et al., (1990, J. Mol. Biol. 215:403-410), respectively. BLAST and BLAST 2.0 are used, with the parameters described herein, to determine percent sequence identity for the nucleic acids and proteins of the invention. For example the BLASTN program (for nucleotide sequences) may use as defaults a wordlength (W) of 11, an expectation (E) of 10, M=5, N=−4 and a comparison of both strands. For amino acid sequences, the BLASTP program may use as defaults a word length of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands. Software for performing BLAST analyses is publicly available through the National Center for Biotechnology Information (see URL: ncbi.nlm.nih.gov/).

The term "nucleic acid segment" as used herein refers to a sequence of nucleic acids that encodes a protein of interest. In addition to the sequence of nucleic acids, the nucleic acid segment comprise a regulatory region and a terminator that are operatively linked to the sequence of nucleic acids. The regulatory region may comprise a promoter, and an enhancer element (expression enhancer) operatively linked to the promoter.

The term "nucleic acid complex" as used herein refers to a combination of two or more than two nucleic acid segments. The two or more than two nucleic acid segments may be present in a single nucleic acid, so that the nucleic acid complex comprises two, or more than two nucleic acid segments, with each nucleic acid segment under the control of a regulatory region and a terminator. Alternatively, the nucleic acid complex may comprise two or more separate nucleic acids, each of the nucleic acids comprising one or more than one nucleic acid segment, where each nucleic acid segment is under the control of a regulatory region and a terminator. For example a nucleic acid complex may comprise one nucleic acid that comprises two nucleic acid segments, a nucleic acid complex may comprise two nucleic acids, each nucleic acid comprising one nucleic acid segment, or a nucleic acid complex may comprise two or more than two nucleic acids, with each nucleic acid comprising one or more than one nucleic acid segment.

The terms "vector" or "expression vector" as used herein, refer to a recombinant nucleic acid for transferring exogenous nucleic acid sequences into host cells (e.g. plant cells) and directing expression of the exogenous nucleic acid sequences in the host cells. The vector may be introduced to the plant, the portion of the plant, or a plant cell, directly, or the vectors may be introduced in the plant, the portion of the plant, or a plant cell as part of a plant expression system. The vector or expression vector comprise a construct or an expression construct. The construct or expression construct comprises a nucleotide sequence comprising a nucleic acid of interest under the control of, and operably (or operatively) linked to, an appropriate promoter, an expression enhancer, or other regulatory elements for transcription of the nucleic acid of interest in a host cell. As one of skill in the art would appreciate, the construct or expression cassette may comprise a termination (terminator) sequence that is any sequence that is active in the plant host. For example the termination sequence may be derived from the RNA-2 genome segment of a bipartite RNA virus, e.g. a comovirus, the termination sequence may be a NOS terminator, the terminator sequence may be obtained from the 3'UTR of the alfalfa plastocyanin gene, or a combination thereof.

The constructs of the present disclosure may further comprise a 3' untranslated region (UTR). A 3' untranslated region contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Non-limiting examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes, the small subunit of the ribulose-1, 5-bisphosphate carboxylase gene (ssRUBISCO; U.S. Pat. No. 4,962,028; which is incorporated herein by reference), the promoter and/or terminator used in regulating plastocyanin expression.

For example, which is not to be considered limiting, a CPMV 3'UTR+NOS terminator may be used as a 3'UTR sequence that is operatively linked to the 3' end of the nucleic acid sequence encoding the protein of interest.

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a nucleotide sequence of interest, this may result in expression of the nucleotide sequence of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element may comprise a basal promoter element, responsible for the initiation of transcription, as well as other regulatory elements that modify gene expression.

There are several types of regulatory regions, including those that are developmentally regulated, inducible or constitutive. A regulatory region that is developmentally regulated or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example seed-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically, the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358). Examples, of potential inducible promoters include, but not limited to, tetracycline-inducible promoter (Gatz, C., 1997, Ann. Rev. Plant Physiol. Plant Mol. Biol. 48, 89-108), steroid inducible promoter (Aoyama, T. and Chua, N. H., 1997, Plant J. 2, 397-404) and ethanol-inducible promoter (Salter, M. G., et al, 1998, Plant Journal 16, 127-132; Caddick, M. X., et al, 1998, Nature Biotech. 16, 177-180) cytokinin inducible IB6 and CKI1 genes (Brandstatter, I. and Kieber, J. J., 1998, Plant Cell 10, 1009-1019; Kakimoto, T., 1996, Science 274, 982-985) and the auxin inducible element, DRS (Ulmasov, T., et al., 1997, Plant Cell 9, 1963-1971).

A constitutive regulatory region directs the expression of a gene throughout the various parts of a plant and continuously throughout plant development. Examples of known constitutive regulatory elements include promoters associated with the CaMV 35S transcript. (p35S; Odell et al., 1985, Nature, 313: 810-812; which is incorporated herein by reference), the rice actin 1 (Zhang et al, 1991, Plant Cell, 3: 1155-1165), actin 2 (An et al., 1996, *Plant J.,* 10: 107-121), or tms 2 (U.S. Pat. No. 5,428,147), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), the tobacco translational initiation factor 4A gene (Mandel et al, 1995 Plant Mol. Biol. 29: 995-1004); the Cassava Vein Mosaic Virus promoter, pCAS, (Verdaguer et al., 1996); the promoter of the small subunit of ribulose biphosphate carboxylase, pRbcS: (Outchkourov et al., 2003), the pUbi (for monocots and dicots).

The term "constitutive" as used herein does not necessarily indicate that a nucleotide sequence under control of the constitutive regulatory region is expressed at the same level in all cell types, but that the sequence is expressed in a wide range of cell types even though variation in abundance is often observed.

The constructs or expression constructs as described above may be present in a vector (or an expression vector). The vector may comprise border sequences which permit the transfer and integration of the expression cassette into the genome of the organism or host. The construct may be a plant binary vector, for example a binary transformation vector based on pPZP (Hajdukiewicz, et al. 1994). Other example constructs include pBin19 (see Frisch, D. A., L. W. Harris-Haller, et al. 1995, *Plant Molecular Biology* 27: 405-409).

A nucleotide sequence interest that encodes a protein requires the presence of a "translation initiation site" or "initiation site" or "translation start site" or "start site" or "start codon" located upstream of the gene to be expressed. Such initiation sites may be provided either as part of an enhancer sequence or as part of a nucleotide sequence encoding the protein of interest.

The term "native", "native protein" or "native domain", as used herein, refers to a protein or domain having a primary amino acid sequence identical to wildtype. Native proteins or domains may be encoded by nucleotide sequences having 100% sequence similarity to the wildtype sequence. A native amino acid sequence may also be encoded by a human codon (hCod) optimized nucleotide sequence or a nucleotide sequence comprising an increased GC content when compared to the wild type nucleotide sequence provided that the amino acid sequence encoded by the hCod-nucleotide sequence exhibits 100% sequence identity with the native amino acid sequence.

By a nucleotide sequence that is "human codon optimized" or an "hCod" nucleotide sequence, it is meant the selection of appropriate DNA nucleotides for the synthesis of an oligonucleotide sequence or fragment thereof that approaches the codon usage generally found within an oligonucleotide sequence of a human nucleotide sequence. By "increased GC content" it is meant the selection of appropriate DNA nucleotides for the synthesis of an oligonucleotide sequence or fragment thereof in order to approach codon usage that, when compared to the corresponding native oligonucleotide sequence, comprises an increase of GC content, for example, from about 1 to about 30%, or any amount therebetween, over the length of the coding portion of the oligonucleotide sequence. For example, from about 1, 2, 4, 6, 8, 10, 12, 14, 16, 18, 20, 22, 24, 26, 28, 30%, or any amount therebetween, over the length of the coding portion of the oligonucleotide sequence. As described below, a human codon optimized nucleotide sequence, or a nucleotide sequence comprising an increased GC content (when compared to the wild type nucleotide sequence) exhibits increased expression within a plant, portion of a plant, or a plant cell, when compared to expression of the non-human optimized (or lower GC content) nucleotide sequence.

The term "single construct" or "single constructs", as used herein, refers to a nucleic acid comprising a single nucleic acid sequence. The term "dual construct" or "dual constructs", as used herein, refers to a nucleic acid comprising two nucleic acid sequences.

By co-expression it is meant the introduction and expression of two or more nucleotide sequences, each of the two or more nucleotide sequences encoding a protein of interest, or a fragment of a protein of interest within a plant, portion of a plant or a plant cell. The two or more nucleotide sequences may be introduced into the plant, portion of the plant or the plant cell within one vector, so that each of the two or more nucleotide sequences is under the control of a separate regulatory region (e.g. comprising a dual construct). Alternatively, the two or more nucleotide sequences may be introduced into the plant, portion of the plant or the plant cell within separate vectors (e.g. comprising single constructs), and each vector comprising appropriate regulatory regions for the expression of the corresponding nucleic acid. For example, two nucleotide sequences, each on a separate vector and introduced into separate *Agrobacterium*

*tumefaciens* hosts, may be co-expressed by mixing suspensions of each *A. tumefaciens* host in a desired volume (for example, an equal volume, or the ratios of each *A. tumefaciens* host may be altered) before vacuum infiltration. In this manner, co-infiltration of multiple *A. tumifaciens* suspensions permits co-expression of multiple transgenes.

The nucleic acid encoding a protein of interest as described herein may further comprise sequences that enhance expression of the protein of interest in the plant, portion of the plant, or plant cell. Sequences that enhance expression are described herein and for example, may include one or more of, an expression enhancer element obtained from a nucleic acid encoding a secretory protein (SPEE) or an expression enhancer element obtained from a nucleic acid encoding a cytosolic protein (CPEE), in operative association with the nucleic acid encoding the protein of interest. Non-limiting examples of using the expression enhancer as described herein for the expression of a secreted protein includes any protein of interest comprising a signal peptide or signal sequence that targets the protein of interest to the extracellular compartment, for example an antibody (see FIG. 3C), or virus like particles (VLPs) that are known to bud from the plasma membrane, for example, influenza HA (see for example FIGS. 3A and 3B). Non-limiting examples of proteins that are produced cytosolically include any protein of interest that do not comprise a secretory peptide or signal sequence (see for example FIG. 2A), or VLPs that are known to be produced and retained within the cytsol, for example norovirus (see FIG. 2B).

The sequence encoding the protein of interest may also be optimized for human codon usage, increased GC content, or a combination thereof. Co-expression of a nucleic acid encoding a second protein of interest may lead to functional multimeric protein, for example an antibody comprising heavy and light chain components, or to an increased yield of protein. If the protein of interest results in the production of a VLP, then co-expression of two or more proteins may result in an increase yield, increased density, increased integrity, or combination thereof, of the VLPs that comprise the protein of interest. The increase in yield, density, integrity, or combination thereof, may be determined by comparing the yield, density, integrity, or combination thereof, obtained using the expression enhancer as described herein with the yield, density, integrity, or combination thereof, of the same nucleotide sequence encoding the heterologous open reading frame but not operatively linked to an expression enhancer, or for example, when operatively linked to the prior art expression enhancer CPMV 160 (SEQ ID NO:6).

A plant expression system comprising a nucleic acid comprising a regulatory region, operatively linked with one or more than one expression enhancer as described herein and a nucleotide sequence of interest is also provided. The plant expression system may comprise one or more than one vector, one or more than one construct or one or more than one nucleic acid, that comprises the regulatory region operatively linked with one or more than one expression enhancer as described herein and the nucleotide sequence or nucleic acid of interest, along with other components that may be introduced into the plant, the portion of the plant or a plant cell. For example, the plant expression system may also comprise additional vectors, constructs, or nucleic acids, additional Agrobacteria comprising vectors, constructs or nucleic acids for co-expression, one or more than one chemical compound to modify the efficiency of transformation, other components, or a combination thereof.

Furthermore, a nucleic acid comprising a promoter (regulatory region) sequence, operatively linked with an expression enhancer comprising an expression enhancer as described herein, and a nucleotide sequence of interest is described. The nucleic acid may further comprise a sequence encoding a 3'UTR, for example a comovirus 3' UTR, or a plastocyanin 3' UTR, and a terminator sequence, for example a NOS terminator, so that the nucleotide sequence of interest is inserted upstream from the 3'UTR.

"Expression enhancer(s)", "enhancer sequence(s)" or "enhancer element(s)", as referred to herein, when operatively linked to a nucleic acid of interest, for example a heterologous nucleic acid of interest, results in expression of the nucleic acid of interest. The expression enhancer may also enhance or increase expression of a downstream heterologous open reading frame (ORF) to which they are attached. The expression enhancer may be operatively linked at the 5' end of the enhancer sequence with a regulatory region that is active in a plant, and operatively linked to a nucleotide sequence of interest at the 3' end of the expression enhancer in order to drive expression of the nucleotide sequence of interest within a host, for example a plant, portion of a plant or a plant cell. Expression enhancers described herein include sequences derived from, or that share sequence similarity with, a nucleotide sequence selected from nbEPI42 (SEQ ID NO:1); nbSNS46 (SEQ ID NO:2); nbCSY65 (SEQ ID NO:3); nbHEL40 (SEQ ID NO:4); and nbSEP44 (SEQ ID NO:5).

By "operatively linked" it is meant that the particular sequences interact either directly or indirectly to carry out an intended function, such as mediation or modulation of expression of a nucleic acid sequence. The interaction of operatively linked sequences may, for example, be mediated by proteins that interact with the operatively linked sequences.

The term "5'UTR" or "5' untranslated region" or "5' leader sequence" refers to regions of an mRNA that are not translated. The 5'UTR typically begins at the transcription start site and ends just before the translation initiation site or start codon (usually AUG in an mRNA, ATG in a DNA sequence) of the coding region. The 5' UTR may modulate the stability and/or translation of an mRNA transcript. If desired, the length of the 5'UTR may be modified by mutation for example substitution, deletion or insertion of the 5'UTR.

The expression enhancer may further comprise one or more "restriction site(s)" or "restriction recognition site(s)", "multiple cloning site", "MCS", "cloning site(s)", "polylinker sequence", or "polylinker" to facilitate the insertion of the nucleotide of interest into the plant expression system. Restrictions sites are specific sequence motifs that are recognized by restriction enzymes and are well known in the art. The expression enhancer may comprise one or more restriction sites or cloning sites that are located downstream (3') of the 5'UTR. The polylinker sequence (multiple cloning site) may comprise any sequence of nucleic acids that are useful for adding and removing nucleic acid sequences, including a nucleotide sequence encoding a protein of interest, to the 3' end of the 5'UTR. A polylinker sequence may comprise from 4 to about 100 nucleic acids, or any amount therebetween. As would be evident to one of skill in the art, any multiple cloning site (MCS), or an MCS of different length (either shorter or longer) may be used.

Expression systems, or vectors, to produce one or more proteins of interest in a plant using one or more than one expression enhancers as described herein are also provided. The expression systems described herein comprise an expression cassette comprising one or more than one expression enhancer, or a sequence that comprises 80-100% sequence similarity, or any amount therebetween, with the one or more than one expression enhancer. The expression cassette comprising the expression enhancer may further comprise a regulatory region that is active in a plant that is operatively linked to the 5' end of the expression enhancer. A nucleotide sequence of interest may be operatively linked to the 3' end of the expression cassette so that when introduced within a plant, portion of the plant or a plant cell, expression of the nucleotide sequence of interest within a plant is achieved.

Plants, portions of plants, plant cells, plant tissues, whole plants, inoculum, nucleic acids, constructs comprising nucleotide sequences of interest encoding proteins of interest, expression cassettes or expression systems comprising the one or more than one expression enhancer as described herein, and methods of expressing a protein of interest in plants, portions of plants, or plant cells are also provided.

The nucleotide sequence of interest may be fused (operatively linked) to the enhancer sequence comprising a plant regulatory region, using a variety of approaches. For example, which are not to be considered limiting, a nucleotide sequence of interest encoding a protein of interest may be fused to the 3' end of an expression enhancer immediately after the 5' UTR sequence.

The constructs of the present invention can be introduced into plant cells in a stable or transient manner using Ti plasmids, Ri plasmids, plant virus vectors, direct DNA transformation, micro-injection, electroporation, infiltration, and the like. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, Fundamentals of Gene Transfer in Plants. In *Plant Metabolism,* 2d Ed. D T. Dennis, D H Turpin, D D Lefebrve, D B Layzell (eds), Addison-Wesley, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J. Virol Meth, 105:343-348, 2002), U.S. Pat. Nos. 4,945,050; 5,036,006; 5,100,792; 6,403,865; 5,625,136, (all of which are hereby incorporated by reference).

Transient expression methods may be used to express the constructs of the present invention (see Liu and Lomonossoff, 2002, Journal of Virological Methods, 105:343-348; which is incorporated herein by reference). Alternatively, a vacuum-based transient expression method, as described by Kapila et al. 1997 (incorporated herein by reference) may be used. These methods may include, for example, but are not limited to, a method of Agro-inoculation or Agro-infiltration, however, other transient methods may also be used as noted above. With either Agro-inoculation or Agro-infiltration, a mixture of Agrobacteria comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacterium* infect and transfer t-DNA copies into the cells. The t-DNA is episomally transcribed and the mRNA translated, leading to the production of the protein of interest in infected cells, however, the passage oft-DNA inside the nucleus is transient.

If the nucleotide sequence of interest encodes a product that is directly or indirectly toxic to the plant, then by using the method of the present invention, such toxicity may be reduced throughout the plant by selectively expressing the nucleotide sequence of interest within a desired tissue or at a desired stage of plant development. In addition, the limited period of expression resulting from transient expression may reduce the effect when producing a toxic product in the plant. An inducible promoter, a tissue-specific promoter, or a cell specific promoter may be used to selectively direct expression of the sequence of interest.

U.S. Provisional Application No. 62/643,053 (filed Mar. 14, 2018; which is incorporated herein by reference) describes the identification of 15 plant-derived expression enhancer elements (UTRs) identified using polysomal analysis. Two of these UTRs (nbMT78, SEQ ID NO:7; and atHSP69, SEQ ID NO:8) are included herein for comparative purposes. The expression enhancers described herein (endogenous expression enhancers) were identified by analysing the 5' region of UTRs that were identified using the polysomal analysis described in U.S. Provisional Application No. 62/643,053. However, the endogenous expression enhancers described herein were not identified within the group of UTRs identified as a result of the polysomal analysis (described in U.S. Provisional Application No. 62/643,053), nor were the endogenous expression enhancers described herein identified using polysomal analysis.

Examples of expression enhancers (endogenous expression enhancers) as described herein include:

```
nbEPI42;
                                    (SEQ ID NO: 1)
ACTTTAATTTGCTGATTTTCAACAAAATCAAGAATTTCAGCA;

nbSNS46;
                                    (SEQ ID NO: 2)
ATTCAGTGCTTAACTGGTTATTGAGTAAGTTATCAAAAAGCAAAAA;

nbCSY65;
                                    (SEQ ID NO: 3)
ACTTTTCTAATCAATCATCAAACAGAACGCAGAAAATTTCCTAAAAA
CAAAAAAAGGCATACAA;

nbHEL40;
                                    (SEQ ID NO: 4)
ACTCCATTTGAATCTATCAAACCAAAACACATTGAGCAAA;

nbSEP44;
                                    (SEQ ID NO: 5)
ACTTCAATCACTCCACACTTTATTCTCTTTCAAAACCTACACTC;
```

The enhancer sequence may be selected from any one of SEQ ID NO's:1-5, or a nucleotide sequence that exhibits 100%, 99%, 98%, 97%, 96%, 95%, or 90%, or any amount therebetween, sequence identity to the sequence as set forth in any one of SEQ ID NO's:1-15, wherein, the expression enhancer, when operatively linked to a nucleic acid of interest, results in the expression of the nucleic acid of interest, or increases the level of expression of the nucleic acid of interest when compared to the level of expression of the same nucleic acid of interest that is not operatively linked to the expression enhancer, or for example, when operatively linked to the prior art expression enhancer CPMV 160 (SEQ ID NO:6). Each of the enhancer sequences shown in SEQ ID NO's:1-5 may be modified using methods known to one of skill in the art, including deletion, insertion, and/or substitution of one or more than one nucleotide of the enhancer sequence, to produce an expression enhancer that results in a similar or increased enhancer activity, or that results in another beneficial property of the expression enhancer (see for example Diamos et. al., Frontiers in Plant Science. 2016, vol 7 pp. 1-15; Dvir S. et. al., 2013, PNAS published online Jul. 15, 2013; Leppek K et. al., 2018, Nature Reviews Mol. Cell Biol. 19:158-174; which are incorporated herein by reference). For example, a beneficial property may include improved transcriptional initiation, improved mRNA stability, improved mRNA translation, or a combination thereof.

Use of one or more than one of the above expression enhancer of SEQ ID NO's:1-5, was observed to result in the expression of the nucleic acid of interest, or result in an increased expression of a nucleic acid of interest, or a protein of interest (an increase in the yield, the activity, or both the yield and activity, of the protein of interest) as shown with reference to FIGS. 2-5.

Figure 2B:
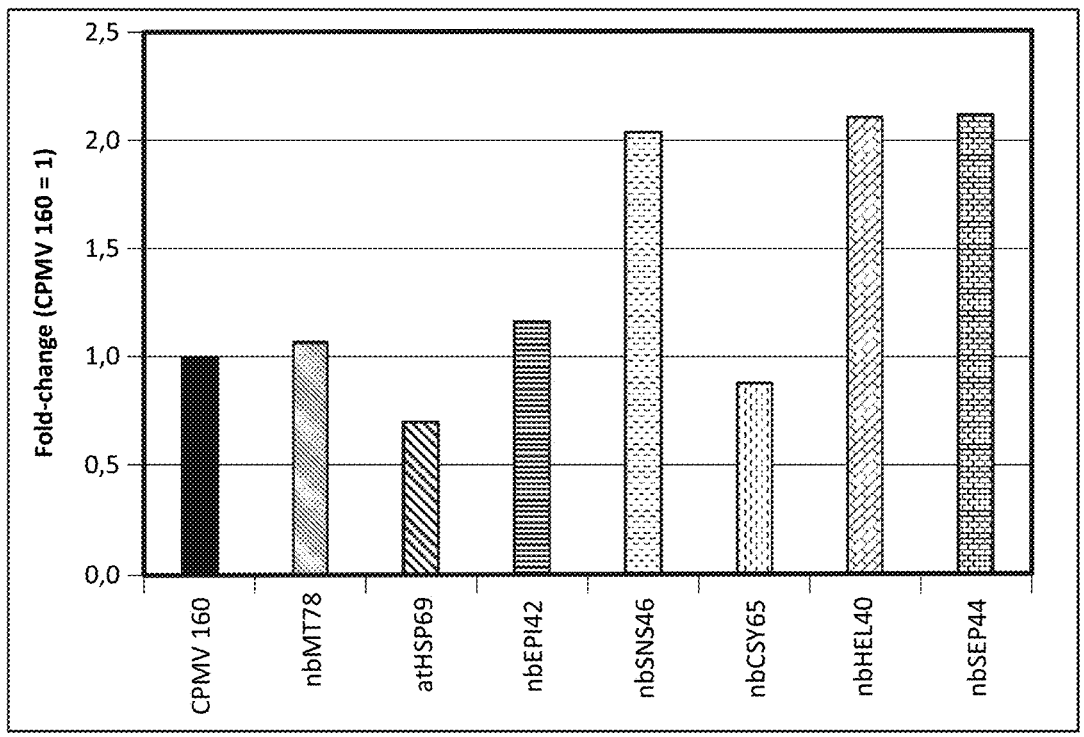
Figure 3A:
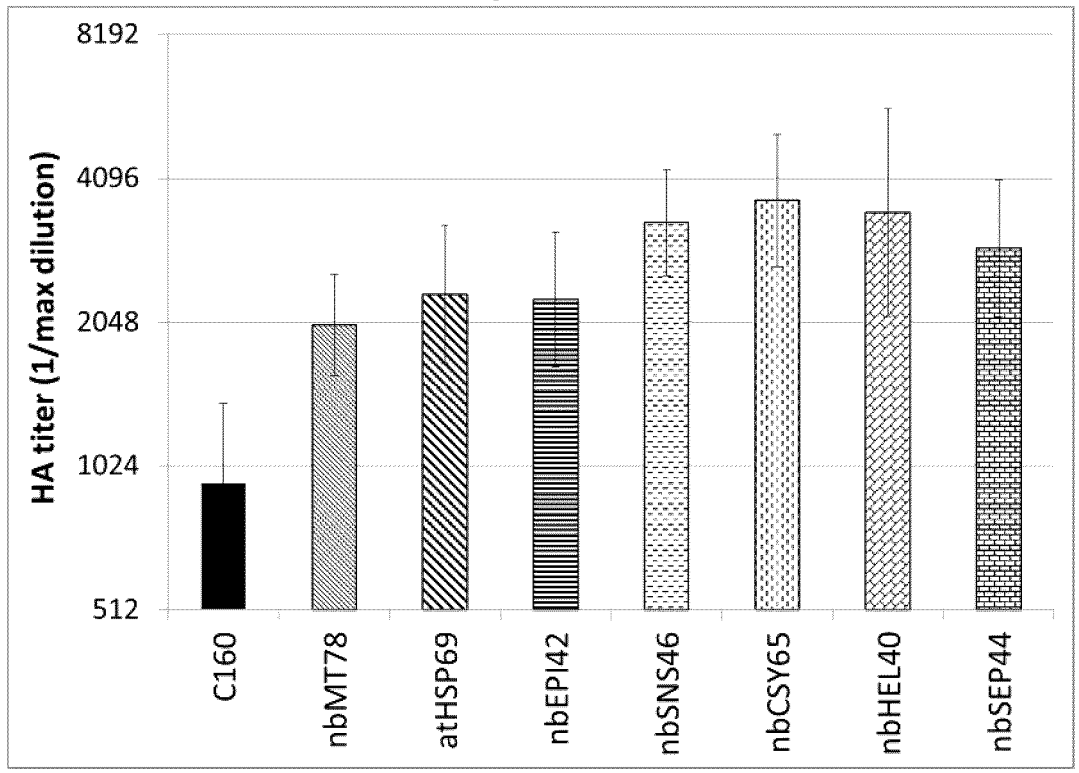
FIG. 3A shows the hemagglutinin titers of the secreted VLP of a H3 A Singapore influenza virus, the VLP produced in plants by expressing a nucleic acid encoding the H3 A Singapore protein wherein the nucleic acid encoding this protein is operatively linked to expression enhancers CP nbCSY65-SpPDI-H3 A-Sing-19-0019-16-CPMV 3'UTR/NOS)
Figure 3B:
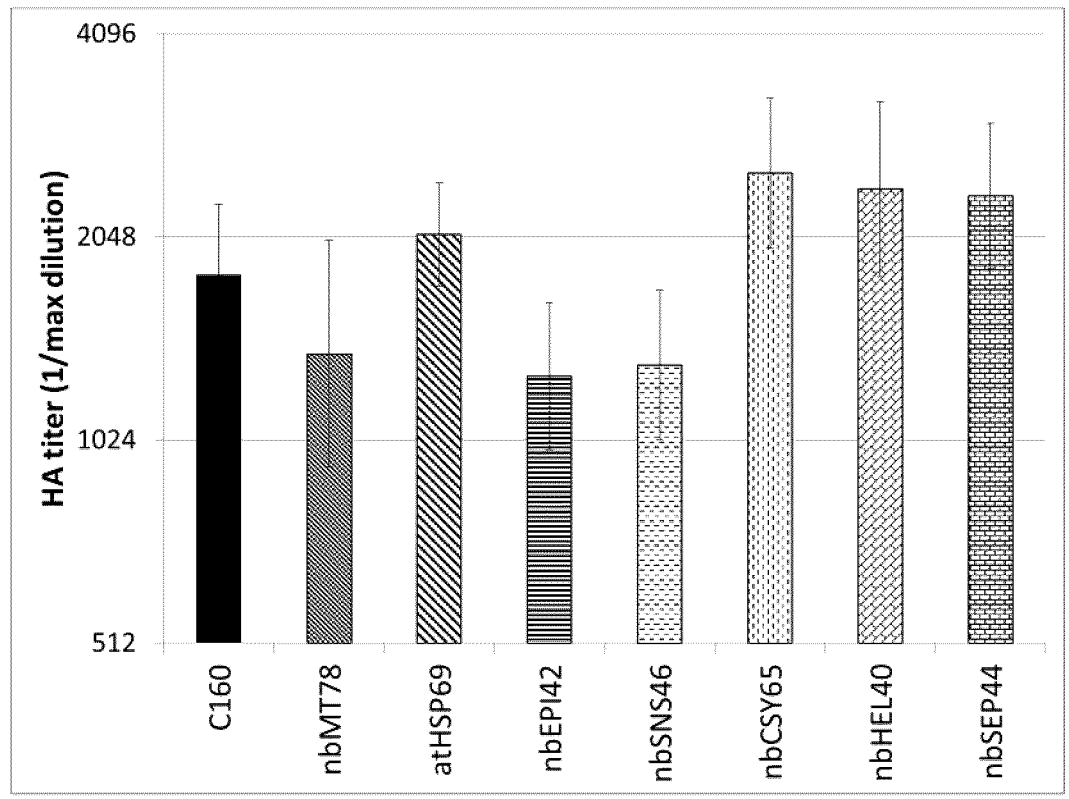
Figure 3C:
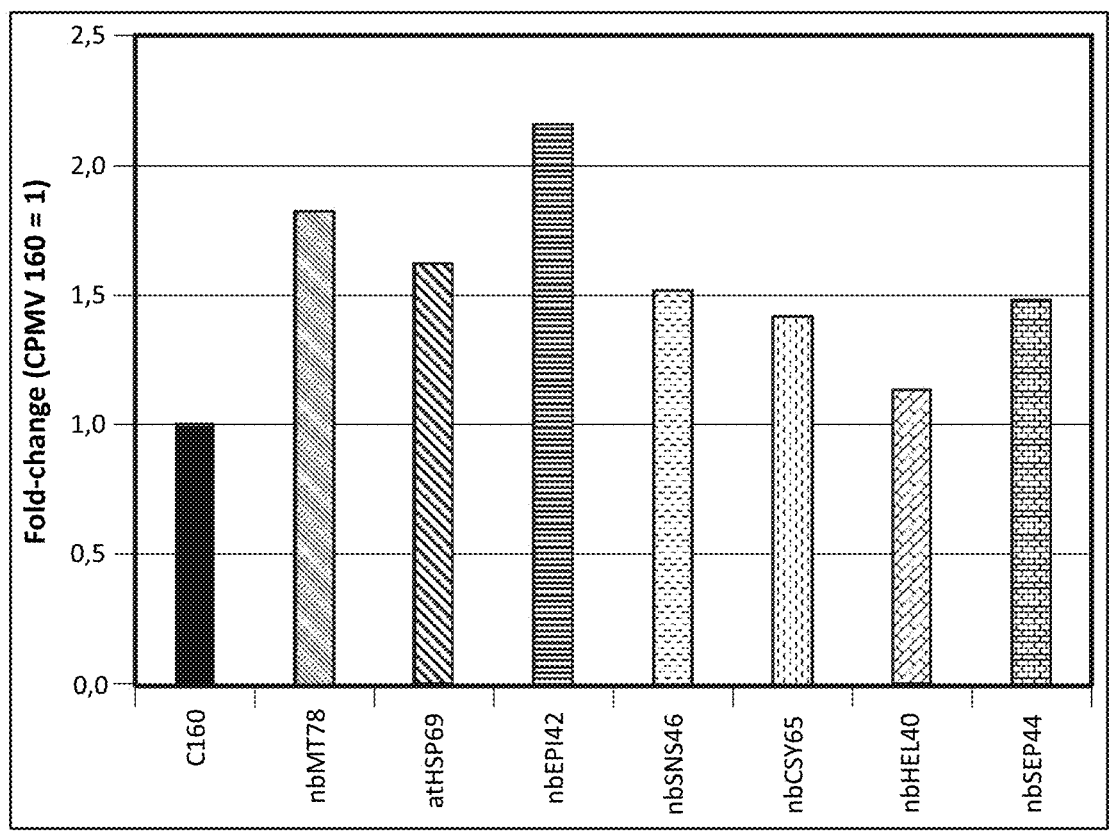
Figure 4A:
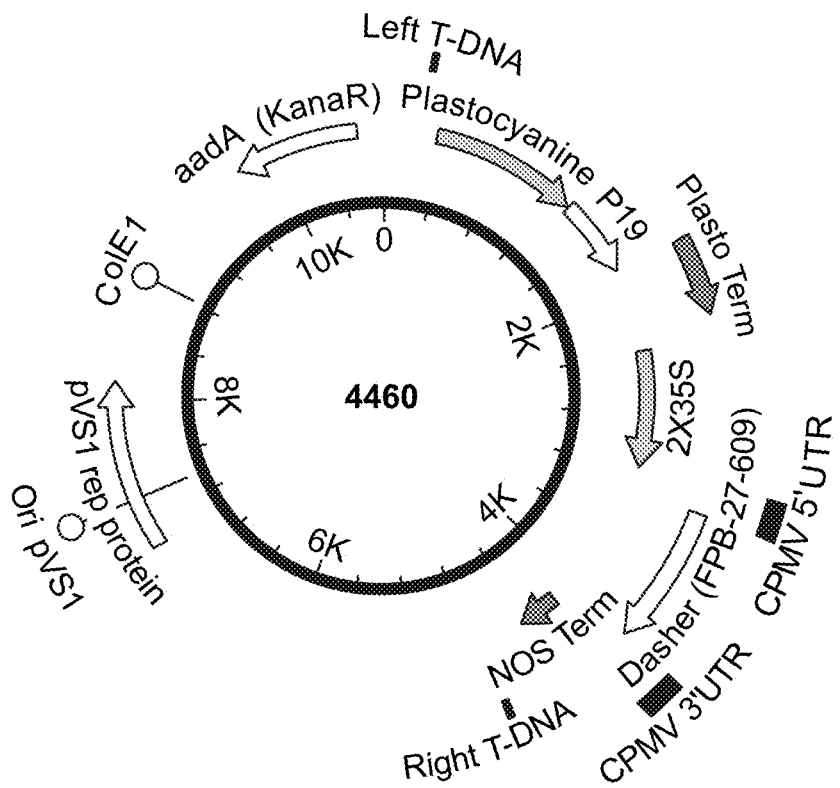
Figure 4B:
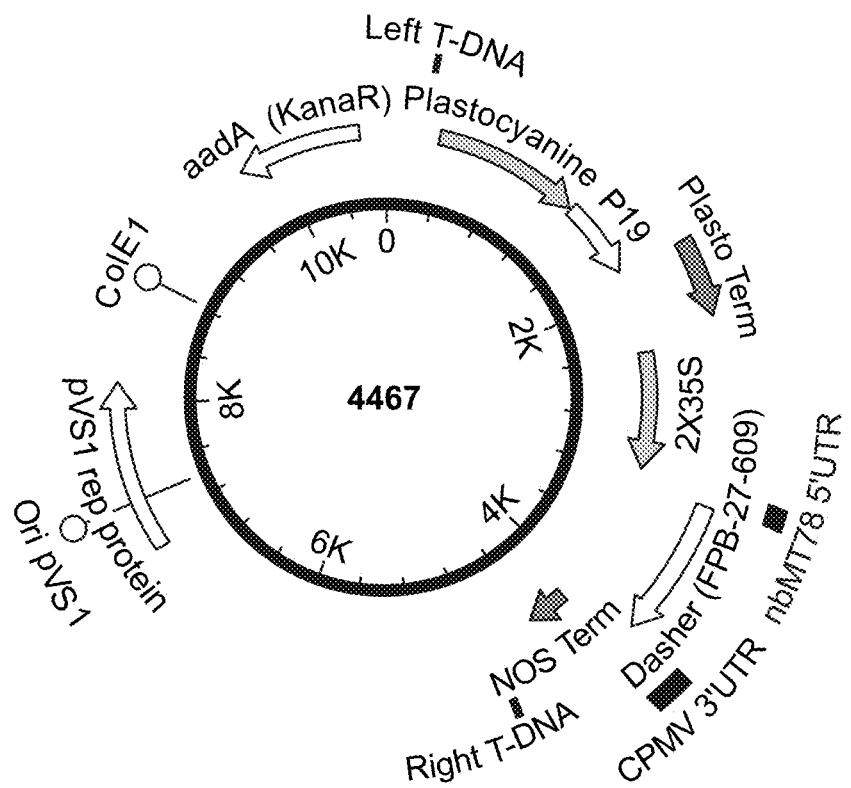
Figure 4C:
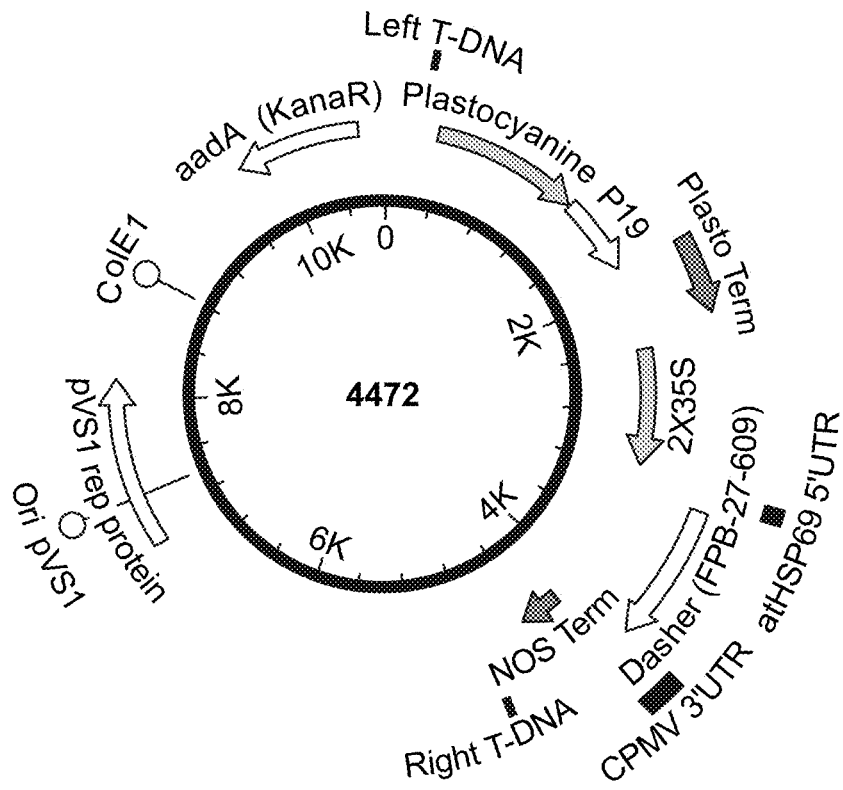
Figure 4D:
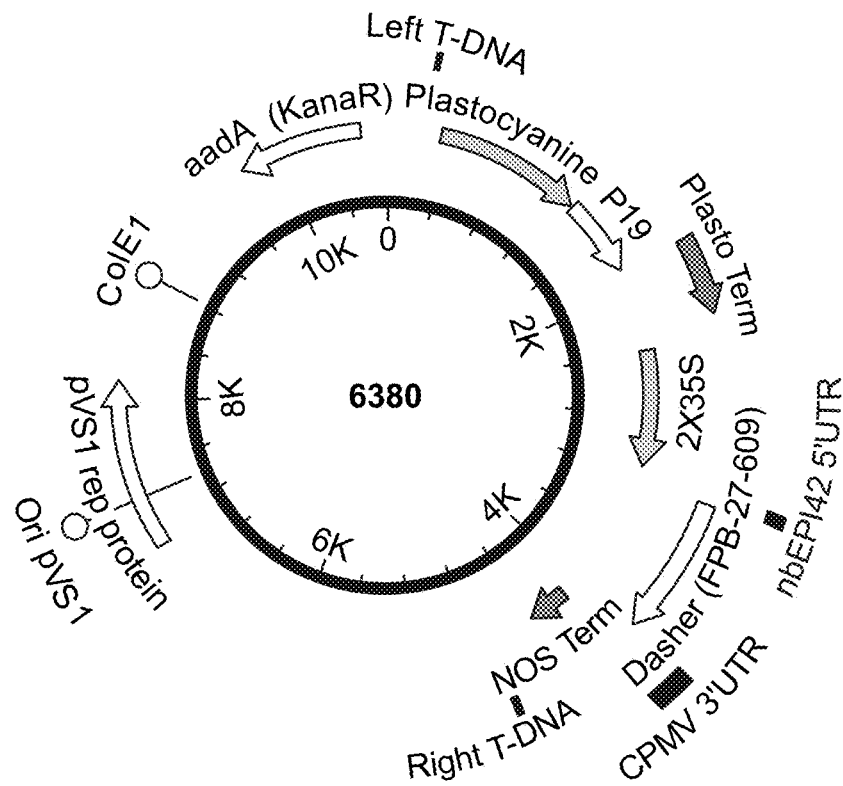
Figure 4E:
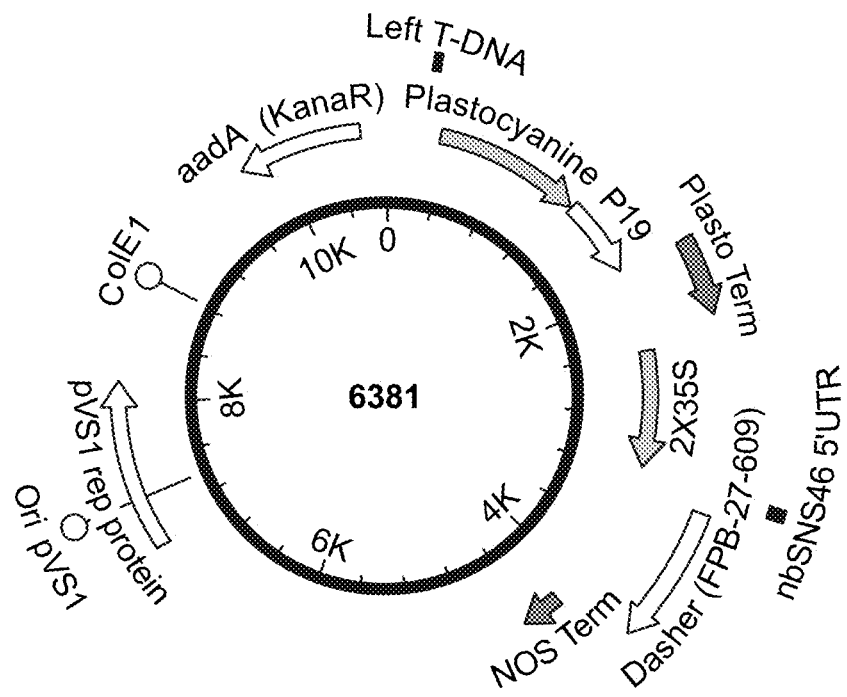
Figure 4F:
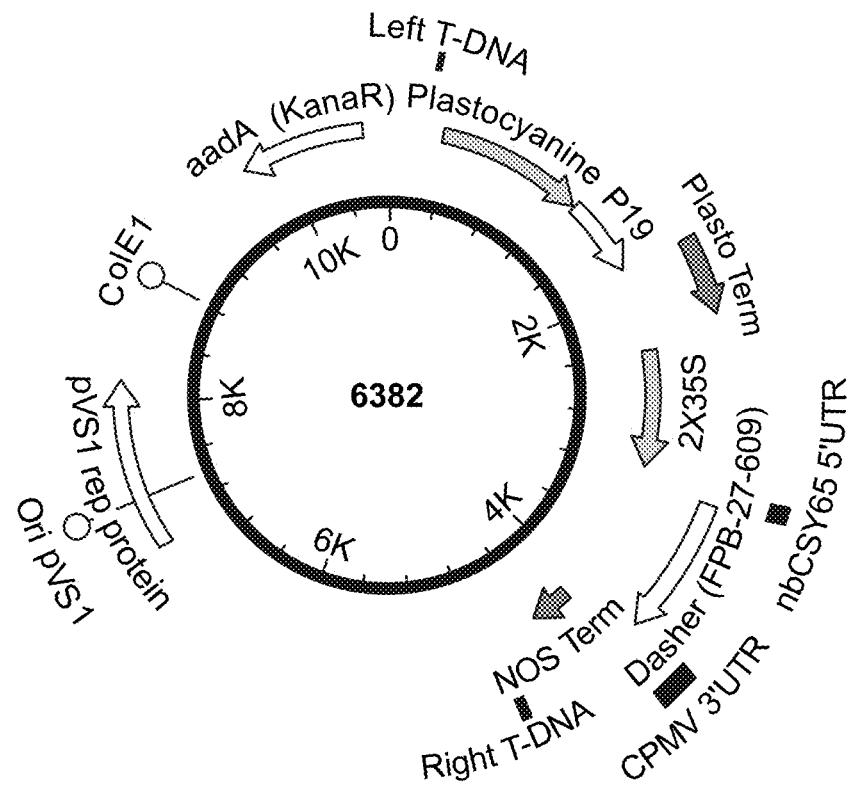
Figure 4G:
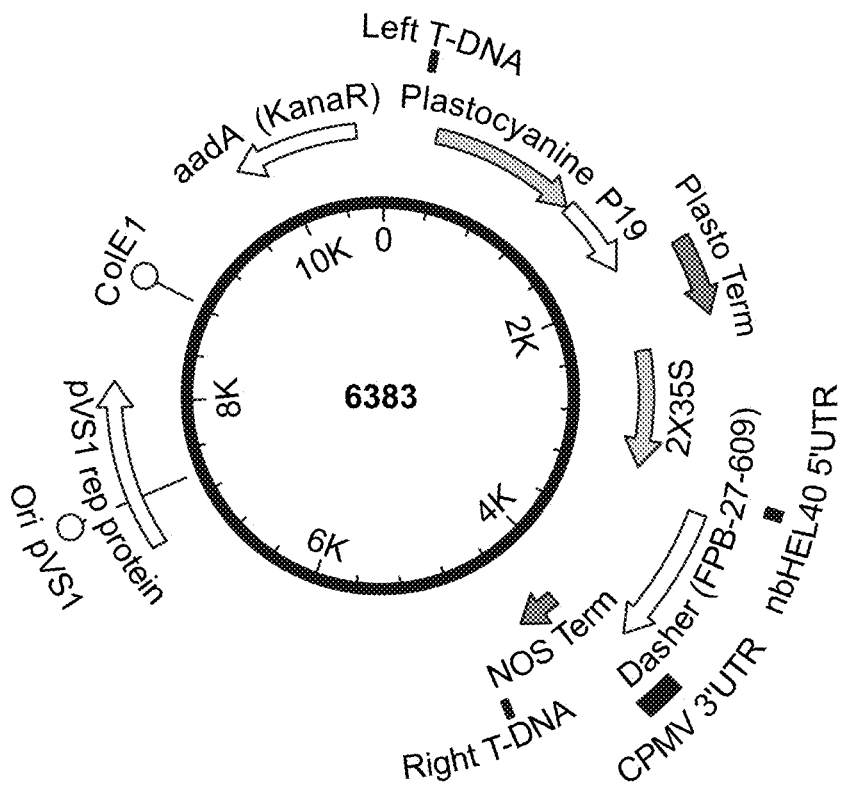
Figure 4H:
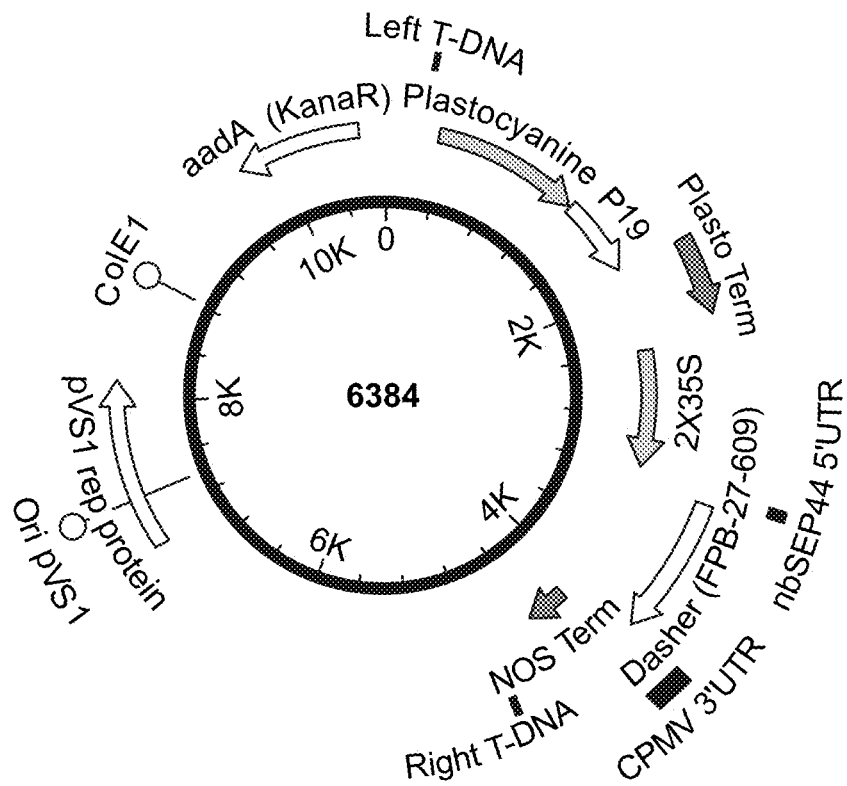
Figure 5A:
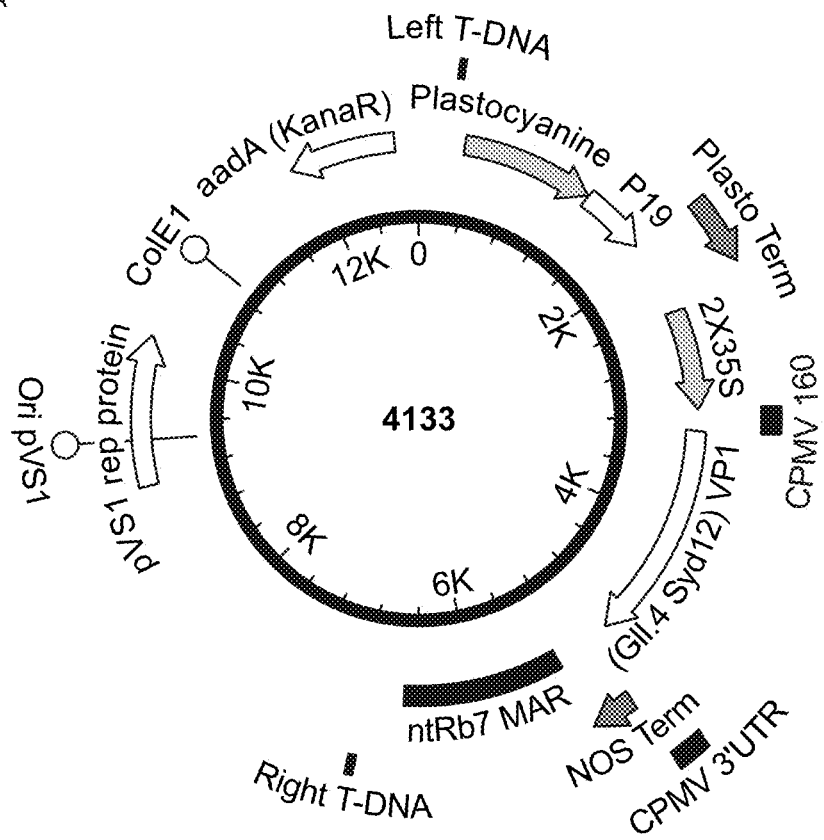
Figure 5B:
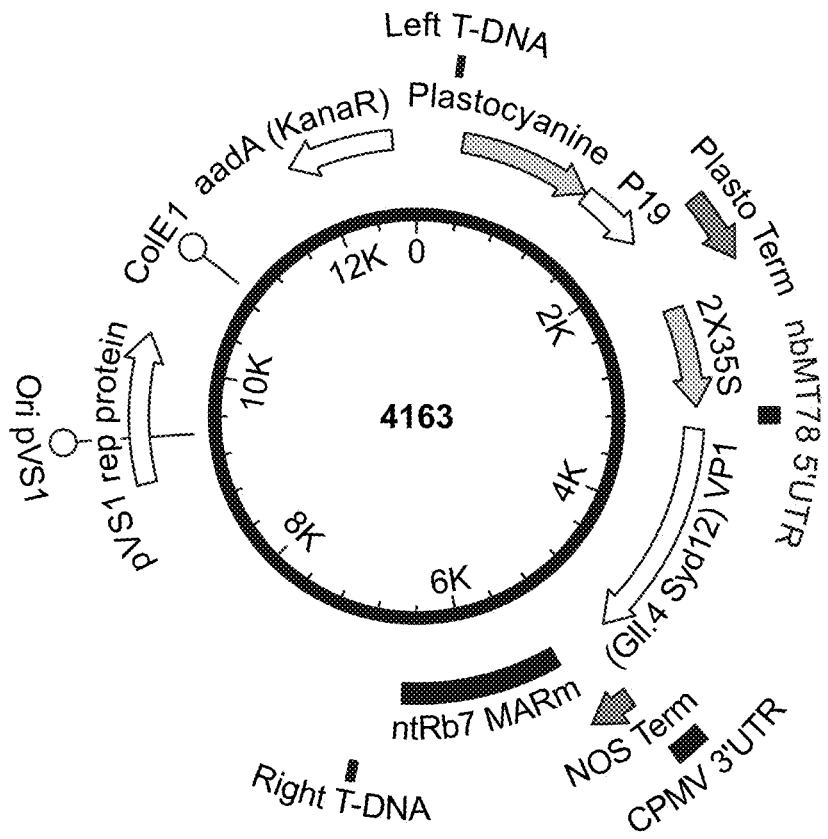
Figure 5C:
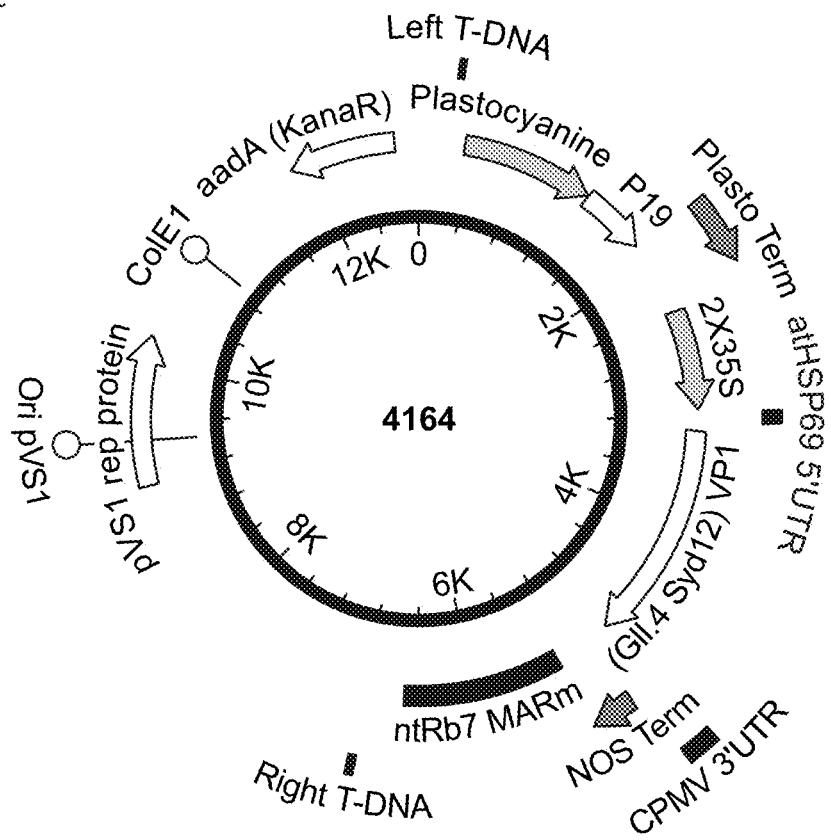
Figure 5D:
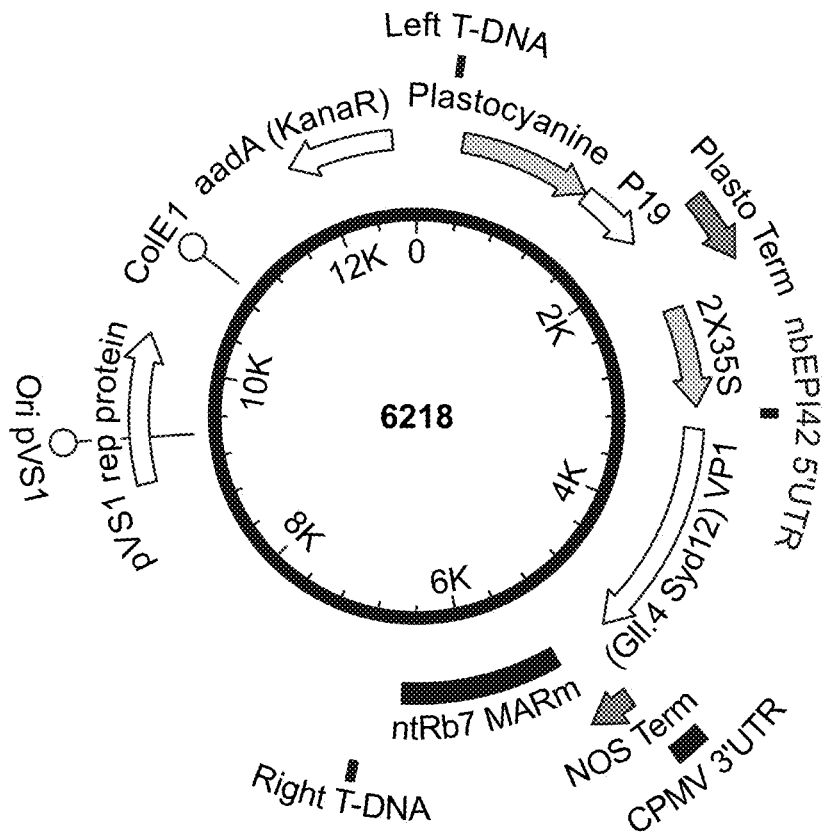
Figure 5E:
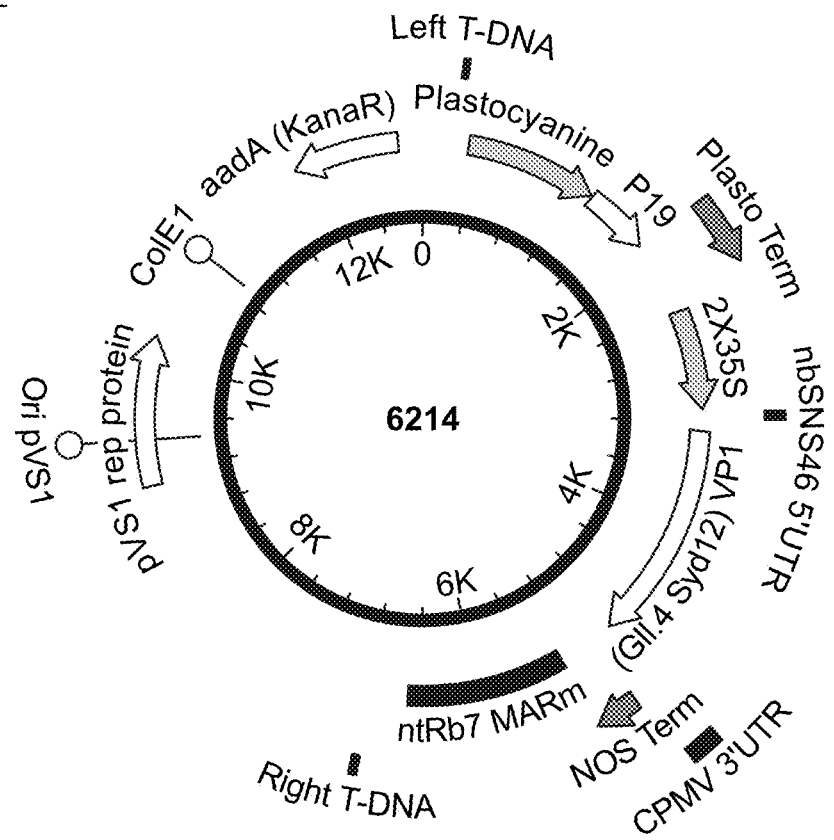
Figure 5F:
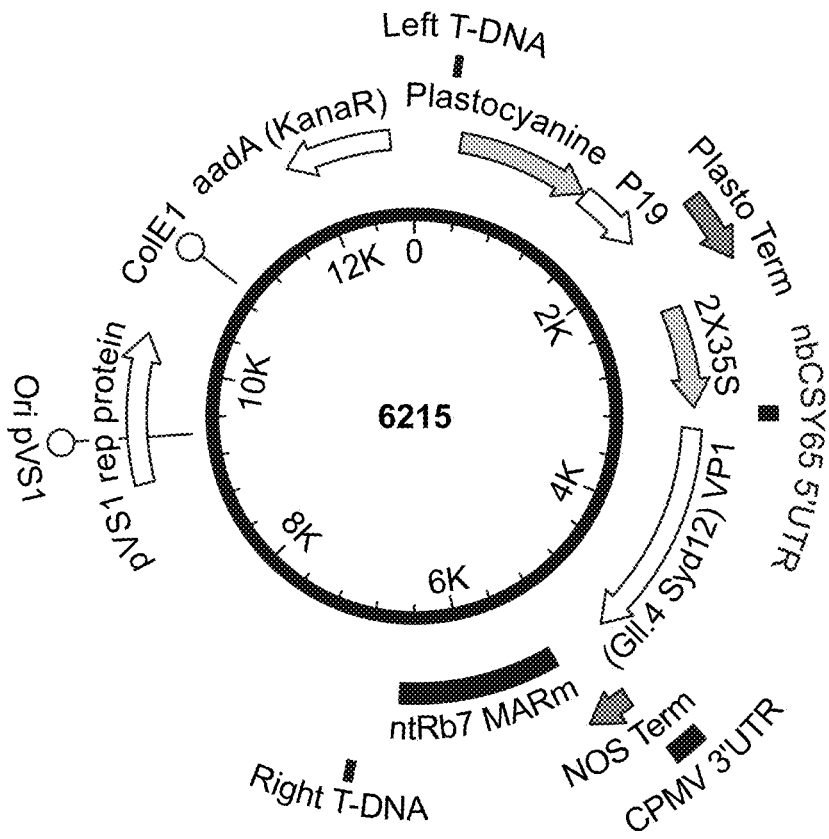
Figure 5G:
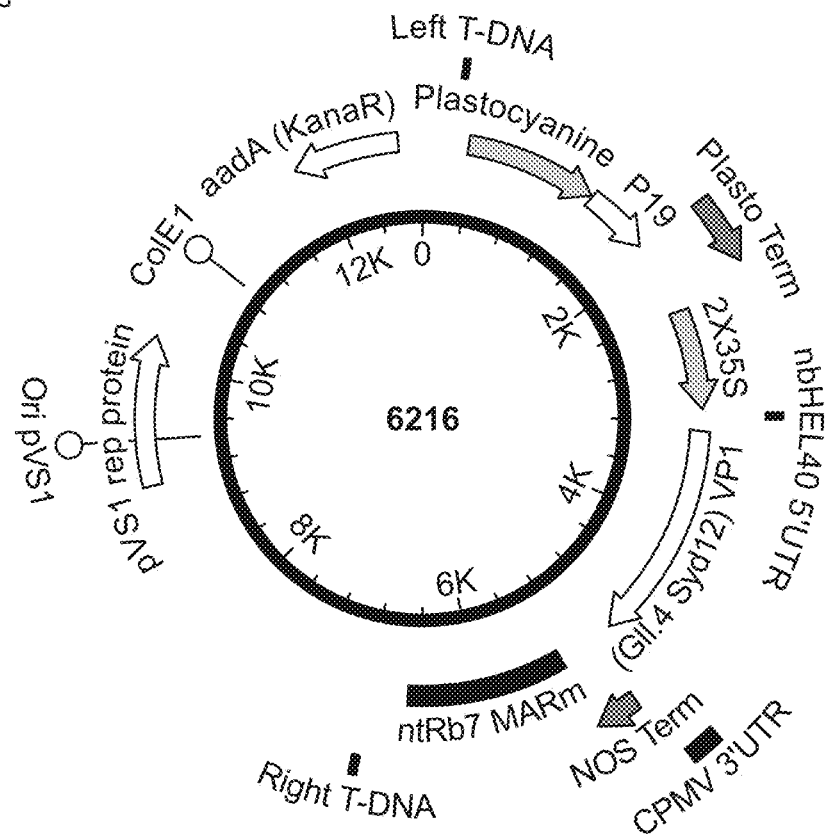
Figure 5H:
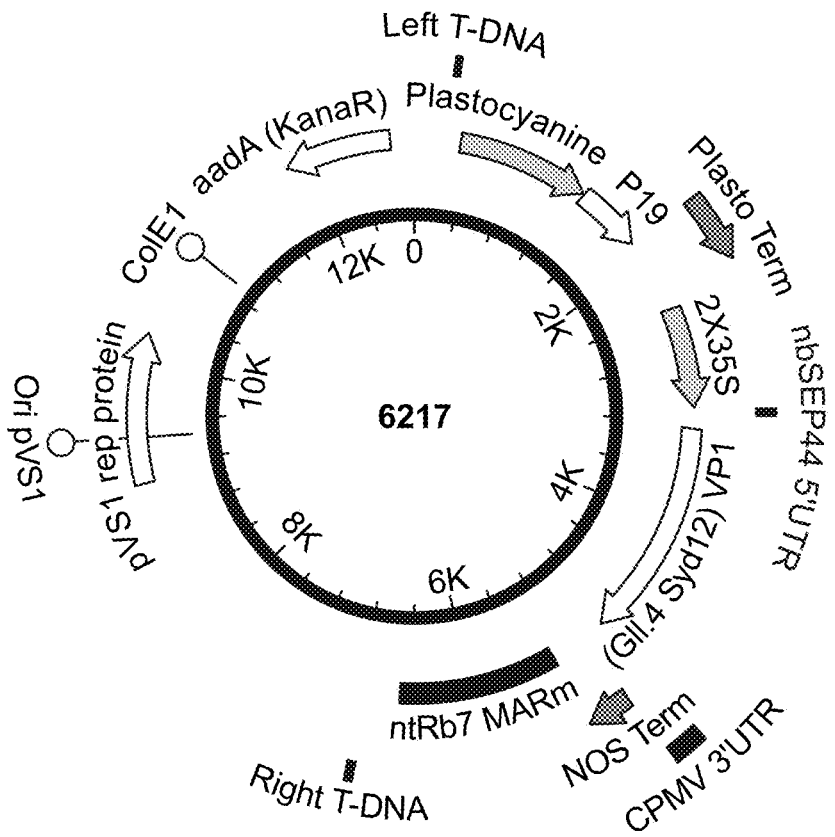
Figure 6A:
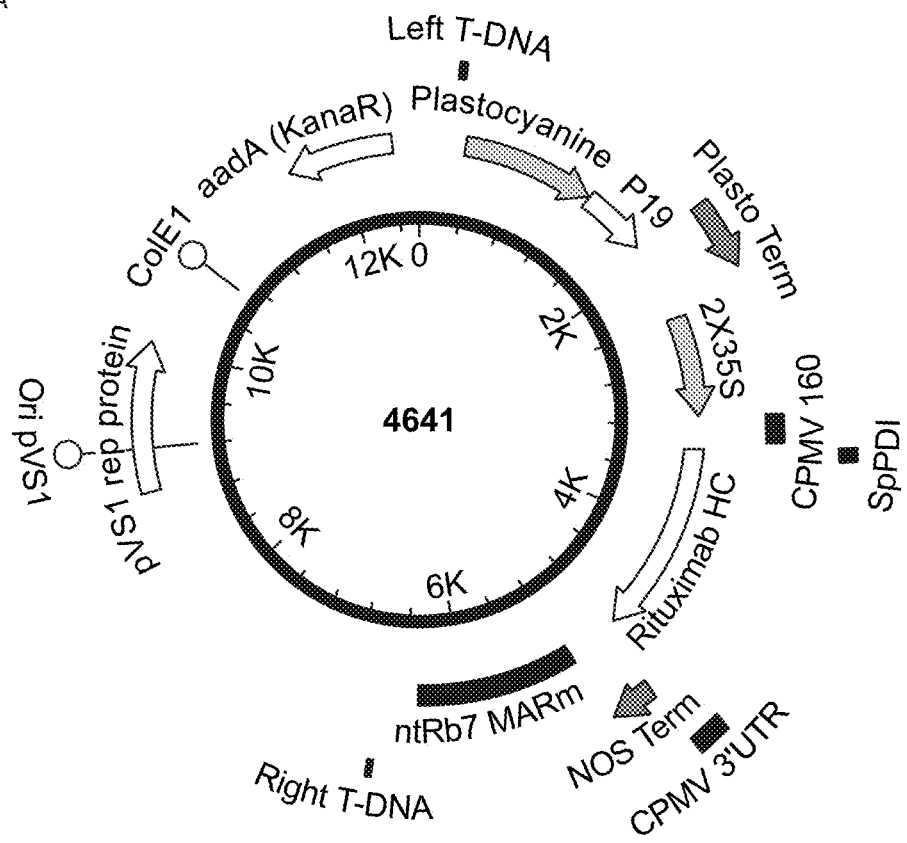
Figure 6B:
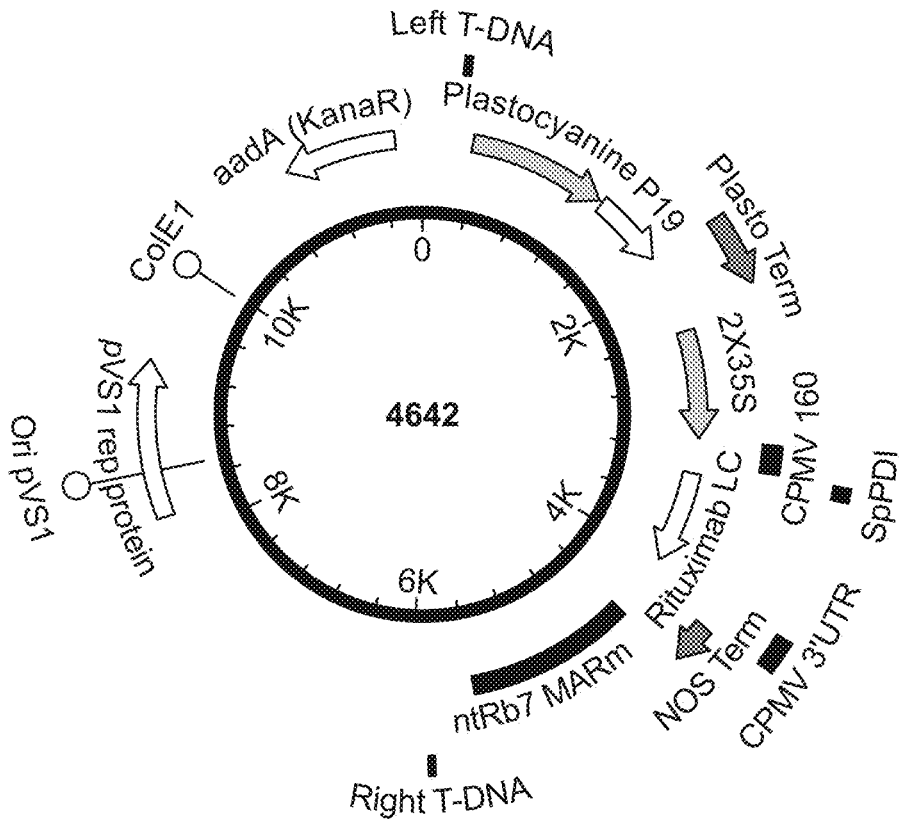
Figure 6C:
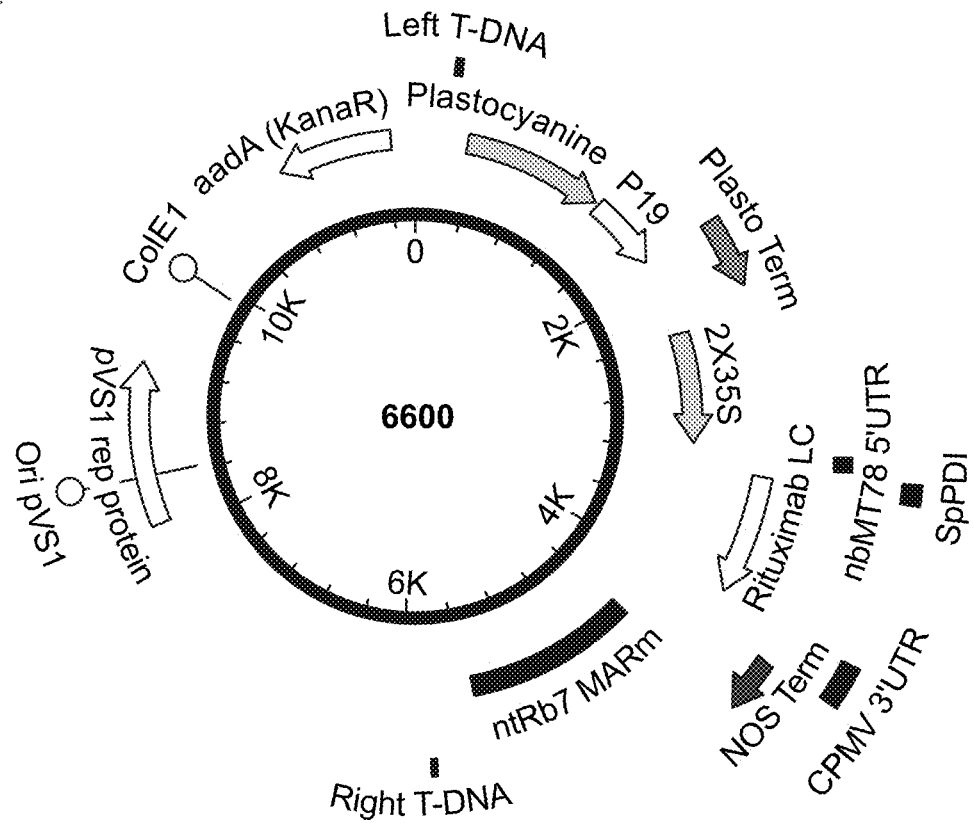
Figure 6D:
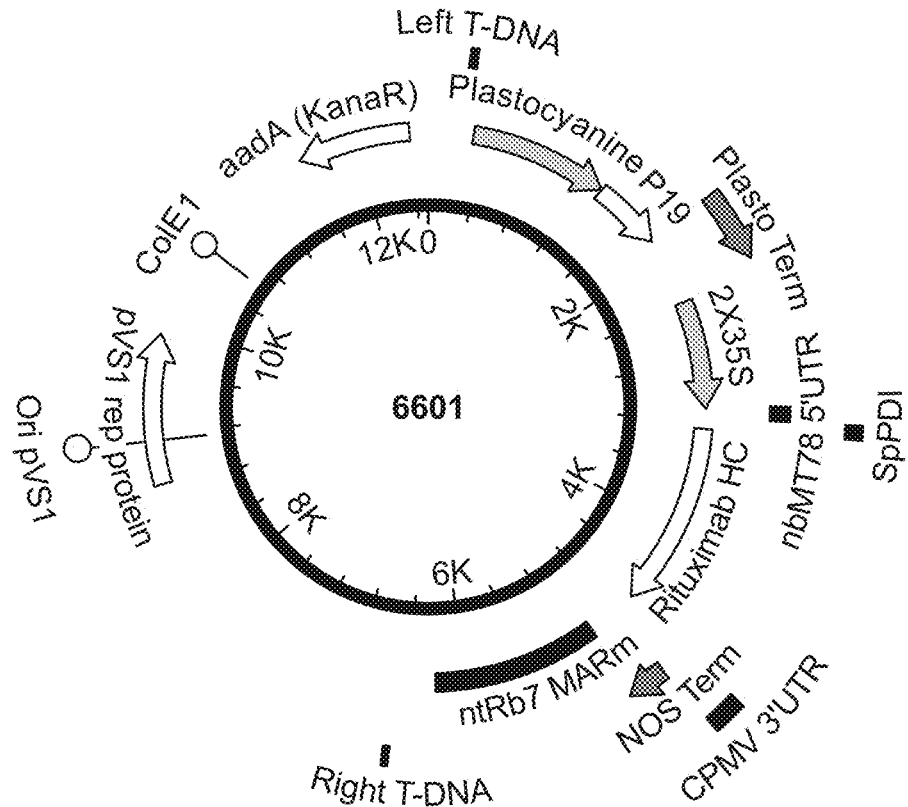
Figure 6E:
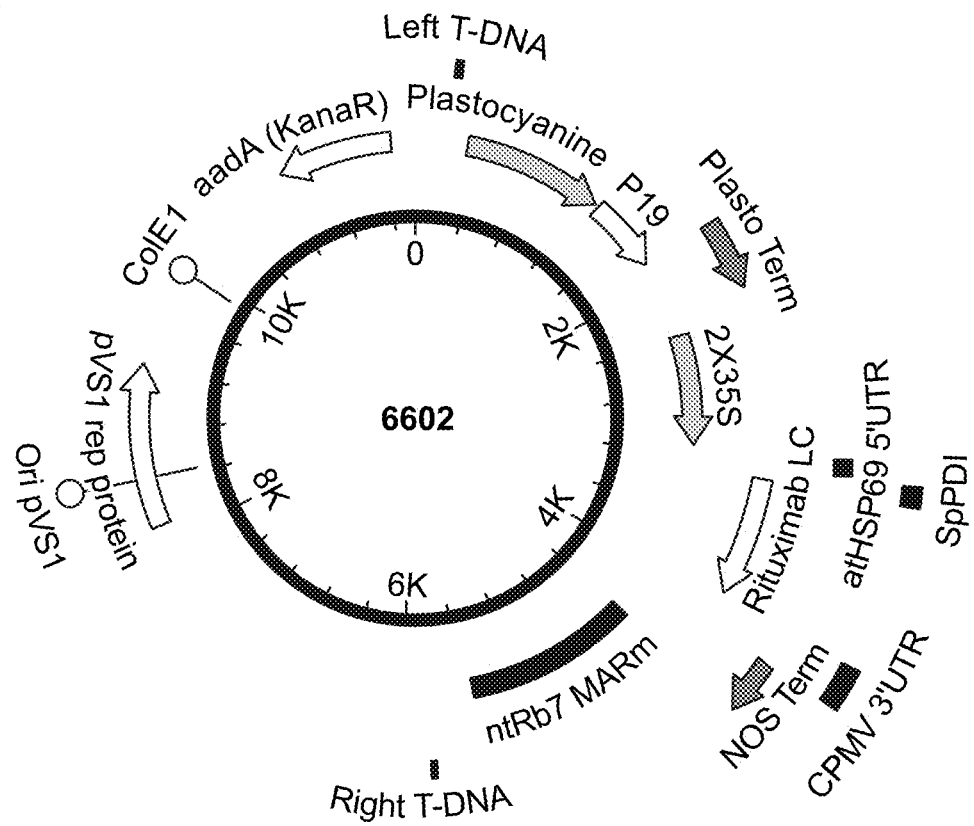
Figure 6F:
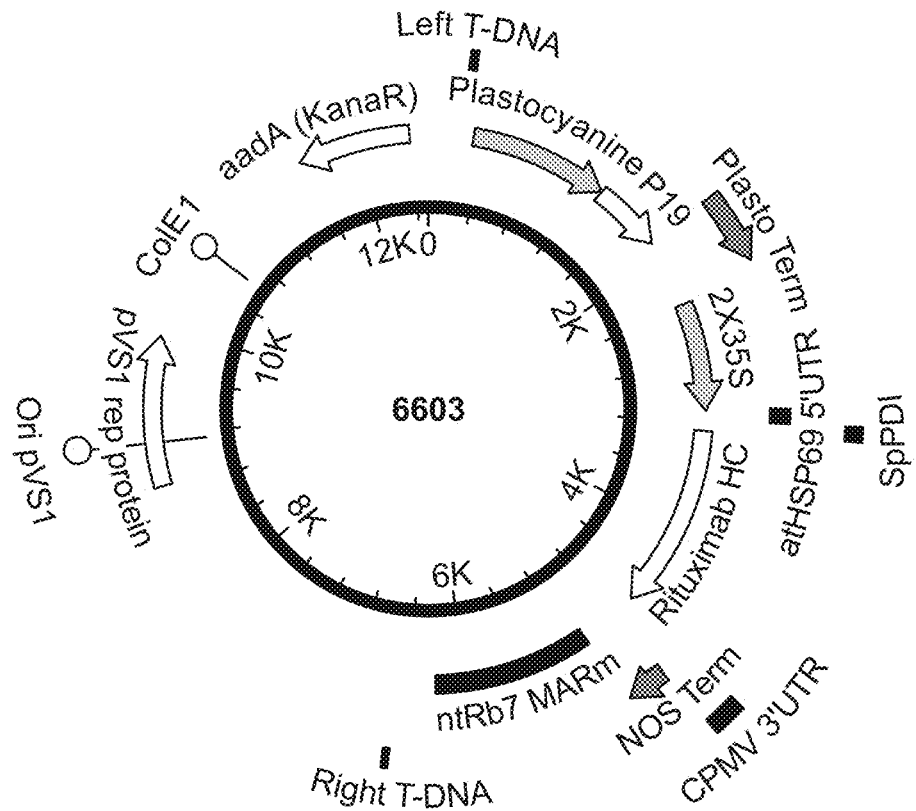
Figure 6G:
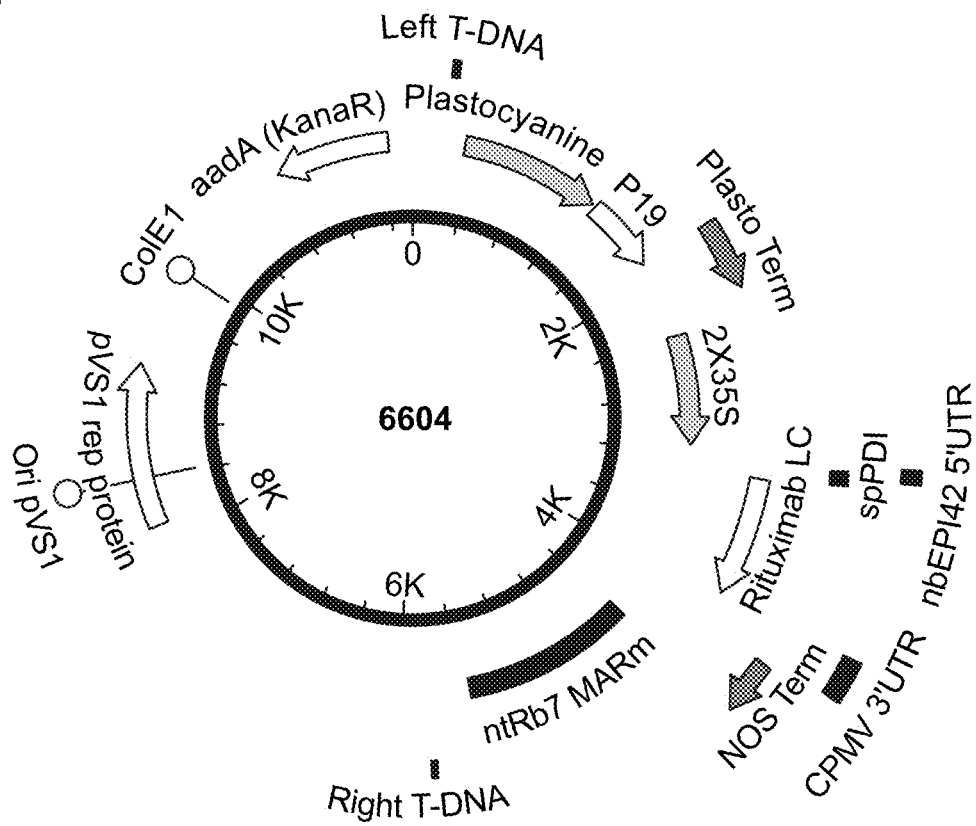
Figure 6H:
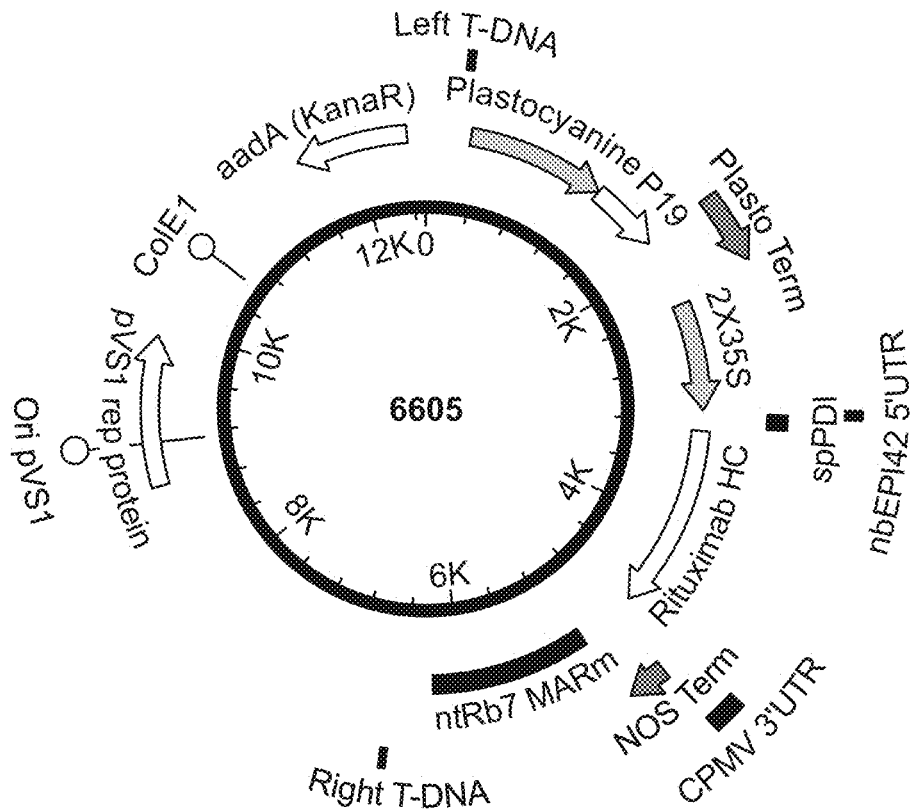
Figure 6I:
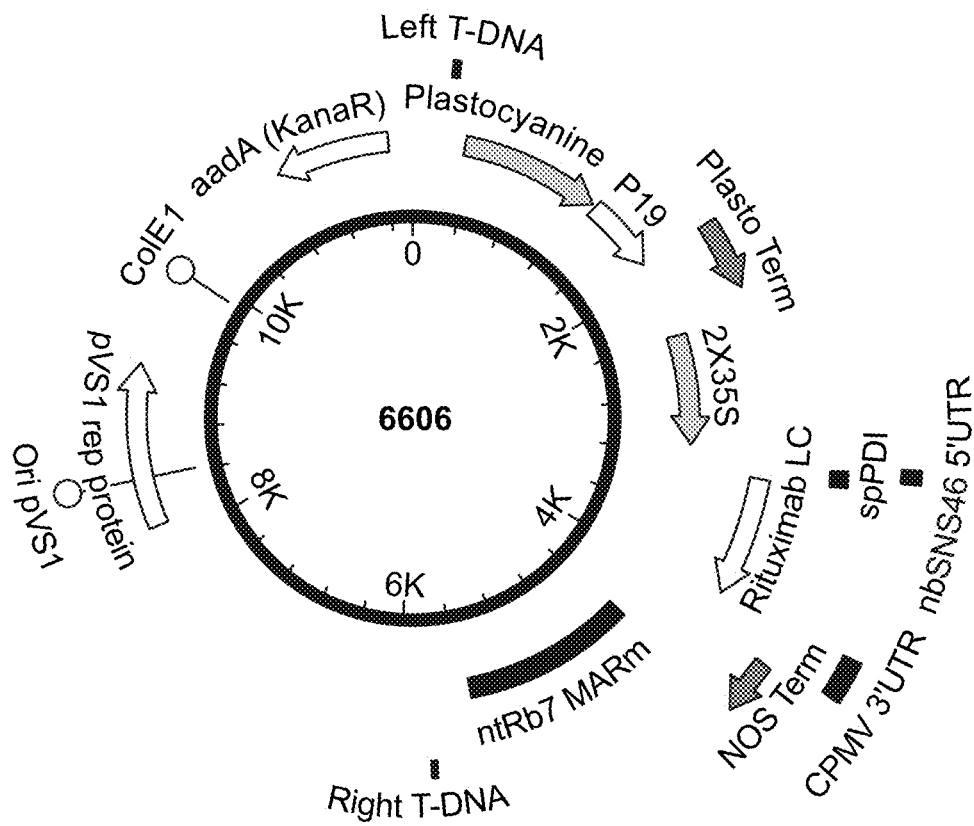
Figure 6J:
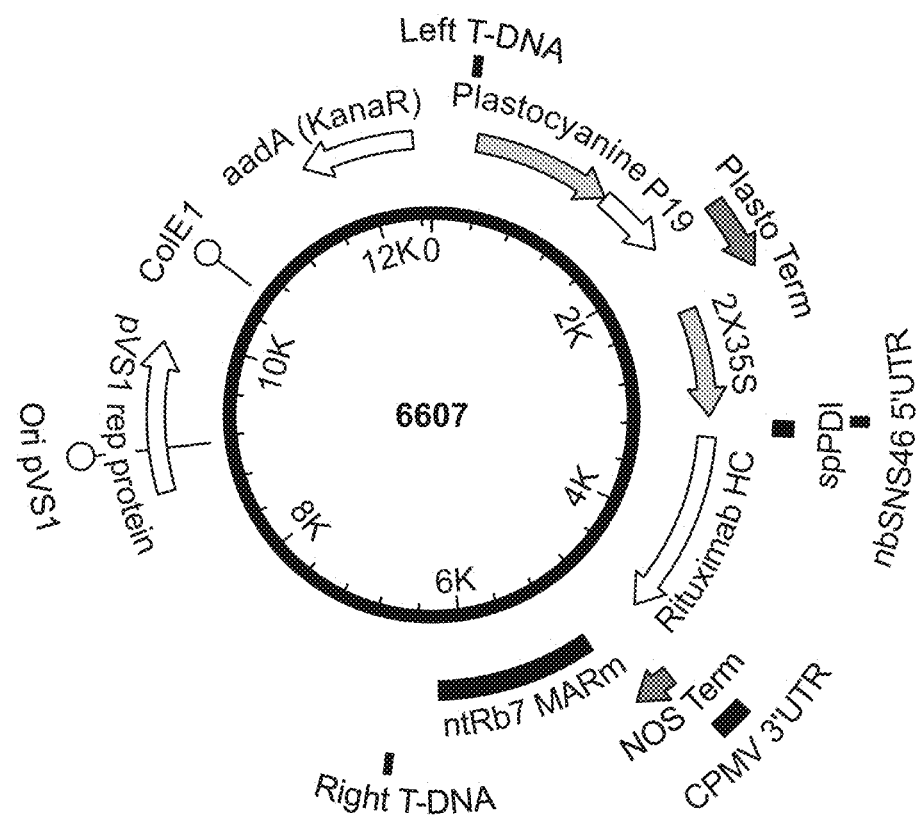
Figure 6K:
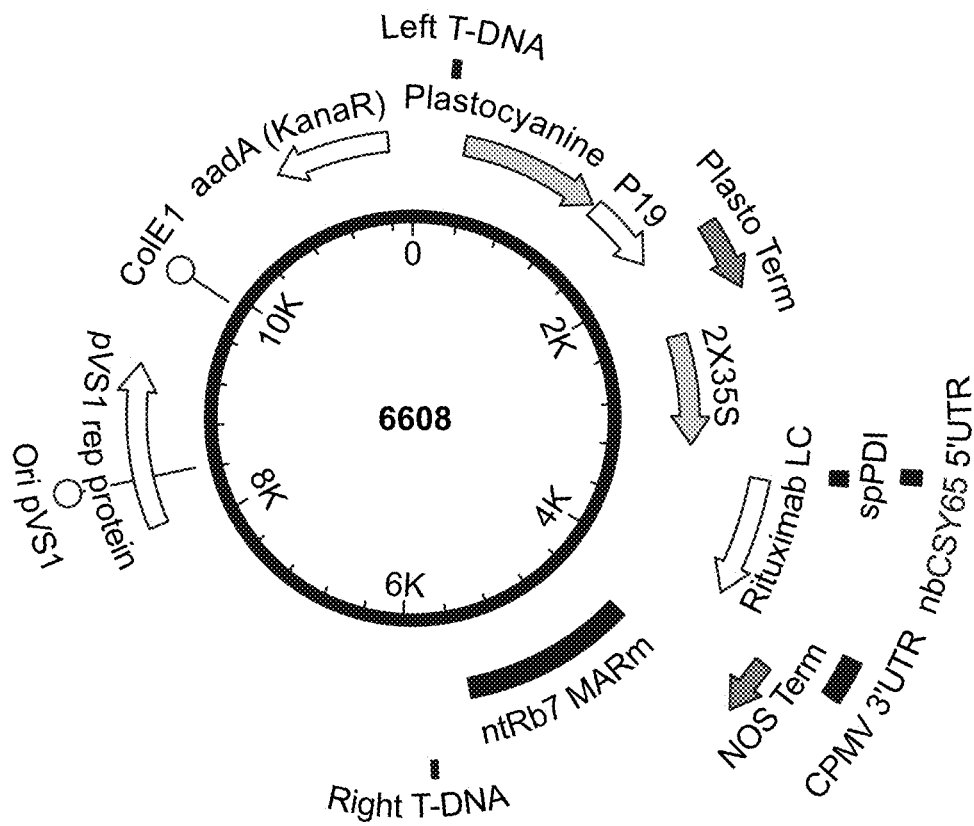
Figure 6L:
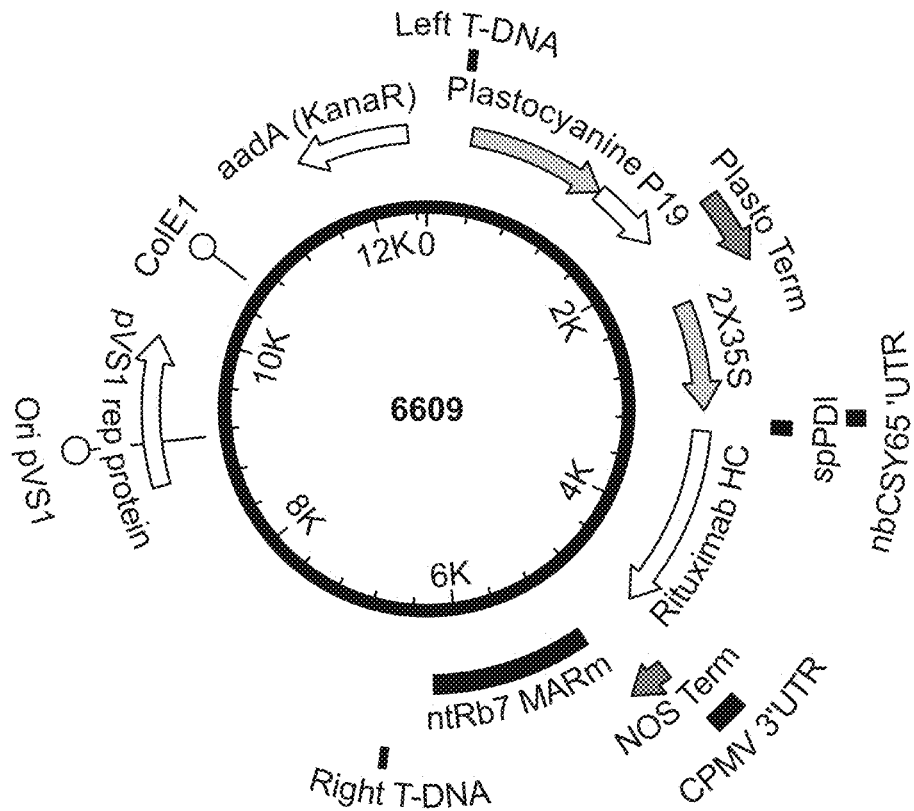
Figure 6M:
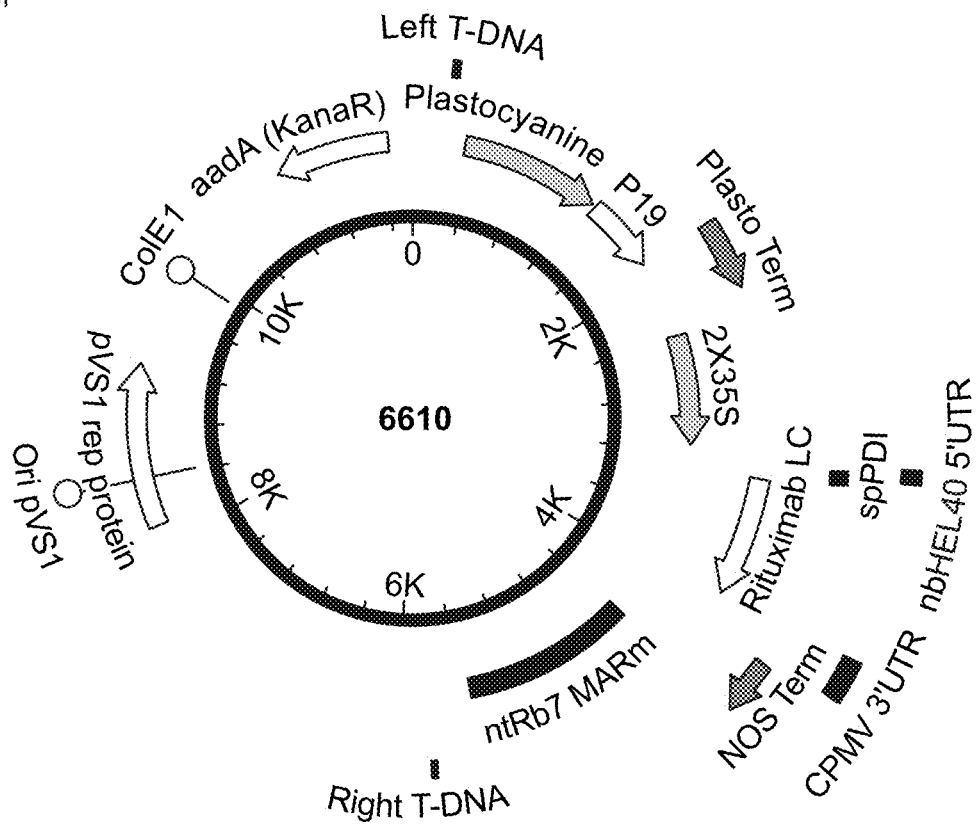
Figure 6N:
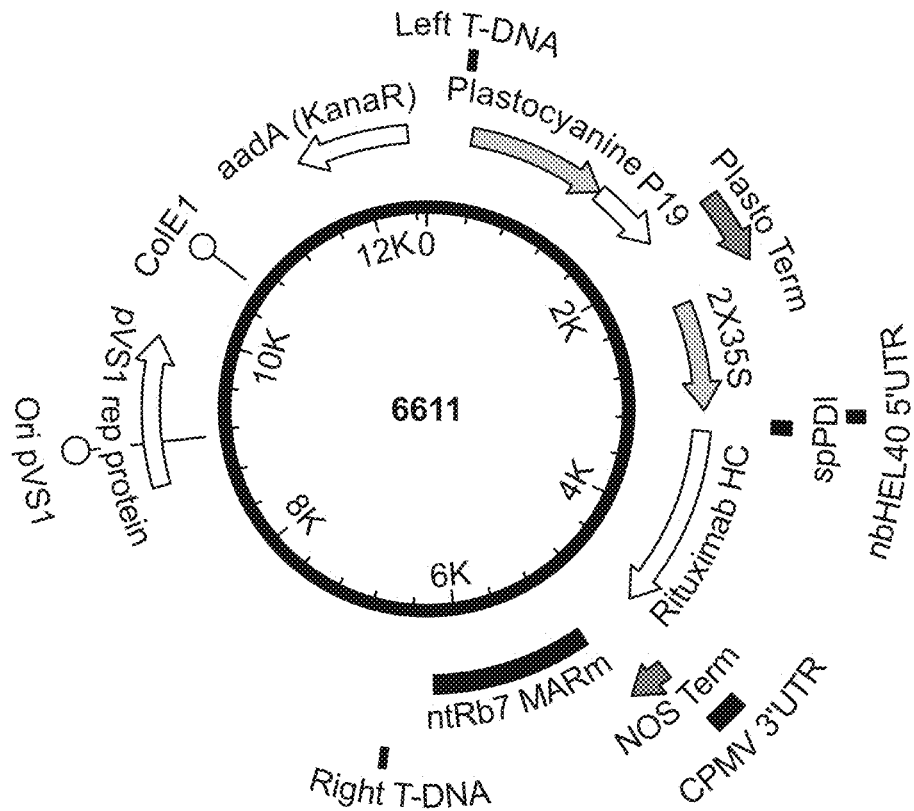
Figure 6O:
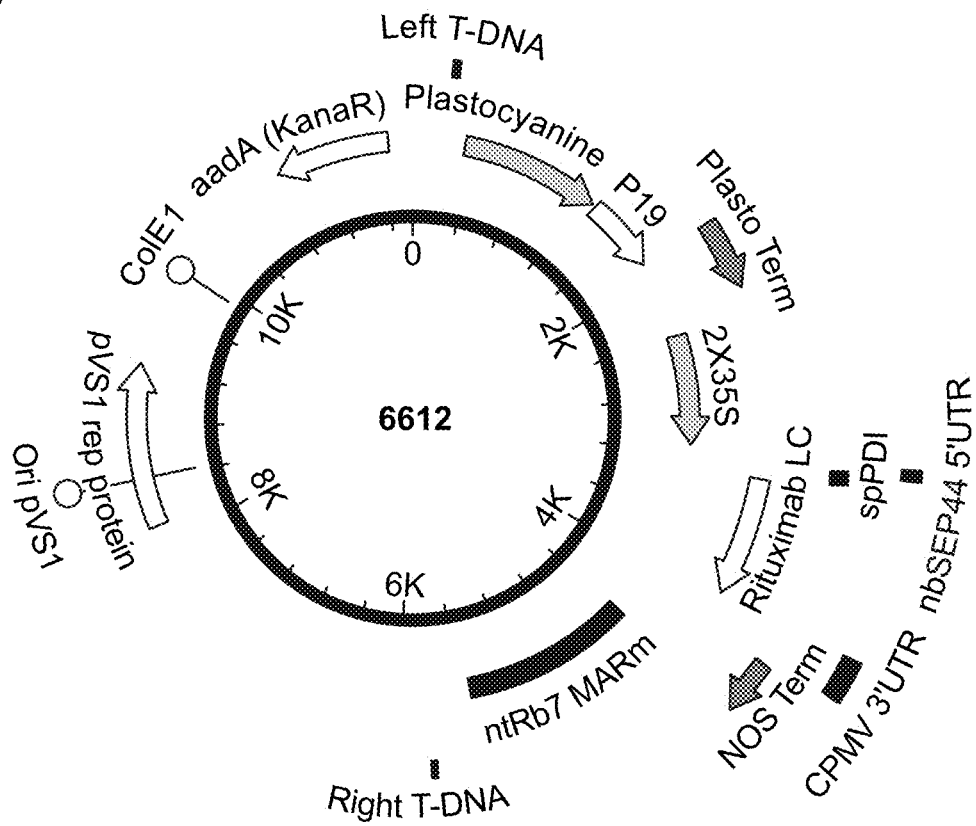
Figure 6P:
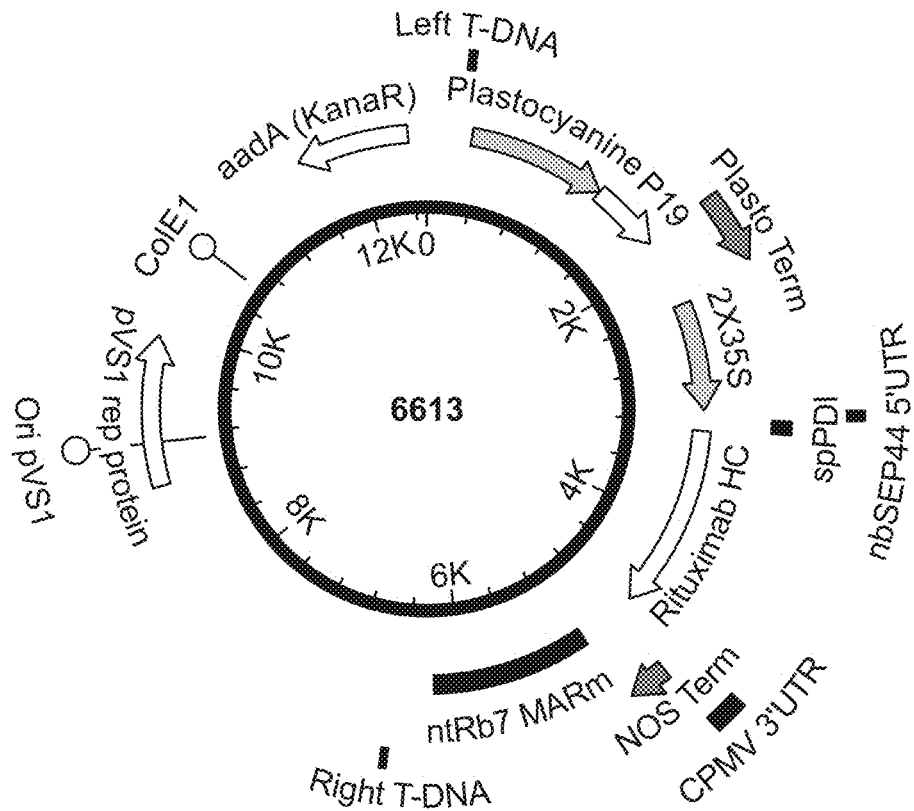
Figure 7A:
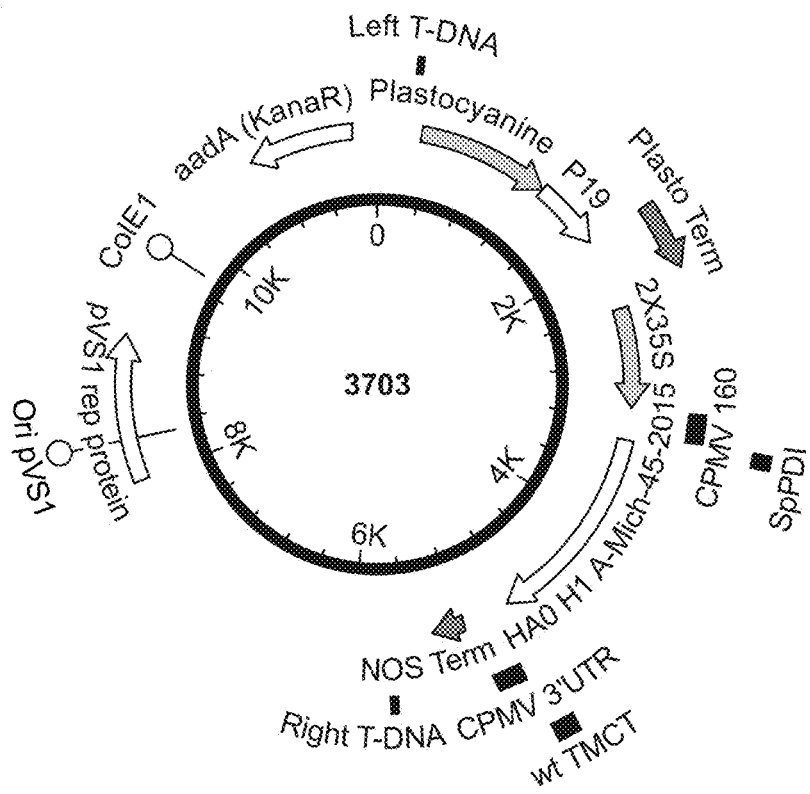
Figure 7B:
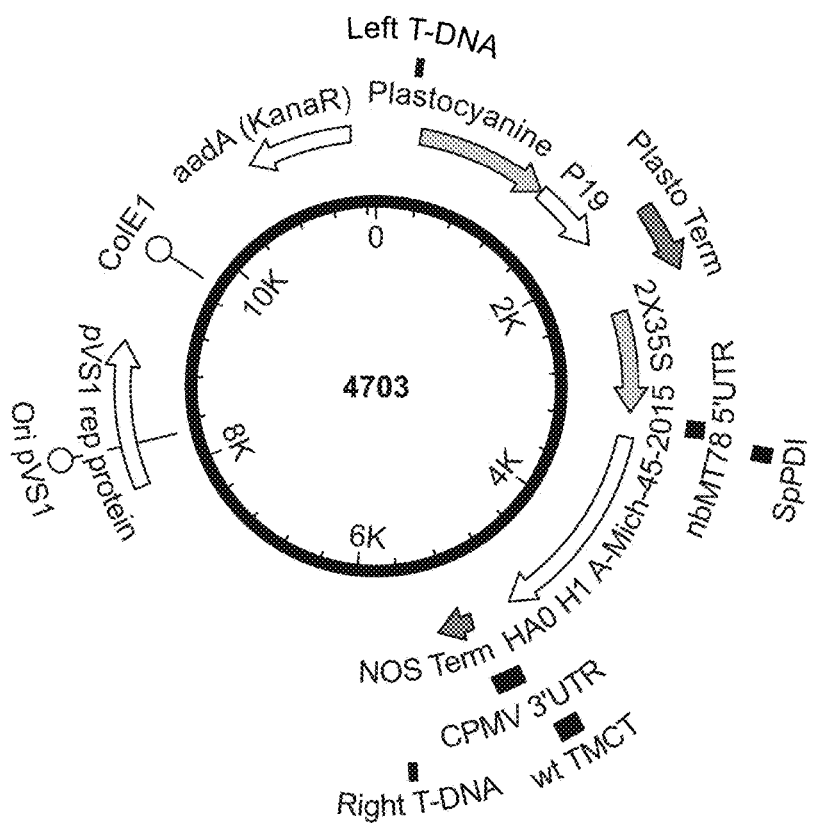
Figure 7C:
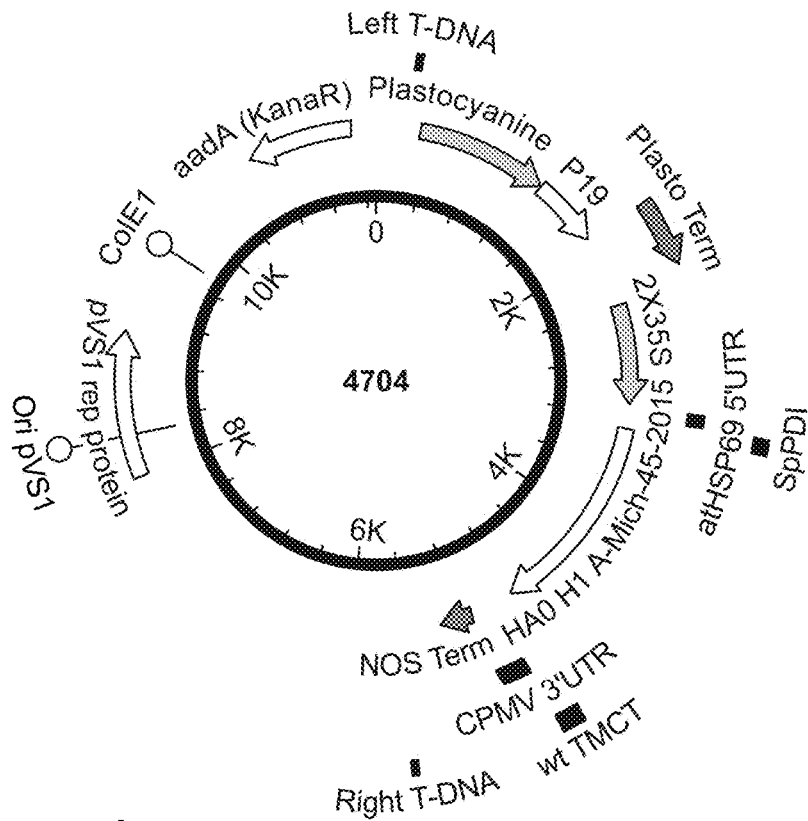
Figure 7D:
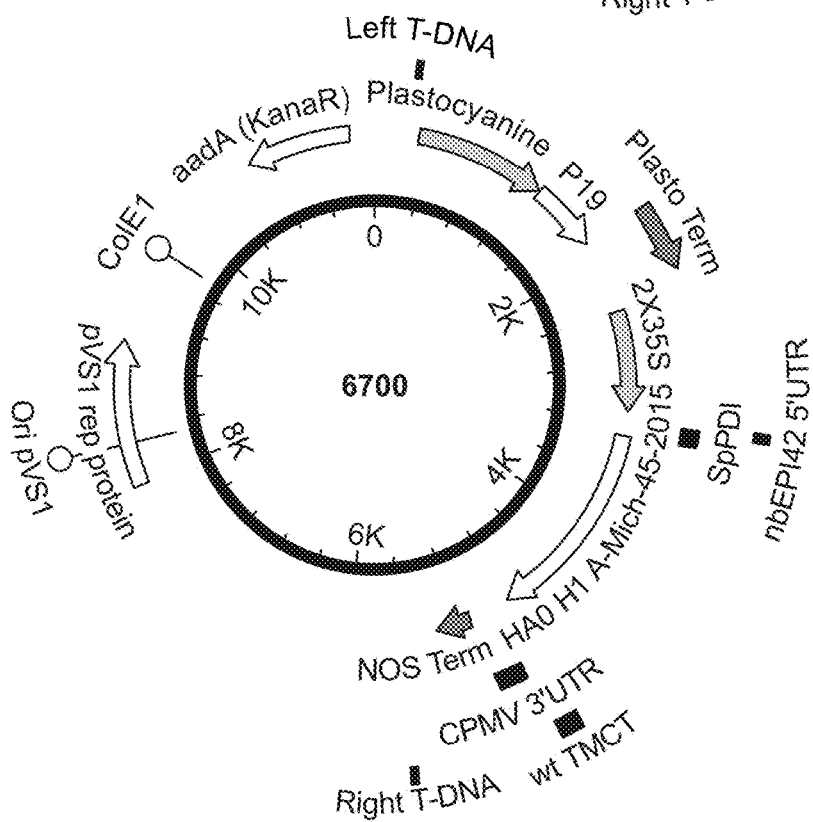
Figure 7E:
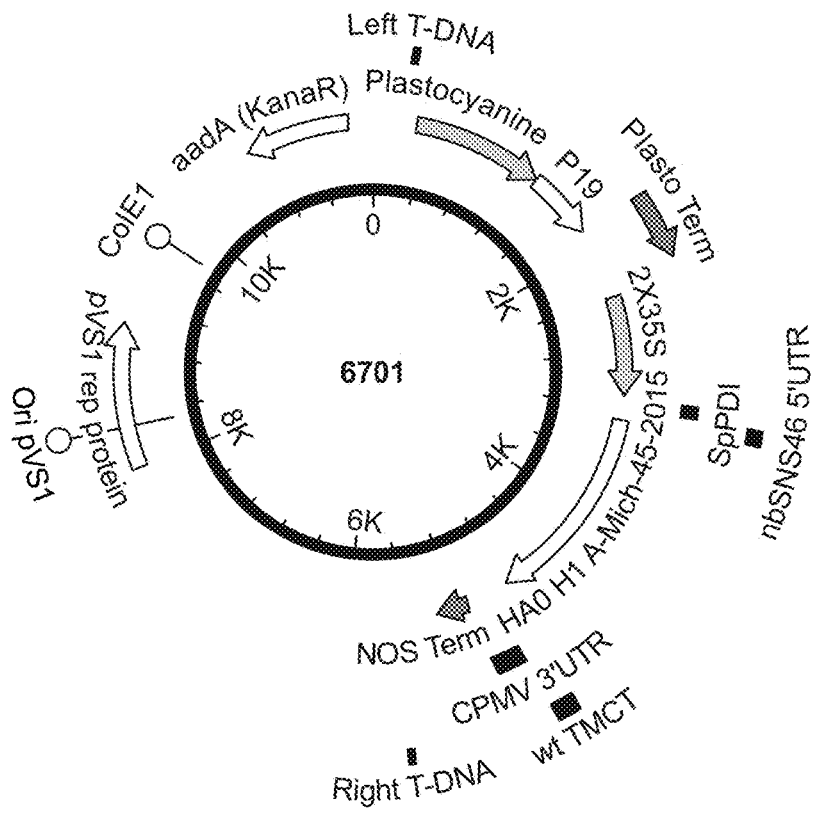
Figure 7F:
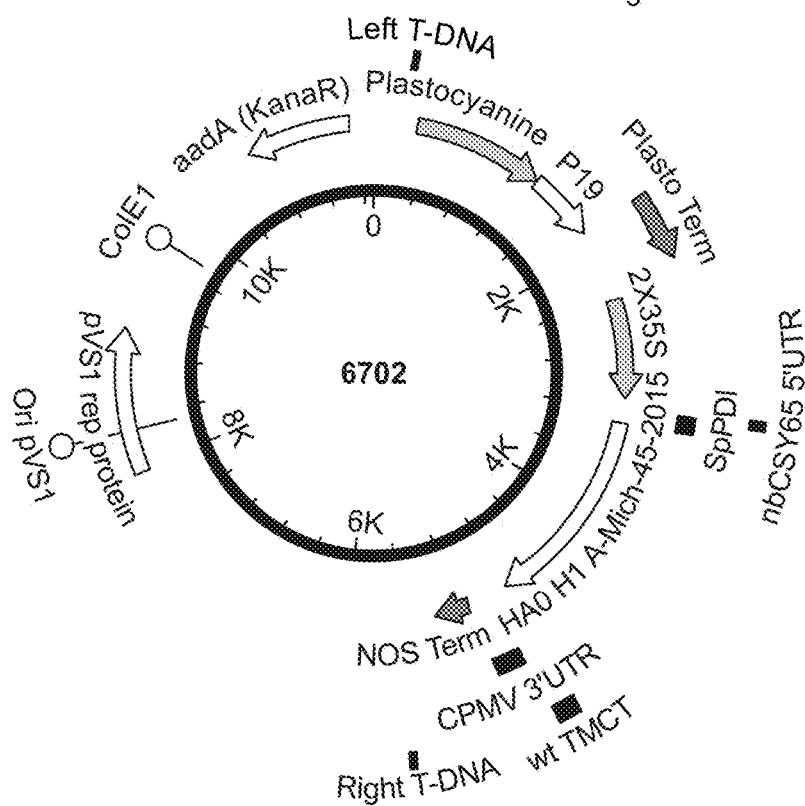
Figure 7G:
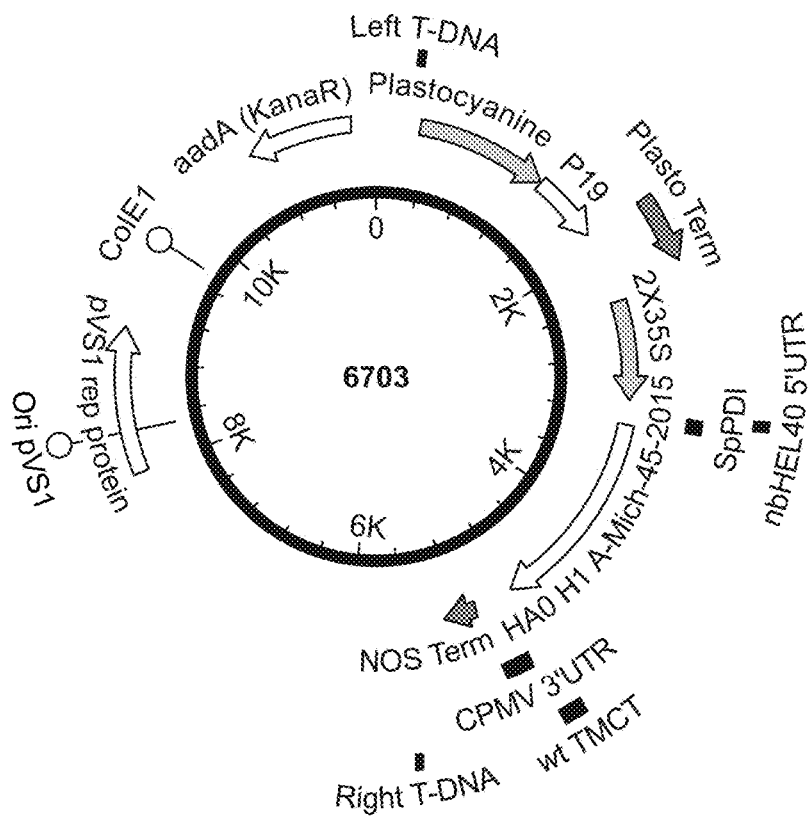
Figure 7H:
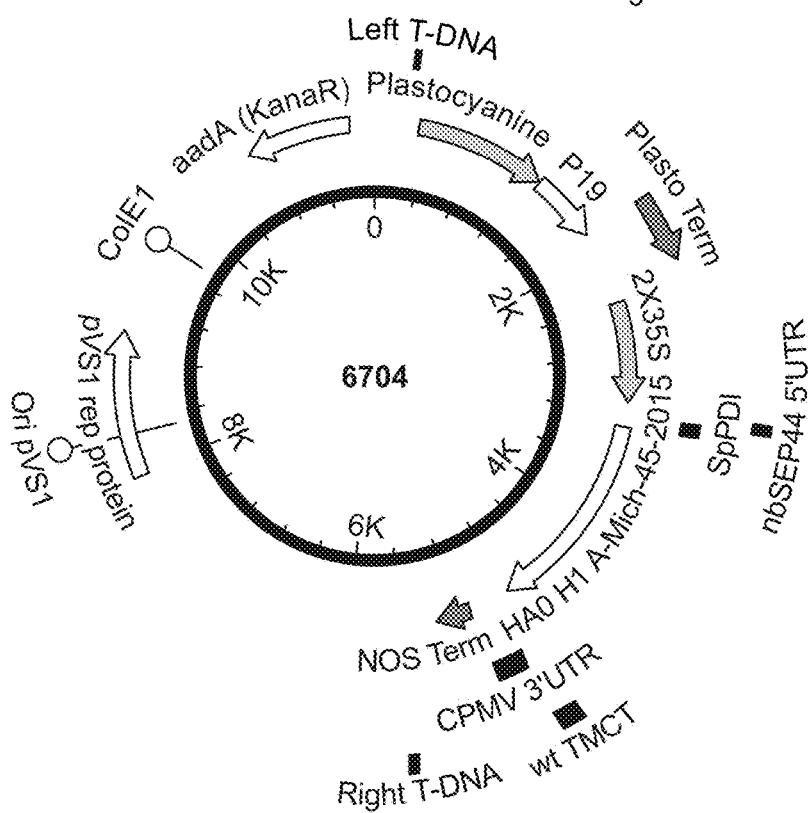
Figure 8A:
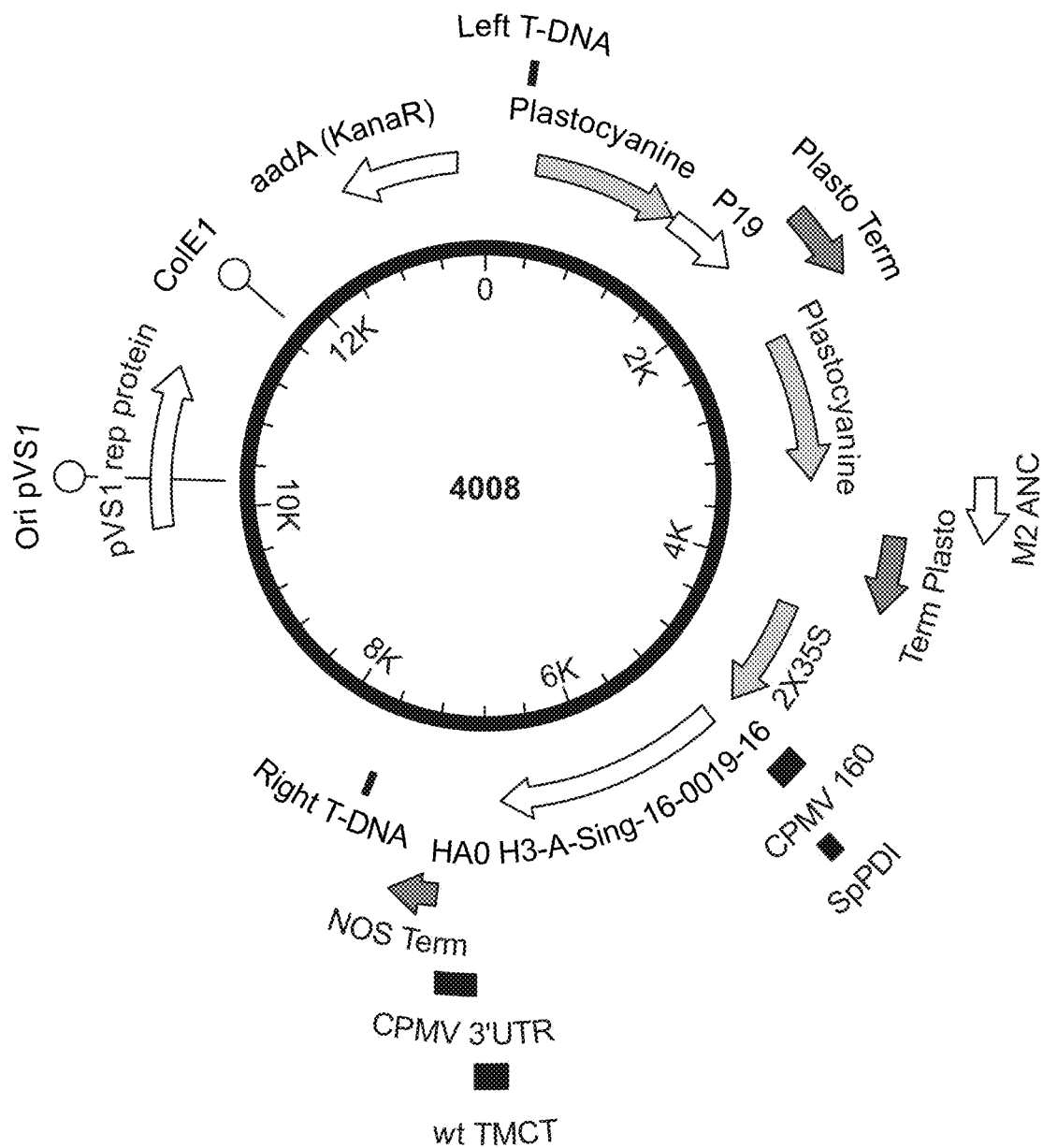
FIG. 8G shows construct 6708 (2X35S-5'UTR nbHEL40-SpPDI-H3 A-Sing-19-0019-16-CPMV 3'UTR/NOS)
FIG. 8H shows construct 6709 (2X35S-5'UTR nbSEP44-SpPDI-H3 A-Sing-19-0019-16-CPMV 3'UTR/NOS).
Figure 8B:
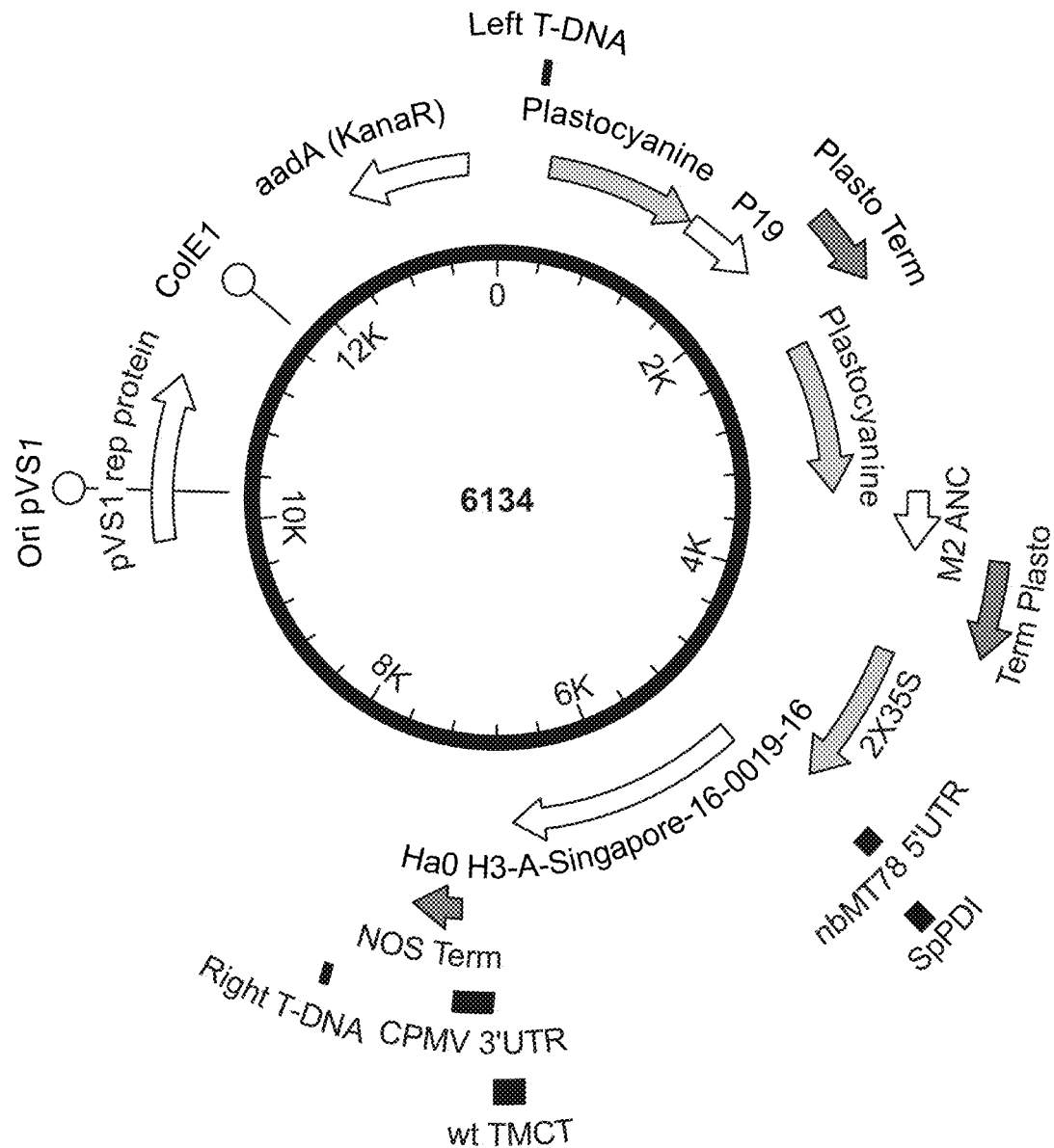
Figure 8C:
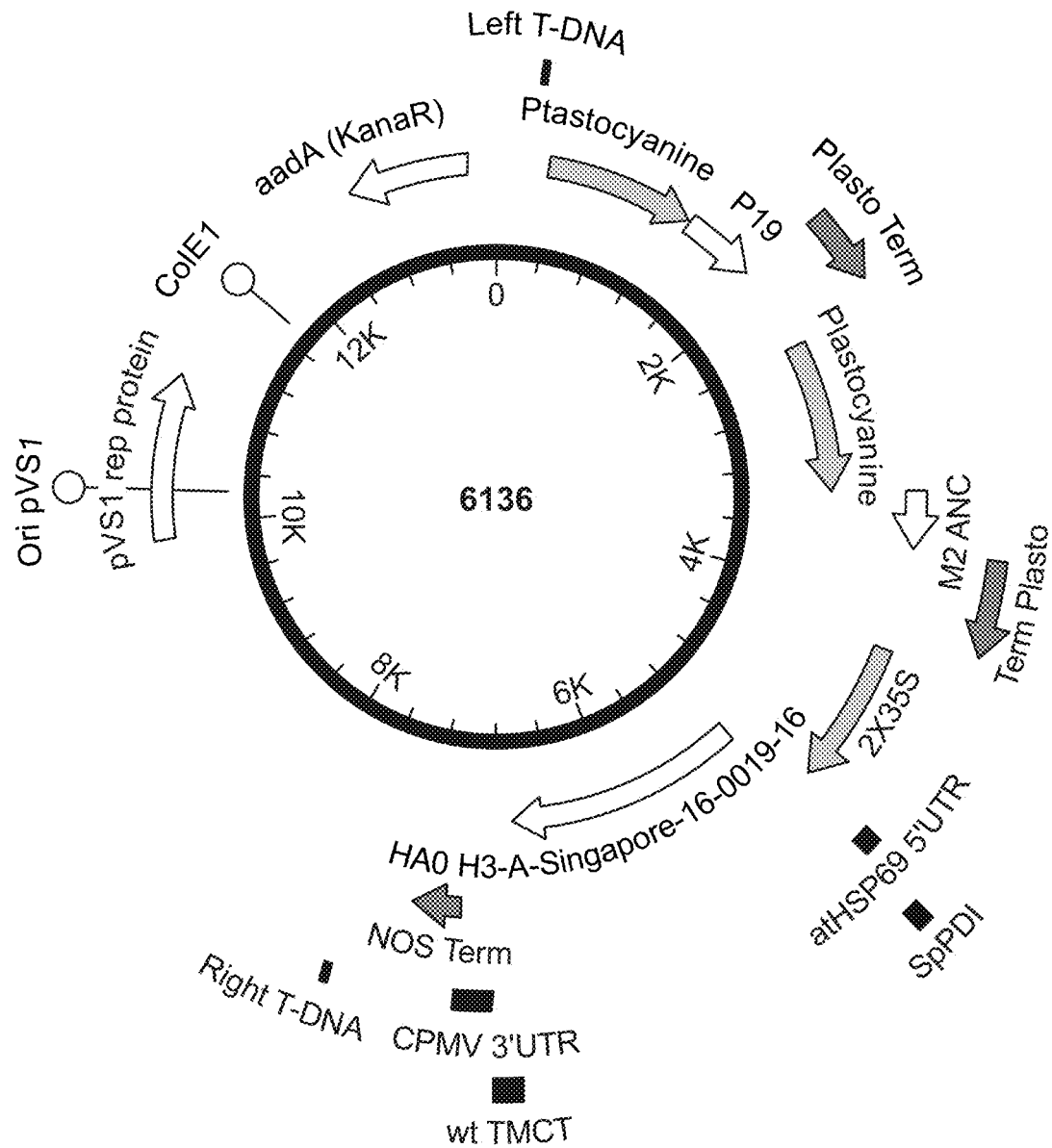
Figure 8D:
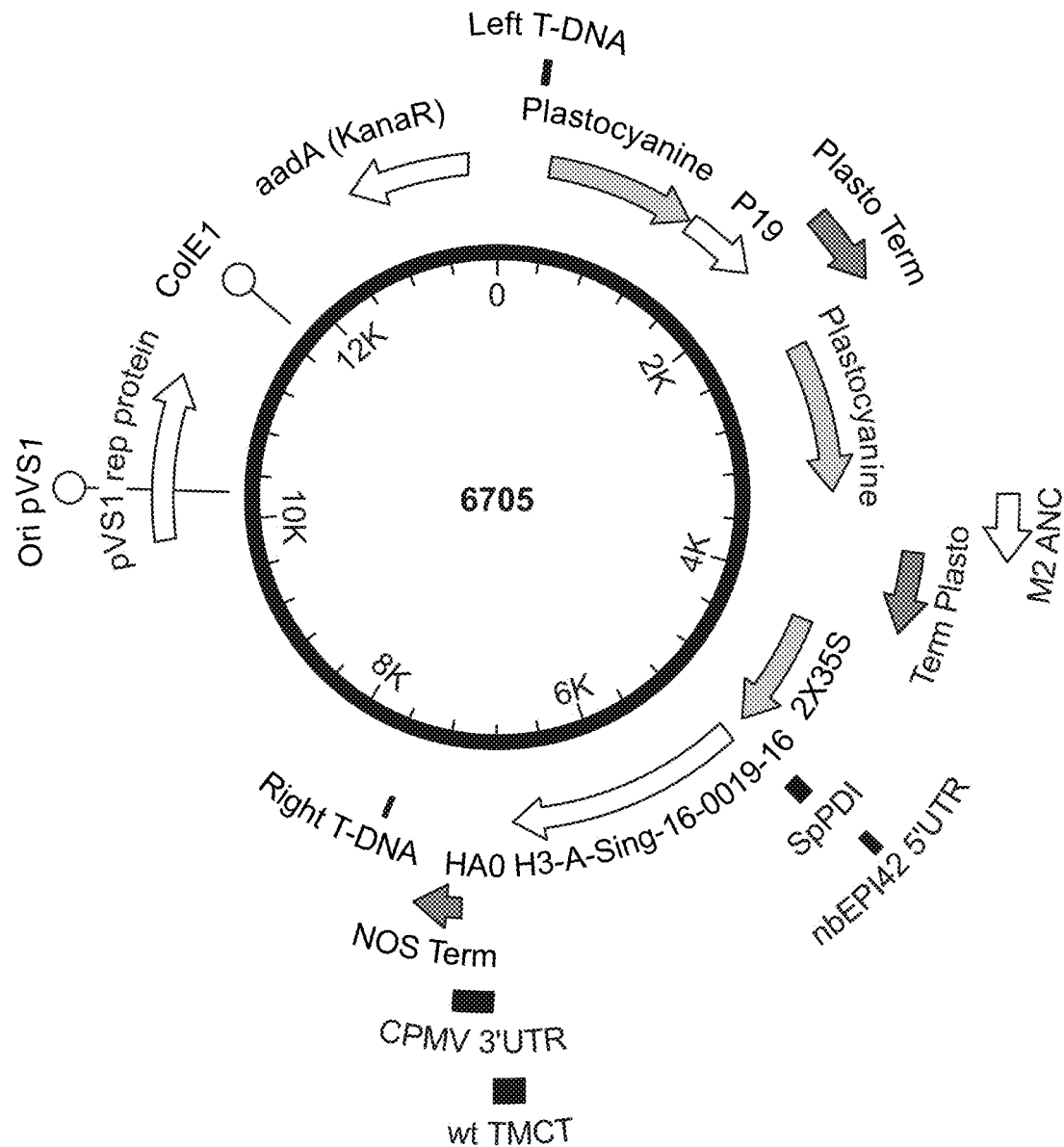
Figure 8E:
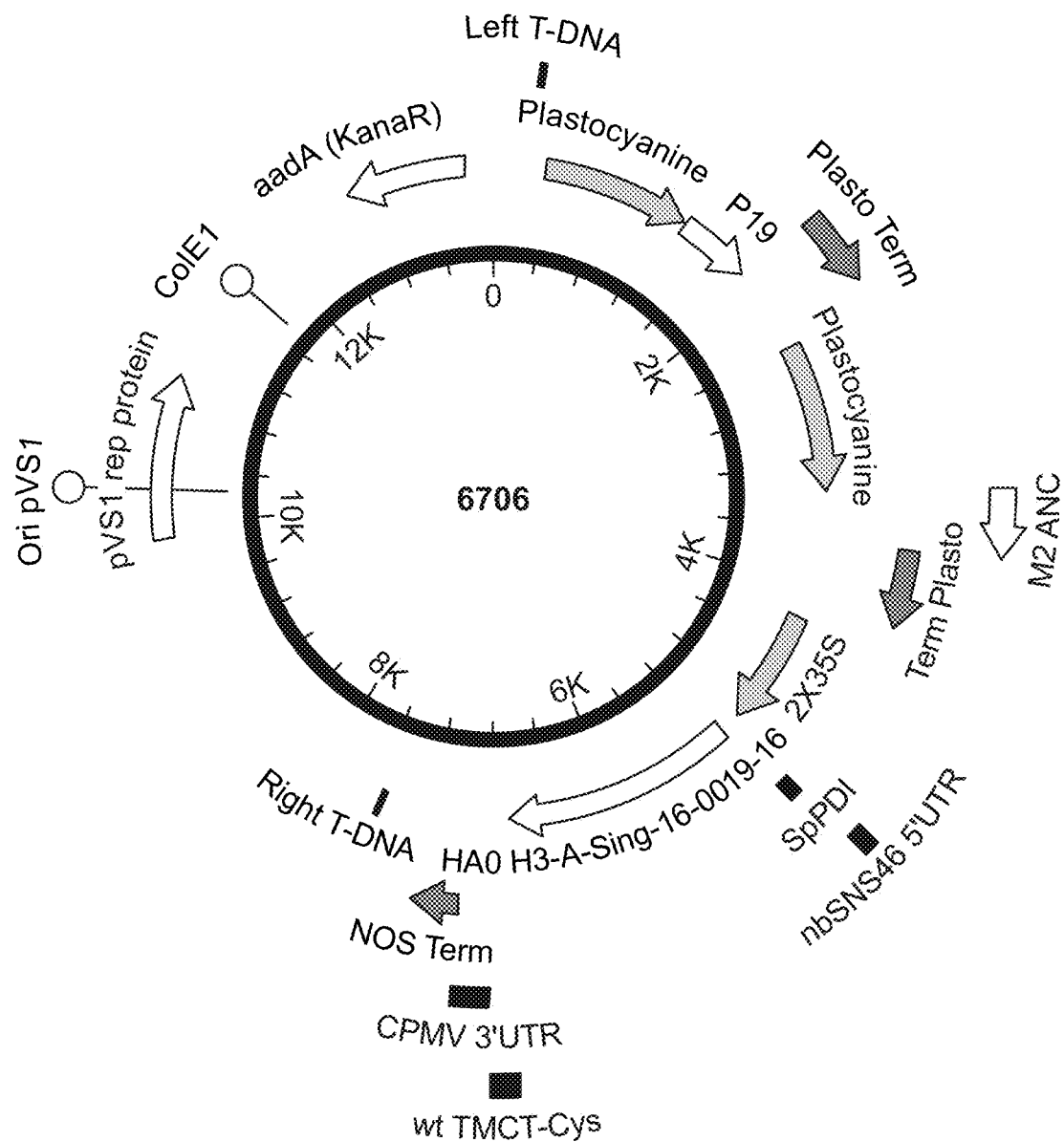
Figure 8F:
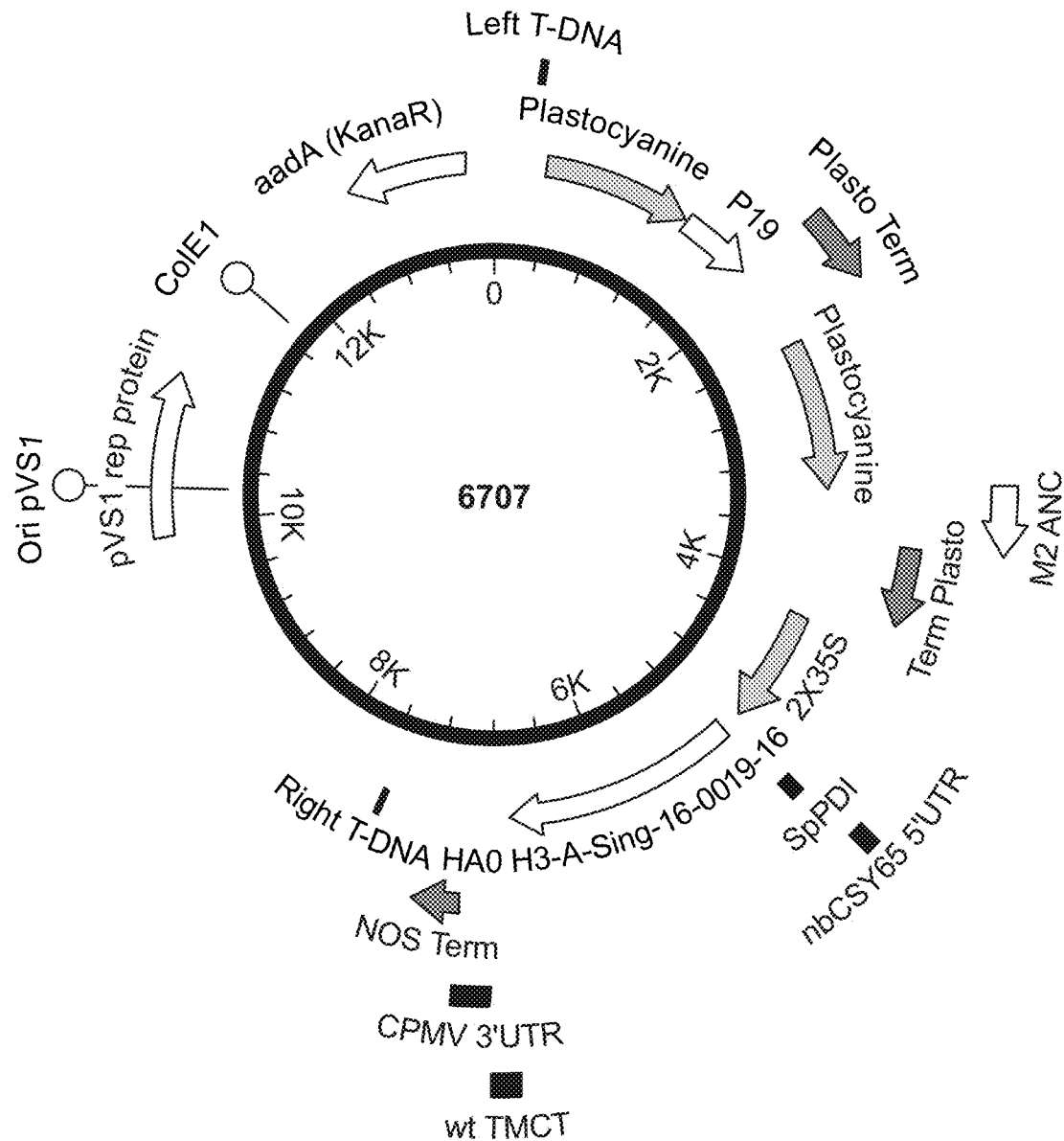
Figure 8G:
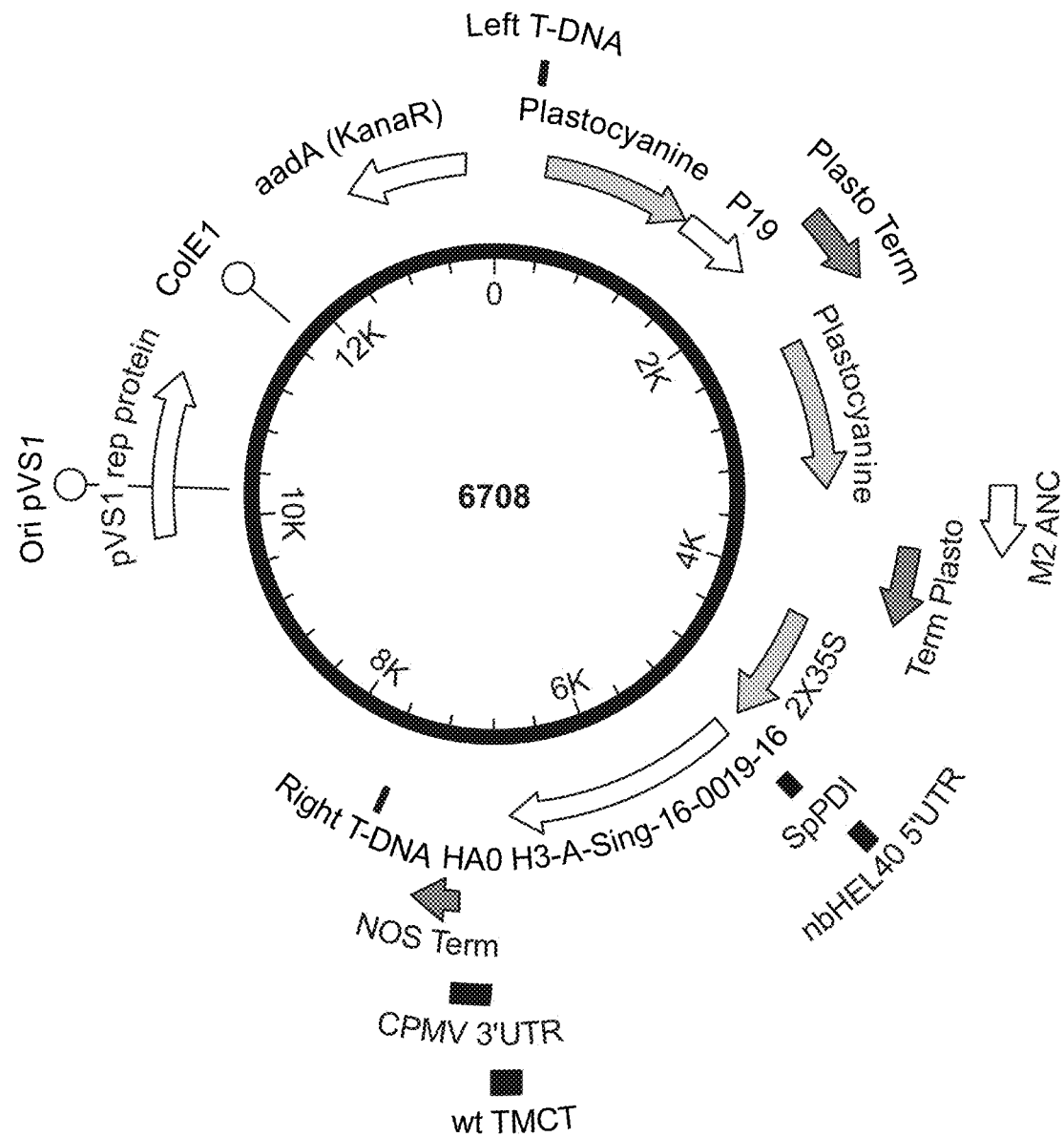
Figure 8H:
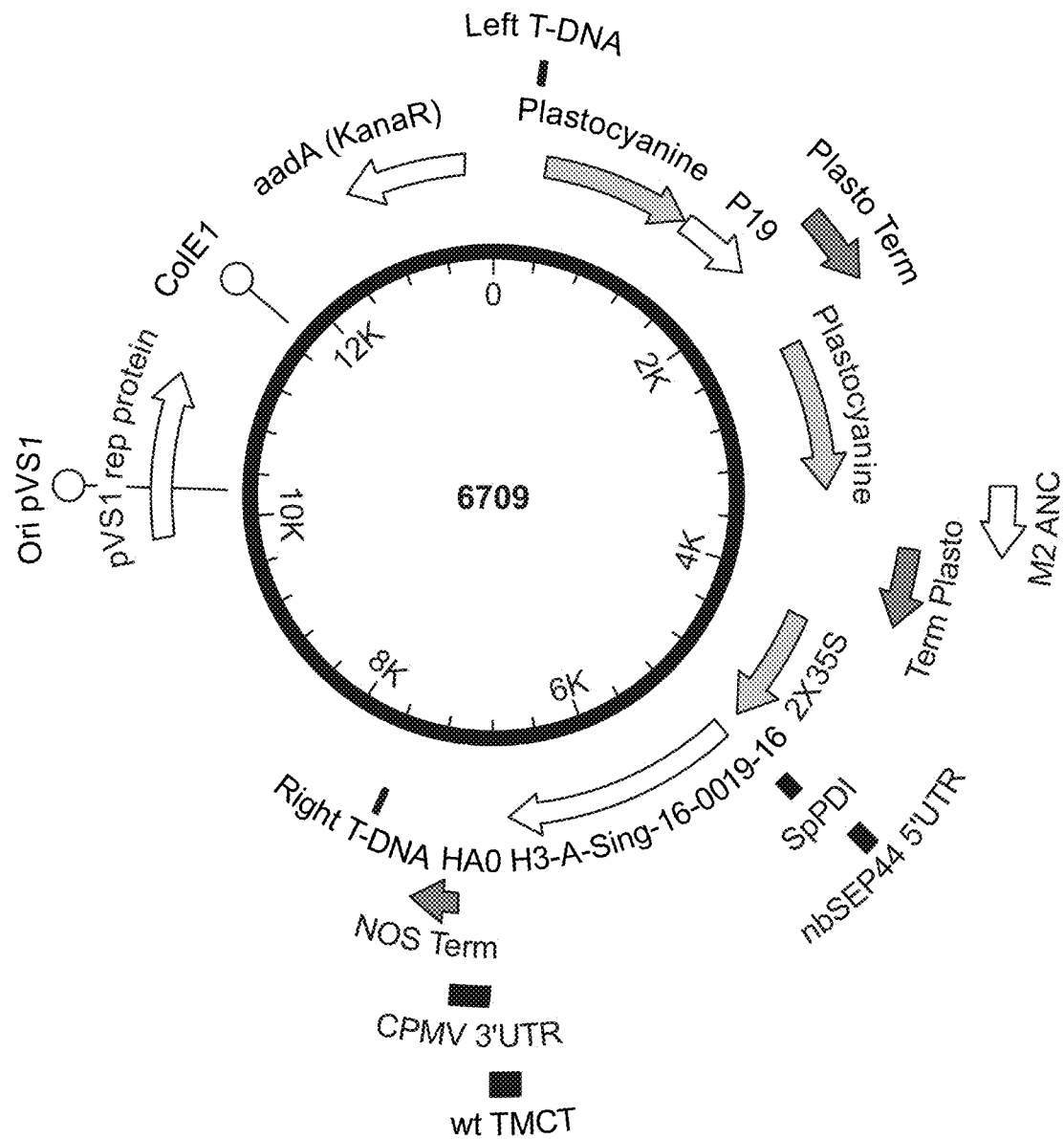

With reference to FIGS. 2A, 2B, 3A and 3B, each of the expression enhancers, nbEPI42 (SEQ ID NO:1); nbSNS46 (SEQ ID NO:2); nbCSY65 (SEQ ID NO:3); nbHEL40 (SEQ ID NO:4); and nSEP44 (SEQ ID NO:5) when operatively linked to a nucleic acid sequence encoding a protein of interest, were observed to result in a similar, or an increased, expression or activity of the protein, either Dasher (Dasher GFP; FPOB-27E-269; from ATUM.bio; FIG. 2A), norovirus (GII.4/Syd/12; FIG. 2B), influenza hemagglutinin (H3 A/Sing 19-0019-16, FIG. 3A; and H1 A/Mich/45/15, FIG. 3B), when compared to the activity of the prior art expression enhancer sequence CMPV 160 (SEQ ID NO:1; WO 2015/103704) operatively linked to the same nucleic acid sequence encoding the same proteins of interest, and expressed under similar conditions, or where indicated, when compared to the activity of the nbMT78 or atHSP69 (both described in U.S. Provisional Application No. 62/643,053, filed Mar. 14, 2018, which is incorporated herein by reference) operatively linked to the same nucleic acid sequence encoding the same proteins of interest, and expressed under similar conditions.

The activity of the prior art expression enhancer CPMV 160 (SEQ ID NO:6), operatively linked to a nucleic acid sequence encoding a protein of interest, is shown relative to the prior art expression enhancer, CPMV-HT, in FIGS. 1A and 1B. The CPMV HT enhancer element refers to a nucleotide sequence encoding the 5'UTR regulating the Cowpea Mosaic Virus (CPMV) RNA2 polypeptide or a modified CPMV sequence as described in WO2009/087391; Sainsbury F., and Lomonossoff G. P., (2008, Plant Physiol. 148: pp. 1212-1218). The CPMV 160 expression enhancer refers to a nucleotide sequence comprising a truncated 5'UTR from CPMV RNA2 as describe in WO 2015/103704. The CPMV 160 and CPMV 160+ expression enhancers both comprise the first 160 nucleic acids of the 5'UTR of CMPV RNA 2, however, the CPMV 160+ expression enhancer further comprises a multiple cloning site and a plant kozak sequence at the 3' end of the expression enhancer.

Therefore, the expression enhancers described herein may be used within a plant expression system comprising a regulatory region that is operatively linked with the expression enhancer sequence and a nucleotide sequence of interest.

For example, the present invention provides a method of producing a protein of interest, or increasing production of a protein of interest, for example but not limited to an influenza HA protein, modified influenza HA protein, norovirus protein, or modified norovirus protein, in plants. The method involves introducing a nucleic acid comprising an expression enhancer as described herein operatively linked to nucleotide sequence encoding the protein of interest, for example the influenza HA protein, a modified influenza HA protein, a norovirus protein, or a modified norovirus protein, into the plant, portion of the plant, or plant cell, and expressing the protein in the plant, portion of the plant, or plant cell in a transient or stable manner. Where, the increase in expression may be determined by comparing the level of expression of the nucleotide sequence operatively linked to an expression enhancer, with the level of expression of the same nucleotide sequence that is not operatively linked to the expression enhancer, or for example, when operatively linked to the prior art expression enhancer CPMV 160 (SEQ ID NO:6). Alternatively, the method may comprise providing a plant, portion of the plant, or plant cell that comprises an expression enhancer as described herein operatively linked to nucleotide sequence encoding the protein of interest, for example the influenza HA protein, modified influenza HA protein, norovirus protein, modified norovirus protein, or multimeric protein, and expressing the nucleic acid encoding the protein in the plant, portion of the plant or plant cell in a transient or stable manner.

Furthermore, the present invention provides plant matter, a plant extract, or a protein extract comprising a protein of interest, for example an influenza HA protein, modified influenza HA protein, norovirus protein, or modified norovirus protein. The plant matter, plant extract, or protein extract may be used to induce immunity, for example, to influenza or norovirus infection in a subject. Alternatively, the protein of interest, for example influenza HA protein, modified influenza HA protein, norovirus protein, or modified norovirus protein may be purified or partially purified, and the purified or partially purified preparation may be used to induce immunity, for example, to influenza or norovirus infection in a subject, or the protein of interest, for example the influenza HA protein, modified influenza HA protein, norovirus protein, or modified norovirus protein may be used within a composition for inducing an immune response, and a pharmaceutically acceptable carrier, adjuvant, vehicle, or excipient.

The expression enhancers described herein may be used for the production of any protein of interest or for the production of virus like particles (VLPs). For example, with reference to FIG. 2B, and FIGS. 3A and 3B, the expression enhancers described herein are shown to be effective for the production of Norovirus, and influenza, VLPs, respectively.

Therefore, the present invention also provides a method of producing, or increasing production of VLPs comprising an influenza HA protein, modified influenza HA protein, norovirus protein, or modified norovirus protein, in plants. For example, the method may involve introducing a nucleic acid comprising an expression enhancer as described herein, for example, one or more than one of SEQ ID NO:1-5, operatively linked to nucleotide sequence encoding an influenza HA protein, a modified influenza HA protein, a norovirus protein, or a modified norovirus protein, into the plant, portion of the plant, or plant cell in a transient or stable manner, and expressing the protein in the plant, portion of the plant, or plant cell, in order to produce a VLP comprising the influenza HA protein, modified influenza HA protein, norovirus protein, or modified norovirus protein. The increase in expression may be determined by comparing the level of expression of the nucleotide sequence operatively linked to an expression enhancer, with the level of expression of the same nucleotide sequence that is not operatively linked to the expression enhancer, or for example, when operatively linked to the prior art expression enhancer CPMV 160 (SEQ ID NO:6). Alternatively, the method may comprise providing a plant, portion of the plant, or plant cell that comprises an expression enhancer as described herein operatively linked to nucleotide sequence encoding the influenza HA protein, modified influenza HA protein, norovirus protein, or modified norovirus protein, and expressing the nucleic acid encoding the protein in order to produce a VLP comprising the influenza HA protein, modified influenza HA protein, norovirus protein, or modified norovirus protein.

Furthermore, the present invention provides plant matter, a plant extract, or a protein extract comprising VLPs comprising an influenza HA protein, modified influenza HA protein, norovirus protein, or modified norovirus protein. The plant matter, plant extract, or protein extract may be used to induce immunity to norovirus infection in a subject. Alternatively, VLPs comprising the influenza HA protein, modified influenza HA protein, norovirus protein, or modified norovirus protein may be purified or partially purified, and the purified or partially purified preparation may be used to induce immunity to a norovirus infection in a subject, or the VLPs comprising influenza HA protein, modified influenza HA protein, norovirus protein, or modified norovirus protein may be used within a composition for inducing an immune response, and a pharmaceutically acceptable carrier, adjuvant, vehicle, or excipient.

The expression enhancers described herein may also be used for the production of a multimeric protein of interest, for example an antibody. As shown with reference to FIG. 3C, co-expression of two nucleic acids encoding the light chain (LC) and the heavy chain (HC) of an antibody, for example Rituximab, may be expressed in a plant, when each of the nucleic acid sequences are operatively linked to the same or different expression enhancers described herein. For example, co-expression of a first nucleic acid, encoding the HC of rituximab, and operatively linked to the expression enhancer nbEPI42 (SEQ ID NO:1); nbSNS46 (SEQ ID NO:2); nbCSY65 (SEQ ID NO:3); nbHEL40 (SEQ ID NO:4); and nbSEP44 (SEQ ID NO:5), along with a second nucleic acid, encoding the LC of rituximab, and operatively linked to either the same expression enhancer, nbEPI42 (SEQ ID NO:1); nbSNS46 (SEQ ID NO:2); nbCSY65 (SEQ ID NO:3); nbHEL40 (SEQ ID NO:4); and nbSEP44 (SEQ ID NO:5), respectively, resulted in expression of the multimeric protein, or an increase in expression of the multimeric protein, when compared to co-expression of first and second nucleic acids encoding the same HC and LC sequences, but each of the first and second nucleic acids operatively linked to the prior art expression enhancer CPMV 160 (SEQ ID NO:6). The first and second nucleic acids may also be co-expressed using other combination of the expression enhancers described herein, in a similar manner as described in U.S. Provisional Application No. 62/643,053 (filed Mar. 14, 2018, which is incorporated herein by reference).

Therefore, the present invention also provides a method of producing, or increasing production of a multimeric protein in plants. For example, the method may involve introducing, in a transient or stable manner, a first nucleic acid comprising an expression enhancer as described herein operatively linked to nucleotide sequence encoding a first protein component, and a second nucleic acid comprising an expression enhancer as described herein operatively linked to nucleotide sequence encoding a second protein component, into the plant, portion of the plant, or plant cell, and co-expressing the first and second nucleic acids in the plant, portion of the plant, or plant cell, in order to produce the multimeric protein. The increase in expression may be determined by comparing the level of expression of the first and second nucleic acid, each operatively linked to an expression enhancer(s), with the level of expression of the same first and second nucleic acids, each of which are not operatively linked to the expression enhancer(s), or for example, when operatively linked to the prior art expression enhancer CPMV 160 (SEQ ID NO:6). Alternatively, the method may comprise providing a plant, portion of the plant, or plant cell that comprises the first nucleic acid comprising an expression enhancer as described herein operatively linked to nucleotide sequence encoding a first protein component, and a second nucleic acid comprising an expression enhancer as described herein operatively linked to nucleotide sequence encoding a second protein component and co-expressing the first and second nucleic acid sequences to produce the multimeric protein.

Furthermore, the present invention provides plant matter, a plant extract, or a protein extract comprising the multimeric protein, or the multimeric protein may be purified or partially purified.

As described herein, there is provided a nucleic acid construct comprising an expression enhancer sequence operatively linked to a nucleotide sequence of interest encoding a protein of interest. Also provided are plant expression systems and vectors, comprising the construct or one or more than one nucleic acid comprising an enhancer sequence as described herein. Also provided is a plant expression system, a vector, a construct, or a nucleic acid, comprising a plant regulatory region, in operative association with an enhancer sequence that is operatively linked to a nucleotide sequence of interest, the nucleotide sequence of interest encoding a protein of interest. The enhancer sequence may be selected from any one of SEQ ID NO's:1, 5, or a nucleotide sequence that exhibits 100%, 99%, 98%, 97%, 96%, 95%, or 90%, or any amount therebetween, sequence identity to the sequence as set forth in any one of SEQ ID NO's:1-5, wherein, the expression enhancer, when operatively linked to a nucleic acid of interest, results in the expression of the nucleic acid of interest, or increases the level of expression of the nucleic acid of interest when compared to the level of expression of the same nucleic acid of interest that is not operatively linked to the expression enhancer, or for example, when operatively linked to the prior art expression enhancer CPMV 160 (SEQ ID NO:6).

The enhancer sequence of any one of SEQ ID NO's:1-5 may be modified using methods known to one of skill in the art, including deletion, insertion, and/or substitution of one or more than one nucleotide of the enhancer sequence, to produce an expression enhancer that results in a similar or increased enhancer activity, or that results in another beneficial property of the expression enhancer. For example, a beneficial property may include improved transcriptional initiation, improved mRNA stability, improved mRNA translation, or a combination thereof.

The enhancer sequence of the present invention may be used to express a protein of interest in a host organism for example a plant. In this case, the protein of interest may also be heterologous to the host organism in question and introduced into the plant cells using transformation techniques know in the art. A heterologous gene in an organism may replace an endogenous equivalent gene, i.e. one which normally performs the same or a similar function, or the inserted sequence may be additional to the endogenous gene or other sequence.

The invention further provides an expression cassette comprising in series, a promoter or plant regulatory region, operatively linked to an expression enhancer sequence as described herein which is fused with a nucleotide sequence of interest, a 3'UTR sequence, and a terminator sequence. The enhancer sequence may be defined by, any one of SEQ ID NO's:1-5, or a nucleotide sequence that exhibits 100%, 99%, 98%, 97%, 96%, 95%, or 90%, sequence identity, or any amount therebetween, to the sequence as set forth in any one of SEQ ID NO's:1-5. The enhancer sequence may also be modified using techniques known to one of skill in the art, provided that the enhancer sequence results in the expression of the nucleic acid of interest, or increases the level of expression of the nucleotide sequence of interest, for example, determined by comparing the level of expression of the nucleotide sequence operatively linked to an expression enhancer, with the level of expression of the same nucleotide sequence that is not operatively linked to the expression enhancer, or for example, when operatively linked to the prior art expression enhancer CPMV 160 (SEQ ID NO:6).

The sequences described in the present application are listed in Table 1.

TABLE 1

List of nucleic acid and amino acid sequences:

|  | SEQ ID NO: | FIG. # |
|---|---|---|
| nbEPI42 | 1 | 9A |
| nbSNS46 | 2 | 9B |
| nbCSY65 | 3 | 9C |
| nbHEL40 | 4 | 9D |
| nbSEP44 | 5 | 9E |
| CPMV 160 | 6 | 9F |
| nbMT78 | 7 | 9G |
| atHSP69 | 8 | 9H |
| IF-(2X35S + C)_CPMV160.c | 9 | 10A |
| IF-Dasher(27-609).r | 10 | 10B |
| CPMV 160 5'UTR-Dasher | 11 | 10C |
| Dasher (na) | 12 | 10D |
| Dasher (aa) | 13 | 10E |
| IF-nbMT78.c | 14 | 10F |
| nbMT78__Dasher.c | 15 | 10G |
| atHSP69__Dasher.c | 16 | 10H |
| IF-atHSP69.c | 17 | 10I |
| nbEPI42 + Dasher.c | 18 | 10J |
| IF-nbEPI42.c | 19 | 10K |
| nbSNS46 + Dasher.c | 20 | 10L |
| IF-nbSNS46.c | 21 | 10M |
| nbCSY65 + Dasher.c | 22 | 10N |
| IF-nbCSY65.c | 23 | 10O |
| nbHEL40 + Dasher.c | 24 | 10P |
| IF-nbHEL40.c | 25 | 10Q |
| nbSEP44 + Dasher.c | 26 | 10R |
| IF-nbSEP44.c | 27 | 10S |
| IF-GII4Syd12VP1.r | 28 | 11A |
| CPMV 160 5'UTR-VP1 (GII.4) | 29 | 11B |
| VP1 (GII.4) (na) | 30 | 11C |
| VP1 (GII.4) (aa) | 31 | 11D |
| nbMT78 + GII4Syd12.c | 32 | 11E |
| atHSP69 + GII4Syd12.c | 33 | 11F |
| nbEPI42 + GII4Syd12.c | 34 | 11G |
| nbSNS46 + GII4Syd12.c | 35 | 11H |
| nbCSY65 + GII4Syd12.c | 36 | 11I |
| nbHEL40 + GII4Syd12.c | 37 | 11J |
| nbSEP44 + GII4Syd12.c | 38 | 11K |
| IF**-HC(Ritux).s1-6r | 39 | 12A |
| CPMV 160 5'UTR-PDI + Rituximab HC | 40 | 12B |

TABLE 1-continued

List of nucleic acid and amino acid sequences:

|  | SEQ ID NO: | FIG. # |
|---|---|---|
| PDI + Rituximab HC (na) | 41 | 12C |
| PDI + Rituximab HC (aa) | 42 | 12D |
| IF**-LC(Ritux).s1-6r | 43 | 12E |
| CPMV 160 5'UTR-PDI + Rituximab LC (na) | 44 | 12F |
| PDI + Rituximab LC (na) | 45 | 12G |
| PDI + Rituximab LC (aa) | 46 | 12H |
| nbMT78__SpPDI.c | 47 | 12I |
| atHSP69__SpPDI.c | 48 | 12J |
| nbEPI42 + PDI.c | 49 | 12K |
| nbSNS46 + PDI.c | 50 | 12L |
| nbCSY65 + PDI.c | 51 | 12M |
| nbHEL40 + PDI.c | 52 | 12N |
| nbSEP44 + PDI.c | 53 | 12O |
| IF-H1cTMCT.s1-4r | 54 | 13A |
| CPMV 160 5'UTR-PDI + H1 Mich (na) | 55 | 13B |
| PDI + H1 Mich (na) | 56 | 13C |
| PDI + H1 Mich (aa) | 57 | 13D |
| IF-H3Minn15.r | 58 | 14A |
| CPMV 160 5'UTR-PDI + H3 sing (na) | 59 | 14B |
| PDI + H3 sing (na) | 60 | 14C |
| PDI + H3 sing (aa) | 61 | 14D |
| Cloning vector 1666 | 62 | 15A |
| Construct 4467 | 63 | 15B |
| Cloning vector 4160 | 64 | 15C |
| Cloning vector 4170 | 65 | 15D |

The present invention will be further illustrated in the following examples.

Example 1: Constructs

The following constructs comprising the enhancers identified above were prepared as follows:
2X35S/nbMT78 5'UTR/Dasher/CPMV 3'UTR/NOS Term (Construct Number 4467; SEQ ID NO:75)

Figure 16A:
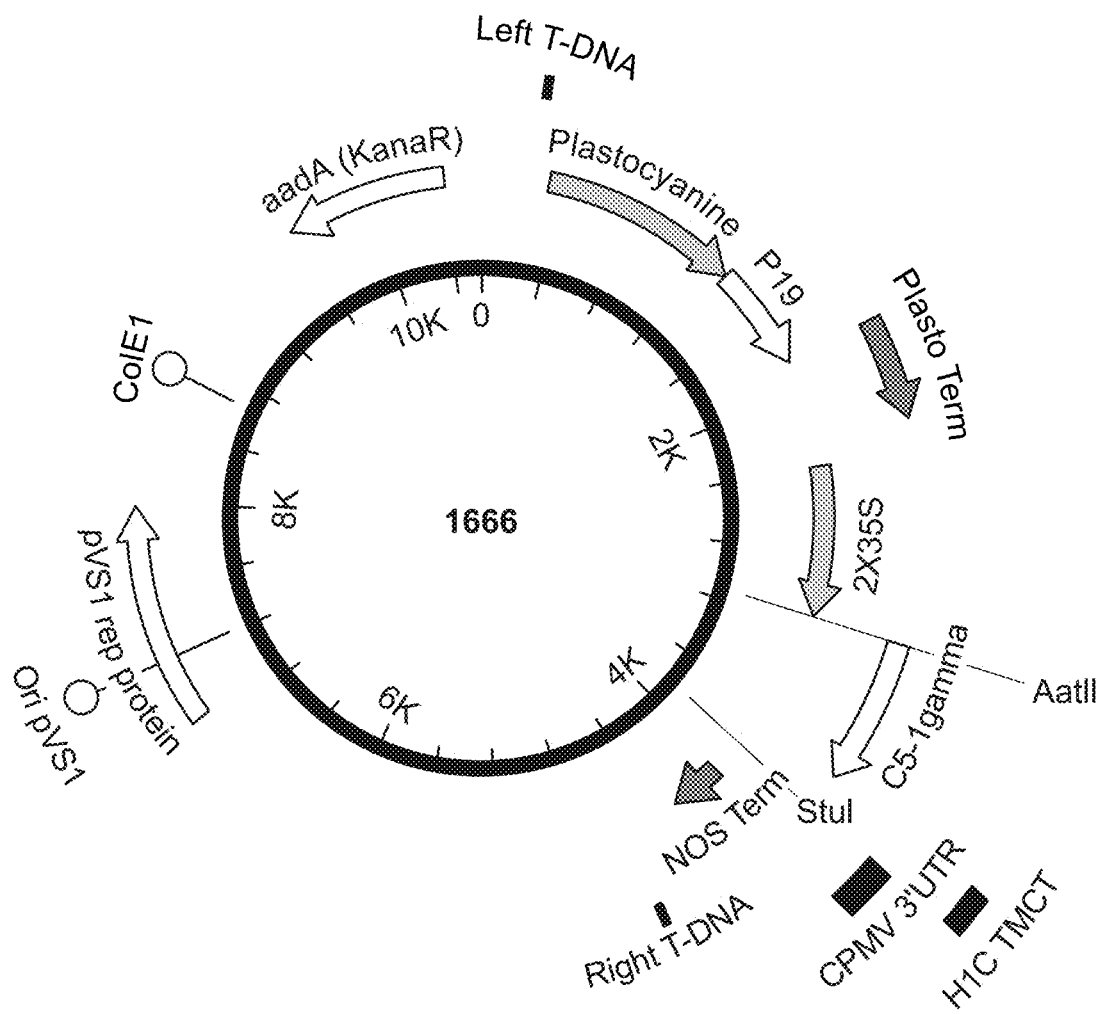
FIG. 16A shows construct 1666.
Figure 16B:
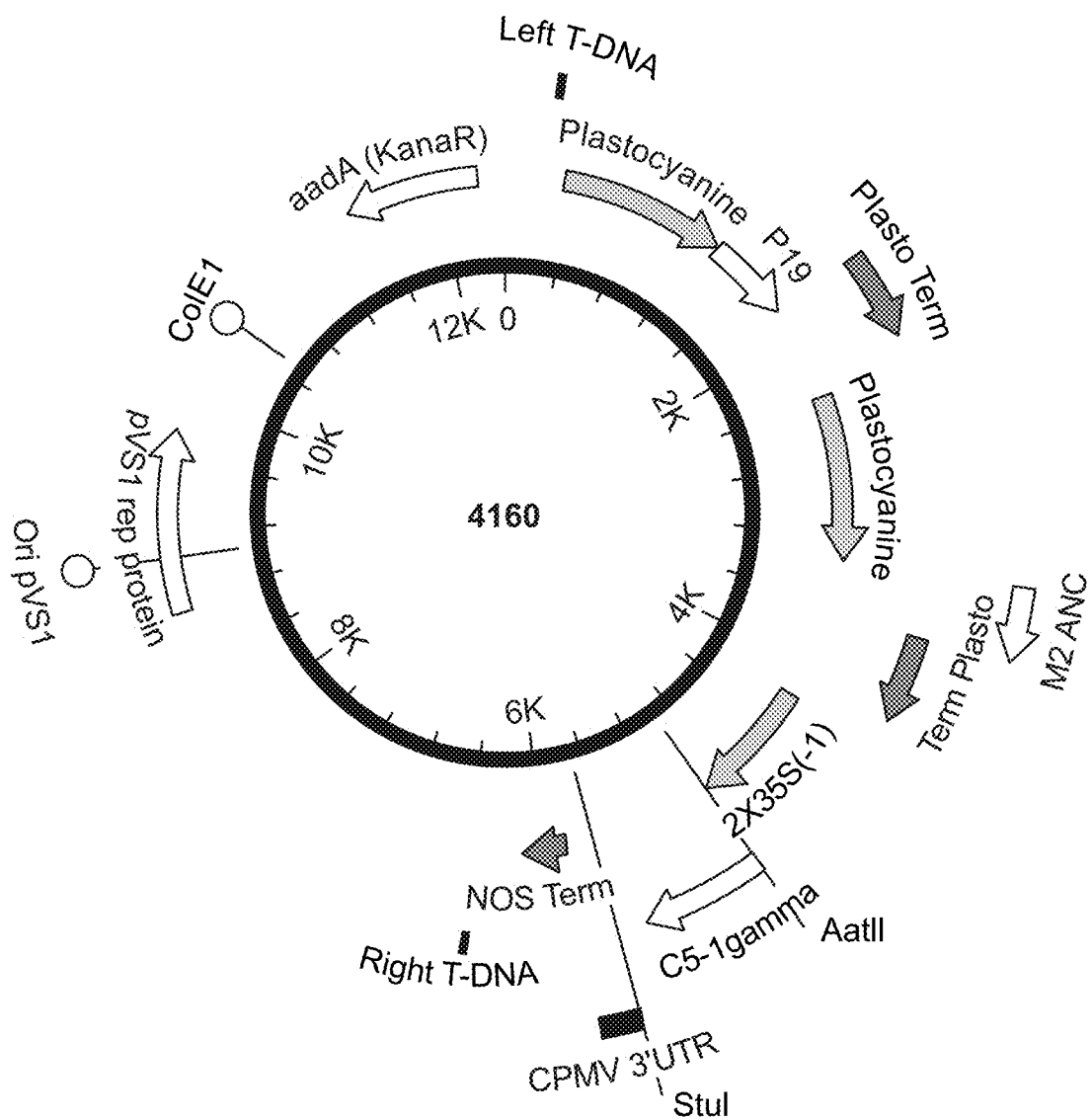
FIG. 16B shows construct 4160.
Figure 16C:
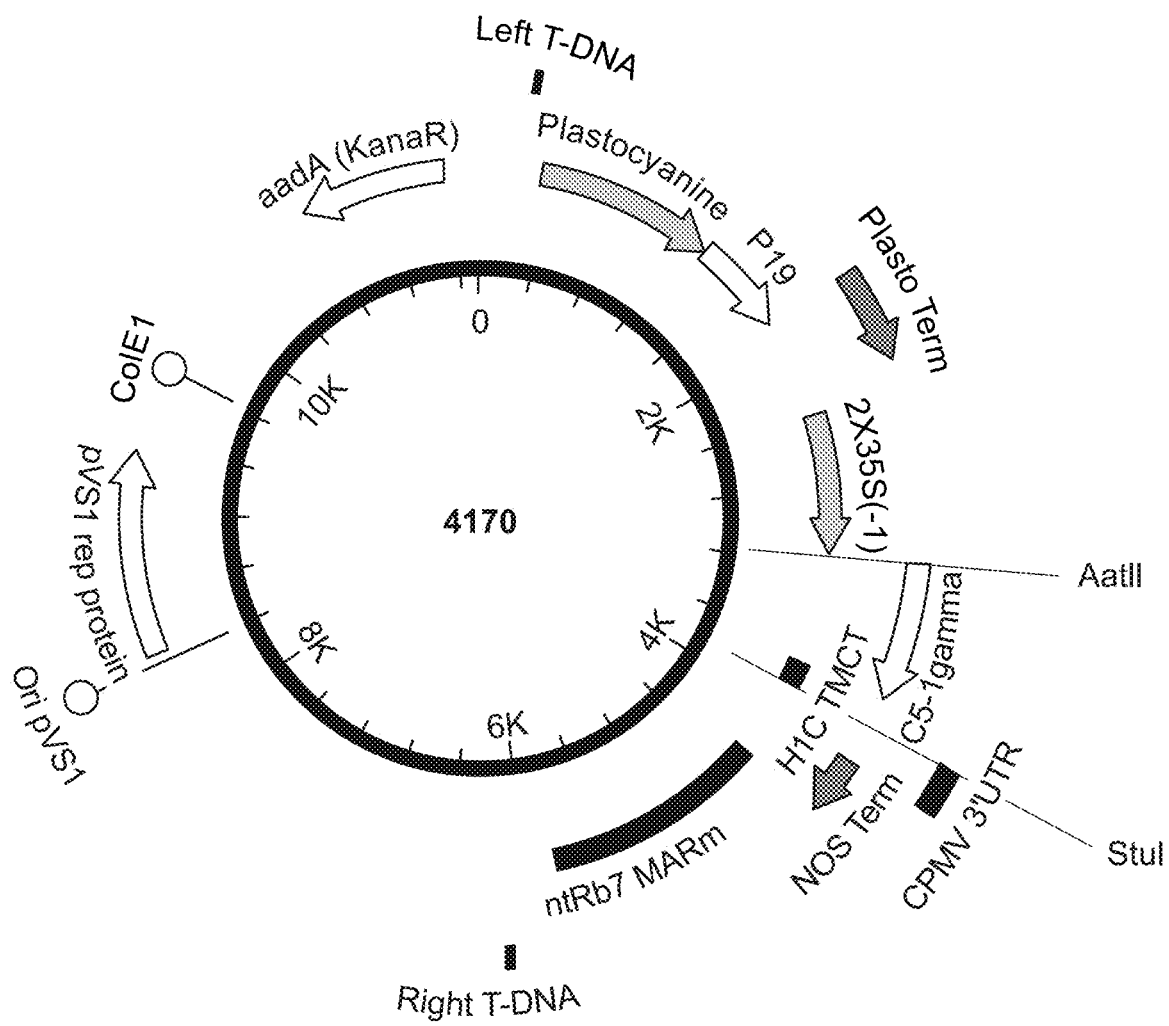
FIG. 16C shows construct 4170.

A sequence encoding Dasher fluorescent protein (Atum, Cat #FPB-27-609) fused to the nbMT78 5'UTR was cloned into 2X35S promoter+CPMV 3'UTR/NOS expression system using the following PCR-based method. In a first round of PCR, a fragment containing the Dasher fluorescent protein was amplified using primers nbMT78_Dasher.c (SEQ ID NO:15) and IF-Dasher (27-609).r (SEQ ID NO: 10) using Dasher gene sequence (SEQ ID NO: 11; FIG. 10C) as template. The PCR product from the first round of amplification (F1 in Table 2) was as used as template to add the atMT78 5'UTR sequence using IF-nbMT78.c (SEQ ID NO:14) and IF-Dasher (27-609).r (SEQ ID NO:10) as primers. The final PCR product (F2 in Table 2) was cloned in 2X35S promoter+CPMV 3'UTR/NOS expression system using In-Fusion cloning system (Clontech, Mountain View, CA). Construct number 1666 (FIG. 16A) was digested with AatII and StuI restriction enzymes and the linearized plasmid was used for the In-Fusion assembly reaction. Construct number 1666 is an acceptor plasmid intended for "In Fusion" cloning of genes of interest in a 2X35S promoter+CPMV 3'UTR/NOS-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO:62 (FIG. 15A). The resulting construct was given number 4467 (SEQ ID NO:63; FIG. 15B). The amino acid sequence of Dasher fluorescent protein is presented in SEQ ID NO:13; FIG. 10E. A representation of construct 4467 is presented in FIG. 4B.

Primers, templates as well as nucleic acid and protein sequences for all constructs described herein, are presented in Table 2.

For influenza H1 construct, the same cloning approach described above for the Dasher fluorescent protein was used.

For Influenza H3 constructs, the cloning vector used, integrates an influenza M2 ion channel gene under the control of Alfalfa Plastocyanin promoter and terminator in addition to the 2X35S promoter+CPMV 3'UTR/NOS-based expression cassette. Plasmid number 4160 (SEQ ID NO: 64; FIG. 15C) was digested with AatII and StuI restriction enzymes and used for the In-Fusion reaction in a similar cloning approach as described above for the Dasher fluorescent protein.

For Norovirus VP1 and Rituximab HC and LC constructs, the cloning vector integrates a Matrix attachment region (MAR) regulatory element from the tobacco RB7 gene after the NOS terminator in addition to the 2X35S promoter+ CPMV 3'UTR/NOS-based expression cassette. Plasmid number 4170 (SEQ ID NO: 65; FIG. 15D) was digested with AatII and StuI restriction enzymes and used for the In-Fusion reaction.

TABLE 2

Primers, templates and sequences of interest (SOI) for construct preparation

| | | | | | | | SEQ ID NO: | | | |
| | | | | | | | | F1 | F2 | | |
| Constructs | | | | | | | | Template | Template | | |
| 5'UT R | Sp | SOI* | Const # | Primer 1* | Primer 2* | Primer 3* | Template | | | SOI NA: | SOI AA |
|---|---|---|---|---|---|---|---|---|---|---|---|
| CPMV 160 | — | Dasher | 4460 | 9 | — | 10 | — | 11 | 12 | 13 |
| nbMT78 | — | Dasher | 4467 | 14 | 15 | 10 | 11 | F1 | 12 | 13 |
| atHSP69 | — | Dasher | 4472 | 17 | 16 | 10 | 11 | F1 | 12 | 13 |
| nbEPI42 | ' | Dasher | 6380 | 19 | 18 | 10 | 11 | F1 | 12 | 13 |
| nbSNS46 | — | Dasher | 6381 | 21 | 20 | 10 | 11 | F1 | 12 | 13 |
| nbCSY65 | — | Dasher | 6382 | 23 | 22 | 10 | 11 | F1 | 12 | 13 |
| nbHEL40 | | Dasher | 6383 | 25 | 24 | 10 | 11 | F1 | 12 | 13 |
| nbSEP44 | — | Dasher | 6384 | 27 | 26 | 10 | 11 | F1 | 12 | 13 |
| CPMV 160 | | VP1 GII.4 Syd 12 | 4133 | 9 | — | 28 | — | 29 | 30 | 31 |
| nbMT78 | | VP1 GII.4 Syd 12 | 4163 | 14 | 32 | 28 | 29 | F1 | 30 | 31 |
| atHSP69 | | VP1 GII.4 Syd 12 | 4164 | 17 | 33 | 28 | 29 | F1 | 30 | 31 |
| nbEPI42 | | VP1 GII.4 Syd 12 | 6218 | 19 | 34 | 28 | 29 | F1 | 30 | 31 |
| nbSNS46 | | VP1 GII.4 Syd 12 | 6214 | 21 | 35 | 28 | 29 | F1 | 30 | 31 |
| nbCSY65 | | VP1 GII.4 Syd 12 | 6215 | 23 | 36 | 28 | 29 | F1 | 30 | 31 |
| nbHEL40 | | VP1 GII.4 Syd 12 | 6216 | 25 | 37 | 28 | 29 | F1 | 30 | 31 |
| nbSEP44 | | VP1 GII.4 Syd 12 | 6217 | 27 | 38 | 28 | 29 | F1 | 30 | 31 |
| CPMV 160 | PDI | HC Rituximab | 4641 | 9 | — | 39 | — | 40 | 41 | 42 |
| CPMV 160 | PDI | LC Rituximab | 4642 | 9 | — | 43 | — | 44 | 45 | 46 |
| nbMT78 | PDI | LC Rituximab | 6600 | 14 | 47 | 43 | 44 | F1 | 45 | 46 |
| nbMT78 | PDI | HC Rituximab | 6601 | 14 | 47 | 39 | 40 | F1 | 41 | 42 |
| atHSP69 | PDI | LC Rituximab | 6602 | 17 | 48 | 43 | 44 | F1 | 45 | 46 |
| atHSP69 | PDI | HC Rituximab | 6603 | 17 | 48 | 39 | 40 | F1 | 41 | 42 |
| nbEPI42 | PDI | LC Rituximab | 6604 | 19 | 49 | 43 | 44 | F1 | 45 | 46 |
| nbEPI42 | PDI | HC Rituximab | 6605 | 19 | 49 | 39 | 40 | F1 | 41 | 42 |
| nbSNS46 | PDI | LC Rituximab | 6606 | 21 | 50 | 43 | 44 | F1 | 45 | 46 |
| nbSNS46 | PDI | HC Rituximab | 6607 | 21 | 50 | 39 | 40 | F1 | 41 | 42 |
| nbCSY65 | PDI | LC Rituximab | 6608 | 23 | 51 | 43 | 44 | F1 | 45 | 46 |
| nbCSY65 | PDI | HC Rituximab | 6609 | 23 | 51 | 39 | 40 | F1 | 41 | 42 |
| nbHEL40 | PDI | LC Rituximab | 6610 | 25 | 52 | 43 | 44 | F1 | 45 | 46 |
| nbHEL40 | PDI | HC Rituximab | 6611 | 25 | 52 | 39 | 40 | F1 | 41 | 42 |
| nbSEP44 | PDI | LC Rituximab | 6612 | 27 | 53 | 43 | 44 | F1 | 45 | 46 |
| nbSEP44 | PDI | HC Rituximab | 6613 | 27 | 53 | 39 | 40 | F1 | 41 | 42 |
| CPMV 160 | PDI | H1 A-Mich-45-2015 | 3703 | 9 | — | 54 | — | 55 | 56 | 57 |
| nbMT78 | PDI | H1 A-Mich-45-2015 | 4703 | 14 | 47 | 54 | 55 | F1 | 56 | 57 |
| atHSP69 | PDI | H1 A-Mich-45-2015 | 4704 | 17 | 48 | 54 | 55 | F1 | 56 | 57 |
| nbEPI42 | PDI | H1 A-Mich-45-2015 | 6700 | 19 | 49 | 54 | 55 | F1 | 56 | 57 |
| nbSNS46 | PDI | H1 A-Mich-45-2015 | 6701 | 21 | 50 | 54 | 55 | F1 | 56 | 57 |
| nbCSY65 | PDI | H1 A-Mich-45-2015 | 6702 | 23 | 51 | 54 | 55 | F1 | 56 | 57 |
| nbHEL40 | PDI | H1 A-Mich-45-2015 | 6703 | 25 | 52 | 54 | 55 | F1 | 56 | 57 |
| nbSEP44 | PDI | H1 A-Mich-45-2015 | 6704 | 27 | 53 | 54 | 55 | F1 | 56 | 57 |
| CPMV 160 | PDI | H3 A-Sing-19-0019-16 | 4008 | 9 | — | 58 | — | 59 | 60 | 61 |
| nbMT78 | PDI | H3 A-Sing-19-0019-16 | 6134 | 14 | 47 | 58 | 59 | F1 | 60 | 61 |
| atHSP69 | PDI | H3 A-Sing-19-0019-16 | 6136 | 17 | 48 | 58 | 59 | F1 | 60 | 61 |
| nbEPI42 | PDI | H3 A-Sing-19-0019-16 | 6705 | 19 | 49 | 58 | 59 | F1 | 60 | 61 |
| nbSNS46 | PDI | H3 A-Sing-19-0019-16 | 6706 | 21 | 50 | 58 | 59 | F1 | 60 | 61 |
| nbCSY65 | PDI | H3 A-Sing-19-0019-16 | 6707 | 23 | 51 | 58 | 59 | F1 | 60 | 61 |
| nbHEL40 | PDI | H3 A-Sing-19-0019-16 | 6708 | 25 | 52 | 58 | 59 | F1 | 60 | 61 |
| nbSEP44 | PDI | H3 A-Sing-19-0019-16 | 6709 | 27 | 53 | 58 | 59 | F1 | 60 | 61 |

*SOI: sequence of interest; Primer 1: Primer 1 (For In-fusion cloning); Primer 2: Primer 2 (to create fragment no 1 to amplify GOI with primer 3): Primer 3: Primer 3 (For In-fusion cloning)

Example 2: Methods

*Agrobacterium tumefaciens* Transfection

*Agrobacterium tumefaciens* strain AGL1 was transfected (transformed) by electroporation with the different expression vectors using the methods described by D'Aoust et al., 2008 (*Plant Biotech.* 1 6:930-40). Transfected *Agrobacterium* were grown in LB medium supplemented with 10 mM 2-(N-morpholino)ethanesulfonic acid (MES) and 50 µg/ml kanamycin pH5.6 to an $OD_{600}$ between 0.6 and 1.6 and frozen in 100 µl aliquots.

Preparation of Plant Biomass, Inoculum and Agro-infiltration

*N. benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions Agrobacteria transfected (transformed) with each expression vector were grown in a LB medium supplemented with 10 mM 2-(N-morpholino)ethanesulfonic acid (MES) and 50 µg/ml kanamycin pH5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 6 or 9 day incubation period until harvest.

Leaf Harvest and Total Protein Extraction

Following incubation, the aerial part of plants was harvested, frozen at −80° C. and crushed into pieces. Total soluble proteins were extracted by homogenizing (Polytron) each sample of frozen-crushed plant material in 2 volumes of cold 50 mM Tris buffer pH 8.0+500 mM NaCl, 0.4 µg/ml Metabisulfite and 1 mM phenylmethanesulfonyl fluoride. After homogenization, the slurries were centrifuged at 10,000 g for 10 min at 4° C. and these clarified crude extracts (supernatant) kept for analyses.

The total protein content of clarified crude extracts was determined by the Bradford assay (Bio-Rad, Hercules, California) using bovine serum albumin as the reference standard. Proteins were separated by SDS-PAGE under reducing conditions using Criterion™ TGX Stain-Free™ precast gels (Bio-Rad Laboratories, Hercules, CA). Proteins were visualized by staining the gels with Coomassie Brilliant Blue. Alternatively, proteins were visualized with Gel Doc™ EZ imaging system (Bio-Rad Laboratories, Hercules, CA) and electrotransferred onto polyvinylene difluoride (PVDF) membranes (Roche Diagnostics Corporation, Indianapolis, Indiana) for immunodetection. Prior to immunoblotting, the membranes were blocked with 5% skim milk and 0.1% Tween-20 in Tris-buffered saline (TBS-T) for 16-18 h at 4° C.

Dasher Expression as Determined by Direct Fluorescence in Crude Extract

Dasher expression was quantified by direct measure of fluorescence in crude extracts. Frozen biomass was extracted using 50 mM Tris+150 mM NaCl pH 7.4 extraction buffer by mechanical extraction and centrifuged 10 minutes at 10000 g at 4° C. to remove insoluble debris. Clarified crude extracts were diluted 1/16, 1/48 and 1/144 in PBS and fluorescence was measured using a Fluoroskan (Ascent) instrument using 485 nm as excitation filter and 518 nm as emission filter.

HA Expression as Determined Using Hemagglutination Assay (HA Titer)

Hemagglutination assay was based on a method described by Nayak and Reichl (2004, *J. Virol. Methods* 122:9-15). Serial double dilutions of the test samples (100 µL) were made in V-bottomed 96-well microtiter plates containing 100 µL PBS, leaving 100 µL of diluted sample per well. One hundred microliters of a 0.25% turkey red blood cells suspension (Bio Link Inc., Syracuse, NY; for all B strains, H1, H5 and H7) or 0.5% guinea pig red blood cells suspension (for H3) were added to each well, and plates were incubated for 2h at room temperature. The reciprocal of the highest dilution showing complete hemagglutination was recorded as HA activity.

Rituximab Expression as Determined by In-Gel Densitometry

For Rituximab expression analysis, crude protein extracts (2 g biomass/EU) were produced from leaves by mechanical extraction in 150 mM Tris, pH 7.4 buffer with 150 mM NaCl and the extracts were electrophoresed on SDS-PAGE under non-reducing conditions for in-gel densitometry quantification of the band corresponding to the fully assembled $H_2L_2$ form of the antibody. Protein electrophoresis was performed in Stain-Free gels from Bio-Rad and gel imaging system was carried-out using Gel Doc XR+ system, including the Image Lab software for image analyses and in-gel quantification.

Analysis of VLP Formation/Iodixanol Gradients

Proteins were extracted from frozen biomass by mechanical extraction in a blender with 2 volumes of extraction buffer (100 mM phosphate buffer pH 7.2+150 mM NaCl). The slurry was filtered through a large pore nylon filter to remove large debris and centrifuged 5000 g for 5 min at 4° C. The supernatant was collected and centrifuged again at 5000 g for 30 min (4° C.) to remove additional debris. The supernatant is then loaded on a discontinuous iodixanol density gradient. Analytical density gradient centrifugation was performed as follows: 38 ml tubes containing discontinuous iodixanol density gradient in acetate buffer (1 ml at 45%, 2 ml at 35%, 2 ml at 33%, 2 ml at 31%, 2 ml at 29% and 5 ml at 25% of iodixanol) were prepared and overlaid with 25 ml of the extracts containing the virus-like particles. The gradients were centrifuged at 175 000 g for 4 hours (4° C.). After centrifugation, 1 ml fractions were collected from the bottom to the top and fractions were analyzed by SDS-PAGE combined with protein staining or Western blot.

Example 3: Protein Production in Plants

*N. benthamiana* leaves were, vacuum infiltrated, as described in Example 2, with *Agrobacterium tumefaciens* comprising expression vectors encoding the protein of interest operatively linked to the defined expression enhancer, to permit expression of the protein of interest, and the leaves examined for the protein of interest production. After 9 days post infiltration (DPI), total crude protein extracts were prepared from leaf homogenates, and hemagglutinin titer was determined as described above.

With reference to FIG. 2A, each of the expression enhancers, nbEPI42 (SEQ ID NO:1); nbSNS46 (SEQ ID NO:2); nbCSY65 (SEQ ID NO:3); nbHEL40 (SEQ ID NO:4); and nbSEP44 (SEQ ID NO:5), operatively linked to a nucleic acid sequence encoding Dasher was observed to result in the same or increased expression of the protein, when compared to the activity of the prior art expression enhancer sequence CMPV 160 (WO 2015/103704) operatively linked to the same nucleic acid sequence encoding the same proteins of interest, and expressed under similar conditions. The activity of these enhancer elements was the same or greater than the expression enhancers nbMT78 and atHSP69 (described in U.S. Provisional Application No. 62/643,053, filed Mar. 14, 2018, which is incorporated herein by reference).

With reference to FIGS. 3A and 3B, each of the expression enhancers, nbEPI42 (SEQ ID NO:1); nbSNS46 (SEQ ID NO:2); nbCSY65 (SEQ ID NO:3); nbHEL40 (SEQ ID NO:4); and nbSEP44 (SEQ ID NO:5), operatively linked to a nucleic acid sequence encoding a H3 A/Singapore, or a H1 Michigan/45/15, was observed to result in a similar, or slightly increased, expression of the protein when compared to the activity of the prior art expression enhancer sequence CMPV 160 (WO 2015/103704) operatively linked to the same nucleic acid sequence encoding the same proteins of interest, and expressed under similar conditions. The activity of these enhancer elements was also the same or greater than the expression enhancers nbMT78 and atHSP69 (described in U.S. Provisional Application No. 62/643,053, filed Mar. 14, 2018, which is incorporated herein by reference).

These results demonstrate the expression enhancer sequences described herein may be used for the expression of a protein of interest that is operatively linked to the expression enhancer, in a plant, portion of plant, or a plant cell.

Example 4: Norovirus VP1 Protein and VLP Production in Plants

*N. benthamiana* leaves were vacuum infiltrated, as described in Example 2, with *Agrobacterium tumefaciens* comprising expression vectors encoding norovirus VP1 from GII.4 genotype, and the leaves examined for VLP production. After 9 days post infiltration (DPI), total crude protein extracts were separated by SDS-PAGE, and stained with Coomassie (VP1 production), or separated using discontinuous iodixanol density gradients as described in Example 2, above (VLP production). Fractions from the density gradients were examined using Coomassie-stained SDS-PAGE. Norovirus VP1 proteins appear at an approximate 55-60 kDa band. The occurrence of the VP1 protein within a fraction of the density gradients is indicative of the fraction(s) to which the VLPs equilibrate during density gradient centrifugation. The yield of VLPs obtained from peak fractions after density gradient centrifugation was also determined.

As shown in FIG. 2B each of the expression enhancers, nbEPI42 (SEQ ID NO:1); nbSNS46 (SEQ ID NO:2); nbCSY65 (SEQ ID NO:3); nbHEL40 (SEQ ID NO:4); and nbSEP44 (SEQ ID NO:5), operatively linked to a nucleic acid sequence encoding norovirus GII.4/Syd/12 VP1 was observed to result in a similar, or slightly increased, expression of the protein when compared to the activity of the prior art expression enhancer sequence CMPV 160 (WO 2015/103704) operatively linked to the same nucleic acid sequence encoding the same proteins of interest, and expressed under similar conditions. The activity of these enhancer elements was also the same or greater than the expression enhancers nbMT78 and atHSP69 (described in U.S. Provisional Application No. 62/643,053, filed Mar. 14, 2018, which is incorporated herein by reference).

Example 5: Multimeric Protein Production in Plants

The expression enhancers described herein may also be used for the production of a multimeric protein of interest, for example an antibody. *N. benthamiana* leaves were, vacuum infiltrated, as described in Example 2, with *Agrobacterium tumefaciens* comprising expression vectors encoding the protein of interest operatively linked to the defined expression enhancer, to permit expression of the protein of interest, and the leaves examined for the protein of interest production. After 9 days post infiltration (DPI), total crude protein extracts were prepared from leaf homogenates were separated by SDS-PAGE and expression levels were determined by in-gel densitometry of complete IgG, as described above.

As shown with reference to FIG. 3C, co-expression of two nucleic acids, the first nucleic acid encoding the light chain (LC) of Rituximab operatively linked to one of the following expression enhancers, nbEPI42 (SEQ ID NO:1); nbSNS46 (SEQ ID NO:2); nbCSY65 (SEQ ID NO:3); nbHEL40 (SEQ ID NO:4); and nbSEP44 (SEQ ID NO:5), and the second nucleic acid encoding the heavy chain (HC) of rituximab operatively linked to one of the following expression enhancers, nbEPI42 (SEQ ID NO:1); nbSNS46 (SEQ ID NO:2); nbCSY65 (SEQ ID NO:3); nbHEL40 (SEQ ID NO:4); and nbSEP44 (SEQ ID NO:5), resulted in the same, or increased, yield of the multimeric protein in a plant, when compared to co-expression of first and second nucleic acids encoding the same HC and LC rituximab sequences, with each of the first and second nucleic acids operatively linked to the prior art expression enhancer CPMV 160. The activity of these enhancer elements was also the same or greater than the expression enhancers nbMT78 and atHSP69 (described in U.S. Provisional Application No. 62/643,053, filed Mar. 14, 2018, which is incorporated herein by reference).

These results demonstrate that the expression enhancers described herein may be used to produce multimeric proteins, such as an antibody, and that the same or different the expression enhancers as described herein may be operatively linked to each of the nucleic acid sequences used to encode the components of the multimeric protein.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A nucleic acid comprising an expression enhancer operatively linked with a heterologous nucleotide sequence encoding a protein of interest, the expression enhancer consisting of:
nbCSY65 (SEQ ID NO:3).

2. The nucleic acid of claim 1, where the heterologous nucleotide sequence encodes a viral protein or an antibody.

3. The nucleic acid of claim 2, wherein the viral protein is an influenza protein or a norovirus protein.

4. The nucleic acid of claim 3, wherein the influenza protein is a hemagglutinin protein selected from the group of H1, H2, H3, H4, H5, H6, H7, H8, H9, H10, H11, H12, H13, H14, H15, H16, and an influenza type B hemagglutinin.

5. The nucleic acid of claim 3, wherein the norovirus protein is a VP1, a VP2, or a combination thereof selected from the group of GI.1, GI.2, GI.3, GI.5, GI.7, GII. 1, GII.2, GII.3, GII.4, GII.5, GII.6, GII. 7, GII. 12, GII. 13, GII. 14, GII. 17 and GII.21.

6. A plant expression system comprising one or more than one of the nucleic acid of claim 1.

7. A plant expression system comprising one or more than one of nucleic acid of claim 2.

8. A plant expression system comprising one or more than one of the nucleic acid of claim 3.

9. A plant expression system comprising one or more than one of the nucleic acid of claim 4.

10. A plant expression system comprising one or more than one of the nucleic acid of claim 5.

11. The plant expression system of claim 6 further comprising a comovirus 3' UTR.

12. A method of producing a protein of interest in a plant, a portion of a plant, or a plant cell, comprising,
introducing into the plant, the portion of a plant, or the plant cell, in a stable or transient manner, the plant expression system of claim 6 comprising the one or more than one nucleic acid, and
incubating the plant or the portion of a plant under conditions that permit expression of each of the heterologous nucleotide sequence encoding the protein of interest.

13. The method of claim 12, wherein the protein of interest is a viral protein.

14. The method of claim 13, wherein the viral protein is an influenza protein or a norovirus protein.

15. The method of claim 14, wherein the influenza protein is a hemagglutinin protein selected from the group of H1, H2, H3, H4, H5, H6, H7, H8, H9, H10, H11, H12, H13, H14, H15, H16, and an influenza type B hemagglutinin.

16. The method of claim 14, wherein the norovirus protein is a VP1, a VP2, or a combination thereof selected from the group of GI.1, GI.2, GI,3, GI.5, GI.7, GII. 1, GII.2, GII.3, GII.4, GII.5, GII.6, GII. 7, GII. 12, GII. 13, GII. 14, GII. 17 and GII.21.

17. The method of claim 12, wherein the protein of interest is a multimeric protein, and the step of introducing involves co-expressing two or more than two of the heterologous nucleotide sequence, each of the two or more than two of the heterologous nucleotide sequence encoding a component of the multimeric protein.

18. A plant, portion of a plant, or a plant cell, transiently transformed or stably transformed with the plant expression system of claim 6.

19. The nucleic acid of claim 1, wherein the expression enhancer increases expression of the heterologous nucleotide sequence encoding the protein of interest in a *Nicotiana benthamiana* plant when compared to the level of expression of the same heterologous nucleotide sequence that is not operatively linked to the expression enhancer.

* * * * *

SEQUENCE LISTING

```
<160> NUMBER OF SEQ ID NOS: 65

<210> SEQ ID NO 1
<211> LENGTH: 42
<212> TYPE: DNA
<213> ORGANISM: Artificial Sequence
<220> FEATURE:
<223> OTHER INFORMATION: Primer nbEP142
```

<400> SEQUENCE: 1
actttaattt gctgattttc aacaaaatca agaatttcag ca    42

<210> SEQ ID NO 2
<211> LENGTH: 46
<212> TYPE: DNA
<213> ORGANISM: Artificial Sequence
<220> FEATURE:
<223> OTHER INFORMATION: Primer nbSNS46

<400> SEQUENCE: 2
attcagtgct taactggtta ttgagtaagt tatcaaaaag caaaaa    46

<210> SEQ ID NO 3
<211> LENGTH: 65
<212> TYPE: DNA
<213> ORGANISM: Artificial Sequence
<220> FEATURE:
<223> OTHER INFORMATION: Primer nbCYS65

<400> SEQUENCE: 3
acttttctaa tcaatcatca aacagaacgc agaaaatttc ctaaaaacaa aaaaaaggca    60
tacaa    65

<210> SEQ ID NO 4
<211> LENGTH: 40
<212> TYPE: DNA
<213> ORGANISM: Artificial Sequence
<220> FEATURE:
<223> OTHER INFORMATION: Primer nbHEL40

<400> SEQUENCE: 4
actccatttg aatctatcaa accaaaacac attgagcaaa    40

<210> SEQ ID NO 5
<211> LENGTH: 44
<212> TYPE: DNA
<213> ORGANISM: Artificial Sequence
<220> FEATURE:
<223> OTHER INFORMATION: Primer nbSEP44

<400> SEQUENCE: 5
acttcaatca ctccacactt tattctcttt caaaacctac actc    44

<210> SEQ ID NO 6
<211> LENGTH: 160
<212> TYPE: DNA
<213> ORGANISM: Cow Pea Mosiac Virus

<400> SEQUENCE: 6
tattaaaatc ttaataggtt ttgataaaag cgaacgtggg gaaacccgaa ccaaaccttc    60
ttctaaactc tctctcatct ctcttaaagc aaacttctct cttgtctttc ttgcgtgagc    120
gatcttcaac gttgtcagat cgtgcttcgg caccagtaca    160

<210> SEQ ID NO 7
<211> LENGTH: 78
<212> TYPE: DNA
<213> ORGANISM: Artificial Sequence
<220> FEATURE:
<223> OTHER INFORMATION: Primer nbMT78

<400> SEQUENCE: 7
acacaatttg ctttagtgat taaactttct tttacaacaa attaaaggtc tattatctcc    60
caacaacata agaaaaca                                                  78

<210> SEQ ID NO 8
<211> LENGTH: 69
<212> TYPE: DNA
<213> ORGANISM: Artificial Sequence
<220> FEATURE:
<223> OTHER INFORMATION: Primer atHSP69

<400> SEQUENCE: 8
aaattcaaaa tttaacacac aaacacaaac acacacacca aaaaaaacac agaccttaaa    60
aaaataaaa                                                            69

<210> SEQ ID NO 9
<211> LENGTH: 48
<212> TYPE: DNA
<213> ORGANISM: Artificial Sequence
<220> FEATURE:
<223> OTHER INFORMATION: Primer IF-(2X35S+C)_CPMV160.c

<400> SEQUENCE: 9
tttcatttgg agaggctatt aaaatcttaa taggttttga taaaagcg                 48

<210> SEQ ID NO 10
<211> LENGTH: 56
<212> TYPE: DNA
<213> ORGANISM: Artificial Sequence
<220> FEATURE:
<223> OTHER INFORMATION: Primer IF-Dasher(27-609).r

<400> SEQUENCE: 10
actaaagaaa ataggccttt actgataggt atcgagatcg acggccttga ccactt        56

<210> SEQ ID NO 11
<211> LENGTH: 871
<212> TYPE: DNA
<213> ORGANISM: Artificial Sequence
<220> FEATURE:
<223> OTHER INFORMATION: CPMV 160 5'UTR-Dasher DNA sequence

<400> SEQUENCE: 11
tattaaaatc ttaataggtt ttgataaaag cgaacgtggg gaaacccgaa ccaaaccttc    60
ttctaaactc tctctcatct ctcttaaagc aaacttctct cttgtctttc ttgcgtgagc   120
gatcttcaac gttgtcagat cgtgcttcgg caccagtaca atgactgccc tgaccgaagg   180
tgctaagctg tttgagaagg agattccgta catcaccgag ctggaagggg acgtcgaagg   240
aatgaagttc atcatcaagg agaaggaac cggggacgct acgactggaa ccattaaggc   300
caagtatatc tgtaccactg agatctgcc agtgccttgg gccacccttg tgtcaaccct   360
ctcgtatgga gtgcagtgtt ttgctaagta ccctagccac attaaggact tcttcaaatc   420
cgccatgccg gaaggttata cccaagagcg caccattttct tttgagggag atggagtgta   480
caagacccgc gcgatggtca cctatgagag gggatctatc tacaaccggg tgactctgac   540
tggagaaaac tttaagaagg acgggcatat tcttcggaag aatgtcgcct tccagtgccc   600
tcccagcatc ctttacattc tccccgacac tgtgaacaac ggaatccgcg tggagttcaa   660
tcaagcctac gacatcgagg gggtgacgga gaagctggtg accaagtgta gccagatgaa   720
tcggccactg gccggttcag cggctgtcca cattccgcgc taccatcata tcacttatca   780
cactaagctc tccaaagacc gcgatgagag gagagatcac atgtgcctgg tggaagtggt   840

```
caaggccgtc gatctcgata cctatcagta a                                        871
```

<210> SEQ ID NO 12
<211> LENGTH: 711
<212> TYPE: DNA
<213> ORGANISM: Artificial Sequence
<220> FEATURE:
<223> OTHER INFORMATION: Dasher DNA sequence

<400> SEQUENCE: 12

```
atgactgccc tgaccgaagg tgctaagctg tttgagaagg agattccgta catcaccgag    60
ctggaagggg acgtcgaagg aatgaagttc atcatcaagg agaaggaac  cggggacgct   120
acgactggaa ccattaaggc caagtatatc tgtaccactg gagatctgcc agtgccttgg   180
gccacccttg tgtcaaccct ctcgtatgga gtgcagtgtt ttgctaagta ccctagccac   240
attaaggact cttcaaatc cgccatgccg aaggttata  cccaagagcg caccatttct   300
tttgagggag atggagtgta caagacccgc gcgatggtca cctatgagag gggatctatc   360
tacaaccggg tgactctgac tggagaaaac tttaagaagg acgggcatat tcttcggaag   420
aatgtcgcct ccagtgccc  tcccagcatc ctttacattc tccccgacac tgtgaacaac   480
ggaatccgcg tggagttcaa tcaagcctac gacatcgagg gggtgacgga agctggtg    540
accaagtgta gccagatgaa tcggccactg gccggttcag cggctgtcca cattccgcgc   600
taccatcata tcacttatca cactaagctc tccaaagacc gcgatgagag gagagatcac   660
atgtgcctgg tggaagtggt caaggccgtc gatctcgata cctatcagta a            711
```

<210> SEQ ID NO 13
<211> LENGTH: 236
<212> TYPE: PRT
<213> ORGANISM: Artificial Sequence
<220> FEATURE:
<223> OTHER INFORMATION: Dasher protein sequence

<400> SEQUENCE: 13

```
Met Thr Ala Leu Thr Glu Gly Ala Lys Leu Phe Glu Lys Glu Ile Pro
1               5                   10                  15

Tyr Ile Thr Glu Leu Glu Gly Asp Val Glu Gly Met Lys Phe Ile Ile
            20                  25                  30

Lys Gly Glu Gly Thr Gly Asp Ala Thr Thr Gly Thr Ile Lys Ala Lys
        35                  40                  45

Tyr Ile Cys Thr Thr Gly Asp Leu Pro Val Pro Trp Ala Thr Leu Val
    50                  55                  60

Ser Thr Leu Ser Tyr Gly Val Gln Cys Phe Ala Lys Tyr Pro Ser His
65                  70                  75                  80

Ile Lys Asp Phe Phe Lys Ser Ala Met Pro Glu Gly Tyr Thr Gln Glu
                85                  90                  95

Arg Thr Ile Ser Phe Glu Gly Asp Gly Val Tyr Lys Thr Arg Ala Met
            100                 105                 110

Val Thr Tyr Glu Arg Gly Ser Ile Tyr Asn Arg Val Thr Leu Thr Gly
        115                 120                 125

Glu Asn Phe Lys Lys Asp Gly His Ile Leu Arg Lys Asn Val Ala Phe
    130                 135                 140

Gln Cys Pro Pro Ser Ile Leu Tyr Ile Leu Pro Asp Thr Val Asn Asn
145                 150                 155                 160

Gly Ile Arg Val Glu Phe Asn Gln Ala Tyr Asp Ile Glu Gly Val Thr
                165                 170                 175
```

```
Glu Lys Leu Val Thr Lys Cys Ser Gln Met Asn Arg Pro Leu Ala Gly
            180                 185                 190

Ser Ala Ala Val His Ile Pro Arg Tyr His Ile Thr Tyr His Thr
        195                 200                 205

Lys Leu Ser Lys Asp Arg Asp Glu Arg Arg Asp His Met Cys Leu Val
    210                 215                 220

Glu Val Val Lys Ala Val Asp Leu Asp Thr Tyr Gln
225                 230                 235

<210> SEQ ID NO 14
<211> LENGTH: 89
<212> TYPE: DNA
<213> ORGANISM: Artificial Sequence
<220> FEATURE:
<223> OTHER INFORMATION: Primer IF-nbMT78.c

<400> SEQUENCE: 14
tttcatttgg agaggcacac aatttgcttt agtgattaaa ctttctttta caacaaatta      60
aaggtctatt atctcccaac aacataaga                                        89

<210> SEQ ID NO 15
<211> LENGTH: 59
<212> TYPE: DNA
<213> ORGANISM: Artificial Sequence
<220> FEATURE:
<223> OTHER INFORMATION: Primer nbMT78_Dasher.c

<400> SEQUENCE: 15
ttaaaggtct attatctccc aacaacataa gaaaacaatg actgccctga ccgaaggtg       59

<210> SEQ ID NO 16
<211> LENGTH: 59
<212> TYPE: DNA
<213> ORGANISM: Artificial Sequence
<220> FEATURE:
<223> OTHER INFORMATION: Primer atHSP69_Dasher.c

<400> SEQUENCE: 16
ccaaaaaaaa cacagaccct taaaaaaataa aaatgactgc cctgaccgaa ggtgctaag      59

<210> SEQ ID NO 17
<211> LENGTH: 84
<212> TYPE: DNA
<213> ORGANISM: Artificial Sequence
<220> FEATURE:
<223> OTHER INFORMATION: Primer IF-atHSP69.c

<400> SEQUENCE: 17
tttcatttgg agaggcaaat tcaaaattta acacacaaac acaaacacac acaccaaaaa      60
aaacacagac cttaaaaaaa taaa                                             84

<210> SEQ ID NO 18
<211> LENGTH: 52
<212> TYPE: DNA
<213> ORGANISM: Artificial Sequence
<220> FEATURE:
<223> OTHER INFORMATION: Primer nbEPI42+Dasher.c

<400> SEQUENCE: 18
tttcaacaaa atcaagaatt tcagcaatga ctgccctgac cgaaggtgct aa              52

<210> SEQ ID NO 19
```

```
<211> LENGTH: 59
<212> TYPE: DNA
<213> ORGANISM: Artificial Sequence
<220> FEATURE:
<223> OTHER INFORMATION: Primer IF-nbEPI42.c

<400> SEQUENCE: 19
atttcatttg gagaggcact ttaatttgct gattttcaac aaaatcaaga atttcagca       59

<210> SEQ ID NO 20
<211> LENGTH: 52
<212> TYPE: DNA
<213> ORGANISM: Artificial Sequence
<220> FEATURE:
<223> OTHER INFORMATION: Primer nbSNS46+Dasher.c

<400> SEQUENCE: 20
ttgagtaagt tatcaaaaag caaaaaatga ctgccctgac cgaaggtgct aa             52

<210> SEQ ID NO 21
<211> LENGTH: 63
<212> TYPE: DNA
<213> ORGANISM: Artificial Sequence
<220> FEATURE:
<223> OTHER INFORMATION: Primer IF-nbSNS46.c

<400> SEQUENCE: 21
atttcatttg gagaggcatt cagtgcttaa ctggttattg agtaagttat caaaaagcaa    60
aaa                                                                  63

<210> SEQ ID NO 22
<211> LENGTH: 52
<212> TYPE: DNA
<213> ORGANISM: Artificial Sequence
<220> FEATURE:
<223> OTHER INFORMATION: Primer nbCSY65+Dasher.c

<400> SEQUENCE: 22
cctaaaaaca aaaaaaaggc atacaaatga ctgccctgac cgaaggtgct aa             52

<210> SEQ ID NO 23
<211> LENGTH: 82
<212> TYPE: DNA
<213> ORGANISM: Artificial Sequence
<220> FEATURE:
<223> OTHER INFORMATION: Primer IF-nbCSY65.c

<400> SEQUENCE: 23
atttcatttg gagaggcact tttctaatca atcatcaaac agaacgcaga aaatttccta    60
aaaacaaaaa aaaggcatac aa                                             82

<210> SEQ ID NO 24
<211> LENGTH: 53
<212> TYPE: DNA
<213> ORGANISM: Artificial Sequence
<220> FEATURE:
<223> OTHER INFORMATION: Primer nbHEL40+Dasher.c

<400> SEQUENCE: 24
ctatcaaacc aaaacacatt gagcaaaatg actgccctga ccgaaggtgc taa            53

<210> SEQ ID NO 25
<211> LENGTH: 56
<212> TYPE: DNA
<213> ORGANISM: Artificial Sequence
```

```
<220> FEATURE:
<223> OTHER INFORMATION: Primer IF-nbHEL40.c

<400> SEQUENCE: 25
atttcatttg gagaggcact ccatttgaat ctatcaaacc aaaacacatt gagcaa        56

<210> SEQ ID NO 26
<211> LENGTH: 53
<212> TYPE: DNA
<213> ORGANISM: Artificial Sequence
<220> FEATURE:
<223> OTHER INFORMATION: Primer nbSEP44+Dasher.c

<400> SEQUENCE: 26
tttattctct ttcaaaacct acactcatga ctgccctgac cgaaggtgct aag           53

<210> SEQ ID NO 27
<211> LENGTH: 61
<212> TYPE: DNA
<213> ORGANISM: Artificial Sequence
<220> FEATURE:
<223> OTHER INFORMATION: Primer IF-nbSEP44.c

<400> SEQUENCE: 27
atttcatttg gagaggcact tcaatcactc cacactttat tctctttcaa aacctacact   60
c                                                                    61

<210> SEQ ID NO 28
<211> LENGTH: 48
<212> TYPE: DNA
<213> ORGANISM: Artificial Sequence
<220> FEATURE:
<223> OTHER INFORMATION: Primer IF-GII4Syd12VP1.r

<400> SEQUENCE: 28
actaaagaaa ataggccttc agacagccct gcgtctgcca gtcccatt                 48

<210> SEQ ID NO 29
<211> LENGTH: 1783
<212> TYPE: DNA
<213> ORGANISM: Artificial Sequence
<220> FEATURE:
<223> OTHER INFORMATION: CPMV 160 5'UTR-VP1 (GII.4) DNA sequence

<400> SEQUENCE: 29
tattaaaatc ttaataggtt ttgataaaag cgaacgtggg gaaacccgaa ccaaaccttc    60
ttctaaactc tctctcatct ctcttaaagc aaacttctct cttgtctttc ttgcgtgagc  120
gatcttcaac gttgtcagat cgtgcttcgg caccagtaca atgaaaatgg cctcgagtga  180
cgctaaccct agtgacggca cgccgccaa tcttgtgcct gaggttaata atgaggtgat   240
ggccctggag cctgtggtgg gcgcagccat agcagcgccc gtggccggtc agcagaatgt  300
gattgacccg tggatacgca caatttttgt ccaagcccct ggtggggagt tcaccgttag  360
cccgagaaat gcgccaggag aaatcctgtg gtcggccagc ttgggacccg atctgaaccc  420
ctatttgtca catctcgctc ggatgtacaa cgggtatgcc ggcggatttg aagtgcaggt  480
gattctggct gggaacgcgt tcactgctgg caaagtgatc tttgcagcgg tgcctccaa   540 cttcccccact gaaggactgt ctccaagcca ggtcacaatg tttccacaca tcgtggtgga  600
cgtacggcag ctagagcctg tcctgattcc cctccctgat gtacgcaata atttctacca  660
ctacaatcaa tccaatgatc cgaccattaa actcatcgcg atgttgtaca cccctctgcg  720
```

```
cgctaacaat gctggagacg acgtattcac cgtgtcatgc agagtgctca ccagaccttc     780
accagacttt gactttatct tcttagtgcc ccccactgtt gagagccgaa ccaagccctt     840
tagtgtcccc gtactcacag tcgaggagat gacaaatagc cgctttccaa tccccttga      900 gaaactgttc acaggacctt cctcggcatt cgtggttcag ccacagaacg gacgctgcac     960
aactgacggc gtgctgctcg gaaccaccca gcttagccct gttaatatct gtacgtttag    1020
aggcgacgta actcacataa ctggctcacg gaactatacc atgaatctgg catcacagaa    1080
ttggaatgac tacgacccaa ccgaagagat tcccgcacct cttggaaccc ccgactttgt    1140
gggaaaaata cagggcgtcc tgacacaaac caccagaacc gatggctcca cacggggaca    1200
caaggcaacc gtctacactg gctctgccga ttttgccccg aaactgggta gagtgcagtt    1260
tgagaccgac actgaccggg actttgaagc caatcagaat actaagttca cacctgtagg    1320
agtgattcag gacgggggca ccactcaccg gaacgagccg caacaatggg tcctgccctc    1380
ttatagcggg aggaatactc ataatgtgca tttggctcct gcagtggctc ccacgtttcc    1440 cgggaacaa ctgctctttt ttcgttcaac catgcctgga tgctccggat atcccaatat     1500
ggatctcgat tgcctgctcc cacaggaatg ggtgcagtat ttttatcaag aggccgcacc    1560
agcccaatcc gacgtcgcac ttctgcggtt cgtgaatcca gacacaggcc gcgtgttgtt    1620
tgagtgcaaa ttgcacaaat caggatacgt tacagtggct catactggac agcatgacct    1680
ggtgatccca cccaacggat attttaggtt cgactcctgg gtgaatcagt tttatacatt    1740
agcccccatg gggaatggga ctggcagacg cagggctgtc tga                      1783

<210> SEQ ID NO 30
<211> LENGTH: 1623
<212> TYPE: DNA
<213> ORGANISM: Artificial Sequence
<220> FEATURE:
<223> OTHER INFORMATION: VP1 (GII.4) DNA sequence

<400> SEQUENCE: 30
atgaaaatgg cctcgagtga cgctaaccct agtgacggca gcgccgccaa tcttgtgcct      60
gaggttaata atgaggtgat ggccctggag cctgtggtgg gcgcagccat agcagcgccc     120
gtggccggtc agcagaatgt gattgacccg tggatacgca acaattttgt ccaagcccct     180 ggtgggagt tcaccgttag cccgagaaat gcgccaggag aaatcctgtg gtcggccagc      240
ttgggacccg atctgaaccc ctatttgtca catctcgctc ggatgtacaa cgggtatgcc     300
ggcggatttg aagtgcaggt gattctggct gggaacgcgt tcactgctgg caaagtgatc     360
tttgcagcgg tgcctcccaa cttccccact gaaggactgt ctccaagcca ggtcacaatg     420
tttccacaca cgtggtgga cgtacggcag ctagagcctg tcctgattcc cctccctgat     480
gtacgcaata atttctacca ctacaatcaa tccaatgatc cgaccattaa actcatcgcg     540
atgttgtaca cccctctgcg cgctaacaat gctggagacg acgtattcac cgtgtcatgc     600
agagtgctca ccagaccttc accagacttt gactttatct tcttagtgcc ccccactgtt     660
gagagccgaa ccaagccctt tagtgtcccc gtactcacag tcgaggagat gacaaatagc     720
cgctttccaa tccccttga gaaactgttc acaggacctt cctcggcatt cgtggttcag      780
ccacagaacg gacgctgcac aactgacggc gtgctgctcg gaaccaccca gcttagccct     840
gttaatatct gtacgtttag aggcgacgta actcacataa ctggctcacg gaactatacc     900
atgaatctgg catcacagaa ttggaatgac tacgacccaa ccgaagagat tcccgcacct     960
cttggaaccc ccgactttgt gggaaaaata cagggcgtcc tgacacaaac caccagaacc    1020
```

-continued

```
gatggctcca cacggggaca caaggcaacc gtctacactg gctctgccga ttttgccccg    1080
aaactgggta gagtgcagtt tgagaccgac actgaccggg actttgaagc caatcagaat    1140
actaagttca cacctgtagg agtgattcag gacgggggca ccactcaccg gaacgagccg    1200
caacaatggg tcctgccctc ttatagcggg aggaatactc ataatgtgca tttggctcct    1260
gcagtggctc ccacgtttcc cggggaacaa ctgctctttt ttcgttcaac catgcctgga    1320
tgctccggat atcccaatat ggatctcgat tgcctgctcc acaggaatg ggtgcagtat    1380 ttttatcaag aggccgcacc agcccaatcc gacgtcgcac ttctgcggtt cgtgaatcca    1440
gacacaggcc gcgtgttgtt tgagtgcaaa ttgcacaaat caggatacgt tacagtggct    1500
catactggac agcatgacct ggtgatccca cccaacggat attttaggtt cgactcctgg    1560
gtgaatcagt tttatacatt agcccccatg gggaatggga ctggcagacg cagggctgtc    1620
tga                                                                  1623
```

<210> SEQ ID NO 31
<211> LENGTH: 540
<212> TYPE: PRT
<213> ORGANISM: Artificial Sequence
<220> FEATURE:
<223> OTHER INFORMATION: VP1 (GII.4) protein sequence

<400> SEQUENCE: 31

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Ser
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
```

```
            245                 250                 255
Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540

<210> SEQ ID NO 32
<211> LENGTH: 59
<212> TYPE: DNA
<213> ORGANISM: Artificial Sequence
<220> FEATURE:
<223> OTHER INFORMATION: Primer nbMT78+GII4Syd12.c

<400> SEQUENCE: 32
tctattatct cccaacaaca taagaaaaca atgaaaatgg cctcgagtga cgctaaccc       59

<210> SEQ ID NO 33
<211> LENGTH: 59
<212> TYPE: DNA
<213> ORGANISM: Artificial Sequence
<220> FEATURE:
<223> OTHER INFORMATION: Primer atHSP69+GII4Syd12.c

<400> SEQUENCE: 33
aaacacagac cttaaaaaaa taaaaatgaa aatggcctcg agtgacgcta accctagtg       59
```

<210> SEQ ID NO 34
<211> LENGTH: 56
<212> TYPE: DNA
<213> ORGANISM: Artificial Sequence
<220> FEATURE:
<223> OTHER INFORMATION: Primer nbEPI42+GII4Syd12.c

<400> SEQUENCE: 34
tgattttcaa caaaatcaag aatttcagca atgaaaatgg cctcgagtga cgctaa        56

<210> SEQ ID NO 35
<211> LENGTH: 52
<212> TYPE: DNA
<213> ORGANISM: Artificial Sequence
<220> FEATURE:
<223> OTHER INFORMATION: nbSNS46+GII4Syd12.c

<400> SEQUENCE: 35
ttgagtaagt tatcaaaaag caaaaaatga aaatggcctc gagtgacgct aa        52

<210> SEQ ID NO 36
<211> LENGTH: 53
<212> TYPE: DNA
<213> ORGANISM: Artificial SEquence
<220> FEATURE:
<223> OTHER INFORMATION: Primer nbCSY65+GII4Syd12.c

<400> SEQUENCE: 36
tcctaaaaac aaaaaaaagg catacaaatg aaaatggcct cgagtgacgc taa        53

<210> SEQ ID NO 37
<211> LENGTH: 56
<212> TYPE: DNA
<213> ORGANISM: Artificial Sequence
<220> FEATURE:
<223> OTHER INFORMATION: Primer nbHEL40+GII4Syd12.c

<400> SEQUENCE: 37
tctatcaaac caaaacacat tgagcaaaat gaaaatggcc tcgagtgacg ctaacc        56

<210> SEQ ID NO 38
<211> LENGTH: 53
<212> TYPE: DNA
<213> ORGANISM: Artificial Sequence
<220> FEATURE:
<223> OTHER INFORMATION: Primer nbSEP44+GII4Syd12.c

<400> SEQUENCE: 38
ctttattctc tttcaaaacc tacactcatg aaaatggcct cgagtgacgc taa        53

<210> SEQ ID NO 39
<211> LENGTH: 51
<212> TYPE: DNA
<213> ORGANISM: Artificial Sequence
<220> FEATURE:
<223> OTHER INFORMATION: Primer IF -HC(Ritux).s1-6r

<400> SEQUENCE: 39
actaaagaaa ataggccttc actttccagg agaaagagaa agggactttt g        51

<210> SEQ ID NO 40
<211> LENGTH: 1588
<212> TYPE: DNA
<213> ORGANISM: Artificial Sequence
<220> FEATURE:

<223> OTHER INFORMATION: CPMV 160 5'UTR-PDI+Rituximab HC DNA sequence

<400> SEQUENCE: 40

```
tattaaaatc ttaataggtt ttgataaaag cgaacgtggg gaaacccgaa ccaaaccttc      60
ttctaaactc tctctcatct ctcttaaagc aaacttctct cttgtctttc ttgcgtgagc     120
gatcttcaac gttgtcagat cgtgcttcgg caccagtaca atggcgaaaa acgttgcgat     180
tttcggctta ttgttttctc ttcttgtgtt ggttccttct cagatcttcg cgcaggtaca     240
actgcagcag cctggggctg agctggtgaa gcctggggcc tcagtgaaga tgtcctgcaa     300
ggcttctggc tacacattta ccagttacaa tatgcactgg gtaaaacaga cacctggtcg     360
gggcctggaa tggattggag ctatttatcc cggaaatggt gatacttcct acaatcagaa     420
gttcaaaggc aaggccacat tgactgcaga caaatcctcc agcacagcct acatgcagct     480
cagcagcctg acatctgagg actctgcggt ctattactgt gcaagatcga cttactacgg     540
cggtgactgg tacttcaatg tctggggcgc agggaccacg gtcaccgtct ctgcagctag     600
caccaagggc ccatcggtct tccccctggc accctcctcc aagagcacct ctgggggcac     660
agcggccctg ggctgcctgg tcaaggacta cttccccgaa ccggtgacgg tgtcgtggaa     720
ctcaggcgcc ctgaccagcg gcgtgcacac cttcccggct gtcctacagt cctcaggact     780
ctactccctc agcagcgtgg tgaccgtgcc ctccagcagc ttgggcaccc agacctacat     840
ctgcaacgtg aatcacaagc ccagcaacac caaggtggac aagaaagttg agcccaaatc     900
ttgtgacaaa actcacacat gcccaccgtg cccagcacct gaactcctgg ggggaccgtc     960
agtcttcctc ttccccccaa aacccaagga caccctcatg atctcccgga cccctgaggt    1020
cacatgcgtg gtggtggacg tgagccacga agaccctgag gtcaagttca actggtacgt    1080
ggacggcgtg gaggtgcata atgccaagac aaagccgcgg gaggagcagt acaacagcac    1140
gtaccgtgtg gtcagcgtcc tcaccgtcct gcaccaggac tggctgaatg caaggagta    1200
caagtgcaag gtctccaaca aagccctccc agccccatc gagaaaacca tctccaaagc    1260
caaagggcag cctagggaac acaagtgta cactcttcca ccatctaggg atgagcttac    1320
taagaaccaa gttctctta cttgtcttgt gaagggattt tatccatctg acatcgccgt    1380
ggaatgggaa tccaacggac aaccagagaa caattacaag actactccac cagttcttga    1440
ttctgatgga tccttctttc tttattccaa gcttactgtt gataagtcca gatggcagca    1500
aggaaatgtg ttctcttgtt ctgttatgca cgaagctctt cataatcatt atactcaaaa    1560
gtccctttct ctttctcctg aaagtga                                        1588
```

<210> SEQ ID NO 41
<211> LENGTH: 1428
<212> TYPE: DNA
<213> ORGANISM: Artificial Sequence
<220> FEATURE:
<223> OTHER INFORMATION: PDI+Rituximab HC DNA sequence

<400> SEQUENCE: 41

```
atggcgaaaa acgttgcgat tttcggctta ttgttttctc ttcttgtgtt ggttccttct      60
cagatcttcg cgcaggtaca actgcagcag cctggggctg agctggtgaa gcctggggcc    120
tcagtgaaga tgtcctgcaa ggcttctggc tacacattta ccagttacaa tatgcactgg    180
gtaaaacaga cacctggtcg gggcctggaa tggattggag ctatttatcc cggaaatggt    240
gatacttcct acaatcagaa gttcaaaggc aaggccacat tgactgcaga caaatcctcc    300
agcacagcct acatgcagct cagcagcctg acatctgagg actctgcggt ctattactgt    360
```

```
gcaagatcga cttactacgg cggtgactgg tacttcaatg tctggggcgc agggaccacg    420
gtcaccgtct ctgcagctag caccaagggc ccatcggtct tccccctggc accctcctcc    480
aagagcacct ctgggggcac agcggccctg ggctgcctgg tcaaggacta cttccccgaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtggac    720
aagaaagttg agcccaaatc ttgtgacaaa actcacacat gcccaccgtg cccagcacct    780
gaactcctgg ggggaccgtc agtcttcctc ttccccccaa acccaaggac accctcatg     840 atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caagtgcaag gtctccaaca aagccctccc agcccccatc   1080
gagaaaacca tctccaaagc caaagggcag cctagggaac cacaagtgta cactcttcca   1140
ccatctaggg atgagcttac taagaaccaa gtttctctta cttgtcttgt gaagggattt   1200
tatccatctg acatcgccgt ggaatgggaa tccaacggac aaccagagaa caattacaag   1260
actactccac cagttcttga ttctgatgga tccttctttc tttattccaa gcttactgtt   1320
gataagtcca gatggcagca aggaaatgtg ttctcttgtt ctgttatgca cgaagctctt   1380
cataatcatt atactcaaaa gtcccttttct ctttctcctg gaaagtga                 1428
```

<210> SEQ ID NO 42  
<211> LENGTH: 475  
<212> TYPE: PRT  
<213> ORGANISM: Artificial Sequence  
<220> FEATURE:  
<223> OTHER INFORMATION: PDI+Rituximab HC protein sequence

<400> SEQUENCE: 42

```
Met Ala Lys Asn Val Ala Ile Phe Gly Leu Leu Phe Ser Leu Leu Val
1               5                   10                  15

Leu Val Pro Ser Gln Ile Phe Ala Gln Val Gln Leu Gln Gln Pro Gly
                20                  25                  30

Ala Glu Leu Val Lys Pro Gly Ala Ser Val Lys Met Ser Cys Lys Ala
            35                  40                  45

Ser Gly Tyr Thr Phe Thr Ser Tyr Asn Met His Trp Val Lys Gln Thr
        50                  55                  60

Pro Gly Arg Gly Leu Glu Trp Ile Gly Ala Ile Tyr Pro Gly Asn Gly
65                  70                  75                  80

Asp Thr Ser Tyr Asn Gln Lys Phe Lys Gly Lys Ala Thr Leu Thr Ala
                85                  90                  95

Asp Lys Ser Ser Ser Thr Ala Tyr Met Gln Leu Ser Ser Leu Thr Ser
            100                 105                 110

Glu Asp Ser Ala Val Tyr Tyr Cys Ala Arg Ser Thr Tyr Tyr Gly Gly
        115                 120                 125

Asp Trp Tyr Phe Asn Val Trp Gly Ala Gly Thr Thr Val Thr Val Ser
    130                 135                 140

Ala Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175
```

Tyr Phe Pro Glu Pro Val Thr Val Ser Trp Asn Ser Gly Ala Leu Thr
                180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
        210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
                370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
450                 455                 460

Thr Gln Lys Ser Leu Ser Leu Ser Pro Gly Lys
465                 470                 475

<210> SEQ ID NO 43
<211> LENGTH: 51
<212> TYPE: DNA
<213> ORGANISM: Artificial Sequence
<220> FEATURE:
<223> OTHER INFORMATION: IF -LC(Ritux).s1-6r

<400> SEQUENCE: 43
actaaagaaa ataggccttc aacactctcc cctgttgaag ctctttgtga c          51

<210> SEQ ID NO 44
<211> LENGTH: 874
<212> TYPE: DNA
<213> ORGANISM: Artificial Sequence
<220> FEATURE:
<223> OTHER INFORMATION: CPMV 160 5'UTR-PDI+Rituximab LC DNA sequence

<400> SEQUENCE: 44

```
tattaaaatc ttaataggtt ttgataaaag cgaacgtggg gaaacccgaa ccaaaccttc      60
ttctaaactc tctctcatct ctcttaaagc aaacttctct cttgtctttc ttgcgtgagc     120
gatcttcaac gttgtcagat cgtgcttcgg caccagtaca atggcgaaaa acgttgcgat     180
tttcggctta ttgttttctc ttcttgtgtt ggttccttct cagatcttcg cgcaaattgt     240
tctctcccag tctccagcaa tcctgtctgc atctccaggg gagaaggtca caatgacttg     300
cagggccagc tcaagtgtaa gttacatcca ctggttccag cagaagccag gatcctcccc     360
caaaccctgg atttatgcca catccaacct ggcttctgga gtccctgttc gcttcagtgg     420
cagtgggtct gggacttctt actctctcac aatcagcaga gtggaggctg aagatgctgc     480
cacttattac tgccagcagt ggactagtaa cccacccacg ttcggagggg ggaccaagct     540
ggaaatcaaa cgtacggtgg ctgcaccatc tgtcttcatc ttcccgccat ctgatgagca     600
gttgaaatct ggaactgcct ctgttgtgtg cctgctgaat aacttctatc ccagagaggc     660
caaagtacag tggaaggtgg ataacgccct ccaatcgggt aactcccagg agagtgtcac     720
agagcaggac agcaaggaca gcacctacag cctcagcagc accctgacgc tgagcaaagc     780
agactacgag aaacacaaag tctacgcctg cgaagtcacc catcagggcc tgagctcgcc     840
cgtcacaaag agcttcaaca ggggagagtg ttga                                 874
```

<210> SEQ ID NO 45
<211> LENGTH: 714
<212> TYPE: DNA
<213> ORGANISM: Artificial Sequence
<220> FEATURE:
<223> OTHER INFORMATION: PDI+Rituximab LC DNA sequence

<400> SEQUENCE: 45

```
atggcgaaaa acgttgcgat tttcggctta ttgttttctc ttcttgtgtt ggttccttct      60
cagatcttcg cgcaaattgt tctctcccag tctccagcaa tcctgtctgc atctccaggg    120
gagaaggtca caatgacttg cagggccagc tcaagtgtaa gttacatcca ctggttccag    180
cagaagccag gatcctcccc caaaccctgg atttatgcca catccaacct ggcttctgga    240
gtccctgttc gcttcagtgg cagtgggtct gggacttctt actctctcac aatcagcaga    300
gtggaggctg aagatgctgc cacttattac tgccagcagt ggactagtaa cccacccacg    360
ttcggagggg ggaccaagct ggaaatcaaa cgtacggtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct caatcgggt    540 aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttga          714
```

<210> SEQ ID NO 46
<211> LENGTH: 237
<212> TYPE: PRT
<213> ORGANISM: Artificial Sequence
<220> FEATURE:
<223> OTHER INFORMATION: PDI+Rituximab LC protein sequence

<400> SEQUENCE: 46

```
Met Ala Lys Asn Val Ala Ile Phe Gly Leu Leu Phe Ser Leu Leu Val
1               5                   10                  15

Leu Val Pro Ser Gln Ile Phe Ala Gln Ile Val Leu Ser Gln Ser Pro
```

```
            20                  25                  30
Ala Ile Leu Ser Ala Ser Pro Gly Glu Lys Val Thr Met Thr Cys Arg
             35                  40                  45

Ala Ser Ser Ser Val Ser Tyr Ile His Trp Phe Gln Gln Lys Pro Gly
 50                  55                  60

Ser Ser Pro Lys Pro Trp Ile Tyr Ala Thr Ser Asn Leu Ala Ser Gly
 65                  70                  75                  80

Val Pro Val Arg Phe Ser Gly Ser Gly Ser Gly Thr Ser Tyr Ser Leu
                 85                  90                  95

Thr Ile Ser Arg Val Glu Ala Glu Asp Ala Ala Thr Tyr Tyr Cys Gln
             100                 105                 110

Gln Trp Thr Ser Asn Pro Pro Thr Phe Gly Gly Gly Thr Lys Leu Glu
            115                 120                 125

Ile Lys Arg Thr Val Ala Ala Pro Ser Val Phe Ile Phe Pro Pro Ser
        130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 47
<211> LENGTH: 59
<212> TYPE: DNA
<213> ORGANISM: Artificial Sequence
<220> FEATURE:
<223> OTHER INFORMATION: nbMT78_SpPDI.c

<400> SEQUENCE: 47
tattatctcc caacaacata agaaaacaat ggcgaaaaac gttgcgattt tcggcttat     59

<210> SEQ ID NO 48
<211> LENGTH: 59
<212> TYPE: DNA
<213> ORGANISM: Artificial Sequence
<220> FEATURE:
<223> OTHER INFORMATION: atHSP69_SpPDI.c

<400> SEQUENCE: 48
caaaaaaaac acagacctta aaaaaataaa aatggcgaaa aacgttgcga ttttcggct     59

<210> SEQ ID NO 49
<211> LENGTH: 54
<212> TYPE: DNA
<213> ORGANISM: Artificial Sequence
<220> FEATURE:
<223> OTHER INFORMATION: nbEPI42+PDI.c

<400> SEQUENCE: 49
tttcaacaaa atcaagaatt tcagcaatgg cgaaaaacgt tgcgattttc ggct           54

<210> SEQ ID NO 50
```

```
<211> LENGTH: 53
<212> TYPE: DNA
<213> ORGANISM: Artificial Sequence
<220> FEATURE:
<223> OTHER INFORMATION: nbSNS46+PDI.c

<400> SEQUENCE: 50
ttgagtaagt tatcaaaaag caaaaaatgg cgaaaaacgt tgcgattttc ggc          53

<210> SEQ ID NO 51
<211> LENGTH: 53
<212> TYPE: DNA
<213> ORGANISM: Artificial Sequence
<220> FEATURE:
<223> OTHER INFORMATION: nbCSY65 plus PDI.c

<400> SEQUENCE: 51
cctaaaaaca aaaaaaggc atacaaatgg cgaaaaacgt tgcgattttc ggc           53

<210> SEQ ID NO 52
<211> LENGTH: 55
<212> TYPE: DNA
<213> ORGANISM: Artificial Sequence
<220> FEATURE:
<223> OTHER INFORMATION: nbHEL40+PDI.c

<400> SEQUENCE: 52
ctatcaaacc aaaacacatt gagcaaaatg gcgaaaaacg ttgcgatttt cggct        55

<210> SEQ ID NO 53
<211> LENGTH: 57
<212> TYPE: DNA
<213> ORGANISM: Artificial Sequence
<220> FEATURE:
<223> OTHER INFORMATION: nbSEP44+PDI.c

<400> SEQUENCE: 53
tttattctct ttcaaaacct acactcatgg cgaaaaacgt tgcgattttc ggcttat     57

<210> SEQ ID NO 54
<211> LENGTH: 46
<212> TYPE: DNA
<213> ORGANISM: Artificial Sequence
<220> FEATURE:
<223> OTHER INFORMATION: IF-H1cTMCT.s1-4r

<400> SEQUENCE: 54
actaaagaaa ataggccttt aaatacatat tctacactgt agagac                 46

<210> SEQ ID NO 55
<211> LENGTH: 1882
<212> TYPE: DNA
<213> ORGANISM: Artificial Sequence
<220> FEATURE:
<223> OTHER INFORMATION: CPMV 160 5'UTR-PDI+H1 Mich DNA sequence

<400> SEQUENCE: 55
tattaaaatc ttaataggtt ttgataaaag cgaacgtggg gaaacccgaa ccaaaccttc   60
ttctaaactc tctctcatct ctcttaaagc aaacttctct cttgtctttc ttgcgtgagc  120
gatcttcaac gttgtcagat cgtgcttcgg caccagtaca atggcgaaaa acgttgcgat  180 ttcggctta tgttttctc ttcttgtgtt ggttccttct cagatcttcg cggacacatt   240
atgtataggt tatcatgcga acaattcaac agacactgta gacacagtac tagaaaagaa  300
tgtaacagta acacactctg ttaaccttct ggaagacaag cataacggaa aactatgcaa  360
```

-continued

```
actaagaggg gtagccccat tgcatttggg taaatgtaac attgctggct ggatcctggg        420
aaatccagag tgtgaatcac tctccacagc aagttcatgg tcctacattg tggaaacatc        480
taattcagac aatggaacgt gttacccagg agatttcatc aattatgagg agctaagaga        540
gcaattgagc tcagtgtcat catttgaaag gtttgagata ttccccaaga caagttcatg        600
gcccaatcat gactcgaaca aaggtgtaac ggcagcatgt cctcacgctg agcaaaaag         660 cttctacaaa aacttgatat ggctagttaa aaaaggaaat tcatacccaa agcttaacca        720
atcctacatt aatgataaag ggaagaagt cctcgtgctg tggggcattc accatccatc         780
tactactgct gaccaacaaa gtctctatca gaatgcagat gcatatgttt ttgtggggac        840
atcaagatac agcaagaagt tcaagccgga aatagcaaca agacccaaag tgagggatca        900
agaagggaga atgaactatt actggacact agtagagccg ggagacaaaa taacattcga        960
agcaactgga aatctagtgg taccgagata tgcattcaca atggaaagaa atgctggatc       1020
tggtattatc atttcagata caccagtcca cgattgcaat acaacttgtc agacacccga       1080
gggtgctata aacaccagcc tcccatttca gaatatacat ccgatcacaa ttggaaaatg       1140
tccaaagtat gtaaaagca caaaattgag actggccaca ggattgagga atgttccgtc        1200
tattcaatct agaggcctat tcggggccat tgccggcttc attgaagggg ggtggacagg       1260
gatggtagat ggatggtacg gttatcacca tcaaaatgag cagggtcag gatatgcagc        1320 cgacctgaag agcacacaaa atgccattga caagattact aacaaagtaa attctgttat       1380
tgaaaagatg aatacacagg acacagcagt gggtaaagag ttcaaccacc tggaaaaaag       1440
aatagagaat ctaaataaaa aagttgatga tggttccctg gacatttgga cttacaatgc       1500
cgaactgttg gttctaatgg aaaatgaaag aactttggac tatcacgatt caaatgtgaa       1560
gaacttgtat gaaaaagtaa gaaccagtt aaaaaacaat gccaaggaaa ttggaaacgg       1620
ctgctttgaa ttttaccaca atgcgataa cacgtgcatg gaaagtgtca aaaatgggac        1680
ttatgactac ccaaaatact cagaggaagc aaaattaaac agagaaaaaa tagatggggt       1740
aaagctggaa tcaacaagga tttaccagat tttggcgatc tattcaactg tcgccagttc       1800
attggtactg gtagtctccc tgggggcaat cagcttctgg atgtgctcta atgggtctct       1860
acagtgtaga atatgtattt aa                                                1882
```

<210> SEQ ID NO 56
<211> LENGTH: 1722
<212> TYPE: DNA
<213> ORGANISM: Artificial Sequence
<220> FEATURE:
<223> OTHER INFORMATION: PDI+H1 Mich DNA sequence

<400> SEQUENCE: 56

```
atggcgaaaa acgttgcgat tttcggctta ttgttttctc ttcttgtgtt ggttccttct         60
cagatcttcg cggacacatt atgtataggt tatcatgcga acaattcaac agacactgta        120
gacacagtac tagaaaagaa tgtaacagta acacactctg ttaaccttct ggaagacaag        180
cataacggaa actatgcaa actaagaggg gtagccccat tgcatttggg taaatgtaac        240
attgctggct ggatcctggg aaatccagag tgtgaatcac tctccacagc aagttcatgg        300
tcctacattg tggaaacatc taattcagac aatggaacgt gttacccagg agatttcatc        360
aattatgagg agctaagaga gcaattgagc tcagtgtcat catttgaaag gtttgagata        420
ttccccaaga caagttcatg gcccaatcat gactcgaaca aaggtgtaac ggcagcatgt        480
```

```
cctcacgctg gagcaaaaag cttctacaaa aacttgatat ggctagttaa aaaggaaat      540 tcatacccaa agcttaacca atcctacatt aatgataaag ggaaagaagt cctcgtgctg     600
tggggcattc accatccatc tactactgct gaccaacaaa gtctctatca gaatgcagat     660
gcatatgttt ttgtggggac atcaagatac agcaagaagt tcaagccgga atagcaaca     720 agacccaaag tgagggatca agaagggaga atgaactatt actggacact agtagagccg    780
ggagacaaaa taacattcga agcaactgga atctagtgg taccgagata tgcattcaca     840
atggaaagaa atgctggatc tggtattatc atttcagata caccagtcca cgattgcaat    900
acaacttgtc agacacccga gggtgctata acaccagcc tcccatttca gaatatacat     960
ccgatcacaa ttggaaaatg tccaaagtat gtaaaaagca caaaattgag actggccaca    1020
ggattgagga atgttccgtc tattcaatct agaggcctat tcggggccat tgccggcttc    1080
attgaagggg ggtggacagg gatggtagat ggatggtacg gttatcacca tcaaaatgag    1140 cagggggtcag gatatgcagc cgacctgaag agcacacaaa atgccattga caagattact    1200
aacaaagtaa attctgttat tgaaaagatg aatacacagg acacagcagt gggtaaagag    1260
ttcaaccacc tggaaaaaag aatagagaat ctaaataaaa aagttgatga tggtttcctg    1320
gacatttgga cttacaatgc cgaactgttg gttctaatgg aaaatgaaag aactttggac    1380
tatcacgatt caaatgtgaa gaacttgtat gaaaaagtaa gaaaccagtt aaaaaacaat    1440
gccaaggaaa ttgaaacgg ctgctttgaa ttttaccaca aatgcgataa cacgtgcatg     1500
gaaagtgtca aaatgggac ttatgactac ccaaaatact cagaggaagc aaaattaaac     1560
agagaaaaaa tagatgggt aaagctggaa tcaacaagga tttaccagat tttggcgatc    1620
tattcaactg tcgccagttc attggtactg gtagtctccc tgggggcaat cagcttctgg    1680
atgtgctcta atgggtctct acagtgtaga atatgtattt aa                        1722
```

<210> SEQ ID NO 57
<211> LENGTH: 573
<212> TYPE: PRT
<213> ORGANISM: Artificial Sequence
<220> FEATURE:
<223> OTHER INFORMATION: PDI plus H1 Mich protein sequence

<400> SEQUENCE: 57

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
    130                 135                 140
```

```
Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Met Glu Asn Glu Arg Thr Leu Asp Tyr His Asp Ser
    450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
```

<210> SEQ ID NO 58
<211> LENGTH: 55
<212> TYPE: DNA
<213> ORGANISM: Artificial Sequence
<220> FEATURE:
<223> OTHER INFORMATION: IF-H3Minn15.r

<400> SEQUENCE: 58

```
actaaagaaa ataggccttc aaatgcaaat gttgcatcta atgttgccct tttgg        55
```

<210> SEQ ID NO 59
<211> LENGTH: 1885
<212> TYPE: DNA
<213> ORGANISM: Artificial Sequence
<220> FEATURE:
<223> OTHER INFORMATION: CPMV 160 5'UTR-PDI+H3 sing DNA sequence

<400> SEQUENCE: 59

```
tattaaaatc ttaataggtt ttgataaaag cgaacgtggg gaaacccgaa ccaaaccttc     60
ttctaaactc tctctcatct ctcttaaagc aaacttctct cttgtctttc ttgcgtgagc    120
gatcttcaac gttgtcagat cgtgcttcgg caccagtaca atggcgaaaa acgttgcgat    180
tttcggctta tgttttctc ttcttgtgtt ggttccttct cagatcttcg cgcaaaaaat    240
tcctggaaat gacaatagca cggcaacgct gtgccttggg caccatgcag taccaaacgg    300
aacgatagtg aaaacaatca caaatgaccg aattgaagtt actaatgcta ctgagttggt    360
tcagaattcc tcaataggtg aaatatgcga cagtcctcat cagatccttg atggagagaa    420
ctgcacacta atagatgctc tattgggaga ccctcagtgt gatggctttc aaaataagaa    480
atgggacctt tttgttgaac gaagcaaagc ctacagcaac tgttaccctt atgatgtgcc    540
ggattatgcc tcccttaggt cactagttgc ctcatccggc acactggagt ttaaaaatga    600
aagcttcaat tggactggag tcactcaaaa cggaacaagt tctgcttgca taaggggctc    660
tagtagtagt ttctttagta gattaaattg gttgacccac ttaaactaca catatccagc    720
attgaacgtg actatgccaa acaaggaaca atttgacaaa ttgtacattt ggggggttca    780
ccacccgggt acggacaagg accaaatctt cctgtatgct caatcatcag aagaatcac    840
agtatctacc aaaagaagcc aacaagctgt aatcccaaat atcggatcta gacccagaat    900
aagggatatc cctagcagaa taagcatcta ttggacaata gtaaaaccgg agacatact    960
tttgattaac agcacaggga atctaattgc tcctagggt tacttcaaaa tacgaagtgg   1020
gaaaagctca ataatgagat cagatgcacc cattggcaaa tgcaagtctg aatgcatcac   1080
tccaaatgga agcattccca atgacaaacc attccaaaat gtaaacagga tcacatacgg   1140
ggcctgtccc agatatgtta agcatagcac tctgaaattg caacaggaa tgcgaaatgt   1200
accagagaaa caaactagag gcatatttgg cgcaatagcg gtttcatag aaaatggttg   1260
ggagggaatg gtggatggtt ggtacggttt caggcatcaa aattctgagg gaagaggaca   1320
agcagcagat ctcaaaagca ctcaagcagc aatcgatcaa atcaatggga agctggctcg   1380
ggtgatcggg aaaccaacg agaaattcca tcagattgaa aaagaattct cagaagtaga   1440
aggaagagtt caagaccttg agaaatatgt tgaggacact aaaatagatc tctggtcata   1500
caacgcggag cttcttgttg ccctggagaa ccaacataca attgatctaa ctgactcaga   1560
aatgaacaaa ctgtttgaaa aacaaagaa gcaactgagg gaaatgctg aggatatggg   1620
aaatggttgt ttcaaaatat accacaaatg tgacaatgcc tgcataggat caataagaaa   1680
```

```
tgaaacttat gaccacaatg tgtacaggga tgaagcatta acaaccggt tccagatcaa    1740 gggagttgag ctgaagtcag ggtacaaaga ttggatccta tggatttcct ttgccatatc    1800
atcccttgta ctgttagttg ctttgttggg gttcatcatg tgggcctgcc aaaagggcaa    1860
cattagatgc aacatttgca tttga                                          1885

<210> SEQ ID NO 60
<211> LENGTH: 1725
<212> TYPE: DNA
<213> ORGANISM: Artificial Sequence
<220> FEATURE:
<223> OTHER INFORMATION: PDI+H3 sing DNA sequence

<400> SEQUENCE: 60
atggcgaaaa acgttgcgat ttcggctta ttgttttctc ttcttgtgtt ggttccttct      60
cagatcttcg cgcaaaaaat tcctggaaat gacaatagca cggcaacgct gtgccttggg    120
caccatgcag taccaaacgg aacgatagtg aaaacaatca caatgaccg aattgaagtt     180 actaatgcta ctgagttggt tcagaattcc tcaataggtg aaatatgcga cagtcctcat    240
cagatccttg atggagagaa ctgcacacta atagatgctc tattgggaga ccctcagtgt    300
gatggctttc aaaataagaa atgggacctt tttgttgaac gaagcaaagc ctacagcaac    360
tgttaccctt atgatgtgcc ggattatgcc tcccttaggt cactagttgc ctcatccggc    420
acactggagt ttaaaaatga agcttcaat ggactggag tcactcaaaa cggaacaagt     480
tctgcttgca aaggggctc tagtagtagt ttctttagta gattaaattg gttgacccac    540
ttaaactaca catatccagc attgaacgtg actatgccaa caaggaaca atttgacaaa    600 ttgtacattt gggggttca ccacccgggt acggacaagg accaaatctt cctgtatgct    660
caatcatcag gaagaatcac agtatctacc aaaagaagcc aacaagctgt aatcccaaat    720
atcggatcta gacccagaat aagggatatc cctagcagaa taagcatcta ttggacaata    780
gtaaaaccgg gagacatact tttgattaac agcacaggga atctaattgc tcctaggggt    840
tacttcaaaa tacgaagtgg gaaaagctca ataatgagat cagatgcacc cattggcaaa    900
tgcaagtctg aatgcatcac tccaaatgga agcattccca atgacaaacc attccaaaat    960
gtaaacagga tcacatacgg ggcctgtccc agatatgtta agcatagcac tctgaaattg   1020
gcaacaggaa tgcgaaatgt accagagaaa caaactagag catatttgg cgcaatagcg    1080 ggtttcatag aaaatggttg ggagggaatg gtggatggtt ggtacggttt caggcatcaa    1140
aattctgagg gaagaggaca agcagcagat ctcaaagcac tcaagcagc aatcgatcaa    1200 atcaatggga agctggctcg ggtgatcggg aaaaccaacg agaaattcca tcagattgaa    1260
aaagaattct cagaagtaga aggaagagtt caagaccttg agaaatatgt tgaggacact    1320
aaaatagatc tctggtcata caacgcggag cttcttgttg ccctggagaa ccaacataca    1380
attgatctaa ctgactcaga aatgaacaaa ctgtttgaaa aacaaagaa gcaactgagg    1440 gaaaatgctg aggatatggg aaatggttgt ttcaaaatat accacaaatg tgacaatgcc    1500
tgcataggat caataagaaa tgaaacttat gaccacaatg tgtacaggga tgaagcatta    1560
aacaaccggt tccagatcaa gggagttgag ctgaagtcag ggtacaaaga ttggatccta    1620
tggatttcct ttgccatatc atcccttgta ctgttagttg ctttgttggg gttcatcatg    1680
tgggcctgcc aaaagggcaa cattagatgc aacatttgca tttga                   1725

<210> SEQ ID NO 61
```

<211> LENGTH: 574
<212> TYPE: PRT
<213> ORGANISM: Artificial Sequence
<220> FEATURE:
<223> OTHER INFORMATION: PDI+H3 sing protein sequence

<400> SEQUENCE: 61

```
Met Ala Lys Asn Val Ala Ile Phe Gly Leu Leu Phe Ser Leu Leu Val
1               5                   10                  15

Leu Val Pro Ser Gln Ile Phe Ala Gln Lys Ile Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Arg Ile Glu Val Thr Asn Ala Thr
50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
130                 135                 140

Lys Asn Glu Ser Phe Asn Trp Thr Gly Val Thr Gln Asn Gly Thr Ser
145                 150                 155                 160

Ser Ala Cys Ile Arg Gly Ser Ser Ser Phe Phe Ser Arg Leu Asn
                165                 170                 175

Trp Leu Thr His Leu Asn Tyr Thr Tyr Pro Ala Leu Asn Val Thr Met
            180                 185                 190

Pro Asn Lys Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asp Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Lys Ser Glu
290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys His Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
370                 375                 380
```

```
Arg Gly Gln Ala Ala Asp Leu Lys Ser Thr Gln Ala Ala Ile Asp Gln
385                 390                 395                 400

Ile Asn Gly Lys Leu Ala Arg Val Ile Gly Lys Thr Asn Glu Lys Phe
            405                 410                 415

His Gln Ile Glu Lys Glu Phe Ser Glu Val Glu Gly Arg Val Gln Asp
        420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
            485                 490                 495

Cys Asp Asn Ala Cys Ile Gly Ser Ile Arg Asn Glu Thr Tyr Asp His
        500                 505                 510

Asn Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Ser Leu Val Leu Leu Val Ala Leu Leu Gly Phe Ile Met
545                 550                 555                 560

Trp Ala Cys Gln Lys Gly Asn Ile Arg Cys Asn Ile Cys Ile
            565                 570

<210> SEQ ID NO 62
<211> LENGTH: 4337
<212> TYPE: DNA
<213> ORGANISM: Artificial Sequence
<220> FEATURE:
<223> OTHER INFORMATION: Cloning vector 1666 from left to right T-DNA

<400> SEQUENCE: 62
tggcaggata tattgtggtg taaacaaatt gacgcttaga caacttaata acacattgcg      60
gacgttttta atgtactgaa ttaacgccga atcccgggct ggtatattta tatgttgtca     120 ataactcaa aaaccataaa agtttaagtt agcaagtgtg tacatttta cttgaacaaa      180 aatattcacc tactactgtt ataaatcatt attaaacatt agagtaaaga aatatggatg     240
ataagaacaa gagtagtgat attttgacaa caattttgtt gcaacatttg agaaaattt      300 gttgttctct cttttcattg gtcaaaaaca atagagagag aaaaaggaag agggagaata     360
aaaacataat gtgagtatga gagagaaagt tgtacaaaag ttgtaccaaa atagttgtac     420
aaatatcatt gaggaatttg acaaaagcta cacaaataag ggttaattgc tgtaaataaa     480
taaggatgac gcattagaga gatgtaccat tagagaattt ttggcaagtc attaaaaaga     540
aagaataaat tattttttaaa attaaaagtt gagtcatttg attaaacatg tgattattta     600
atgaattgat gaaagagttg gattaaagtt gtattagtaa ttagaatttg gtgtcaaatt     660
taatttgaca tttgatcttt tcctatatat tgccccatag agtcagttaa ctcatttta     720 tatttcatag atcaaataag agaaataacg gtatattaat ccctccaaaa aaaaaaacg     780 gtatatttac taaaaaatct aagccacgta ggaggataac aggatcccg taggaggata     840 acatccaatc caaccaatca caacaatcct gatgagataa cccactttaa gcccacgcat     900
ctgtggcaca tctacattat ctaaatcaca cattcttcca cacatctgag ccacacaaaa     960
```

```
accaatccac atctttatca cccattctat aaaaaatcac actttgtgag tctacacttt      1020
gattcccttc aaacacatac aaagagaaga gactaattaa ttaattaatc atcttgagag      1080
aaaatggaac gagctataca aggaaacgac gctagggaac aagctaacag tgaacgttgg      1140
gatggaggat caggaggtac cacttctccc ttcaaacttc ctgacgaaag tccgagttgg      1200
actgagtggc ggctacataa cgatgagacg aattcgaatc aagataatcc ccttggtttc      1260
aaggaaagct ggggtttcgg gaaagttgta tttaagagat atctcagata cgacaggacg      1320
gaagcttcac tgcacagagt ccttggatct tggacgggag attcggttaa ctatgcagca      1380
tctcgatttt tcggtttcga ccagatcgga tgtacctata gtattcggtt tcgaggagtt      1440
agtatcaccg tttctggagg gtcgcgaact cttcagcatc tctgtgagat ggcaattcgg      1500
tctaagcaag aactgctaca gcttgcccca atcgaagtgg aaagtaatgt atcaagagga      1560
tgccctgaag gtactcaaac cttcgaaaaa gaaagcgagt aagttaaaat gcttcttcgt      1620
ctcctattta taatatggtt tgttattgtt aattttgttc ttgtagaaga gcttaattaa      1680
tcgttgttgt tatgaaatac tatttgtatg agatgaactg gtgtaatgta attcatttac      1740
ataagtggag tcagaatcag aatgtttcct ccataactaa ctagacatga agacctgccg      1800
cgtacaattg tcttatattt gaacaactaa aattgaacat cttttgccac aactttataa      1860
gtggttaata tagctcaaat atatggtcaa gttcaataga ttaataatgg aaatatcagt      1920
tatcgaaatt cattaacaat caacttaacg ttattaacta ctaattttat atcatcccct      1980
ttgataaatg atagtacacc aattaggaag gagcatgctc gcctaggaga ttgtcgtttc      2040
ccgccttcag tttgcaagct gctctagccg tgtagccaat acgcaaaccg cctctccccg      2100
cgcgttggga attactagcg cgtgtcgaca agcttgcatg ccggtcaaca tggtggagca      2160
cgacacactt gtctactcca aaaatatcaa agatacagtc tcagaagacc aaagggcaat      2220
tgagactttt caacaagggg taatatccgg aaacctcctc ggattccatt gcccagctat      2280
ctgtcacttt attgtgaaga tagtggaaaa ggaaggtggc tcctacaaat gccatcattg      2340
cgataaagga aaggccatcg ttgaagatgc ctctgccgac agtggtccca agatggacc       2400 cccacccacg aggagcatcg tggaaaaaga agacgttcca accacgtctt caaagcaagt      2460
ggattgatgt gataacatgg tggagcacga cacacttgtc tactccaaaa atatcaaaga      2520
tacagtctca gaagaccaaa gggcaattga cttttcaa caaagggtaa tatccggaaa      2580
cctcctcgga ttccattgcc cagctatctg tcactttatt gtgaagatag tggaaaagga      2640
aggtggctcc tacaaatgcc atcattgcga taaggaaag gccatcgttg aagatgcctc       2700
tgccgacagt ggtcccaaag atggaccccc acccacgagg agcatcgtgg aaaaagaaga      2760
cgttccaacc acgtcttcaa agcaagtgga ttgatgtgat atctccactg acgtaaggga      2820
tgacgcacaa tcccactatc cttcgcaaga cccttcctct ataaggaa gttcatttca        2880 tttggagagg acgtcactcc tcagccaaaa cgacaccccc atctgtctat ccactggccc      2940
ctggatctgc tgcccaaact aactccatgg tgaccctggg atgcctggtc aagggctatt      3000
tccctgagcc agtgacagtg acctggaact ctggatccct gtccagcggt gtgcacacct      3060
tcccagctgt cctgcagtct gacctctaca ctctgagcag ctcagtgact gtcccctcca      3120
gcacctggcc cagcgagacc gtcacctgca acgttgccca ccggccagc agcaccaagg       3180 tggacaagaa aattgtgccc agggattgtg gttgtaagcc ttgcatatgt acagtcccag      3240
aagtatcatc tgtcttcatc ttcccccaa agcccaagga tgtgctcacc attactctga       3300
ctcctaaggt cacgtgtgtt gtggtagaca tcagcaagga tgatcccgag gtccagttca      3360
```

```
gctggtttgt agatgatgtg gaggtgcaca cagctcagac gcaaccccgg gaggagcagt    3420
tcaacagcac tttccgctca gtcagtgaac ttcccatcat gcaccaggac tggctcaatg    3480
gcaaggagac gtccagattt tggcgatcta ttcaactgtc gccagttcat tggtactggt    3540
agtctccctg ggggcaatca gtttctggat gtgctctaat gggtctctac agtgtagaat    3600
atgtatttaa aggcctattt tctttagttt gaatttactg ttattcggtg tgcatttcta    3660
tgtttggtga gcggttttct gtgctcagag tgtgttattt tatgtaatt taatttcttt    3720 gtgagctcct gtttagcagg tcgtcccttc agcaaggaca caaaaagatt ttaattttat    3780
tatcgttcaa acatttggca ataaagtttc ttaagattga atcctgttgc cggtcttgcg    3840
atgattatca tataatttct gttgaattac gttaagcatg taataattaa catgtaatgc    3900
atgacgttat ttatgagatg ggttttatg attagagtcc cgcaattata catttaatac    3960
gcgatagaaa acaaaatata gcgcgcaaac taggataaat tatcgcgcgc ggtgtcatct    4020
atgttactag atctctagag tctcaagctt ggcgcgccca cgtgactagt ggcactggcc    4080
gtcgttttac aacgtcgtga ctgggaaaac cctggcgtta cccaacttaa tcgccttgca    4140
gcacatcccc ctttcgccag ctggcgtaat agcgaagagg cccgcaccga tcgcccttcc    4200
caacagttgc gcagcctgaa tggcgaatgc tagagcagct tgagcttgga tcagattgtc    4260
gtttcccgcc ttcagtttaa actatcagtg tttgacagga tatattggcg ggtaaaccta    4320
agagaaaaga gcgttta                                                   4337

<210> SEQ ID NO 63
<211> LENGTH: 1959
<212> TYPE: DNA
<213> ORGANISM: Artificial Sequence
<220> FEATURE:
<223> OTHER INFORMATION: Construct 4467 from 2X35S promoter to NOS
      terminator

<400> SEQUENCE: 63
gtcaacatgg tggagcacga cacacttgtc tactccaaaa atatcaaaga tacagtctca      60
gaagaccaaa gggcaattga gacttttcaa caaagggtaa tatccggaaa cctcctcgga     120
ttccattgcc cagctatctg tcactttatt gtgaagatag tggaaaagga aggtggctcc     180
tacaaatgcc atcattgcga taaaggaaag gccatcgttg aagatgcctc tgccgacagt     240
ggtcccaaag atggaccccc acccacgagg agcatcgtgg aaaaagaaga cgttccaacc     300
acgtcttcaa gcaagtgga ttgatgtgat aacatggtgg agcacgacac acttgtctac     360
tccaaaaata tcaaagatac agtctcagaa gaccaaaggg caattgagac ttttcaacaa     420
agggtaatat ccggaaacct cctcggattc cattgcccag ctatctgtca ctttattgtg     480
aagatagtgg aaaaggaagg tggctcctac aaatgccatc attgcgataa aggaaaggcc     540
atcgttgaag atgcctctgc cgacagtggt cccaaagatg gacccccacc cacgaggagc     600
atcgtggaaa aagaagacgt tccaaccacg tcttcaaagc aagtggattg atgtgatatc     660
tccactgacg taagggatga cgcacaatcc cactatcctt cgcaagaccc ttcctctata     720
taaggaagtt catttcattt ggagaggcac acaatttgct ttagtgatta aacttctctt     780
tacaacaaat taaaggtcta ttatctccca acaacataag aaaacaatga ctgccctgac     840
cgaaggtgct aagctgtttg agaaggagat tccgtacatc accgagctgg aaggggacgt     900
cgaaggaatg aagttcatca tcaagggaga aggaaccggg gacgctacga ctggaaccat     960
taaggccaag tatatctgta ccactggaga tctgccagtg ccttgggcca cccttgtgtc    1020
```

```
aaccctctcg tatggagtgc agtgttttgc taagtaccct agccacatta aggacttctt   1080
caaatccgcc atgccggaag gttatacccca agagcgcacc atttcttttg agggagatgg   1140
```

```
aaccctctcg tatggagtgc agtgttttgc taagtaccct agccacatta aggacttctt   1080
caaatccgcc atgccggaag gttatacccca agagcgcacc atttcttttg agggagatgg   1140
agtgtacaag acccgcgcga tggtcaccta tgagagggga tctatctaca accgggtgac   1200
tctgactgga gaaaacttta agaaggacgg gcatattctt cggaagaatg tcgccttcca   1260
gtgccctccc agcatccttt acattctccc cgacactgtg aacaacggaa tccgcgtgga   1320
gttcaatcaa gcctacgaca tcgagggggt gacggagaag ctggtgacca agtgtagcca   1380
gatgaatcgg ccactggccg gttcagcggc tgtccacatt ccgcgctacc atcatatcac   1440
ttatcacact aagctctcca agaccgcga tgagaggaga tcacatgt gcctggtgga   1500 agtggtcaag gccgtcgatc tcgataccta tcagtaaagg cctattttct ttagtttgaa   1560
tttactgtta ttcggtgtgc atttctatgt ttggtgagcg gttttctgtg ctcagagtgt   1620
gtttatttta tgtaatttaa tttctttgtg agctcctgtt tagcaggtcg tcccttcagc   1680
aaggacacaa aaagatttta attttattat cgttcaaaca tttggcaata aagtttctta   1740
agattgaatc ctgttgccgg tcttgcgatg attatcatat aatttctgtt gaattacgtt   1800
aagcatgtaa taattaacat gtaatgcatg acgttattta tgagatgggt ttttatgatt   1860
agagtcccgc aattatacat ttaatacgcg atagaaaaca aaatatagcg cgcaaactag   1920
gataaattat cgcgcgcggt gtcatctatg ttactagat                          1959
```

<210> SEQ ID NO 64
<211> LENGTH: 6156
<212> TYPE: DNA
<213> ORGANISM: Artificial Sequence
<220> FEATURE:
<223> OTHER INFORMATION: Cloning vector 4160 from left to right T-DNA

<400> SEQUENCE: 64

```
tggcaggata tattgtggtg taaacaaatt gacgcttaga caacttaata acacattgcg     60
gacgttttta atgtactgaa ttaacgccga atcccgggct ggtatattta tatgttgtca    120 ataactcaa aaaccataaa agtttaagtt agcaagtgtg tacatttta cttgaacaaa     180 aatattcacc tactactgtt ataaatcatt attaaacatt agagtaaaga aatatggatg    240
ataagaacaa gagtagtgat attttgacaa caattttgtt gcaacatttg agaaaatttt    300
gttgttctct cttttcattg gtcaaaaaca atagagagag aaaaaggaag agggagaata    360
aaaacataat gtgagtatga gagagaaagt tgtacaaaag ttgtaccaaa atagttgtac    420
aaatatcatt gaggaatttg acaaaagcta cacaaataag ggttaattgc tgtaaataaa    480
taaggatgac gcattagaga gatgtaccat tagagaattt ttggcaagtc attaaaaaga    540
aagaataaat tattttttaaa attaaaagtt gagtcatttg attaaacatg tgattattta    600
atgaattgat gaaagagttg gattaaagtt gtattagtaa ttagaatttg gtgtcaaatt    660
taatttgaca tttgatcttt tcctatatat gccccatag agtcagttaa ctcatttta    720 tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacactt    1020 gattcccttc aaacacatac aaagagaaga gactaattaa ttaattaatc atcttgagag   1080
```

```
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaaggaga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca cgcgtggcgc gccctggtat atttatatgt   2160
tgtcaaataa ctcaaaaacc ataaaagttt aagttagcaa gtgtgtacat ttttacttga   2220
acaaaaatat tcacctacta ctgttataaa tcattattaa acattagagt aaagaaatat   2280
ggatgataag aacaagagta gtgatatttt gacaacaatt tgttgcaac atttgagaaa   2340 attttgttgt tctctctttt cattggtcaa aaacaataga gagagaaaaa ggaagaggga   2400
gaataaaaac ataatgtgag tatgagagag aaagttgtac aaaagttgta ccaaaatagt   2460
tgtacaaata tcattgagga atttgacaaa agctacacaa ataagggtta attgctgtaa   2520
ataaataagg atgacgcatt agagagatgt accattagag aatttttggc aagtcattaa   2580
aaagaaagaa taaattattt ttaaaattaa agttgagtc atttgattaa acatgtgatt   2640
atttaatgaa ttgatgaaag agttggatta agttgtatt agtaattaga atttggtgtc   2700
aaatttaatt tgacatttga tcttttccta tatattgccc catagagtca gttaactcat   2760
ttttatattt catagatcaa ataagagaaa taacggtata ttaatccctc caaaaaaaaa   2820
aaacggtata tttactaaaa aatctaagcc acgtaggagg ataacaggat ccccgtagga   2880
ggataacatc caatccaacc aatcacaaca atcctgatga gataacccac tttaagccca   2940
cgcatctgtg gcacatctac attatctaaa tcacacattc ttccacacat ctgagccaca   3000
caaaaaccaa tccacatctt tatcacccat tctataaaaa atcacacttt gtgagtctac   3060
actttgattc ccttcaaaca catacaaaga gaagagacta attaattaat taatcatctt   3120
gagagaaaat gagtcttcta accgaggtcg aaacgcctat cagaaacgaa tgggggtgca   3180
gatgcaacga ttcaagtgat cctcttgttg ttgccgcaag tataattggg attgtgcacc   3240
tgatattgtg gattattgat cgccttttt ccaaaagcat ttatcgtatc tttaaacacg   3300
gtttaaaaag agggccttct acggaaggag taccagagtc tatgagggaa gaatatcgag   3360
aggaacagca gaatgctgtg gatgctgacg atggtcattt tgtcagcata gagctggagt   3420
aagagctcta agttaaaatg cttcttcgtc tcctatttat aatatggttt gttattgtta   3480
```

```
attttgttct tgtagaagag cttaattaat cgttgttgtt atgaaatact atttgtatga    3540
gatgaactgg tgtaatgtaa ttcatttaca taagtggagt cagaatcaga atgtttcctc    3600
cataactaac tagacatgaa gacctgccgc gtacaattgt cttatatttg aacaactaaa    3660
attgaacatc ttttgccaca actttataag tggttaatat agctcaaata tatggtcaag    3720
ttcaatagat taataatgga aatatcagtt atcgaaattc attaacaatc aacttaacgt    3780
tattaactac taattttata tcatccccct tgataaatga tagtacacca attaggaagg    3840
aactaggaga ttgtcgtttc ccgccttcag tttgcaagct gctctagccg tgtagccaat    3900
acgcaaaccg cctctccccg cgcgttggga attactagcg cgtgtcgaca agcttgcatg    3960
ccggtcaaca tggtggagca cgacacactt gtctactcca aaaatatcaa agatacagtc    4020
tcagaagacc aaagggcaat tgagactttt caacaaaggg taatatccgg aaacctcctc    4080
ggattccatt gcccagctat ctgtcacttt attgtgaaga tagtggaaaa ggaaggtggc    4140
tcctacaaat gccatcattg cgataaagga aggccatcg ttgaagatgc ctctgccgac    4200
agtggtccca aagatggacc cccacccacg aggagcatcg tggaaaaaga agacgttcca    4260
accacgtctt caaagcaagt ggattgatgt gataacatgg tggagcacga cacacttgtc    4320
tactccaaaa atatcaaaga tacagtctca gaagaccaaa gggcaattga gacttttcaa    4380
caaagggtaa tatccggaaa cctcctcgga ttccattgcc cagctatctg tcactttatt    4440
gtgaagatag tggaaaagga aggtggctcc tacaaatgcc atcattgcga taaggaaag    4500 gccatcgttg aagatgcctc tgccgacagt ggtcccaaag atggaccccc acccacgagg    4560
agcatcgtgg aaaaagaaga cgttccaacc acgtcttcaa agcaagtgga ttgatgtgat    4620
atctccactg acgtaaggga tgacgcacaa tcccactatc cttcgcaaga cccttcctct    4680
atataaggaa gttcatttca tttggagaga cgtcactcct cagccaaaac gacaccccca    4740
tctgtctatc cactggcccc tggatctgct gcccaaacta actccatggt gaccctggga    4800
tgcctggtca agggctattt ccctgagcca gtgacagtga cctggaactc tggatccctg    4860
tccagcggtg tgcacacctt cccagctgtc ctgcagtctg acctctacac tctgagcagc    4920
tcagtgactg tcccctccag cacctggccc agcgagaccg tcacctgcaa cgttgcccac    4980
ccggccagca gcaccaaggt ggacaagaaa attgtgccca gggattgtgg ttgtaagcct    5040
tgcatatgta cagtcccaga agtatcatct gtcttcatct tcccccaaa gcccaaggat    5100 gtgctcacca ttactctgac tcctaaggtc acgtgtgttg tggtagacat cagcaaggat    5160
gatcccgagg tccagttcag ctggtttgta gatgatgtgg aggtgcacac agctcagacg    5220
caaccccggg aggagcagtt caacagcact ttccgctcag tcagtgaact tcccatcatg    5280
caccaggact ggctcaatgg caaggagacg tccagatttt ggcgatctat tcaactgtcg    5340
ccagttcatt ggtactggta gtctccctgg gggcaatcag tttctggatg tgctctaatg    5400
ggtctctaca gtgtagaata tgtatttaaa ggcctatttt ctttagtttg aatttactgt    5460
tattcggtgt gcatttctat gtttggtgag cggttttctg tgctcagagt gtgtttattt    5520
tatgtaattt aatttctttg tgagctcctg tttagcaggt cgtcccttca gcaaggacac    5580
aaaaagattt taatttttatt atcgttcaaa catttggcaa taaagtttct taagattgaa    5640
tcctgttgcc ggtcttgcga tgattatcat ataatttctg ttgaattacg ttaagcatgt    5700
aataattaac atgtaatgca tgacgttatt tatgagatgg gtttttatga ttagagtccc    5760
gcaattatac atttaatacg cgatagaaaa caaaatatag cgcgcaaact aggataaatt    5820
```

```
atcgcgcgcg gtgtcatcta tgttactaga tctctagagt ctcaagcttg gcgcgcccac    5880
gtgactagtg gcactggccg tcgttttaca acgtcgtgac tgggaaaacc ctggcgttac    5940
ccaacttaat cgccttgcag cacatccccc tttcgccagc tggcgtaata gcgaagaggc    6000
ccgcaccgat cgcccttccc aacagttgcg cagcctgaat ggcgaatgct agagcagctt    6060
gagcttggat cagattgtcg tttcccgcct tcagtttaaa ctatcagtgt ttgacaggat    6120
atattggcgg gtaaacctaa gagaaaagag cgttta                              6156
```

<210> SEQ ID NO 65  
<211> LENGTH: 5502  
<212> TYPE: DNA  
<213> ORGANISM: Artificial Sequence  
<220> FEATURE:  
<223> OTHER INFORMATION: Cloning vector 4170 from left to right T-DNA

<400> SEQUENCE: 65

```
tggcaggata tattgtggtg taaacaaatt gacgcttaga caacttaata acacattgcg      60
gacgttttta atgtactgaa ttaacgccga atcccgggct ggtatattta tatgttgtca     120
aataactcaa aaaccataaa agtttaagtt agcaagtgtg tacattttta cttgaacaaa     180
aatattcacc tactactgtt ataaatcatt attaaacatt agagtaaaga aatatggatg     240
ataagaacaa gagtagtgat attttgacaa caattttgtt gcaacatttg agaaaatttt     300
gttgttctct cttttcattg gtcaaaaaca atagagagag aaaaaggaag agggagaata     360
aaaacataat gtgagtatga gagagaaagt tgtacaaaag ttgtaccaaa atagttgtac     420
aaatatcatt gaggaatttg acaaaagcta cacaaataag ggttaattgc tgtaaataaa     480
taaggatgac gcattagaga gatgtaccat tagagaattt ttggcaagtc attaaaaaga     540
aagaataaat tattttttaaa attaaaagtt gagtcatttg attaaacatg tgattatttta    600
atgaattgat gaaagagttg gattaaagtt gtattagtaa ttagaatttg gtgtcaaatt     660
taatttgaca tttgatcttt tcctatatat tgccccatag agtcagttaa ctcattttta     720
tatttcatag atcaaataag agaataacg gtatattaat ccctccaaaa aaaaaaaacg      780
gtatatttac taaaaaatct aagccacgta ggaggataac aggatccccg taggaggata     840
acatccaatc caaccaatca caacaatcct gatgagataa cccactttaa gcccacgcat     900
ctgtggcaca tctacattat ctaaatcaca cattcttcca cacatctgag ccacacaaaa     960
accaatccac atctttatca cccattctat aaaaaatcac actttgtgag tctacacttt    1020
gattcccttc aaacacatac aaagagaaga gactaattaa ttaattaatc atcttgagag    1080
aaaatggaac gagctataca aggaaacgac gctagggaac aagctaacag tgaacgttgg    1140
gatggaggat caggaggtac cacttctccc ttcaaacttc ctgacgaaag tccgagttgg    1200
actgagtggc ggctacataa cgatgagacg aattcgaatc aagataatcc ccttggtttc    1260
aaggaaagct ggggtttcgg gaagttgta tttaagagat atctcagata cgacaggacg     1320
gaagcttcac tgcacagagt ccttggatct tggacgggag attcggttaa ctatgcagca    1380
tctcgatttt tcggtttcga ccagatcgga tgtacctata gtattcggtt tcgaggagtt    1440
agtatcaccg tttctggagg gtcgcgaact cttcagcatc tctgtgagat ggcaattcgg    1500
tctaagcaag aactgctaca gcttgcccca atcgaagtgg aaagtaatgt atcaagagga    1560
tgccctgaag gtactcaaac cttgaaaaaa gaaagcgagt aagttaaaat gcttcttcgt    1620
ctcctatttta taatatggtt tgttattgtt aattttgttc ttgtagaaga gcttaattaa    1680
tcgttgttgt tatgaaatac tatttgtatg agatgaactg gtgtaatgta attcatttac    1740
```

```
ataagtggag tcagaatcag aatgtttcct ccataactaa ctagacatga agacctgccg    1800
cgtacaattg tcttatattt gaacaactaa aattgaacat cttttgccac aactttataa    1860
gtggttaata tagctcaaat atatggtcaa gttcaataga ttaataatgg aaatatcagt    1920
tatcgaaatt cattaacaat caacttaacg ttattaacta ctaattttat atcatcccct    1980
ttgataaatg atagtacacc aattaggaag gagcatgctc gcctaggaga ttgtcgtttc    2040
ccgccttcag tttgcaagct gctctagccg tgtagccaat acgcaaaccg cctctccccg    2100
cgcgttggga attactagcg cgtgtcgaca agcttgcatg ccggtcaaca tggtggagca    2160
cgacacactt gtctactcca aaaatatcaa agatacagtc tcagaagacc aaagggcaat    2220
tgagactttt caacaagggt aatatccgg aaacctcctc ggattccatt gcccagctat    2280
ctgtcacttt attgtgaaga tagtggaaaa ggaaggtggc tcctacaaat gccatcattg    2340
cgataaagga aaggccatcg ttgaagatgc ctctgccgac agtggtccca agatggacc    2400 cccacccacg aggagcatcg tggaaaaaga agacgttcca accacgtctt caaagcaagt    2460
ggattgatgt gataacatgg tggagcacga cacacttgtc tactccaaaa atatcaaaga    2520
tacagtctca gaagaccaaa gggcaattga cttttcaa caaagggtaa tatccggaaa    2580
cctcctcgga ttccattgcc cagctatctg tcactttatt gtgaagatag tggaaaagga    2640
aggtggctcc tacaaatgcc atcattgcga taaaggaaag gccatcgttg aagatgcctc    2700
tgccgacagt ggtcccaaag atggaccccc acccacgagg agcatcgtgg aaaaagaaga    2760
cgttccaacc acgtcttcaa agcaagtgga ttgatgtgat atctccactg acgtaaggga    2820
tgacgcacaa tcccactatc cttcgcaaga cccttcctct ataaggaa gttcatttca    2880 tttggagaga cgtcactcct cagccaaaac gacaccccca tctgtctatc cactggcccc    2940
tggatctgct gcccaaacta actccatggt gaccctggga tgcctggtca agggctattt    3000
ccctgagcca gtgacagtga cctggaactc tggatccctg tccagcggtg tgcacacctt    3060
cccagctgtc ctgcagtctg acctctacac tctgagcagc tcagtgactg tcccctccag    3120
cacctggccc agcgagaccg tcacctgcaa cgttgcccac ccggccagca gcaccaaggt    3180
ggacaagaaa attgtgccca gggattgtgg ttgtaagcct tgcatatgta cagtcccaga    3240
agtatcatct gtcttcatct ccccccaaa gcccaaggat gtgctcacca ttactctgac    3300
tcctaaggtc acgtgtgttg tggtagacat cagcaaggat gatcccgagg tccagttcag    3360
ctggtttgta gatgatgtgg aggtgcacac agctcagacg caaccccggg aggagcagtt    3420
caacagcact ttccgctcag tcagtgaact tcccatcatg caccaggact ggctcaatgg    3480
caaggagacg tccagatttt ggcgatctat tcaactgtcg ccagttcatt ggtactggta    3540
gtctccctgg gggcaatcag tttctggatg tgctctaatg ggtctctaca gtgtagaata    3600
tgtatttaaa ggcctatttt ctttagtttg aatttactgt tattcggtgt gcatttctat    3660
gtttggtgag cggttttctg tgctcagagt gtgtttattt tatgtaattt aatttctttg    3720
tgagctcctg tttagcaggt cgtcccttca gcaaggacac aaaaagattt aatttttatt    3780
atcgttcaaa catttggcaa taaagtttct taagattgaa tcctgttgcc ggtcttgcga    3840
tgattatcat ataatttctg ttgaattacg ttaagcatgt aataattaac atgtaatgca    3900
tgacgttatt tatgagatgg gtttttatga ttagagtccc gcaattatac atttaatacg    3960
cgatagaaaa caaatatag cgcgcaaact aggataaatt atcgcgcgcg gtgtcatcta    4020
tgttactaga tctctaggta aaaatcccaa ttatatttgg tctaatttag tttggtattg    4080
```

```
agtaaaacaa attcgaacca aaccaaaata taaatatata gtttttatat atatgccttt    4140
aagacttttt atagaatttt cttaaaaaa tatcaagaaa tatttgcgac tcttctggca    4200
tgtaatattt cgttaaatat gaagtgctcc atttttatta actttaaata attggttgta    4260
cgatcacttt cttatcaagt gttactaaaa tgcgtcaatc tctttgttct tccatattca    4320
tatgtcaaaa tctatcaaaa ttcttatata tcttttcga atttgaagtg aaatttcgat    4380
aatttaaaat taaatagaac atatcattat ttaggtatca tattgatttt tatacttaat    4440
tactaaattt ggttaacttt gaaagtgtac atcaacgaaa aattagtcaa acgactaaaa    4500
taaataaata tcatgtgtta ttaagaaaat tctcctataa gaatatttta atagatcata    4560
tgtttgtaaa aaaaattaat ttttactaac acatatattt acttatcaaa aatttgacaa    4620
agtaagatta aaataatatt catctaacaa aaaaaaaacc agaaaatgct gaaaacccgg    4680
caaaaccgaa ccaatccaaa ccgatatagt tggtttggtt tgattttgat ataaaccgaa    4740
ccaactcggt ccatttgcac ccctaatcat aatagcttta atatttcaag atattattaa    4800
gttaacgttg tcaatatcct ggaaattttg caaaatgaat caagcctata tggctgtaat    4860
atgaatttaa aagcagctcg atgtggtggt aatatgtaat ttacttgatt ctaaaaaaat    4920
atcccaagta ttaataattt ctgctaggaa gaaggttagc tacgatttac agcaaagcca    4980
gaatacaaag aaccataaag tgattgaagc tcgaaatata cgaaggaaca aatattttta    5040
aaaaaatacg caatgacttg gaacaaaaga aagtgatata ttttttgttc ttaaacaagc    5100
atcccctcta aagaatggca gttttccttt gcatgtaact attatgctcc cttcgttaca    5160
aaaattttgg actactattg ggaacttctt ctgaaaattc tagagtctca agcttggcgc    5220
gcccacgtga ctagtggcac tggccgtcgt tttacaacgt cgtgactggg aaaaccctgg    5280
cgttacccaa cttaatcgcc ttgcagcaca tccccctttc gccagctggc gtaatagcga    5340
agaggcccgc accgatcgcc cttcccaaca gttgcgcagc ctgaatggcg aatgctagag    5400
cagcttgagc ttggatcaga ttgtcgtttc ccgccttcag tttaaactat cagtgtttga    5460
caggatatat tggcgggtaa acctaagaga aaagagcgtt ta                      5502
```